(12) United States Patent
Ammendola et al.

(10) Patent No.: US 11,702,674 B2
(45) Date of Patent: Jul. 18, 2023

(54) SIMIAN ADENOVIRUS VECTORS COMPRISING THE CHAD-157 FIBER PROTEIN

(71) Applicant: GLAXOSMITHKLINE BIOLOGICALS SA, Rixensart (BE)

(72) Inventors: Virginia Ammendola, Rome (IT); Stefania Capone, Rome (IT); Stefano Colloca, Rome (IT); Antonella Folgori, Rome (IT); Rossella Merone, Rome (IT)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 16/973,630

(22) PCT Filed: Jun. 11, 2019

(86) PCT No.: PCT/IB2019/054857
§ 371 (c)(1),
(2) Date: Dec. 9, 2020

(87) PCT Pub. No.: WO2019/239311
PCT Pub. Date: Dec. 19, 2019

(65) Prior Publication Data
US 2021/0246468 A1 Aug. 12, 2021

(30) Foreign Application Priority Data
Jun. 12, 2018 (EP) .................................... 18177412

(51) Int. Cl.
| | |
|---|---|
| *C12N 15/86* | (2006.01) |
| *A61K 39/235* | (2006.01) |
| *A61P 37/04* | (2006.01) |
| *A61K 39/21* | (2006.01) |
| *A61K 39/00* | (2006.01) |
| *A61K 39/12* | (2006.01) |

(52) U.S. Cl.
CPC ............ *C12N 15/86* (2013.01); *A61K 39/235* (2013.01); *A61K 39/12* (2013.01); *A61K 39/21* (2013.01); *A61K 2039/5256* (2013.01); *A61P 37/04* (2018.01); *C12N 2710/10322* (2013.01); *C12N 2710/10334* (2013.01); *C12N 2710/10343* (2013.01); *C12N 2740/16034* (2013.01); *C12N 2740/16071* (2013.01)

(58) Field of Classification Search
CPC .................................................... A61K 39/235
See application file for complete search history.

(56) References Cited

U.S. PATENT DOCUMENTS

| | | | | |
|---|---|---|---|---|
| 8,216,834 B2* | 7/2012 | Colloca | ............ | C07K 14/70503 |
| | | | | 435/456 |
| 8,470,310 B2* | 6/2013 | Roy | ........................ | C12N 7/00 |
| | | | | 435/235.1 |

FOREIGN PATENT DOCUMENTS

| | | |
|---|---|---|
| JP | 2012-516679 A | 7/2012 |
| WO | WO 2010/086189 A2 | 8/2010 |
| WO | WO 2016/198599 A1 * | 12/2016 |
| WO | WO 2016/198599 A1 | 12/2016 |
| WO | WO 2018/104911 A1 | 6/2018 |

OTHER PUBLICATIONS

International Search Report issued in PCT/IB2019/054857 (PCT/ISA/210), dated Oct. 14, 2019.
Written Opinion of the International Searching Authority issued in PCT/IB2019/054857 (PCT/ISA/237), dated Oct. 14, 2019.

* cited by examiner

*Primary Examiner* — Jeffrey S Parkin
(74) *Attorney, Agent, or Firm* — Birch, Stewart, Kolasch & Birch, LLP

(57) ABSTRACT

The present invention relates to isolated polynucleotide and polypeptide sequences derived from novel chimpanzee adenovirus ChAd157, as well as to recombinant polynucleotides, vectors, adenoviruses, cells and compositions comprising said polynucleotide and polypeptide sequences.

24 Claims, 10 Drawing Sheets

Specification includes a Sequence Listing.

SEQUENCE LISTING

<160> NUMBER OF SEQ ID NOS: 42

<210> SEQ ID NO 1
<211> LENGTH: 561
<212> TYPE: PRT
<213> ORGANISM: Pan troglodytes

<400> SEQUENCE: 1

```
Met Ser Asp Ser Cys Ser Cys Pro Ser Ala Pro Thr Ile Phe Met Leu
1               5                   10                  15

Leu Gln Met Lys Arg Thr Lys Thr Ser Asp Glu Ser Phe Asn Pro Val
            20                  25                  30

Tyr Pro Tyr Asp Thr Glu Ser Gly Pro Pro Ser Val Pro Phe Leu Thr
        35                  40                  45

Pro Pro Phe Val Ser Pro Asp Gly Phe Gln Glu Ser Pro Pro Gly Val
    50                  55                  60

Leu Ser Leu Asn Leu Ala Glu Pro Leu Val Thr Ser His Gly Met Leu
65                  70                  75                  80

Ala Leu Lys Met Gly Ser Gly Leu Ser Leu Asp Asp Ala Gly Asn Leu
                85                  90                  95

Thr Ser Gln Asp Ile Thr Thr Ala Ser Pro Pro Leu Lys Lys Thr Lys
            100                 105                 110

Thr Asn Leu Ser Leu Glu Thr Ser Ser Pro Leu Thr Val Ser Thr Ser
            115                 120                 125

Gly Ala Leu Thr Val Ala Ala Ala Pro Leu Ala Val Ala Gly Thr
        130                 135                 140

Ser Leu Thr Met Gln Ser Glu Ala Pro Leu Thr Val Gln Asp Ala Lys
145                 150                 155                 160

Leu Thr Leu Ala Thr Lys Gly Pro Leu Thr Val Ser Glu Gly Lys Leu
                165                 170                 175

Ala Leu Gln Thr Ser Ala Pro Leu Thr Ala Ala Asp Ser Ser Thr Leu
            180                 185                 190

Thr Val Ser Ala Thr Pro Pro Ile Asn Val Ser Ser Gly Ser Leu Gly
        195                 200                 205

Leu Asp Met Glu Asp Pro Met Tyr Thr His Asn Gly Lys Leu Gly Ile
```

```
                  210                 215                 220
Arg Ile Gly Gly Pro Leu Arg Val Val Asp Ser Leu His Thr Leu Thr
225                 230                 235                 240

Val Val Thr Gly Asn Gly Leu Thr Val Asp Asn Ala Leu Gln Thr
                245                 250                 255

Lys Val Thr Gly Ala Leu Gly Tyr Asp Thr Ser Gly Asn Leu Gln Leu
                260                 265                 270

Arg Ala Ala Gly Gly Met Arg Ile Asp Ala Asn Gly Gln Leu Ile Leu
            275                 280                 285

Asn Val Ala Tyr Pro Phe Asp Ala Gln Asn Asn Leu Ser Leu Arg Leu
            290                 295                 300

Gly Gln Gly Pro Leu Tyr Ile Asn Thr Asp His Asn Leu Asp Leu Asn
305                 310                 315                 320

Cys Asn Arg Gly Leu Thr Thr Thr Thr Asn Thr Lys Lys Leu
                325                 330                 335

Glu Thr Lys Ile Ser Ser Gly Leu Asp Tyr Asp Thr Asn Gly Ala Val
                340                 345                 350

Ile Ile Lys Leu Gly Thr Gly Leu Ser Phe Asp Asn Thr Gly Ala Leu
            355                 360                 365

Thr Val Gly Asn Thr Gly Asp Asp Lys Leu Thr Leu Trp Thr Thr Pro
370                 375                 380

Asp Pro Ser Pro Asn Cys Arg Ile His Ser Asp Lys Asp Cys Lys Phe
385                 390                 395                 400

Thr Leu Val Leu Thr Lys Cys Gly Ser Gln Ile Leu Ala Ser Val Ala
                405                 410                 415

Ala Leu Ala Val Ser Gly Asn Leu Ala Ser Ile Thr Gly Thr Val Ala
                420                 425                 430

Ser Val Thr Ile Phe Leu Arg Phe Asp Gln Asn Gly Val Leu Met Glu
            435                 440                 445

Asn Ser Ser Leu Asp Arg Gln Tyr Trp Asn Phe Arg Asn Gly Asn Ser
            450                 455                 460

Thr Asn Ala Ala Pro Tyr Thr Asn Ala Val Gly Phe Met Pro Asn Leu
465                 470                 475                 480

Ala Ala Tyr Pro Lys Thr Gln Ser Gln Thr Ala Lys Asn Asn Ile Val
                485                 490                 495

Ser Gln Val Tyr Leu Asn Gly Asp Lys Ser Lys Pro Met Thr Leu Thr
            500                 505                 510

Ile Thr Leu Asn Gly Thr Asn Glu Ser Ser Glu Thr Ser Gln Val Ser
            515                 520                 525

His Tyr Ser Met Ser Phe Thr Trp Ala Trp Glu Ser Gly Gln Tyr Ala
            530                 535                 540

Thr Glu Thr Phe Ala Thr Asn Ser Phe Thr Phe Ser Tyr Ile Ala Glu
545                 550                 555                 560

Gln

<210> SEQ ID NO 2
<211> LENGTH: 1683
<212> TYPE: DNA
<213> ORGANISM: Pan troglodytes

<400> SEQUENCE: 2
atgtcagatt cttgctcctg tccctccgca cccactatct tcatgttgtt gcagatgaag    60
cgcaccaaaa cgtctgacga gagcttcaac cccgtgtacc cctatgacac ggaaagcggc   120
```

```
cctccctccg tccctttcct caccccctccc ttcgtgtctc ccgatggatt ccaagaaagt    180
ccccccgggg tcctgtctct gaacctggcc gagcccctgg tcacttccca cggcatgctc    240
gccctgaaaa tgggaagtgg cctctccctg gacgacgctg caacctcac ctctcaagat     300
atcaccaccg ctagccctcc cctcaaaaaa accaagacca acctcagcct agaaacctca    360
tccccctaa ctgtgagcac ctcaggcgcc ctcaccgtag cagccgccgc tcccctggcg     420
gtggccggca cctccctcac catgcaatca gaggcccccc tgacagtaca ggatgcaaaa    480
ctcacccctg gccaccaaagg ccccctgacc gtgtctgaag caaactggc cttgcaaaca    540
tcggccccgc tgacggccgc tgacagcagc accctcaccg ttagcgccac accaccaatt    600
aatgtaagca gtggaagttt aggcttagac atggaagacc ctatgtatac tcacaatgga    660
aaactgggaa taagaattgg gggtccacta agagtagtag acagcttgca tacactcact    720
gtagttaccg gaaatggact aactgtagat aacaatgccc tccaaactaa agttacgggc    780
gccctaggtt atgacacatc aggaaaatcta caattaagag ctgcaggagg tatgcgaatt    840
gacgcaaatg ccaacttat ccttaatgtg gcatacccat ttgatgctca gaacaatctc     900
agccttagac ttggtcaggg accccctgtat ataaacacag accacaaacct ggatttgaat  960
tgcaacagag gtctaaccac aactaccacc aacaacacaa aaaacttga gactaaaatt    1020
agctcaggct tagactatga caccaatggt gctgtcatta ttaaacttgg cactggtcta    1080
agcttcgaca acacaggcgc cctaactgtg gaaacactg gtgatgataa actgactctg    1140
tggacgaccc cagacccatc tccaaattgc agaattcact cagacaaaga ctgcaagttt    1200
actctagtcc taactaagtg tggaagccaa atcctggcct ctgtcgccgc cctagcggta    1260
tcaggaaatc tggcttcgat aacaggcacc gttgccagcg ttaccatctt tctcagattt    1320
gatcagaatg gagtgcttat ggaaaactcc tcgctagaca ggcagtactg gaacttcaga    1380
aatggcaact caactaacgc tgccccctac accaatgcag ttgggttcat gccaaacctc    1440
gcagcatacc ccaaaacgca aagccagact gctaaaaaca acattgtaag tcaggtttac    1500
ttgaatggag acaaatccaa acccatgacc cttaccatca ccctcaatgg aactaatgaa    1560
tccagtgaaa ctagccaggt gagtcactac tccatgtcat ttacatgggc ttgggaaagt    1620
gggcaatatg ccactgaaac cttttgccacc aactccttca cctttttctta cattgctgaa    1680
caa                                                                  1683
```

<210> SEQ ID NO 3
<211> LENGTH: 593
<212> TYPE: PRT
<213> ORGANISM: Pan troglodytes

<400> SEQUENCE: 3

Met Arg Arg Ala Ala Met Tyr Gln Glu Gly Pro Pro Ser Tyr Glu
1               5                   10                  15

Ser Val Val Gly Ala Ala Ala Ala Pro Ser Ser Pro Phe Ala Ser
                20                  25                  30

Gln Leu Leu Glu Pro Pro Tyr Val Pro Pro Arg Tyr Leu Arg Pro Thr
            35                  40                  45

Gly Gly Arg Asn Ser Ile Arg Tyr Ser Glu Leu Ala Pro Leu Phe Asp
        50                  55                  60

Thr Thr Arg Val Tyr Leu Val Asp Asn Lys Ser Ala Asp Val Ala Ser
65                  70                  75                  80

Leu Asn Tyr Gln Asn Asp His Ser Asn Phe Leu Thr Thr Val Ile Gln
                85                  90                  95

```
Asn Asn Asp Tyr Ser Pro Ser Glu Ala Ser Thr Gln Thr Ile Asn Leu
            100                 105                 110
Asp Asp Arg Ser His Trp Gly Gly Asp Leu Lys Thr Ile Leu His Thr
            115                 120                 125
Asn Met Pro Asn Val Asn Glu Phe Met Phe Thr Asn Lys Phe Lys Ala
130                 135                 140
Arg Val Met Val Ser Arg Ser His Thr Lys Glu Asp Arg Val Glu Leu
145                 150                 155                 160
Lys Tyr Glu Trp Val Glu Phe Glu Leu Pro Glu Gly Asn Tyr Ser Glu
                    165                 170                 175
Thr Met Thr Ile Asp Leu Met Asn Asn Ala Ile Val Glu His Tyr Leu
            180                 185                 190
Lys Val Gly Arg Gln Asn Gly Val Leu Glu Ser Asp Ile Gly Val Lys
            195                 200                 205
Phe Asp Thr Arg Asn Phe Arg Leu Gly Leu Asp Pro Val Thr Gly Leu
210                 215                 220
Val Met Pro Gly Val Tyr Thr Asn Glu Ala Phe His Pro Asp Ile Ile
225                 230                 235                 240
Leu Leu Pro Gly Cys Gly Val Asp Phe Thr Tyr Ser Arg Leu Ser Asn
                    245                 250                 255
Leu Leu Gly Ile Arg Lys Arg Gln Pro Phe Gln Glu Gly Phe Arg Ile
            260                 265                 270
Thr Tyr Glu Asp Leu Glu Gly Gly Asn Ile Pro Ala Leu Leu Asp Val
            275                 280                 285
Glu Ala Tyr Gln Asp Ser Leu Lys Glu Asn Glu Ala Gly Gln Glu Asp
            290                 295                 300
Thr Ala Pro Ala Ala Ser Ala Ala Ala Glu Gln Gly Glu Asp Ala Ala
305                 310                 315                 320
Asp Thr Ala Ala Ala Asp Gly Ala Glu Ala Asp Pro Ala Met Val Val
                    325                 330                 335
Glu Ala Ala Glu Gln Glu Glu Asp Met Asn Asp Ser Ala Val Arg Gly
            340                 345                 350
Asp Thr Phe Val Thr Arg Gly Glu Glu Lys Gln Ala Glu Ala Glu Ala
            355                 360                 365
Ala Ala Glu Glu Lys Gln Leu Ala Ala Ala Ala Ala Ala Ala Ala Leu
370                 375                 380
Ala Ala Ala Glu Ala Glu Ser Glu Gly Thr Lys Pro Ala Lys Glu Pro
385                 390                 395                 400
Val Ile Lys Pro Leu Thr Glu Asp Ser Lys Lys Arg Ser Tyr Asn Leu
                    405                 410                 415
Leu Lys Asp Ser Thr Asn Thr Ala Tyr Arg Ser Trp Tyr Leu Ala Tyr
            420                 425                 430
Asn Tyr Gly Asp Pro Ser Thr Gly Val Arg Ser Trp Thr Leu Leu Cys
            435                 440                 445
Thr Pro Asp Val Thr Cys Gly Ser Glu Gln Val Tyr Trp Ser Leu Pro
            450                 455                 460
Asp Met Met Gln Asp Pro Val Thr Phe Arg Ser Thr Arg Gln Val Ser
465                 470                 475                 480
Asn Phe Pro Val Val Gly Ala Glu Leu Leu Pro Val His Ser Lys Ser
                    485                 490                 495
Phe Tyr Asn Asp Gln Ala Val Tyr Ser Gln Leu Ile Arg Gln Phe Thr
            500                 505                 510
```

```
Ser Leu Thr His Val Phe Asn Arg Phe Pro Glu Asn Gln Ile Leu Ala
    515                 520                 525
Arg Pro Pro Ala Pro Thr Ile Thr Thr Val Ser Glu Asn Val Pro Ala
    530                 535                 540
Leu Thr Asp His Gly Thr Leu Pro Leu Arg Asn Ser Ile Gly Gly Val
545                 550                 555                 560
Gln Arg Val Thr Val Thr Asp Ala Arg Arg Arg Thr Cys Pro Tyr Val
                565                 570                 575
Tyr Lys Ala Leu Gly Ile Val Ser Pro Arg Val Leu Ser Ser Arg Thr
            580                 585                 590
Phe
```

<210> SEQ ID NO 4
<211> LENGTH: 1779
<212> TYPE: DNA
<213> ORGANISM: Pan troglodytes

<400> SEQUENCE: 4

```
atgcggcgcg cggcgatgta ccaggaggga cctcctccct cttacgagag cgtggtgggc    60
gcggcggcgg cggcgccctc ttctcccttt gcgtcgcagc tgctggagcc gccgtacgtg   120
cctccgcgct acctgcggcc tacggggggg agaaacagca tccgttactc ggagctggcg   180
cccctgttcg acaccacccg ggtgtacctg gtggacaaca agtcggcgga cgtggcctcc   240
ctgaactacc agaacgacca cagcaatttt ttgaccacgg tcatccagaa caatgactac   300
agcccgagcg aggccagcac ccagaccatc aatctggatg accggtcgca ctggggcggc   360
gacctgaaaa ccatcctgca caccaacatg cccaacgtga acgagttcat gttcaccaat   420
aagttcaagg cgcgggtgat ggtgtcgcgc tcgcacacca aggaagaccg ggtggagctg   480
aagtacgagt gggtggagtt cgagctgcca gagggcaact actccgagac catgaccatt   540
gacctgatga caacgcgat cgtggagcac tatctgaaag tgggcaggca gaacggggtc   600
ctggagagcg acatcggggt caagttcgac accaggaact tccgcctggg gctggacccc   660
gtgaccgggc tggttatgcc cggggtgtac accaacgagg ccttccatcc cgacatcatc   720
ctgctgcccg gctgcggggt ggacttcact tacagccgcc tgagcaacct cctgggcatc   780
cgcaagcggc agcccttcca ggagggcttc aggatcacct acgaggacct ggagggggggc   840
aacatccccg cgctcctcga tgtggaggcc taccaggata gcttgaagga aaatgaggcg   900
ggacaggagg ataccgcccc cgccgcctcc gccgccgccg agcagggcga ggatgctgct   960
gacaccgcgc cgcggacgg gcggaggcc gaccccgcta tggtggtgga ggctgccgag  1020
caggaggagg acatgaatga cagtgcggtg cgcggagaca ccttcgtcac ccgggggggag  1080
gaaaagcaag cggaggccga ggccgcgcc gaggaaaagc aactggcggc agcagcggcg  1140
gcggcggcgt tggccgcggc ggaggctgag tctgagggga ccaagcccgc caaggagccc  1200
gtgattaagc ccctgaccga agatagcaag aagcgcagtt acaacctgct caaggacagc  1260
accaacaccg cgtaccgcag ctggtacctg gcctacaact acggcgaccc gtcgacgggg  1320
gtgcgctcct ggaccctgct gtgcacgccg acgtgacct gcggctcgga gcaggtgtac  1380
tggtcgctgc ccgacatgat gcagacccc gtgaccttcc gctccacgcg gcaggtcagc  1440
aacttcccgg tggtgggcgc cgagctgctg ccgtgcact caagagctt ctacaacgac  1500
caggccgtct actcccagct catccgccag ttcacctctc tgacccacgt gttcaatcgc  1560
tttcctgaga ccagattct ggcgcgcccg ccgccccca ccatcaccac cgtcagtgaa  1620
```

```
aacgttcctg ctctcacaga tcacgggacg ctaccgctgc gcaacagcat cggaggagtc      1680
cagcgagtga ccgttactga cgccagacgc cgcacctgcc cctacgttta caaggccttg      1740
ggcatagtct cgccgcgcgt cctttccagc cgcactttt                              1779
```

<210> SEQ ID NO 5
<211> LENGTH: 958
<212> TYPE: PRT
<213> ORGANISM: Pan troglodytes

<400> SEQUENCE: 5

```
Met Ala Thr Pro Ser Met Met Pro Gln Trp Ser Tyr Met His Ile Ser
1               5                  10                  15

Gly Gln Asp Ala Ser Glu Tyr Leu Ser Pro Gly Leu Val Gln Phe Ala
            20                  25                  30

Arg Ala Thr Glu Ser Tyr Phe Ser Leu Ser Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ser Leu Ala Pro Lys Gly
        115                 120                 125

Ala Pro Asn Ser Cys Glu Trp Glu Gln Leu Glu Glu Ala Gln Ala Ala
    130                 135                 140

Val Glu Asp Glu Glu Leu Glu Asp Glu Glu Glu Pro Gln Asp Glu
145                 150                 155                 160

Ala Pro Val Lys Lys Thr His Val Tyr Ala Gln Ala Pro Leu Ser Gly
                165                 170                 175

Glu Glu Ile Thr Lys Asn Gly Leu Gln Ile Gly Ser Asp Asn Thr Glu
            180                 185                 190

Ala Gln Ser Lys Pro Ile Tyr Ala Asp Pro Thr Phe Gln Pro Glu Pro
        195                 200                 205

Gln Ile Gly Glu Ser Gln Trp Asn Glu Ala Asp Ala Thr Val Ala Gly
    210                 215                 220

Gly Arg Val Leu Lys Lys Ser Thr Pro Met Lys Pro Cys Tyr Gly Ser
225                 230                 235                 240

Tyr Ala Arg Pro Thr Asn Ser Asn Gly Gly Gln Gly Val Leu Val Ala
                245                 250                 255

Asp Asp Lys Gly Val Leu Gln Ser Lys Val Glu Leu Gln Phe Phe Ser
            260                 265                 270

Asn Thr Thr Thr Leu Asn Gln Arg Glu Gly Asn Asp Thr Lys Pro Lys
        275                 280                 285

Val Val Leu Tyr Ser Glu Asp Val His Met Glu Thr Pro Asp Thr His
    290                 295                 300

Ile Ser Tyr Lys Pro Thr Lys Ser Asp Asp Asn Ser Lys Ile Met Leu
305                 310                 315                 320

Gly Gln Gln Ser Met Pro Asn Arg Pro Asn Tyr Ile Gly Phe Arg Asp
                325                 330                 335

Asn Phe Ile Gly Leu Met Tyr Tyr Asn Ser Thr Gly Asn Met Gly Val
            340                 345                 350
```

```
Leu Ala Gly Gln Ala Ser Gln Leu Asn Ala Val Val Asp Leu Gln Asp
            355                 360                 365

Arg Asn Thr Glu Leu Ser Tyr Gln Leu Leu Leu Asp Ser Met Gly Asp
            370                 375                 380

Arg Thr Arg Tyr Phe Ser Met Trp Asn Gln Ala Val Asp Ser Tyr Asp
385                 390                 395                 400

Pro Asp Val Arg Ile Ile Glu Asn His Gly Thr Glu Asp Glu Leu Pro
                405                 410                 415

Asn Tyr Cys Phe Pro Leu Gly Gly Ile Gly Val Thr Asp Thr Tyr Gln
            420                 425                 430

Ala Ile Lys Thr Asn Gly Asn Gly Gln Glu Asn Pro Thr Trp Glu Lys
            435                 440                 445

Asp Thr Glu Phe Ala Asp Arg Asn Glu Ile Gly Val Gly Asn Asn Phe
450                 455                 460

Ala Met Glu Ile Asn Leu Ser Ala Asn Leu Trp Arg Asn Phe Leu Tyr
465                 470                 475                 480

Ser Asn Val Ala Leu Tyr Leu Pro Asp Lys Leu Lys Tyr Asn Pro Ser
                485                 490                 495

Asn Val Asp Ile Ser Asp Asn Pro Asn Thr Tyr Asp Tyr Met Asn Lys
                500                 505                 510

Arg Val Val Ala Pro Gly Leu Val Asp Cys Tyr Ile Asn Leu Gly Ala
            515                 520                 525

Arg Trp Ser Leu Asp Tyr Met Asp Asn Val Asn Pro Phe Asn His His
            530                 535                 540

Arg Asn Ala Gly Leu Arg Tyr Arg Ser Met Leu Leu Gly Asn Gly Arg
545                 550                 555                 560

Tyr Val Pro Phe His Ile Gln Val Pro Gln Lys Phe Phe Ala Ile Lys
                565                 570                 575

Asn Leu Leu Leu Leu Pro Gly Ser Tyr Thr Tyr Glu Trp Asn Phe Arg
            580                 585                 590

Lys Asp Val Asn Met Val Leu Gln Ser Ser Leu Gly Asn Asp Leu Arg
            595                 600                 605

Val Asp Gly Ala Ser Ile Lys Phe Glu Ser Ile Cys Leu Tyr Ala Thr
            610                 615                 620

Phe Phe Pro Met Ala His Asn Thr Ala Ser Thr Leu Glu Ala Met Leu
625                 630                 635                 640

Arg Asn Asp Thr Asn Asp Gln Ser Phe Asn Asp Tyr Leu Ser Ala Ala
                645                 650                 655

Asn Met Leu Tyr Pro Ile Pro Ala Asn Ala Thr Asn Val Pro Ile Ser
                660                 665                 670

Ile Pro Ser Arg Asn Trp Ala Ala Phe Arg Gly Trp Ala Phe Thr Arg
            675                 680                 685

Leu Lys Thr Lys Glu Thr Pro Ser Leu Gly Ser Gly Phe Asp Pro Tyr
            690                 695                 700

Tyr Thr Tyr Ser Gly Ser Ile Pro Tyr Leu Asp Gly Thr Phe Tyr Leu
705                 710                 715                 720

Asn His Thr Phe Lys Lys Val Ser Val Thr Phe Asp Ser Ser Val Ser
                725                 730                 735

Trp Pro Gly Asn Asp Arg Leu Leu Thr Pro Asn Glu Phe Glu Ile Lys
            740                 745                 750

Arg Ser Val Asp Gly Glu Gly Tyr Asn Val Ala Gln Cys Asn Met Thr
            755                 760                 765
```

Lys Asp Trp Phe Leu Val Gln Met Leu Ala Asn Tyr Asn Ile Gly Tyr
        770                 775                 780

Gln Gly Phe Tyr Ile Pro Glu Ser Tyr Lys Asp Arg Met Tyr Ser Phe
785                 790                 795                 800

Phe Arg Asn Phe Gln Pro Met Ser Arg Gln Val Val Asp Gln Thr Lys
                805                 810                 815

Tyr Lys Asp Tyr Gln Glu Val Gly Ile Ile His Gln His Asn Asn Ser
            820                 825                 830

Gly Phe Val Gly Tyr Leu Ala Pro Thr Met Arg Glu Gly Gln Ala Tyr
        835                 840                 845

Pro Ala Asn Phe Pro Tyr Pro Leu Ile Gly Lys Thr Ala Val Asp Ser
850                 855                 860

Ile Thr Gln Lys Lys Phe Leu Cys Asp Arg Thr Leu Trp Arg Ile Pro
865                 870                 875                 880

Phe Ser Ser Asn Phe Met Ser Met Gly Ala Leu Ser Asp Leu Gly Gln
                885                 890                 895

Asn Leu Leu Tyr Ala Asn Ser Ala His Ala Leu Asp Met Thr Phe Glu
            900                 905                 910

Val Asp Pro Met Asp Glu Pro Thr Leu Leu Tyr Val Leu Phe Glu Val
        915                 920                 925

Phe Asp Val Val Arg Val His Gln Pro His Arg Gly Val Ile Glu Thr
930                 935                 940

Val Tyr Leu Arg Thr Pro Phe Ser Ala Gly Asn Ala Thr Thr
945                 950                 955

<210> SEQ ID NO 6
<211> LENGTH: 2874
<212> TYPE: DNA
<213> ORGANISM: Pan troglodytes

<400> SEQUENCE: 6
atggcgaccc catcgatgat gccgcagtgg tcgtacatgc acatctcggg ccaggacgcc      60
tcggagtacc tgagccccgg gctggtgcag ttcgcccgcg ccaccgagag ctacttcagc     120
ctgagtaaca gtttaggaa ccccacggtg gcgcccacgc acgatgtgac caccgaccgg     180
tctcagcgcc tgacgctgcg gttcattccc gtggaccgcg aggacaccgc gtactcgtac     240
aaggcgcggt tcaccctggc cgtgggcgac aaccgcgtgc tggacatggc ctccacctac     300
tttgacatcc gcggggtgct ggaccggggc cccactttca gccttactc tggcaccgcc     360 tacaactccc tggcccccaa gggcgctccc aactcctgcg agtgggagca attagaagaa     420
gcccaggccg ctgtggaaga cgaagaatta gaagatgaag acgaggaacc acaggatgag     480
gcacctgtga aaaaaccca tgtatacgct caggctcccc tttctggaga agaaattact     540
aaaaacggtt tgcaaatagg gtcagataac acagaagccc agtctaagcc catatatgca     600
gatcctacat tccagcctga accccaaatc ggggaatccc agtggaatga ggcagatgct     660
acagttgccg gcggtagagt gctaaagaaa tccactccca tgaagccatg ctatggttcc     720
tatgcaagac ccacaaactc caatggaggt caaggtgtgc tggtggctga tgataagggg     780
gttcttcaat ctaaagttga attgcaattt ttttcaaata ctactactct taatcagcgg     840
gagggtaacg atacaaaacc aaaagtggtg ctgtatagcg aagatgtgca catggaaact     900
ccagacaccc acatttctta caagcccaca aaaagcgatg acaattcaaa aatcatgctg     960
ggtcagcagt ccatgcccaa cagacctaat tacatcggct tcagagacaa ctttatcggc    1020
ctcatgtatt acaatagcac tggcaacatg ggagtgcttg caggtcaggc ctctcagttg    1080

-continued

```
aatgcagtgg tggacttgca agacagaaac acagaactgt cctaccagct cttgcttgat    1140
tccatgggtg acagaaccag atactttttcc atgtggaatc aggcagtgga cagttatgac   1200
ccagatgtca gaattattga aaatcatgga actgaagacg agctccccaa ctattgtttc    1260
cctctgggcg cataggggt aactgacact taccaggcca ttaaaaccaa tggcaatggt     1320
caagaaaacc caacctggga aaagataca gagtttgcag accgcaatga aatagggtg      1380 ggaaacaatt cgctatgga gatcaacctc agtgccaacc tgtggagaaa cttcctgtac     1440
tccaacgtgg cgctgtacct gccagacaag cttaagtaca ccccctccaa tgtggacatc    1500
tctgacaacc ccaacaccta cgattacatg aacaagcgag tggtggcccc ggggctggtg    1560
gactgctaca tcaacctggg cgcgcgctgg tcgctggact acatggacaa cgtcaacccc    1620
ttcaaccacc accgcaatgc gggcctgcgc taccgctcca tgctcctggg caacgggcgc    1680
tacgtgccct tccacatcca ggtgccccag aagttctttg ccatcaagaa cctcctcctc    1740
ctgccgggct cctacaccta cgagtggaac ttcaggaagg atgtcaacat ggtcctccag    1800
agctctctgg gtaacgatct cagggtggac ggggccagca tcaagttcga gagcatctgc    1860
ctctacgcca ccttcttccc catggcccac aacacggcct ccacgctcga ggccatgctc    1920
aggaacgaca ccaacgacca gtccttcaat gactacctct ccgccgccaa catgctctac    1980
cccatacccg ccaacgccac caacgtcccc atctccatcc cctcgcgcaa ctgggcggcc    2040
ttccgcggct gggccttcac ccgcctcaag accaaggaga ccccctccct gggctcggga    2100
ttcgacccct actacaccta ctcgggctcc attccctacc tggacggcac cttctacctc    2160
aaccacactt tcaagaaggt ctcggtcacc ttcgactcct cggtcagctg gccgggcaac    2220
gaccgtctgc tcaccccaa cgagttcgaa atcaagcgct cggtcgacgg ggagggctac     2280
aacgtggccc agtgcaacat gaccaaggac tggttcctgg tccagatgct ggccaactac    2340
aacatcggct accagggctt ctacatccca gagagctaca aggacaggat gtactccttc    2400
ttcaggaact tccagcccat gagccggcag gtggtggacc agaccaagta caaggactac    2460
caggaggtgg gcatcatcca ccagcacaac aactcgggct cgtgggcta cctcgccccc    2520 accatgcgcg agggacaggc ctaccccgcc aacttcccct acccgctcat aggcaagacc    2580
gcggtcgaca gcatcaccca gaaaaagttc ctctgcgatc gcaccctctg gcgcatcccc    2640
ttctccagca acttcatgtc catgggtgcg ctctcggacc tgggcagaa cttgctctac     2700 gccaactccg cccacgcccct cgacatgacc ttcgaggtcg accccatgga cgagcccacc    2760
cttctctatg tttctgttcga agtctttgac gtggtccggg tccaccagcc gcaccgcggc   2820
gtcatcgaga ccgtgtacct gcgtacgccc ttctcggccg gcaacgccac cacc          2874
```

<210> SEQ ID NO 7
<211> LENGTH: 578
<212> TYPE: PRT
<213> ORGANISM: Pan troglodytes

<400> SEQUENCE: 7

```
Met Lys Arg Thr Lys Thr Ser Asp Glu Ser Phe Asn Pro Val Tyr Pro
 1               5                  10                  15

Tyr Asp Thr Glu Ser Gly Pro Pro Ser Val Pro Phe Leu Thr Pro Pro
            20                  25                  30

Phe Val Ser Pro Asp Gly Phe Gln Glu Ser Pro Pro Gly Val Leu Ser
        35                  40                  45

Leu Asn Leu Ala Glu Pro Leu Val Thr Ser His Gly Met Leu Ala Leu
```

-continued

```
                 50                  55                  60
        Lys Met Gly Ser Gly Leu Ser Leu Asp Asp Ala Gly Asn Leu Thr Ser
        65                  70                  75                  80

Gln Asp Ile Thr Thr Ala Ser Pro Pro Leu Lys Lys Thr Lys Thr Asn
                            85                  90                  95

Leu Ser Leu Glu Thr Ser Ser Pro Leu Thr Val Ser Thr Ser Gly Ala
                            100                 105                 110

Leu Thr Val Ala Ala Ala Ala Pro Leu Ala Val Ala Gly Thr Ser Leu
                            115                 120                 125

Thr Met Gln Ser Glu Ala Pro Leu Thr Val Gln Asp Ala Lys Leu Thr
                    130                 135                 140

Leu Ala Thr Lys Gly Pro Leu Thr Val Ser Glu Gly Lys Leu Ala Leu
        145                 150                 155                 160

Gln Thr Ser Ala Pro Leu Thr Ala Ala Asp Ser Ser Thr Leu Thr Val
                            165                 170                 175

Ser Ala Thr Pro Pro Leu Ser Thr Ser Asn Gly Ser Leu Gly Ile Asp
                            180                 185                 190

Met Gln Ala Pro Ile Tyr Thr Thr Asn Gly Lys Leu Gly Leu Asn Phe
                    195                 200                 205

Gly Ala Pro Leu His Val Val Asp Ser Leu Asn Ala Leu Thr Val Val
        210                 215                 220

Thr Gly Gln Gly Leu Thr Ile Asn Gly Thr Ala Leu Gln Thr Arg Val
        225                 230                 235                 240

Ser Gly Ala Leu Asn Tyr Asp Thr Ser Gly Asn Leu Glu Leu Arg Ala
                            245                 250                 255

Ala Gly Gly Met Arg Val Asp Ala Asn Gly Gln Leu Ile Leu Asp Val
                    260                 265                 270

Ala Tyr Pro Phe Asp Ala Gln Asn Asn Leu Ser Leu Arg Leu Gly Gln
                    275                 280                 285

Gly Pro Leu Phe Val Asn Ser Ala His Asn Leu Asp Val Asn Tyr Asn
                    290                 295                 300

Arg Gly Leu Tyr Leu Phe Thr Ser Gly Asn Thr Lys Lys Leu Glu Val
        305                 310                 315                 320

Asn Ile Lys Thr Ala Lys Gly Leu Ile Tyr Asp Thr Ala Ile Ala
                            325                 330                 335

Ile Asn Ala Gly Asp Gly Leu Gln Phe Asp Ser Gly Ser Asp Thr Asn
                    340                 345                 350

Pro Leu Lys Thr Lys Leu Gly Leu Gly Leu Asp Tyr Asp Ser Ser Arg
                    355                 360                 365

Ala Ile Ile Ala Lys Leu Gly Thr Gly Leu Ser Phe Asp Asn Thr Gly
        370                 375                 380

Ala Ile Thr Val Gly Asn Lys Asn Asp Asp Lys Leu Thr Leu Trp Thr
        385                 390                 395                 400

Thr Pro Asp Pro Ser Pro Asn Cys Arg Ile Tyr Ser Glu Lys Asp Ala
                    405                 410                 415

Lys Phe Thr Leu Val Leu Thr Lys Cys Gly Ser Gln Val Leu Ala Ser
                            420                 425                 430

Val Ser Val Leu Ser Val Lys Gly Ser Leu Ala Pro Ile Ser Gly Thr
                    435                 440                 445

Val Thr Ser Ala Gln Ile Val Leu Arg Phe Asp Glu Asn Gly Val Leu
                    450                 455                 460

Leu Ser Asn Ser Ser Leu Asp Pro Gln Tyr Trp Asn Tyr Arg Lys Gly
        465                 470                 475                 480
```

```
Asp Leu Thr Glu Gly Thr Ala Tyr Thr Asn Ala Val Gly Phe Met Pro
            485                 490                 495

Asn Leu Thr Ala Tyr Pro Lys Thr Gln Ser Gln Thr Ala Lys Ser Asn
        500                 505                 510

Ile Val Ser Gln Val Tyr Leu Asn Gly Asp Lys Ser Lys Pro Met Thr
    515                 520                 525

Leu Thr Ile Thr Leu Asn Gly Thr Asn Glu Thr Gly Asp Ala Thr Val
        530                 535                 540

Ser Thr Tyr Ser Met Ser Phe Ser Trp Asn Trp Asn Gly Ser Asn Tyr
545                 550                 555                 560

Ile Asn Glu Thr Phe Gln Thr Asn Ser Phe Thr Phe Ser Tyr Ile Ala
                565                 570                 575

Gln Glu
```

<210> SEQ ID NO 8
<211> LENGTH: 1734
<212> TYPE: DNA
<213> ORGANISM: Pan troglodytes

<400> SEQUENCE: 8

| | |
|---|---:|
| atgaagcgca ccaaaacgtc tgacgagagc ttcaaccccg tgtacccta tgacacggaa | 60 |
| agcggccctc cctccgtccc tttcctcacc cctcccttcg tgtctcccga tggattccaa | 120 |
| gaaagtcccc ccggggtcct gtctctgaac ctggccgagc ccctggtcac ttcccacggc | 180 |
| atgctcgccc tgaaaatggg aagtggcctc tccctggacg acgctggcaa cctcaccctct | 240 |
| caagatatca ccaccgctag ccctcccctc aaaaaaacca agaccaacct cagcctagaa | 300 |
| acctcatccc ccctaactgt gagcacctca ggcgccctca ccgtagcagc cgccgctccc | 360 |
| ctggcggtgg ccggcaccctc cctcaccatg caatcagagg ccccctgac agtacaggat | 420 |
| gcaaaactca ccctggccac caaaggcccc ctgaccgtgt ctgaaggcaa actggccttg | 480 |
| caaacatcgg ccccgctgac ggccgctgac agcagcaccc tcacagtcag tgccacacca | 540 |
| cccttagca aagcaatgg cagcttgggt attgacatgc aagccccccat ttacaccacc | 600 |
| aatggaaaac taggacttaa ctttggcgct ccctgcatg tggtagacag cctaaatgca | 660 |
| ctgactgtag ttactggcca aggtcttacg ataaacggaa cagccctaca aactagagtc | 720 |
| tcaggtgccc tcaactatga cacatcagga aacctagaat tgagagctgc aggggggtatg | 780 |
| cgagttgatg caaatggtca acttatcctt gatgtagctt acccatttga tgcacaaaac | 840 |
| aatctcagcc ttaggcttgg acagggaccc ctgtttgtta actctgccca caacttggat | 900 |
| gttaactaca acagaggcct ctacctgttc acatctggaa ataccaaaaa gctagaagtt | 960 |
| aatatcaaaa cagccaaggg tctcatttat gatgacactg ctatagcaat caatgcgggt | 1020 |
| gatgggctac agtttgactc aggctcagat acaaatccat aaaaactaa acttggatta | 1080 |
| ggactggatt atgactccag cagagccata attgctaaac tgggaactgg cctaagcttt | 1140 |
| gacaacacag gtgccatcac agtaggcaac aaaaatgatg acaagcttac cttgtggacc | 1200 |
| acaccagacc catccctaa ctgtagaatc tattcagaga aagatgctaa attcacactt | 1260 |
| gttttgacta atgcggcag tcaggtgttg gccagcgttt ctgttttatc tgtaaaaggt | 1320 |
| agccttgcgc ccatcagtgg cacagtaact agtgctcaga ttgtcctcag atttgatgaa | 1380 |
| aatggagttc tactaagcaa ttcttcccctt gaccctcaat actggaacta cagaaaaggt | 1440 |
| gaccttacag agggcactgc atataccaac gcagtgggat ttatgcccaa cctcacagca | 1500 |

```
tacccaaaaa cacagagcca aactgctaaa agcaacattg taagtcaggt ttacttgaat   1560
ggggacaaat ccaaacccat gaccctcacc attaccctca atggaactaa tgaaacagga   1620
gatgccacag taagcactta ctccatgtca ttctcatgga actggaatgg aagtaattac   1680
attaatgaaa cgttccaaac caactccttc accttctcct acatcgccca agaa         1734
```

```
<210> SEQ ID NO 9
<211> LENGTH: 593
<212> TYPE: PRT
<213> ORGANISM: Pan troglodytes

<400> SEQUENCE: 9

Met Arg Arg Ala Ala Met Tyr Gln Glu Gly Pro Pro Ser Tyr Glu
1               5                   10                  15

Ser Val Val Gly Ala Ala Ala Ala Pro Ser Ser Pro Phe Ala Ser
                20                  25                  30

Gln Leu Leu Glu Pro Pro Tyr Val Pro Pro Arg Tyr Leu Arg Pro Thr
            35                  40                  45

Gly Gly Arg Asn Ser Ile Arg Tyr Ser Glu Leu Ala Pro Leu Phe Asp
        50                  55                  60

Thr Thr Arg Val Tyr Leu Val Asp Asn Lys Ser Ala Asp Val Ala Ser
65                  70                  75                  80

Leu Asn Tyr Gln Asn Asp His Ser Asn Phe Leu Thr Thr Val Ile Gln
                85                  90                  95

Asn Asn Asp Tyr Ser Pro Ser Glu Ala Ser Thr Gln Thr Ile Asn Leu
                100                 105                 110

Asp Asp Arg Ser His Trp Gly Gly Asp Leu Lys Thr Ile Leu His Thr
            115                 120                 125

Asn Met Pro Asn Val Asn Glu Phe Met Phe Thr Asn Lys Phe Lys Ala
        130                 135                 140

Arg Val Met Val Ser Arg Ser His Thr Lys Glu Asp Arg Val Glu Leu
145                 150                 155                 160

Lys Tyr Glu Trp Val Glu Phe Glu Leu Pro Glu Gly Asn Tyr Ser Glu
                165                 170                 175

Thr Met Thr Ile Asp Leu Met Asn Asn Ala Ile Val Glu His Tyr Leu
            180                 185                 190

Lys Val Gly Arg Gln Asn Gly Val Leu Glu Ser Asp Ile Gly Val Lys
        195                 200                 205

Phe Asp Thr Arg Asn Phe Arg Leu Gly Leu Asp Pro Val Thr Gly Leu
    210                 215                 220

Val Met Pro Gly Val Tyr Thr Asn Glu Ala Phe His Pro Asp Ile Ile
225                 230                 235                 240

Leu Leu Pro Gly Cys Gly Val Asp Phe Thr Tyr Ser Arg Leu Ser Asn
                245                 250                 255

Leu Leu Gly Ile Arg Lys Arg Gln Pro Phe Gln Glu Gly Phe Arg Ile
            260                 265                 270

Thr Tyr Glu Asp Leu Glu Gly Gly Asn Ile Pro Ala Leu Leu Asp Val
        275                 280                 285

Glu Ala Tyr Gln Asp Ser Leu Lys Glu Asn Glu Ala Gly Gln Glu Asp
    290                 295                 300

Thr Ala Pro Ala Ala Ser Ala Ala Glu Gln Gly Glu Asp Ala Ala
305                 310                 315                 320

Asp Thr Ala Ala Ala Asp Gly Ala Glu Ala Asp Pro Ala Met Val Val
                325                 330                 335
```

```
Glu Ala Pro Glu Gln Glu Asp Met Asn Asp Ser Ala Val Arg Gly
                340                 345                 350

Asp Thr Phe Val Thr Arg Gly Glu Lys Gln Ala Glu Ala Glu Ala
            355                 360                 365

Ala Ala Glu Glu Lys Gln Leu Ala Ala Ala Ala Ala Ala Ala Leu
        370                 375                 380

Ala Ala Ala Glu Ala Glu Ser Glu Gly Thr Lys Pro Ala Lys Glu Pro
385                 390                 395                 400

Val Ile Lys Pro Leu Thr Glu Asp Ser Lys Lys Arg Ser Tyr Asn Leu
                405                 410                 415

Leu Lys Asp Ser Thr Asn Thr Ala Tyr Arg Ser Trp Tyr Leu Ala Tyr
                420                 425                 430

Asn Tyr Gly Asp Pro Ser Thr Gly Val Arg Ser Trp Thr Leu Leu Cys
            435                 440                 445

Thr Pro Asp Val Thr Cys Gly Ser Glu Gln Val Tyr Trp Ser Leu Pro
    450                 455                 460

Asp Met Met Gln Asp Pro Val Thr Phe Arg Ser Thr Arg Gln Val Ser
465                 470                 475                 480

Asn Phe Pro Val Val Gly Ala Glu Leu Leu Pro Val His Ser Lys Ser
                485                 490                 495

Phe Tyr Asn Asp Gln Ala Val Tyr Ser Gln Leu Ile Arg Gln Phe Thr
            500                 505                 510

Ser Leu Thr His Val Phe Asn Arg Phe Pro Glu Asn Gln Ile Leu Ala
        515                 520                 525

Arg Pro Pro Ala Pro Thr Ile Thr Thr Val Ser Glu Asn Val Pro Ala
530                 535                 540

Leu Thr Asp His Gly Thr Leu Pro Leu Arg Asn Ser Ile Gly Gly Val
545                 550                 555                 560

Gln Arg Val Thr Val Thr Asp Ala Arg Arg Arg Thr Cys Pro Tyr Val
                565                 570                 575

Tyr Lys Ala Leu Gly Ile Val Ser Pro Arg Val Leu Ser Ser Arg Thr
            580                 585                 590

Phe
```

<210> SEQ ID NO 10
<211> LENGTH: 1779
<212> TYPE: DNA
<213> ORGANISM: Pan troglodytes

<400> SEQUENCE: 10

```
atgcggcgcg cggcgatgta ccaggaggga cctcctccct cttacgagag cgtggtgggc    60
gcggcggcgg cggcgccctc ttctcccttt gcgtcgcagc tgctggagcc gccgtacgtg   120
cctccgcgct acctgcggcc tacggggggg agaaacagca tccgttactc ggagctggcg   180
cccctgttcg acaccacccg ggtgtacctg gtggacaaca gtcggcgga cgtggcctcc   240 ctgaactacc agaacgacca cagcaatttt ttgaccacgg tcatccagaa caatgactac   300
agcccgagcg aggccagcac ccagaccatc aatctggatg accggtcgca ctggggcggc   360
gacctgaaaa ccatcctgca caccaacatg cccaacgtga acgagttcat gttcaccaat   420
aagttcaagg cgcgggtgat ggtgtcgcgc tcgcacacca aggaagaccg ggtggagctg   480
aagtacgagt gggtggagtt cgagctgcca gagggcaact actccgagac catgaccatt   540
gacctgatga caacgcgat cgtggagcac tatctgaaag tgggcaggca gaacggggtc   600
ctggagagcg acatcggggt caagttcgac accaggaact tccgcctggg gctggacccc   660
```

```
gtgaccgggc tggttatgcc cggggtgtac accaacgagg ccttccatcc cgacatcatc      720
ctgctgcccg gctgcggggt ggacttcact tacagccgcc tgagcaacct cctgggcatc      780
cgcaagcggc agcccttcca ggagggcttc aggatcacct acgaggacct ggagggggc       840 aacatccccg cgctcctcga tgtggaggcc taccaggata gcttgaagga aaatgaggcg      900
ggacaggagg ataccgcccc cgccgcctcc gccgccgccg agcagggcga ggatgctgct      960
gacaccgcgc ccgcggacgg ggcagaggcc gaccccgcta tggtggtgga ggctcccgag     1020
caggaggagg acatgaatga cagtgcggtg cgcggagaca ccttcgtcac ccggggggag     1080
gaaaagcaag cggaggccga ggccgcgccc gaggaaaagc aactggcggc agcagcggcg     1140
gcggcggcgt tggccgcggc ggaggctgag tctgaggga ccaagcccgc caaggagccc      1200
gtgattaagc ccctgaccga agatagcaag aagcgcagtt acaacctgct caaggacagc     1260
accaacaccg cgtaccgcag ctggtacctg gcctacaact acggcgaccc gtcgacgggg     1320
gtgcgctcct ggaccctgct gtgcacgccg acgtgacct cggctcgga gcaggtgtac       1380 tggtcgctgc ccgacatgat gcaagacccc gtgaccttcc gctccacgcg gcaggtcagc     1440
aacttcccgg tggtgggcgc cgagctgctg cccgtgcact ccaagagctt ctacaacgac     1500
caggccgtct actcccagct catccgccag ttcacctctc tgacccacgt gttcaatcgc     1560
tttcctgaga accagattct ggcgcgcccg ccgcccccca ccatcaccac cgtcagtgaa     1620
aacgttcctg ctctcacaga tcacgggacg ctaccgctgc gcaacagcat cggaggagtc     1680
cagcgagtga ccgttactga cgccagacgc cgcacctgcc cctacgttta caaggccttg     1740
ggcatagtct cgccgcgcgt cctttccagc cgcactttt                             1779

<210> SEQ ID NO 11
<211> LENGTH: 960
<212> TYPE: PRT
<213> ORGANISM: Pan troglodytes

<400> SEQUENCE: 11

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
                20                  25                  30

Arg Ala Thr Glu Ser Tyr Phe Ser Leu Ser Asn Lys Phe Arg Asn Pro
            35                  40                  45

Thr Val Ala Pro Thr His Asp Val Thr Thr Asp Arg Ser Gln Arg Leu
        50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ser Leu Ala Pro Lys Gly
        115                 120                 125

Ala Pro Asn Ser Cys Glu Trp Glu Gln Glu Thr Gln Ala Val Glu
    130                 135                 140

Glu Ala Ala Glu Glu Glu Glu Asp Ala Asp Gly Gln Ala Glu Glu
145                 150                 155                 160

Glu Gln Ala Ala Thr Lys Lys Thr His Val Tyr Ala Gln Ala Pro Leu
                165                 170                 175
```

-continued

Ser Gly Glu Lys Ile Ser Lys Asp Gly Leu Gln Ile Gly Thr Asp Ala
            180                 185                 190

Thr Ala Thr Glu Gln Lys Pro Ile Tyr Ala Asp Pro Thr Phe Gln Pro
            195                 200                 205

Glu Pro Gln Ile Gly Glu Ser Gln Trp Asn Glu Ala Asp Ala Thr Val
        210                 215                 220

Ala Gly Gly Arg Val Leu Lys Lys Ser Thr Pro Met Lys Pro Cys Tyr
225                 230                 235                 240

Gly Ser Tyr Ala Arg Pro Thr Asn Ala Asn Gly Gly Gln Gly Val Leu
                245                 250                 255

Thr Ala Asn Ala Gln Gly Gln Leu Glu Ser Gln Val Glu Met Gln Phe
                260                 265                 270

Phe Ser Thr Ser Glu Asn Ala Arg Asn Glu Ala Asn Asn Ile Gln Pro
            275                 280                 285

Lys Leu Val Leu Tyr Ser Glu Asp Val His Met Glu Thr Pro Asp Thr
        290                 295                 300

His Leu Ser Tyr Lys Pro Ala Lys Ser Asp Asp Asn Ser Lys Ile Met
305                 310                 315                 320

Leu Gly Gln Gln Ser Met Pro Asn Arg Pro Asn Tyr Ile Gly Phe Arg
                325                 330                 335

Asp Asn Phe Ile Gly Leu Met Tyr Tyr Asn Ser Thr Gly Asn Met Gly
            340                 345                 350

Val Leu Ala Gly Gln Ala Ser Gln Leu Asn Ala Val Val Asp Leu Gln
        355                 360                 365

Asp Arg Asn Thr Glu Leu Ser Tyr Gln Leu Leu Asp Ser Met Gly
        370                 375                 380

Asp Arg Thr Arg Tyr Phe Ser Met Trp Asn Gln Ala Val Asp Ser Tyr
385                 390                 395                 400

Asp Pro Asp Val Arg Ile Ile Glu Asn His Gly Thr Glu Asp Glu Leu
                405                 410                 415

Pro Asn Tyr Cys Phe Pro Leu Gly Gly Ile Gly Val Thr Asp Thr Tyr
            420                 425                 430

Gln Ala Val Lys Thr Asn Asn Gly Asn Asn Gly Gly Gln Val Thr Trp
        435                 440                 445

Thr Lys Asp Glu Thr Phe Ala Asp Arg Asn Glu Ile Gly Val Gly Asn
        450                 455                 460

Asn Phe Ala Met Glu Ile Asn Leu Ser Ala Asn Leu Trp Arg Asn Phe
465                 470                 475                 480

Leu Tyr Ser Asn Val Ala Leu Tyr Leu Pro Asp Lys Leu Lys Tyr Asn
                485                 490                 495

Pro Ser Asn Val Asp Ile Ser Asp Asn Pro Asn Thr Tyr Asp Tyr Met
            500                 505                 510

Asn Lys Arg Val Val Ala Pro Gly Leu Val Asp Cys Tyr Ile Asn Leu
        515                 520                 525

Gly Ala Arg Trp Ser Leu Asp Tyr Met Asp Asn Val Asn Pro Phe Asn
        530                 535                 540

His His Arg Asn Ala Gly Leu Arg Tyr Arg Ser Met Leu Leu Gly Asn
545                 550                 555                 560

Gly Arg Tyr Val Pro Phe His Ile Gln Val Pro Gln Lys Phe Phe Ala
                565                 570                 575

Ile Lys Asn Leu Leu Leu Leu Pro Gly Ser Tyr Thr Tyr Glu Trp Asn
            580                 585                 590

```
Phe Arg Lys Asp Val Asn Met Val Leu Gln Ser Ser Leu Gly Asn Asp
            595                 600                 605

Leu Arg Val Asp Gly Ala Ser Ile Lys Phe Glu Ser Ile Cys Leu Tyr
610                 615                 620

Ala Thr Phe Phe Pro Met Ala His Asn Thr Ala Ser Thr Leu Glu Ala
625                 630                 635                 640

Met Leu Arg Asn Asp Thr Asn Asp Gln Ser Phe Asn Asp Tyr Leu Ser
            645                 650                 655

Ala Ala Asn Met Leu Tyr Pro Ile Pro Ala Asn Ala Thr Asn Val Pro
                660                 665                 670

Ile Ser Ile Pro Ser Arg Asn Trp Ala Ala Phe Arg Gly Trp Ala Phe
            675                 680                 685

Thr Arg Leu Lys Thr Lys Glu Thr Pro Ser Leu Gly Ser Gly Phe Asp
690                 695                 700

Pro Tyr Tyr Thr Tyr Ser Gly Ser Ile Pro Tyr Leu Asp Gly Thr Phe
705                 710                 715                 720

Tyr Leu Asn His Thr Phe Lys Lys Val Ser Val Thr Phe Asp Ser Ser
            725                 730                 735

Val Ser Trp Pro Gly Asn Asp Arg Leu Leu Thr Pro Asn Glu Phe Glu
                740                 745                 750

Ile Lys Arg Ser Val Asp Gly Glu Gly Tyr Asn Val Ala Gln Cys Asn
            755                 760                 765

Met Thr Lys Asp Trp Phe Leu Val Gln Met Leu Ala Asn Tyr Asn Ile
770                 775                 780

Gly Tyr Gln Gly Phe Tyr Ile Pro Glu Ser Tyr Lys Asp Arg Met Tyr
785                 790                 795                 800

Ser Phe Phe Arg Asn Phe Gln Pro Met Ser Arg Gln Val Val Asp Gln
            805                 810                 815

Thr Lys Tyr Lys Asp Tyr Gln Glu Val Gly Ile Ile His Gln His Asn
                820                 825                 830

Asn Ser Gly Phe Val Gly Tyr Leu Ala Pro Thr Met Arg Glu Gly Gln
            835                 840                 845

Ala Tyr Pro Ala Asn Phe Pro Tyr Pro Leu Ile Gly Lys Thr Ala Val
850                 855                 860

Asp Ser Ile Thr Gln Lys Lys Phe Leu Cys Asp Arg Thr Leu Trp Arg
865                 870                 875                 880

Ile Pro Phe Ser Ser Asn Phe Met Ser Met Gly Ala Leu Ser Asp Leu
            885                 890                 895

Gly Gln Asn Leu Leu Tyr Ala Asn Ser Ala His Ala Leu Asp Met Thr
                900                 905                 910

Phe Glu Val Asp Pro Met Asp Glu Pro Thr Leu Leu Tyr Val Leu Phe
            915                 920                 925

Glu Val Phe Asp Val Val Arg Val His Gln Pro His Arg Gly Val Ile
930                 935                 940

Glu Thr Val Tyr Leu Arg Thr Pro Phe Ser Ala Gly Asn Ala Thr Thr
945                 950                 955                 960

<210> SEQ ID NO 12
<211> LENGTH: 2880
<212> TYPE: DNA
<213> ORGANISM: Pan troglodytes

<400> SEQUENCE: 12
atggcgaccc catcgatgat gccgcagtgg tcgtacatgc acatctcggg ccaggacgcc      60
```

```
tcggagtacc tgagccccgg gctggtgcag ttcgcccgcg ccaccgagag ctacttcagc    120
ctgagtaaca agtttaggaa ccccacggtg gcgcccacgc acgatgtgac caccgaccgg    180
tctcagcgcc tgacgctgcg gttcattccc gtggaccgcg aggacaccgc gtactcgtac    240
aaggcgcggt tcaccctggc cgtgggcgac aaccgcgtgc tggacatggc ctccacctac    300
tttgacatcc gcggggtgct ggaccggggt cccactttca gccctactc tggcaccgcc    360 tacaactccc tggcccccaa gggcgctccc aactcctgcg agtgggagca agaggaaact    420
caggcagttg aagaagcagc agaagaggaa gaagaagatg ctgacggtca agctgaggaa    480
gagcaagcag ctaccaaaaa gactcatgta tatgctcagg ctcccctttc tggcgaaaaa    540
attagtaaag atggtctgca aataggaacg gacgctacag ctacagaaca aaaacctatt    600
tatgcagacc ctacattcca gcccgaaccc caaatcgggg agtcccagtg aatgaggca    660 gatgctacag tcgccggcgg tagagtgcta aagaaatcta ctcccatgaa accatgctat    720
ggttcctatg caagacccac aaatgctaat ggaggtcagg gtgtactaac ggcaaatgcc    780
cagggacagc tagaatctca ggttgaaatg caattctttt caacttctga aaacgcccgt    840
aacgaggcta acaacattca gcccaaattg gtgctgtata gtgaggatgt gcacatggag    900
accccggata cgcacctttc ttacaagccc gcaaaaagcg atgacaattc aaaaatcatg    960
ctgggtcagc agtccatgcc caacagacct aattacatcg gcttcagaga caactttatc   1020
ggcctcatgt attacaatag cactggcaac atggagtgc ttgcaggtca ggcctctcag   1080
ttgaatgcag tggtggactt gcaagacaga aacacagaac tgtcctacca gctcttgctt   1140
gattccatgg gtgacagaac cagatacttt tccatgtgga tcaggcagt ggacagttat   1200 gacccagatg ttagaattat tgaaaatcat ggaactgaag acgagctccc caactattgt   1260
ttccctctgg gtggcatagg ggtaactgac acttaccagg ctgttaaaac caacaatggc   1320
aataacgggg gccaggtgac ttggacaaaa gatgaaactt ttgcagatcg caatgaaata   1380
ggggtgggaa acaatttcgc tatggagatc aacctcagtg ccaacctgtg agaaacttc   1440 ctgtactcca acgtggcgct gtacctacca gacaagctta agtacaaccc ctccaatgtg   1500
gacatctctg acaaccccaa cacctacgat tacatgaaca agcgagtggt ggccccgggg   1560
ctggtggact gctacatcaa cctgggcgcg cgctggtcgc tggactacat ggacaacgtc   1620
aaccccttca ccaccaccg caatgcgggc ctgcgctacc gctccatgct cctgggcaac   1680
gggcgctacg tgcccttcca catccaggtg ccccagaagt tctttgccat caagaacctc   1740
ctcctcctgc cgggctccta cacctacgag tggaacttca ggaaggatgt caacatggtc   1800
ctccagagct ctctgggtaa cgatctcagg gtggacgggg ccagcatcaa gttcgagagc   1860
atctgcctct acgccacctt cttccccatg gcccacaaca cggcctccac gctcgaggcc   1920
atgctcagga acgacaccaa cgaccagtcc ttcaatgact acctctccgc cgccaacatg   1980
ctctacccca tacccgccaa cgccaccaac gtccccatct ccatcccctc gcgcaactgg   2040
gcggccttcc gcgctgggc cttcacccgc tcaagacca aggagaccccc ctccctgggc   2100 tcgggattcg accctactaa cacctactcg gctccattc cctacctgga cggcaccttc   2160
tacctcaacc acactttcaa gaaggtctcg gtcaccttcg actcctcggt cagctggccg   2220
ggcaacgacc gtctgctcac ccccaacgag ttcgagatca agcgctcggt cgacggggag   2280
ggctacaacg tggcccagtg caacatgacc aaggactggt tcctggtcca gatgctggcc   2340
aactacaaca tcggctacca gggcttctac atcccagaga gctacaagga caggatgtac   2400
tccttcttca ggaacttcca gcccatgagc cggcaggtgg tggaccagac caagtacaag   2460
```

```
gactaccagg aggtgggcat catccaccag cacaacaact cgggcttcgt gggctacctc   2520
gcccccacca tgcgcgaggg acaggcctac cccgccaact tccccctatcc gctcataggc   2580 aagaccgcgg tcgacagcat cacccagaaa aagttcctct gcgaccgcac cctctggcgc   2640 atcccccttct ccagcaactt catgtccatg ggtgcgctct cggacctggg ccagaacttg   2700
ctctacgcca actccgccca cgccctcgac atgaccttcg aggtcgaccc catggacgag   2760
cccacccttc tctatgttct gttcgaagtc tttgacgtgg tccgggtcca ccagccgcac   2820
cgcggcgtca tcgagaccgt gtacctgcgt acgcccttct cggccggcaa cgccaccacc   2880
```

<210> SEQ ID NO 13
<211> LENGTH: 37830
<212> TYPE: DNA
<213> ORGANISM: Pan troglodytes

<400> SEQUENCE: 13

```
catcatcaat aatataccctt attttggatt gaagccaata tgataatgag atgggcggcg     60
cggggcggga ggcgggtccg ggggcgggcc ggcgggcggg gcggtgtggc ggaagtggac    120
tttgtaagtg tggcggatgt gacttgctag tgccgggcgc ggtaaaagtg acgttttccg    180
tgcgcgacaa cgcccacggg aagtgacatt tttcccgcgg ttttttaccgg atgttgtagt    240 gaatttgggc gtaaccaagt aagatttggc cattttcgcg ggaaaactga acggggaag    300 tgaaatctga ttaatttcgc gttagtcata ccgcgtaata tttgtcgagg gccgagggac    360
tttggccgat tacgtggagg actcgcccag gtgttttttg aggtgaattt ccgcgttccg    420
ggtcaaagtc tccgttttat tattatagtc agctgacgcg gagtgtattt ataccctctg    480
atctcgtcaa gtggccactc ttgagtgcca gcgagtagag ttttctcctc tgccgctctc    540
cgctccgctc cgctcggctc tgacaccggg gaaaaaatga gacatttcac ctacgatggc    600
ggtgtgctca ccggccagct ggctgctgaa gtcctggaca ccctgatcga ggaggtattg    660
gccgataatt atcctccctc gactccttttt gagccaccta cacttcacga actctacgat    720
ctggatgtgg tggggcccag cgatccgaac gagcaggcgg tttccagttt ttttccagag    780
tccatgttgt tggccagcca ggaggggggtc gaacttgaga cccctcctcc gatcgtggat    840
tcccccgatc cgccgcagct gactaggcag cccgagcgct gtgcgggacc tgagactatg    900
ccccagctgc tacctgaggt gatcgatctc acctgtaatg agtctggttt tccacccagc    960
gaggatgagg acgaagaggg tgagcagttt gtgttagatt ctgtggaaca acccgggcga   1020
ggatgcaggt cttgtcaata tcaccggaaa aacacaggag actcccagat tatgtgttct   1080
ctgtgttata tgaagatgac ctgtatgttt atttacagta agtttatcat ctgtgggcag   1140
gtgggctata gtgtgggtgg tggtctttgg ggggtttttt aatatatgtc aggggttatg   1200
ctgaagactt ttttattgtg attttttaaag gtccagtgtc tgagcccgag caagaacctg   1260
aaccggagcc tgagccttct cgccccagga gaaagcctgt aatcttaact agacccagcg   1320
caccggtagc gagaggcctc agcagcgcgg agaccaccga ctccggtgct tcctcatcac   1380
ccccggagat tcacccccctg gtgccccctgt gtcccgttaa gcccgttgcc gtgagagtca   1440
gtgggcggcg gtctgctgtg gagtgcattg aggacttgct ttttgattca caggaacctt   1500
tggacttgag cttgaaacgc cccaggcatt aaacctggtc acctggactg aatgagttga   1560
cgcctatgtt tgcttttgaa tgacttaatg tgtatagata ataaagagtg agataatgtt   1620
ttaattgcat ggtgtgttta acttgggcgg agtctgctgg gtatataagc ttccctgggc   1680
```

```
taaacttggt tacacttgac ctcatggagg cctgggagtg tttggagaac tttgccggag    1740
ttcgtgcctt gctggacgag agctctaaca atacctcttg gtggtggagg tatttgtggg    1800
gctctcccca gggcaagtta gtttgtagaa tcaaggagga ttacaagtgg gaatttgaag    1860
agcttttgaa atcctgtggt gagctattgg attctttgaa tctaggccac caggctctct    1920
tccaggagaa ggtcatcagg actttggatt tttccacacc ggggcgcatt gcagccgcgg    1980
ttgcttttct agcttttttg aaggatagat ggagcgaaga gacccacttg agttcgggct    2040
acgtcctgga ttttctggcc atgcaactgt ggagagcatg gatcagacac aagaacaggc    2100
tgcaactgtt gtcttccgtc cgcccgttgc tgattccggc ggaggagcaa caggccgggt    2160
cagaggaccg ggcccgtcgg gatccggagg agagggcacc gaggccgggc gagaggagcg    2220
cgctgaacct gggaaccggg ctgagcggcc atccacatcg ggagtgaatg tcgggcaggt    2280
ggtggatctt tttccagaac tgcggcggat tttgactatt agggaggatg ggcaatttgt    2340
taagggtctt aagagggaga gggggcttc tgagcataac gaggaggcca gtaatttagc    2400
ttttagcttg atgaccagac accgtccaga gtgcatcact tttcagcaga ttaaggacaa    2460
ttgtgccaat gagttggatc tgttgggtca gaagtatagc atagagcagc tgaccactta    2520
ctggctgcag ccgggtgatg atctggagga agctattagg gtgtatgcta aggtggccct    2580
gcggcccgat tgcaagtaca agctcaaggg gctggtgaat atcaggaatt gttgctacat    2640
ttctggcaac ggggcggagg tggagataga gaccgaagac agggtggctt tcagatgcag    2700
catgatgaat atgtggccgg gggtgctggg catggacggg gtggtgatta tgaatgtgag    2760
gttcacgggg cccaactta acggcacggt gttttgggg aacaccaacc tggtcctgca    2820
cggggtgagc ttctatgggt ttaacaacac ctgtgtggag gcctggaccg atgtgaaggt    2880
ccgcggttgc gccttttatg gatgttggaa ggccatagtg agccgcccta agagcaggag    2940
ttccattaag aaatgcttgt ttgagaggtg caccttgggg atcctggccg agggcaactg    3000
cagggtgcgc cacaatgtgg cctccgagtg cggttgcttc atgctagtca agagcgtggc    3060
ggtaatcaag cataatatgg tgtgcggcaa cagcgaggac aaggcctcac agatgctgac    3120
ctgcacggat ggcaactgcc acttgctgaa gaccatccat gtaaccagcc acagccggaa    3180
ggcctggccc gtgttcgagc acaacttgct gacccgctgc tccttgcatc tgggcaacag    3240
gcggggggtg ttcctgccct atcaatgcaa ctttagtcac accaagatct tgctagagcc    3300
cgagagcatg tccaaggtga acttgaacgg ggtgtttgac atgaccatga agatctggaa    3360
ggtgctgagg tacgacgaga ccaggtcccg gtgcagaccc tgcgagtgcg ggggcaagca    3420
tatgaggaac cagcccgtga tgctggatgt gaccgaggag ctgaggacag accacttggt    3480
tctggcctgc accagggccg agtttggttc tagcgatgaa gacacagatt gaggtgggtg    3540
agtgggcgtg gcctggggtg gtcatgaaaa tatataagtt gggggtctta gggtctcttt    3600
atttgtgttg cagagaccgc cggagccatg agcgggagca gcagcagcag cagtagcagc    3660
agcgccttgg atggcagcat cgtgagccct tatttgacga cgcggatgcc ccactgggcc    3720
ggggtgcgtc agaatgtgat gggctccagc atcgacggcc gacccgtcct gcccgcaaat    3780
tccgccacgc tgacctatgc gaccgtcgcg ggacgccgt tggacgccac cgccgccgcc    3840
gccgccaccg cagccgcctc ggccgtgcgc agcctggcca cggactttgc attcctggga    3900
ccactgcgca caggggctac ttctcggggc gctgctgccg ccgttcgcga tgacaagctg    3960
accgccctgc tggcgcagtt ggatgcgctt actcgggaac tgggtgacct ttctcagcag    4020
gtcatggccc tgcgccagca ggtctcctcc ctgcaagctg gcgggaatgc ttctcccaca    4080
```

```
aatgccgttt aagataaata aaaccagact ctgtttggat taaagaaaag tagcaagtgc    4140
attgctctct ttatttcata attttccgcg cgcgataggc cctagaccag cgttctcggt    4200
cgttgagggt gcggtgtatc ttctccagga cgtggtagag gtggctctgg acgttgagat    4260
acatgggcat gagcccgtcc cggggtggaa ggtagcacca ctgcagagct tcatgctccg    4320
gggtggtgtt gtagatgatc cagtcgtagc aggagcgctg gcatggtgc ctaaaaatgt     4380
ccttcagcag caggccgatg gccaggggga ggcccttggt gtaagtgttt acaaaacggt    4440
taagttggga agggtgcatt cggggagaga tgatgtgcat cttggactgt attttttagat   4500
tggcgatgtt tccgcccaga tcccttctgg gattcatgtt gtgcaggacc accagtacag    4560
tgtatccggt gcacttgggg aatttgtcat gcagcttaga gggaaaagcg tggaagaact    4620
tggagacgcc tttgtggcct cccagatttt ccatgcattc gtccatgatg atggcaatgg    4680
gcccgcggga ggcagcttgg gcaaagatat ttctggggtc gctgacgtcg tagttgtgtt    4740
ccagggtgag gtcgtcatag gccattttta caaagcgcgg gcggagggtg cccgactggg    4800
ggatgatggt cccctctggc cctggggcgt agttgccctc gcagatctgc atttcccagg    4860
ccttaatctc ggagggggga atcatatcca cctgcggggc gatgaagaaa acggtttccg    4920
gagccgggga gattaactgg gatgagagca ggtttctaag cagctgtgat tttccacaac    4980
cggtgggccc ataaataaca cctataaccg gttgcagctg gtagtttaga gagctgcagc    5040
tgccgtcgtc ccggaggagg ggggccacct cgttgagcat gtccctgacg cgcatgttct    5100
ccccgaccag atccgccaga aggcgctcgc cgcccaggga cagcagctct tgcaaggaag    5160
caaagttttt cagcggcttg aggccgtccg ccgtgggcat gttttttcagg gtctggctca    5220
gcagctccag gcggtcccag agctcggtga cgtgctctac ggcatctcta tccagcatat    5280
ctcctcgttt cgcgggttgg ggcgactttc gctgtagggc accaagcggt ggtcgtccag    5340
cggggccaga gtcatgtcct tccatgggcg caggtcctc gtcagggtgg tctgggtcac     5400
ggtgaagggg tgcgctccgg gctgagcgct tgccaaggtg cgcttgaggc tggttctgct    5460
ggtgctgaag cgctgccggt cttcgccctg cgcgtcggcc aggtagcatt tgaccatggt    5520
gtcatagtcc agcccctccg cggcgtgtcc cttggcgcgc agcttgccct tggaggtggc    5580
gccgcacgag gggcagagca ggctcttgag cgcgtagagc ttgggggcga ggaagaccga    5640
ttcgggggag taggcgtccg cgccgcagac cccgcacacg gtctcgcact ccaccagcca    5700
ggtgagctcg gggcgcgccg ggtcaaaaac caggtttccc ccatgctttt tgatgcgttt    5760
cttacctcgg gtctccatga ggtggtgtcc ccgctcggtg acgaagaggc tgtccgtgtc    5820
tccgtagacc gacttgaggg gtcttttctc caggggggtc cctcggtctt cctcgtagag    5880
gaactcggac cactctgaga cgaaggcccg cgtccaggcc aggacgaagg aggctatgtg    5940
ggaggggtag cggtcgttgt ccactagggg gtccaccttc tccaaggtgt gaagacacat    6000
gtcgccttcc tcgcgtccaa ggaagtgat tggcttgtag gtgtaggcca cgtgaccggg     6060
ggttcctgac ggggggtat aaaagggggt ggggcgcgc tcgtcgtcac tctcttccgc      6120
atcgctgtct gcgagggcca gctgctgggg tgagtattcc ctctcgaagg cgggcatgac    6180
ctccgcgctg aggttgtcag tttccaaaaa cgaggaggat ttgatgttca cctgtcccga    6240
ggtgatacct ttgagggtac ccgcgtccat ctggtcagaa aacacgatct ttttattgtc    6300
cagcttggtg gcgaacgacc cgtagagggc gttgagagc agcttggcga tggagcgcag    6360
ggtctggttc ttgtccctgt cggcgcgctc cttggccgcg atgttgagct gcacgtactc    6420
```

```
gcgcgcgacg cagcgccact cggggaagac ggtggtgcgc tcgtcgggca ccaggcgcac   6480
gcgccagccg cggttgtgca gggtgaccag gtccacgctg gtggcgacct cgccgcgcag   6540
gcgctcgttg gtccagcaga gacggccgcc cttgcgcgag cagaaggggg gcaggggtc    6600 gagctgggtc tcgtccgggg ggtccgcgtc cacggtgaaa accccgggc gcaggcgcgc    6660 gtcgaagtag tctatcttgc aaccttgcat gtccagcgcc tgctgccagt cgcgggcggc   6720
gagcgcgcgc tcgtaggggt tgagcggcgg gccccagggc atgggtggg tgagtgcgga    6780 ggcgtacatg ccgcagatgt catagacgta gaggggctcc cgcaggaccc cgatgtaggt   6840
ggggtagcag cggccgccgc ggatgctggc gcgcacgtag tcatacagct cgtgcgaggg   6900
ggcgaggagg tcggggccca ggttggtgcg ggcggggcgc tccgcgcgga agacgatctg   6960
cctgaagatg gcatgcgagt tggaagagat ggtggggcgc tggaagacgt tgaagctggc   7020
gtcctgcagg ccgacggcgt cgcgcacgaa ggaggcgtag gagtcgcgca gcttgtgtac   7080
cagctcggcg gtgacctgca cgtcgagcgc gcagtagtcg agggtctcgc ggatgatgtc   7140
atatttagcc tgcccttct tttccacag ctcgcggttg aggacaaact cttcgcggtc     7200
tttccagtac tcttggatcg ggaaaccgtc cggttccgaa cggtaagagc ctagcatgta   7260
gaactggttg acgccggt aggcgcagca gcccttctcc acggggaggg cgtaggcctg     7320
cgcggccttg cggagcgagg tgtgggtcag ggcgaaggtg tccctgacca tgactttgag   7380
gtactggtgc ttgaagtcgg agtcgtcgca gccgccccgc tcccagagcg agaagtcggt   7440
gcgcttcttg gagcgggggt tgggcagagc gaaggtgaca tcgttgaaga ggattttgcc   7500 cgcgcgggc atgaagttgc gggtgatgcg gaagggcccc ggcacttcag agcggttgtt   7560
gatgacctgg gcggcgagca cgatctcgtc gaagccgttg atgttgtggc ccacgatgta   7620
gagttccagg aagcggggcc ggcccttac ggtgggcagc ttctttagct cttcgtaggt    7680
gagctcctcg ggcgaggcga ggccgtgctc ggccagggcc cagtccgcga ggtgcgggtt   7740
gtctctgagg aaggacttcc agaggtcgcg ggccaggagg gtctgcaggc ggtctctgaa   7800
ggtcctgaac tggcggccca cggccatttt tcgggggtg atgcagtaga aggtgagggg    7860
gtcttgctgc cagcggtccc agtcgagctg caggggcgagg tcgcgcgcgg cggtgaccag   7920
gcgctcgtcg cccccgaatt tcatgaccag catgaagggc acgagctgct tccgaaggc    7980 ccccatccaa gtgtaggtct ctacatcgta ggtgacaaag aggcgctccg tgcgaggatg   8040
cgagccgatc gggaagaact ggatctcccg ccaccagttg gaggagtggc tgttgatgtg   8100
gtggaagtag aagtcccgtc gccgggccga acactcgtgc tggcttttgt aaaagcgagc   8160
gcagtactgg cagcgctgca cgggctgtac ctcatgcacg agatgcacct ttcgcccgcg   8220
cacgaggaag ccgagggaa atctgagccc ccgcctggc tcgcggcatg gctggttctc     8280
ttctactttg gatgcgtgtc cgtctccgtc tggctcctcg agggggtgtta cggtggagcg   8340 gaccaccacg ccgcgcgagc cgcaggtcca gatatcggcg cgcggcggtc ggagtttgat   8400
gacgacatcg cgcagctggg agctgtccat ggtctggagc tcccgcggcg gcggcaggtc   8460
agccgggagt tcttgcaggt tcacctcgca gagtcgggcc agggcgcggg gcaggtctag   8520
gtggtacctg atctctaggg gcgtgttggt ggcggcgtcg atggcttgca ggagcccgca   8580
gccccggggg gcgacgacgg tgccccgcgg ggtggtggtg gtggtggcgg tgcagctcag   8640
aagcggtgcc gcgggcgggc ccccggaggt agggggggct ccggtccgc gggcaggggc    8700 ggcagcggca cgtcggcgtg gagcgcgggc aggagttggt gctgtgcccg gaggttgctg   8760
gcgaaggcga cgacgcggcg gttgatctcc tggatctggc gcctctgcgt gaagacgacg   8820
```

-continued

```
ggcccggtga gcttgaacct gaaagagagt tcgacagaat caatctcggt gtcattgacc    8880
gcggcctggc gcaggatctc ctgcacgtct cccgagttgt cttggtaggc gatctccggcc    8940 atgaactgct cgatctcttc ctcctggagg tctccgcgtc cggcgcgttc cacggtggcc    9000
gccaggtcgt tggagatgcg ccccatgagc tgcgagaagg cgttgagtcc gccctcgttc    9060
cagactcggc tgtagaccac gccccctgg tcatcgcggg cgcgcatgac cacctgcgcg    9120
aggttgagct ccacgtgccg cgcgaagacg gcgtagttgc gcagacgctg gaagaggtag    9180
ttgagggtgg tggcggtgtg ctcggccacg aagaagttca tgacccagcg gcgcaacgtg    9240
gattcgttga tgtcccccaa ggcctccagc cgttccatgg cctcgtagaa gtccacggcg    9300
aagttgaaaa actgggagtt gcgcgccgac acggtcaact cctcctccag aagacggatg    9360
agctcggcga cggtgtcgcg cacctcgcgc tcgaaggcta tggggatctc ttcctccgct    9420
agcatcacca cctcctcctc ttcctcctct tctggcactt ccatgatggc ttcctcctct    9480 tcgggggtg gcggcggcgg cggtgggggga ggggcgctc tgcgccggcg gcggcgcacc    9540
gggaggcggt ccacgaagcg cgcgatcatc tccccgcggc ggcggcgcat ggtctcggtg    9600
acggcgcggc cgttctcccg ggggcgcagt tggaagacgc cgccggacat ctggtgctgg    9660
ggcgggtggc cgtgaggcag cgagacggcg ctgacgatgc atctcaacaa ttgctgcgta    9720
ggtacgccgc cgagggacct gagggagtcc atatccaccg gatccgaaaa ccttttcgagg    9780 aaggcgtcta accagtcgca gtcgcaaggt aggctgagca ccgtggcggg cggcgggggg    9840
tggggggagt gtctggcgga ggtgctgctg atgatgtaat tgaagtaggc ggacttgaca    9900
cggcggatgg tcgacaggag caccatgtcc ttgggtccgg cctgctggat gcggaggcgg    9960
tcggctatgc cccaggcttc gttctggcat cggcgcaggt ccttgtagta gtcttgcatg   10020
agcctttcca ccggcacctc ttctccttcc tcttctgctt cttccatgtc tgcttcggcc   10080
ctggggcggc gccgcgcccc cctgccccc atgcgcgtga ccccgaaccc cctgagcggt   10140
tggagcaggg ccaggtcggc gacgacgcgc tcggccagga tggcctgctg cacctgcgtg   10200
aggtggtttt ggaagtcatc caagtccacg aagcggtggt aggcgcccgt gttgatggtg   10260
taggtgcagt tggccatgac ggaccagttg acggtctggt ggcccggttg cgacatctcg   10320
gtgtacctga gtcgcgagta ggcgcgggag tcgaagacgt agtcgttgca agtccgcacc   10380
aggtactggt agcccaccag gaagtgcggc ggcggctggc ggtagagggg ccagcgcagg   10440
gtggcggggg ctccggggc caggtcttcc agcatgaggc ggtggtaggc gtagatgtac   10500
ctggacatcc aggtgatacc cgcggcggtg gtggaggcgc gcgggaagtc gcgcacccgg   10560
ttccagatgt tgcgcagggg cagaaagtgc tccatggtag gcgtgctctg tccagtcaga   10620
cgcgcgcagt cgttgatact ctagaccagg gaaaacgaaa gccggtcagc gggcactctt   10680
ccgtggtctg gtgaatagat cgcaagggta tcatggcgga gggcctcggt tcgagccccg   10740
ggtccgggcc ggacggtccg ccatgatcca cgcggttacc gcccgcgtgt cgaacccagg   10800
tgtgcgacgt cagacaacgg tggagtgttc ctttttggcgt ttttctggcc gggcgccggc   10860
gccgcgtaag agactaagcc gcgaaagcga aagcagtaag tggctcgctc cccgtagccg   10920
gagggatcct tgctaagggt tgcgttgcgg cgaaccccgg ttcgaatccc gtactcgggc   10980
cggccggacc cgcggctaag gtgttggatt ggcctccccc tcgtataaag accccgcttg   11040
cggattgact ccggacacgg ggacgagccc ctttttatttt tgctttcccc agatgcatcc   11100
ggtgctgcgg cagatgcgcc ccccgccccca gcagcagcaa caacaccagc aagagcggca   11160
```

-continued

```
gcaacagcag cgggagtcat gcagggcccc ctcacccacc ctcggcgggc cggccacctc    11220
ggcgtccgcg gccgtgtctg gcgcctgcgg cggcggcggg gggccggctg acgaccccga    11280 ggagccccg cggcgcaggg ccagacacta cctggacctg gaggagggcg agggcctggc     11340
gcggctgggg gcgccgtctc ccgagcgcca cccgcgggtg cagctgaagc gcgactcgcg    11400
cgaggcgtac gtgcctcggc agaacctgtt cagggaccgc gcgggcgagg agcccgagga    11460
gatgcgggac aggaggttca gcgcagggcg ggagctgcgg caggggctga accgcgagcg    11520
gctgctgcgc gaggaggact ttgagcccga cgcgcggacg gggatcagcc ccgcgcgcgc    11580
gcacgtggcg gccgccgacc tggtgacggc gtacgagcag acggtgaacc aggagatcaa    11640
cttccaaaag agtttcaaca accacgtgcg cacgctggtg gcgcgcgagg aggtgaccat    11700
cgggctgatg cacctgtggg actttgtaag cgcgctggtg cagaacccca acagcaagcc    11760
tctgacggcg cagctgttcc tgatagtgca gcacagcagg gacaacgagg cgtttaggga    11820
cgcgctgctg aacatcaccg agcccgaggg tcggtggctg ctggacctga ttaacatcct    11880
gcagagcata gtggtgcagg agcgcagcct gagcctggcc gacaaggtgg cggccatcaa    11940
ctactcgatg ctgagcctgg gcaagtttta cgcgcgcaag atctaccaga cgccgtacgt    12000
gcccatagac aaggaggtga agatcgacgg ttttttacatg cgcatggcgc tgaaggtgct    12060
caccctgagc gacgacctgg gcgtgtaccg caacgagcgc atccacaagg ccgtgagcgt    12120
gagccggcgg cgcgagctga gcgaccgcga gctgatgcac agcctgcagc gggcgctggc    12180
gggcgccggc agcggcgaca gggaggcgga gtcctacttc gatgcggggg cggacctgcg    12240
ctgggcgccc agccggcggg ccctggaggc cgcggggtc cgcgaggact atgacgagga     12300
cggcgaggag gatgaggagt acgagctaga ggagggcgag tacctggact aaaccgcggg    12360
tggtgtttcc ggtagatgca agacccgaac gtggtggacc cggcgctgcg ggcggctctg    12420
cagagccagc cgtccggcct taactcctca gacgactggc gacaggtcat ggaccgcatc    12480
atgtcgctga cggcgcgtaa cccggacgcg ttccggcagc agccgcaggc caacaggctc    12540
tccgccatcc tggaggcggt ggtgcctgcg cgctcgaacc ccacgcacga aaggtgctg    12600 gccatagtga acgcgctggc cgagaacagg gccatccgcc cggacgaggc cgggctggtg    12660
tacgacgcgc tgctgcagcg cgtggcccgc tacaacagcg gcaacgtgca gaccaacctg    12720
gaccggctgg tggggacgt gcgcgaggcg gtggcgcagc gcgagcgcgc ggatcggcag     12780
ggcaacctgg gctccatggt ggcgctgaat gccttcctga gcacgcagcc ggccaacgtg    12840
ccgcgggggc aggaagacta caccaacttt gtgagcgcgc tgcggctgat ggtgaccgag    12900 acccccaga gcgaggtgta ccagtcgggc ccggactact tcttccagac cagcagacag     12960
ggcctgcaga cggtgaacct gagccaggct ttcaagaacc tgcgggggct gtggggcgtg    13020
aaggcgccca ccggcgaccg ggcgacggtg tccagcctgc tgacgcccaa ctcgcgcctg    13080
ctgctgctgc tgatcgcgcc gttcacggac agcggcagcg tgtcccggga cacctacctg    13140
gggcacctgc tgaccctgta ccgcgaggcc atcgggcagg cgcaggtgga cgagcacacc    13200
ttccaggaga tcaccagcgt gagccgcgcg ctggggcagg aggacacgag cagcctggag    13260
gcgactctga actacctgct gaccaaccgg cggcagaaga ttccctcgct gcacagcctg    13320
acctccgagg aggagcgcat cttgcgctac gtgcagcaga gcgtgagcct gaacctgatg    13380
cgcgacgggg tgacgcccag cgtggcgctg acatgaccg cgcgcaacat ggaacgggc      13440 atgtacgccg cgcaccggcc ttacatcaac cgcctgatgg actacctgca tcgcgcggcg    13500
gccgtgaacc ccgagtactt taccaacgcc atcctgaacc cgcactggct cccgccgccc    13560
```

```
gggttctaca gcggggcttt cgaggtcccg gagaccaacg atggcttcct gtgggacgac    13620
atggacgaca gcgtgttctc cccgcggccg caggcgctgg cggaagcgtc cctgctgcgt    13680
cccaagaagg aggaggagga ggaggcgagt cgccgccgcg gcagcagcgg cgtggcttct    13740
ctgtccgagc tgggggcggc agccgccgcg cgccccgggt ccctgggcgg cagccccttt    13800
ccgagcctgg tggggtctct gcacagcgag cgcaccaccc gccctcggct gctgggcgag    13860
gacgagtacc tgaataactc cctgctgcag ccggtgcggg agaaaaacct gcctcccgcc    13920
ttccccaaca acgggataga gagcctggtg gacaagatga gcagatggaa gacctatgcg    13980
caggagcaca gggacgcgcc tgcgctccgg ccgcccacgc ggcgccagcg ccacgaccgg    14040
cagcgggggc tggtgtggga tgacgaggac tccgcggacg atagcagcgt gctggacctg    14100
ggagggagcg gcaacccgtt cgcgcacctg cgccccgcc tggggaggat gttttaaaaa    14160 aaaaaaaaa aagcaagaag catgatgcaa aaattaaata aaactcacca aggccatggc    14220
gaccgagcgt tggtttcttg tgttcccttc agtatgcggc gcgcggcgat gtaccaggag    14280
ggacctcctc cctcttacga gagcgtggtg ggcgcggcgg cggcggcgcc ctcttctccc    14340
tttgcgtcgc agctgctgga gccgccgtac gtgcctccgc gctacctgcg gcctacgggg    14400
gggagaaaca gcatccgtta ctcggagctg gcgcccctgt tcgacaccac ccgggtgtac    14460
ctggtggaca acaagtcggc ggacgtggcc tccctgaact accagaacga ccacagcaat    14520 ttttttgacca cggtcatcca gaacaatgac tacagcccga gcgaggccag cacccagacc    14580
atcaatctgg atgaccggtc gcactggggc ggcgacctga aaaccatcct gcacaccaac    14640
atgcccaacg tgaacgagtt catgttcacc aataagttca aggcgcgggt gatggtgtcg    14700
cgctcgcaca ccaaggaaga ccgggtggag ctgaagtacg agtgggtgga gttcgagctg    14760
ccagagggca actactccga gaccatgacc attgacctga tgaacaacgc gatcgtggag    14820
cactatctga aagtgggcag gcagaacggg gtcctggaga gcgacatcgg ggtcaagttc    14880
gacaccagga acttccgcct ggggctggac ccgtgaccg ggctggttat gcccggggtg    14940
tacaccaacg aggccttcca tcccgacatc atcctgctgc ccggctgcgg ggtggacttc    15000
acttacagcc gcctgagcaa cctcctgggc atccgcaagc ggcagcccctt ccaggagggc    15060 ttcaggatca cctacgagga cctggagggg gcaacatcc ccgcgctcct cgatgtggag    15120
gcctaccagg atagcttgaa ggaaaatgag gcggacagg aggataccgc ccccgccgcc    15180
tccgccgccg ccgagcaggg cgaggatgct gctgacaccg cggccgcgga cggggcagag    15240
gccgaccccg ctatggtggt ggaggctccc gagcaggagg aggacatgaa tgacagtgcg    15300
gtgcgcggag acaccttcgt cacccggggg gaggaaaagc aagcggaggc cgaggccgcg    15360
gccgaggaaa gcaactggc ggcagcagcg gcggcggcgc cgttggccgc ggcggaggct    15420
gagtctgagg ggaccaagcc cgccaaggag cccgtgatta gcccctgac cgaagatagc    15480 aagaagcgca gttacaacct gctcaaggac agcaccaaca ccgcgtaccg cagctggtac    15540
ctggcctaca actacggcga cccgtcgacg ggggtgcgct cctggaccct gctgtgcacg    15600
ccggacgtga cctgcggctc ggagcaggtg tactggtcgc tgcccgacat gatgcaagac    15660
cccgtgacct tccgctccac gcggcaggtc agcaacttcc cggtggtggg cgccgagctg    15720
ctgcccgtgc actccaagag cttctacaac gaccaggccg tctactccca gctcatccgc    15780
cagttcacct ctctgaccca cgtgttcaat cgctttcctg agaaccagat tctgcgcgcg    15840
ccgcccgccc ccaccatcac caccgtcagt gaaaacgttc ctgctctcac agatcacggg    15900
```

```
acgctaccgc tgcgcaacag catcggagga gtccagcgag tgaccgttac tgacgccaga   15960
cgccgcacct gccccuacgt ttacaaggcc ttgggcatag tctcgccgcg cgtcctttcc   16020
agccgcactt tttgagcaac accaccatca tgtccatcct gatctcaccc agcaataact   16080
ccggctgggg actgctgcgc gcgcccagca agatgttcgg aggggcgagg aagcgttccg   16140
agcagcaccc cgtgcgcgtg cgcgggcact tccgcgcccc ctggggagcg cacaaacgcg   16200
gccgcgcggg gcgcaccacc gtggacgacg ccatcgactc ggtggtggag caggcgcgca   16260
actacaggcc cgcggtctct accgtggacg cggccatcca gaccgtggtg cggggcgcgc   16320
ggcggtacgc caagctgaag agccgccgga agcgcgtggc ccgccgccac cgccgccgac   16380
ccggggccgc cgccaaacgc gccgccgcgg ccctgcttcg ccgggccaag cgcacgggcc   16440
gccgcgccgc catgagggcc gcgcgccgct tggccgccgg catcaccgcc gccaccatgg   16500
ccccccgtac ccgaagacgc gcggccgccg ccgccgccgc cgccatcagt gacatggcca   16560
gcaggcgccg gggcaacgtg tactgggtgc gcgactcggt gaccggcacg cgcgtgcccg   16620
tgcgcttccg ccccccgcgg acttgagatg atgtgaaaaa acaacactga gtctcctgct   16680
gttgtgtgta tcccagcggc ggcggcgcgc gcagcgtcat gtccaagcgc aaaatcaaag   16740
aagagatgct ccaggtcgtc gcgccggaga tctatgggcc cccgaagaag gaagagcagg   16800
attcgaagcc ccgcaagata aagcgggtca aaagaaaaa gaaagatgat gacgatgccg   16860
atggggaggt ggagttcctg cgcgccacgg cgcccaggcg cccggtgcag tggaagggcc   16920
ggcgcgtaaa gcgcgtcctg cgccccggca ccgcggtggt cttcacgccc ggcgagcgct   16980
ccacccggac tttcaagcgc gtctatgacg aggtgtacgg cgacgaagac ctgctggagc   17040
aggccaacga gcgcttcgga gagtttgctt acgggaagcg tcagcgggcg ctggggaagg   17100
aggacctgct ggcgctgccg ctggaccagg gcaaccccac ccccagtctg aagcccgtga   17160
ccctgcagca ggtgctgccg agcagcgcac cctccgaggc gaagcggggt ctgaagcgcg   17220
agggcggcga cctggcgccc accgtgcagc tcatggtgcc caagcggcag aggctggagg   17280
atgtgctgga gaaaatgaaa gtagaccccg gtctgcagcc ggacatcagg gtccgcccca   17340
tcaagcaggt ggcgccgggc ctcggcgtgc agaccgtgga cgtggtcatc cccaccggca   17400 actccccgc cgccgccacc actaccgctg cctccacgga catggagaca cagaccgatc   17460
ccgccgcagc cgcagccgca gccgccgccg cgacctcctc ggcggaggtg cagacggacc   17520
cctggctgcc gccggcgatg tcagctcccc gcgcgcgtcg cgggcgcagg aagtacggcg   17580
ccgccaacgc gctcctgccc gagtacgcct tgcatccttc catcgcgccc acccccggct   17640
accgaggcta tacctaccgc ccgcgaagag ccaagggttc caccccgccgt ccccgccgac   17700 gcgccgccgc caccacccgc cgccgccgcc gcagacgcca gcccgcactg gctccagtct   17760
ccgtgaggaa agtggcgcgc gacggacaca ccctggtgct gcccagggcg cgctaccacc   17820
ccagcatcgt ttaaaagcct gttgtggttc ttgcagatat ggccctcact tgccgcctcc   17880
gtttcccggt gccgggatac cgaggaggaa gatcgcgccg caggagggt ctggccggcc   17940 gcggcctgag cggaggcagc cgccgcgcgc accggcggcg acgcgccacc agccgacgca   18000
tgcgcggcgg ggtgctgccc ctgttaatcc ccctgatcgc cgcggcgatc ggcgccgtgc   18060
ccgggatcgc ctccgtggcc ttgcaagcgt cccagaggca ttgacagact tgcaaacttg   18120
caaatatgga aaaaaaaacc ccaataaaaa agtctagact ctcacgctcg cttggtcctg   18180
tgactatttt gtagaatgga agacatcaac tttgcgtcgc tggccccgcg tcacggctcg   18240
cgcccgttcc tgggacactg gaacgatatc ggcaccagca acatgagcgg tggcgccttc   18300
```

```
agttggggct ctctgtggag cggcattaaa agtatcgggt ctgccgttaa aaattacggc    18360
tcccgggcct ggaacagcag cacgggccag atgttgagag acaagttgaa agagcagaac    18420
ttccagcaga aggtggtgga gggcctggcc tccggcatca acggggtggt ggacctggcc    18480
aaccaggccg tgcagaataa gatcaacagc agactggacc cccggccgcc ggtggaggag    18540
gtgccgccgg cgctggagac ggtgtccccc gatgggcgtg gcgagaagcg cccgcggccc    18600
gatagggaag agaccactct ggtcacgcag accgatgagc cgcccccgta tgaggaggcc    18660
ctgaagcaag gtctgcccac cacgcggccc atcgcgccca tggccaccgg ggtggtgggc    18720
cgccacaccc ccgccacgct ggacttgcct ccgcccgccg atgtgccgca gcagcagaag    18780
gcggcacagc cgggcccgcc cgcgaccgcc tcccgttcct ccgccggtcc tctgcgccgc    18840
gcggccagcg gcccccgcgg gggggtcgcg aggcacggca actggcagag cacgctgaac    18900
agcatcgtgg gtctgggggt gcggtccgtg aagcgccgcc gatgctactg aatagcttag    18960
ctaacgtgtt gtatgtgtgt atgcgcccta tgtcgccgcc agaggagctg ctgagtcgcc    19020
gccgttcgcg cgcccaccac caccgccact ccgcccctca agatggcgac cccatcgatg    19080
atgccgcagt ggtcgtacat gcacatctcg ggccaggacg cctcggagta cctgagcccc    19140
gggctggtgc agttcgcccg cgccaccgag agctacttca gcctgagtaa caagtttagg    19200
aaccccacgg tggcgcccac gcacgatgtg accaccgacc ggtctcagcg cctgacgctg    19260
cggttcattc ccgtggaccg cgaggacacc gcgtactcgt acaaggcgcg gttcacccctg   19320
gccgtgggcg acaaccgcgt gctggacatg gcctccacct actttgacat ccgcggggtg    19380
ctggaccggg gtcccacttt caagccctac tctggcaccg cctacaactc cctggccccc    19440
aagggcgctc ccaactcctg cgagtgggag caagaggaaa ctcaggcagt tgaagaagca    19500
gcagaagagg aagaagaaga tgctgacggt caagctgagg aagagcaagc agctaccaaa    19560
aagactcatg tatatgctca ggctccccctt tctggcgaaa aaattagtaa agatggtctg    19620
caaataggaa cggacgctac agctacagaa caaaaaccta tttatgcaga ccctacattc    19680
cagcccgaac cccaaatcgg ggagtcccag tggaatgagg cagatgctac agtcgccggc    19740
ggtagagtgc taaagaaatc tactcccatg aaaccatgct atggttccta tgcaagaccc    19800
acaaatgcta atggaggtca gggtgtacta acggcaaatg cccagggaca gctagaatct    19860
caggttgaaa tgcaattctt ttcaacttct gaaaacgccc gtaacgaggc taacaacatt    19920
cagcccaaat tggtgctgta tagtgaggat gtgcacatgg agaccccgga tacgcacctt    19980
tcttacaagc ccgcaaaaag cgatgacaat tcaaaaatca tgctgggtca gcagtccatg    20040
cccaacagac ctaattacat cggcttcaga gacaacttta tcggcctcat gtattacaat    20100
agcactggca acatgggagt gcttgcaggt caggcctctc agttgaatgc agtggtggac    20160
ttgcaagaca gaaacacaga actgtcctac cagctcttgc ttgattccat gggtgacaga    20220
accagatact tttccatgtg gaatcaggca gtggacagtt atgacccaga tgttagaatt    20280
attgaaaatc atggaactga agacgagctc cccaactatt gtttccctct gggtggcata    20340
ggggtaactg acacttacca ggctgttaaa accaacaatg caataacggg ggccaggtg    20400
acttggacaa aagatgaaac ttttgcagat cgcaatgaaa taggggtggg aaacaatttc    20460
gctatggaga tcaacctcag tgccaacctg tggagaaact tcctgtactc caacgtggcg    20520
ctgtacctac cagacaagct taagtacaac ccctccaatg tggacatctc tgacaacccc    20580
aacacctacg attacatgaa caagcgagtg gtggcccgg ggctggtgga ctgctacatc    20640
```

```
aacctgggcg cgcgctggtc gctggactac atggacaacg tcaacccctt caaccaccac    20700
cgcaatgcgg gcctgcgcta ccgctccatg ctcctgggca acgggcgcta cgtgcccttc    20760
cacatccagg tgccccagaa gttctttgcc atcaagaacc tcctcctcct gccgggctcc    20820
tacacctacg agtggaactt caggaaggat gtcaacatgg tcctccagag ctctctgggt    20880
aacgatctca gggtggacgg ggccagcatc aagttcgaga gcatctgcct ctacgccacc    20940
ttcttcccca tggcccacaa cacggcctcc acgctcgagg ccatgctcag gaacgacacc    21000
aacgaccagt ccttcaatga ctacctctcc gccgccaaca tgctctaccc catcccgcc    21060 aacgccacca acgtccccat ctccatcccc tcgcgcaact gggcggcctt ccgcggctgg    21120
gccttcaccc gcctcaagac caaggagacc ccctccctgg gctcgggatt cgaccctac    21180 tacacctact cgggctccat tccctacctg gacggcacct tctacctcaa ccacactttc    21240
aagaaggtct cggtcacctt cgactcctcg gtcagctggc cgggcaacga ccgtctgctc    21300
acccccaacg agttcgagat caagcgctcg gtcgacgggg agggctacaa cgtggcccag    21360
tgcaacatga ccaaggactg gttcctggtc cagatgctgg ccaactacaa catcggctac    21420
cagggcttct acatcccaga gagctacaag acaggatgt actccttctt caggaacttc    21480
cagcccatga gccggcaggt ggtggaccag accaagtaca aggactacca ggaggtgggc    21540
atcatccacc agcacaacaa ctcgggcttc gtgggctacc tcgcccccac catgcgcgag    21600
ggacaggcct accccgccaa cttccctat ccgctcatag caagaccgc ggtcgacagc    21660 atcacccaga aaaagttcct ctgcgaccgc accctctggc gcatccccctt ctccagcaac    21720 ttcatgtcca tgggtgcgct ctcggacctg gccagaact tgctctacgc caactccgcc    21780
cacgccctcg acatgacctt cgaggtcgac cccatggacg agcccaccct tctctatgtt    21840
ctgttcgaag tctttgacgt ggtccgggtc caccagccgc accgcggcgt catcgagacc    21900
gtgtacctgc gtacgcccctt ctcggccggc aacgccacca cctaaagaag caagccgcag    21960
tcatcgccgc ctgcatgccg tcgggttcca ccgagcaaga gctcagggcc atcgtcagag    22020
acctgggatg cgggccctat ttttgggca ccttcgacaa gcgcttccct ggctttgtct    22080
ccccacacaa gctggcctgc gccatcgtca acacggccgg ccgcgagacc ggggcgtgc    22140 actggctggc cttcgcctgg aacccgcgct ccaaaacatg cttcctcttt gaccccttcg    22200
gcttttcgga ccagcggctc aagcaaatct acgagttcga gtacgagggc ttgctgcgtc    22260
gcagcgccat cgcctcctcg cccgaccgct gcgtcaccct cgaaaagtcc acccagaccg    22320
tgcaggggcc cgactcggcc gcctgcggtc tcttctgctg catgtttctg cacgcctttg    22380
tgcactggcc tcagagtccc atggaccgca accccaccat gaacttgctg acggggggtgc    22440 ccaactccat gctccagagc ccccaggtcg agcccaccct gcgccgcaac caggagcagc    22500
tctacagctt cctggagcgc cactcgcctt acttccgccg ccacagcgca cagatcagga    22560
gggccacctc cttctgccac ttgcaagaga tgcaagaagg gtaataacga tgtacacact    22620
ttttttctca ataaatggca tctttttatt tatacaagct ctctggggta ttcatttccc    22680
accaccaccc gccgttgtcg ccatctggct ctatttagaa atcgaaaggg ttctgccggg    22740
agtcgccgtg cgccacgggc agggacacgt tgcgatactg gtagcgggtg ccccacttga    22800
actcgggcac caccaggcga ggcagctcgg ggaagttttc gctccacagg ctgcgggtca    22860
gcaccagcgc gttcatcagg tcgggcgccg agatcttgaa gtcgcagttg gggccgccgc    22920
cctgcgcgcg cgagttgcgg tacaccgggt tgcagcactg gaacaccaac agcgccgggt    22980
gcttcacgct ggccagcacg ctgcggtcgg agatcagctc ggcgtccagg tcctccgcgt    23040
```

```
tgctcagcgc gaacgggtc  atcttgggca cttgccgccc caggaagggc gcgtgccccg  23100
gtttcgagtt gcagtcgcag cgcagcggga tcagcaggtg cccgtgcccg gactcggcgt  23160
tggggtacag cgcgcgcatg aaggcctgca tctggcggaa ggccatctgg gccttggcgc  23220
cctccgagaa gaacatgccg caggacttgc ccgagaactg gtttgcgggg cagctggcgt  23280
cgtgcaggca gcagcgcgcg tcggtgttgg cgatctgcac cacgttgcgc ccccaccggt  23340
tcttcacgat cttggccttg gacgattgct ccttcagcgc gcgctgcccg ttctcgctgg  23400
tcacatccat ctcgatcaca tgttccttgt tcaccatgct gctgccgtgc agacacttca  23460
gctcgccctc cgtctcggtg cagcggtgct gccacagcgc gcagcccgtg ggctcgaaag  23520
acttgtaggt cacctccgcg aaggactgca ggtaccctg  caaaaagcgg cccatcatgg  23580
tcacgaaggt cttgttgctg ctgaaggtca gctgcagccc gcggtgctcc tcgttcagcc  23640
aggtcttgca cacggccgcc agcgcctcca cctggtcggg cagcatcttg aagttcacct  23700
tcagctcatt ctccacgtgg tacttgtcca tcagcgtgcg cgccgcctcc atgcccttct  23760
cccaggccga caccagcggc aggctcacgg ggttcttcac catcaccgtg ccgccgcct   23820
ccgccgcgct ttcgctttcc gccccgctgt tctcttcctc ttcctcctct tcctcgccgc  23880
cgcccactcg cagccccgc  accacggggt cgtcttcctg caggcgctgc accttgcgct  23940
tgccgttgcg ccctgcttg  atgcgcacgg gcggttgct  gaagcccacc atcaccagcg  24000
cggcctcttc ttgctcgtcc tcgctgtcca gaatgacctc cggggagggg gggttggtca  24060
tcctcagtac cgaggcacgc ttctttttct tcctggggc  gttcgccagc tccgcggctg  24120
cggccgctgc cgaggtcgaa ggccgagggc tgggcgtgcg cggcaccagc gcgtcctgcg  24180
agccgtcctc gtcctcctcg gactcgagac ggaggcgggc ccgcttcttc ggggcgcgc   24240
ggggcggcgg aggcggcggc ggcgacggag acggggacga gacatcgtcc agggtgggtg  24300
gacggcgggc cgcgccgcgt ccgcgctcgg ggtggtctc  gcgctggtcc tcttcccgac  24360
tggccatctc ccactgctcc ttctcctata ggcagaaaga gatcatggag tctctcatgc  24420
gagtcgagaa ggaggaggac agcctaaccg cccctctga  gccctccacc accgccgcca  24480
ccaccgccaa tgccgccgcg gacgacgcgc ccaccgagac caccgccagt accaccctcc  24540
ccagcgacgc accccgctc  gagaatgaag tgctgatcga gcaggacccg gttttgtga   24600
gcggagagga ggatgaggtg gatgagaagg agaaggagga ggtcgccgcc tcagtgccaa  24660
aagaggataa aaagcaagac caggacgacg cagataagga tgagacagca gtcgggcggg  24720
ggaacggaag ccatgatgct gatgacggct acctagacgt gggagacgac gtgctgctta  24780
agcacctgca ccgccagtgc gtcatcgtct gcgacgcgct gcaggagcgc tgcgaagtgc  24840
ccctggacgt ggcggaggtc agccgcgcct acgagcggca cctcttcgcg ccgcacgtgc  24900
cccccaagcg ccgggagaac ggcacctgcg agcccaaccc gcgtctcaac ttctacccgg  24960
tcttcgcggt acccgaggtg ctggccacct accacatctt tttccaaaac tgcaagatcc  25020
ccctctcctg ccgcgccaac cgcacccgcg ccgacaaaac cctgaccctg cggcagggcg  25080
cccacatacc tgatatcgcc tctctggagg aagtgcccaa gatcttcgag ggtctcggtc  25140
gcgacgagaa acgggcggcg aacgctctgc acggagacag cgaaaacgag agtcactcgg  25200
gggtgctggt ggagctcgag ggcgacaacg cgcgcctggc cgtactcaag cgcagcatag  25260
aggtcaccca ctttgcctac ccggcgctca acctgccccc caaggtcatg agtgtggtca  25320
tgggcgagct catcatgcgc cgcgcccagc ccctggccgc ggatgcaaac ttgcaagagt  25380
```

```
cctccgagga aggcctgccc gcggtcagcg acgagcagct ggcgcgctgg ctggagaccc   25440
gcgaccccgc gcagctggag gagcggcgca agctcatgat ggccgcggtg ctggtcaccg   25500
tggagctcga gtgtctgcag cgcttcttcg cggaccccga gatgcagcgc aagctcgagg   25560
agaccctgca ctacaccttc cgccagggct acgtgcgcca ggcctgcaag atctccaacg   25620
tggagctctg caacctggtc tcctacctgg gcatcctgca cgagaaccgc tcgggcaga   25680 acgtcctgca ctccaccctc aaaggggagg cgcgccgcga ctacatccgc gactgcgcct   25740
acctcttcct ctgctacacc tggcagacgg ccatgggggt ctggcagcag tgcctggagg   25800
agcgcaacct caaggagctg aaaagctcc tcaagcgcac cctcagggac ctctggacgg   25860
gcttcaacga gcgctcggtg gccgccgcgc tggcggacat catctttccc gagcgcctgc   25920
tcaagaccct gcagcagggc ctgcccgact tcaccagcca gagcatgctg cagaacttca   25980
ggactttcat cctggagcgc tcgggcatcc tgccggccac ttgctgcgcg ctgcccagcg   26040
acttcgtgcc catcaagtac agggagtgcc cgccgccgct ctgggccac tgctacctct   26100 tccagctggc caactacctc gcctaccact cggacctcat ggaagacgtg agcggcgagg   26160
gcctgctcga gtgccactgc cgctgcaacc tctgcacgcc ccaccgctct ctagtctgca   26220
acccgcagct gctcagcgag agtcagatta tcggtacctt cgagctgcag ggtccctcgc   26280
ctgacgagaa gtccgcggct ccagggctga aactcactcc ggggctgtgg acttccgcct   26340
acctacgcaa atttgtacct gaggactacc acgcccacga gatcaggttc tacgaagacc   26400
aatcccgccc gcccaaggcg gagctcaccg cctgcgtcat cacccagggg cacatcctgg   26460
gccaattgca agccatcaac aaagcccgcc gagagttctt gctgaaaaag ggtcgggggg   26520
tgtacctgga cccccagtcc ggcgaggagc taaacccgct accccgccg ccgccccagc   26580 agcgggacct tgcttcccag gatggcaccc agaaagaagc agcagccgcc gccgccgccg   26640
cagccataca tgcttctgga ggaagaggag gaggactggg acagtcaggc agaggaggtt   26700
tcggacgagg agcaggagga gatgatggaa gactgggagg aggacagcag cctagacgag   26760
gaagcttcag aggccgaaga ggtggcagac gcaacaccat cgccctcggt cgcagccccc   26820
tcgccggggc ccctgaaatc ctccgaaccc agcaccagcg ctataacctc cgctcctccg   26880
gcgccggcgc cacccgcccg cagacccaac cgtagatggg acaccacagg aaccggggtc   26940
ggtaagtcca agtgcccgcc gccgccaccg cagcagcagc agcagcagcg ccagggctac   27000
cgctcgtggc gcgggcacaa gaacgccata gtcgcctgct gcaagactg cggggcaac   27060 atctctttcg cccgccgctt cctgctattc caccacgggg tcgcctttcc ccgcaatgtc   27120
ctgcattact accgtcatct ctacagcccc tactgcagcg gcgacccaga ggcggcagcg   27180
gcagccacag cggcgaccac cacctaggaa gatatcctcc gcgggcaaga cagcggcagc   27240
agcggccagg agaccgcgg cagcagcggc gggagcggtg ggcgcactgc gcctctcgcc   27300
caacgaaccc ctctcgaccc gggagctcag acacaggatc ttccccactt tgtatgccat   27360
cttccaacag agcagaggcc aggagcagga gctgaaaata aaaaacagat ctctgcgctc   27420
cctcacccgc agctgtctgt atcacaaaag cgaagatcag cttcggcgca cgctggagga   27480
cgcggaggca ctcttcagca aatactgcgc gctcactctt aaagactagc tccgcgccct   27540
tctcgaattt aggcgggaga aaactacgtc atcgccggcc gccgcccagc ccgcccagcc   27600
gagatgagca aagagattcc cacgccatac atgtggagct accagccgca gatgggactc   27660
gcggcgggag cggcccagga ctactccacc cgcatgaact acatgagcgc gggacccac   27720 atgatctcac aggtcaacgg gatccgcgcc cagcgaaacc aaatactgct ggaacaggcg   27780
```

```
gccatcaccg ccacgccccg ccataatctc aaccccgaa attggcccgc cgccctcgtg    27840
taccaggaaa ccccctccgc caccaccgta ctacttccgc gtgacgccca ggccgaagtc    27900
cagatgacta actcaggggc gcagctcgcg ggcggctttc gtcacggggc gcggccgctc    27960
cgaccaggta taagacacct gatgatcaga ggccgaggta tccagctcaa cgacgagtcg    28020
gtgagctctt cgctcggtct ccgtccggac ggaactttcc agctcgccgg atccggccgc    28080
tcttcgttca cgcccgcca ggcgtacctg actctgcaga cctcgtcctc ggagccccgc     28140
tccggcggca tcggaaccct ccagttcgtg gaggagttcg tgccctcggt ctacttcaac    28200
cccttctcgg gacctcccgg acgctacccc gaccagttca ttccgaactt tgacgcggtg    28260
aaggactcgg cggacggcta cgactgaatg tcaggtgtcg aggcagagca gcttcgcctg    28320
agacacctcg agcactgccg ccgccacaag tgcttcgccc gcggttctgg tgagttctgc    28380
tactttcagc tacccgagga gcataccgag gggccggcgc acggcgtccg cctgaccacc    28440
cagggcgagg ttacctgttc cctcatccgg gagtttaccc tccgtcccct gctagtggag    28500
cgggagcggg gtccctgtgt cctaactatc gcctgcaact gccctaaccc tggattacat    28560
caagatcttt gctgtcatct ctgtgctgag tttaataaac gctgagatca gaatctactg    28620
gggctcctgt cgccatcctg tgaacgccac cgtcttcacc caccccgacc aggcccaggc    28680
gaacctcacc tgcggtctgc atcggagggc caagaagtac ctcacctggt acttcaacgg    28740
caccccttt gtggtttaca acagcttcga cggggacgga gtctccctga agaccagct     28800
ctccggtctc agctactcca tccacaagaa caccaccctc caactcttcc ctccctacct    28860
gccgggaacc tacgagtgcg tcaccggccg ctgcaccac ctcacccgcc tgatcgtaaa     28920
ccagagcttt ccgggaacag ataactccct cttccccaga acaggaggtg agctcaggaa    28980
actcccggg gaccagggcg gagacgtacc ttcgacccctt gtgggggttag gatttttat     29040
taccgggttg ctggctcttt taatcaaagt ttccttgaga tttgttcttt ccttctacgt    29100
gtatgaacac ctcaacctcc aataactcta ccctttcttc ggaatcaggt gacttctctg    29160
aaatcgggct tggtgtgctg cttactctgt tgatttttttt ccttatcata ctcagccttc   29220
tgtgcctcag gctcgccgcc tgctgcgcac acatctatat ctactgctgg ttgctcaagt    29280
gcagggggtcg ccaccaaga tgaacaggta catggtccta tcgatcctag gcctgctggc   29340
cctggcggcc tgcagcgccg ccaaaaaaga gattaccttt gaggagcccg cttgcaatgt    29400
aactttcaag cccgagggtg accaatgcac caccctcgtc aaatgcgtta ccaatcatga    29460
gaggctgcgc atcgactaca aaaacaaaac tggccagttt gcggtctata gtgtgtttac    29520
gcccggagac ccctctaact actctgtcac cgtcttccag ggcggacagt ctaagatatt    29580
caattacact ttccctttt atgagttatg cgatgcggtc atgtacatgt caaaacagta    29640
caacctgtgg cctccctctc cccaggcgtg tgtggaaaat actgggtctt actgctgtat    29700
ggctttcgca atcactacgc tcgctctaat ctgcacggtg ctatacataa aattcaggca    29760
gaggcgaatc tttatcgatg aaaagaaaat gccttgatcg ctaacaccgg ctttctatct    29820
gcagaatgaa tgcaatcacc tccctactaa tcaccaccac cctccttgcg attgcccatg    29880
ggttgacacg aatcgaagtg ccagtgggt ccaatgtcac catggtgggc cccgccggca     29940
attccaccct catgtgggaa aaatttgtcc gcaatcaatg ggttcatttc tgctctaacc    30000
gaatcagtat caagcccaga gccatctgcg atgggcaaaa tctaactctg atcaatgtgc    30060
aaatgatgga tgctgggtac tattacgggc agcggggaga aatcattaat tactggcgac    30120
```

```
cccacaagga ctacatgctg catgtagtcg aggcacttcc cactaccacc cccactacca    30180
cctctcccac caccaccacc actactacta ctactactac tactactact actaccacta    30240
ccgctgcccg ccatacccgc aaaagcacca tgattagcac aaagcccccct cgtgctcact   30300 cccacgccgg cgggcccatc ggtgcgacct cagaaaccac cgagctttgc ttctgccaat    30360
gcactaacgc cagcgctcat gaactgttcg acctggagaa tgaggatgtc cagcagagct    30420
ccgcttgcct gacccaggag gctgtggagc ccgttgccct gaagcagatc ggtgattcaa    30480
taattgactc ttcttctttt gccactcccg aatacccctcc cgattctact ttccacatca   30540
cgggtaccaa agaccctaac ctctctttct acctgatgct gctgctctgt atctctgtgg    30600
tctcttccgc gctgatgtta ctggggatgt tctgctgcct gatctgccgc agaaagagaa    30660
aagctcgctc tcagggccaa ccactgatgc ccttcccccta cccccccggat tttgcagata   30720 acaagatatg agctcgctgc tgacactaac cgctttacta gcctgcgctc taacccttgt    30780
cgcttgcgac tcgagattcc acaatgtcac agctgtggca ggagaaaatg ttactttcaa    30840
ctccacggcc gatacccagt ggtcgtggag tggctcaggt agctacttaa ctatctgcaa    30900
tagctccact tcccccggca tatccccaac caagtaccaa tgcaatgcca gcctgttcac    30960
cctcatcaac gcttccaccc tggacaatgg actctatgta ggctatgtac cctttggtgg    31020
gcaaggaaag acccacgctt acaacctgga agttcgccag cccagaacca ctacccaagc    31080
ttctcccacc accaccacca ccaccaccat caccagcagc agcagcagca gcagccacag    31140
cagcagcagc agattattga ctttggtttt ggccagctca tctgccgcta cccaggccat    31200
ctacagctct gtgcccgaaa ccactcagat ccaccgccca gaaacgacca ccgccaccac    31260
cctacacacc tccagcgatc agatgccgac caacatcacc cccttggctc ttcaaatggg    31320
acttacaagc cccactccaa aaccagtgga tgcggccgag gtctccgccc tcgtcaatga    31380
ctgggcgggg ctgggaatgt ggtggttcgc cataggcatg atggcgctct gcctgcttct    31440
gctctggctc atctgctgcc tccaccgcag gcgagccaga ccccccatct atagacccat    31500
cattgtcctg aaccccgata atgatgggat ccatagattg gatggcctga aaaacctact    31560
ttttcttttt acagtatgat aaattgagac atgcctcgca ttttcttgta catgttcctt    31620
ctcccacctt ttctggggtg ttctacgctg gccgctgtgt ctcacctgga ggtagactgc    31680
ctctcaccct tcactgtcta cctgctttac ggattggtca ccctcactct catctgcagc    31740
ctaatcacag taatcatcgc cttcatccag tgcattgatt acatctgtgt gcgcctcgca    31800
tacttcagac accaccgcca gtaccgagac aggaacattg cccaacttct aagactgctc    31860
taatcatgca taagactgtg atctgccttc tgatcctctg catcctgccc accctcacct    31920
cctgccagta caccacaaaa tctccgcgca aaagacatgc ctcctgccgc ttcacccaac    31980
tgtggaatat acccaaatgc tacaacgaaa agagcgagct ctccgaagct tggctgtatg    32040
gggtcatctg tgtcttagtt ttctgcagca ctgtctttgc cctcataatc taccccctact   32100 ttgatttggg atggaacgcg atcgatgcca tgaattaccc cacctttccc gcacccgaga    32160
taattccact gcgacaagtt gtacccgttg tcgttaatca acgccccccca tcccctacgc    32220 ccactgaaat cagctacttt aacctaacag gcggagatga ctgacgccct agatctagaa    32280
atggacggca tcagtaccga gcagcgtctc ctagagaggc gcaggcaggc ggctgagcaa    32340
gagcgcctca atcaggagct ccgagatctc gttaacctgc accagtgcaa aagaggcatc    32400
ttttgtctgg taaagcaggc caaagtcacc tacgagaaga ccggcaacag ccaccgcctc    32460
agttacaaat tgcccacccca gcgccagaag ctggtgctca tggtgggtga gaatcccatc    32520
```

```
accgtcaccc agcactcggt agagaccgag gggtgtctgc actcccctg tcggggtcca   32580
gaagacctct gcaccctggt aaagaccctg tgcggtctca gagatttagt cccctttaac   32640
taatcaaaca ctggaatcaa taaaaagaat cacttactta aaatcagaca gcaggtctct   32700
gtccagttta ttcagcagca cctccttccc ctcctcccaa ctctggtact ccaaacgcct   32760
tctggcggca aacttcctcc acaccctgaa gggaatgtca gattcttgct cctgtccctc   32820
cgcacccact atcttcatgt tgttgcagat gaagcgcacc aaaacgtctg acgagagctt   32880
caacccgtg taccctatg acacggaaag cggccctccc tccgtccctt tcctcacccc   32940
tcccttcgtg tctcccgatg gattccaaga aagtccccc ggggtcctgt ctctgaacct   33000
ggccgagccc ctggtcactt cccacggcat gctcgccctg aaaatgggaa gtggcctctc   33060
cctggacgac gctggcaacc tcacctctca agatatcacc accgctagcc ctcccctcaa   33120
aaaaaccaag accaacctca gcctagaaac ctcatccccc ctaactgtga gcacctcagg   33180
cgccctcacc gtagcagccg ccgctcccct ggcggtggcc ggcacctccc tcaccatgca   33240
atcagaggcc cccctgacag tacaggatgc aaaactcacc ctggccacca aaggcccccct   33300
gaccgtgtct gaaggcaaac tggccttgca acatcggcc ccgctgacgg ccgctgacag   33360
cagcaccctc acagtcagtg ccacaccacc ccttagcaca agcaatggca gcttgggtat   33420
tgacatgcaa gccccatttt acaccaccaa tggaaaacta ggacttaact ttggcgctcc   33480
cctgcatgtg gtagacagcc taaatgcact gactgtagtt actggccaag tcttacgat   33540
aaacggaaca gccctacaaa ctagagtctc aggtgccctc aactatgaca catcaggaaa   33600
cctagaattg agagctgcag ggggtatgcg agttgatgca aatggtcaac ttatccttga   33660
tgtagcttac ccatttgatg cacaaaacaa tctcagcctt aggcttggac agggacccct   33720
gtttgttaac tctgcccaca acttggatgt taactacaac agaggcctct acctgttcac   33780
atctggaaat accaaaaagc tagaagttaa tatcaaaaca gccaagggtc tcatttatga   33840
tgacactgct atagcaatca atgcgggtga tgggctacag tttgactcag gctcagatac   33900
aaatccatta aaaactaaac ttggattagg actggattat gactccagca gagccataat   33960
tgctaaactg ggaactggcc taagcttttga caacacaggt gccatcacag taggcaacaa   34020
aaatgatgac aagcttacct tgtggaccac accagaccca tcccctaact gtagaatcta   34080
ttcagagaaa gatgctaaat tcacacttgt tttgactaaa tgcggcagtc aggtgttggc   34140
cagcgtttct gttttatctg taaaaggtag ccttgcgccc atcagtggca cagtaactag   34200
tgctcagatt gtcctcagat ttgatgaaaa tggagttcta ctaagcaatt cttcccttga   34260
ccctcaatac tggaactaca gaaaaggtga ccttacagag ggcactgcat ataccaacgc   34320
agtgggattt atgcccaacc tcacagcata cccaaaaaca cagagccaaa ctgctaaaag   34380
caacattgta agtcaggttt acttgaatgg ggacaaatcc aaacccatga ccctcaccat   34440
taccctcaat ggaactaatg aaacaggaga tgccacagta agcacttact ccatgtcatt   34500
ctcatggaac tggaatggaa gtaattacat taatgaaacg ttccaaacca actccttcac   34560
cttctcctac atcgcccaag aataaaaagc atgacgctgt tgatttgatt caatgtgttt   34620
ctgtttttatt ttcaagcaca acaaaatcat tcaagtcatt cttccatctt agcttaatag   34680
acacagtagc ttaatagacc cagtagtgca aagcccatt ctagcttata gatcagacag   34740
tgataattaa ccaccaccac caccataccct tttgattcag gaaatcatga tcatcacagg   34800
atcctagtct tcaggccgcc ccctccctcc caagacacag aatacacagt cctctccccc   34860
```

```
cgactggctt taaataacac catctggttg gtcacagaca tgttcttagg ggttatattc    34920
cacacggtct cctgccgcgc caggcgctcg tcggtgatgt tgataaactc tcccggcagc    34980
tcgctcaagt tcacgtcgct gtccagcggc tgaacctccg gctgacgcga taactgtgcg    35040
accggctgct ggacgaacgg aggccgcgcc tacaaggggg tagagtcata atcctcggtc    35100
aggatagggc ggtgatgcag cagcagcgag cgaaacatct gctgccgccg ccgctccgtc    35160
cggcaggaaa acaacacgcc ggtggtctcc tccgcgataa tccgcaccgc ccgcagcatc    35220
agcttcctcg ttctccgcgc gcagcacctc acccttatct cgctcaaatc ggcgcagtag    35280
gtacagcaca gcaccacgat gttattcatg atcccacagt gcagggcgct gtatccaaag    35340
ctcatgccgg gaaccaccgc ccccacgtgg ccatcgtacc acaagcgcac gtaaatcaag    35400
tgtcgacccc tcatgaacgc gctggacaca acattactt ccttgggcat gttgtaattc     35460
accacctccc ggtaccagat aaacctctgg ttgaacaggg caccttccac caccatcctg    35520
aaccaagagg ccagaacctg cccaccggct atgcactgca gggaacccgg gttggaacaa    35580
tgacaatgca gactccaagg ctcgtaaccg tggatcatcc ggctgctgaa ggcatcgatg    35640
ttggcacaac acagacacac gtgcatgcac tttctcatga ttagcagctc ttccctcgtc    35700
aggatcatat cccaaggaat aacccattct tgaatcaacg taaaacccac acagcaggga    35760
aggcctcgca cataactcac gttgtgcatg gtcagcgtgt tgcattccgg aaacagcgga    35820
tgatcctcca gtatcgaggc gcgggtctcc ttctcacagg gaggtaaagg gtccctgctg    35880
tacggactgc gccgggacga ccgagatcgt gttgagcgta gtgtcatgga aaagggaacg    35940
ccggacgtgg tcatacttct tgaagcagaa ccaggttcgc gcgtggcagg cctccttgcg    36000
tctgcggtct cgccgtctag ctcgctccgt gtgatagttg tagtacagcc actcccgcag    36060
agcgtcgagg cgcaccctgg cttccggatc tatgtagact ccgtcttgca ccgcggccct    36120
gataatatcc accaccgtag aataagcaac acccagccaa gcaatacact cgctctgcga    36180
gcggcagaca ggaggagcgg gcagagatgg gagaaccatg ataaaaaact tttttttaaag    36240
aatattttcc aattcttcga agtaagatc tatcaagtgg cagcgctccc ctccactggc     36300
gcggtcaaac tctacggcca aagcacagac aacggcattt ctaagatgtt ccttaatggc    36360
gtccaaaaga cacaccgctc tcaagttgca gtaaactatg aatgaaaacc catccggctg    36420
attttccaat atagacgcgc cggcagcgtc caccaaaccc agataatttt cttctctcca    36480
gcggtttacg atctgtctaa gcaaatccct tatatcaagt ccgaccatgc caaaaatctg    36540
ctcaagagcg ccctccacct tcatgtacaa gcagcgcatc atgattgcaa aaattcaggt    36600
tcttcagaga cctgtataag attcaaaatg ggaacattaa caaaaattcc tctgtcgcgc    36660
agatcccttc gcagggcaag ctgaacataa tcagacaggt ccgaacggac cagtgaggcc    36720
aaatccccac caggaaccag atccagagac cctatactga ttatgacgcg catactcggg    36780
gctatgctga ccagcgtagc gccgatgtag gcgtgctgca tgggcggcga gataaaatgc    36840
aaagtgctgg ttaaaaaatc aggcaaagcc tcgcgcaaaa aagctaacac atcataatca    36900
tgctcatgca ggtagttgca ggtaagctca ggaaccaaaa cggaataaca cacgatttc     36960
ctctcaaaca tgacttcgcg gatactgcgt aaaacaaaaa attataaata aaaaattaat    37020
taaataactt aaacattgga agcctgtctc acaacaggaa aaaccacttt aatcaacata    37080
agacgggcca cggcatgcc ggcatagccg taaaaaaatt ggtccccgtg attaacaagt      37140
accacagaca gctcccggt catgtcgggg gtcatcatgt gagactctgt atacacgtct      37200
ggattgtgaa catcagacaa acaaagaaat cgagccacgt agcccggagg tataatcacc    37260
```

```
cgcaggcgga ggtacagcaa aacgaccccc ataggaggaa tcacaaaatt agtaggagaa    37320
aaaaatacat aaacaccaga aaaaccctgt tgctgaggca aaatagcgcc ctcccgatcc    37380
aaaacaacat aaagcgcttc cacaggagca gccataacaa agacccgagt cttaccagta    37440
aaagaaaaaa gatctctcaa cgcagcacca gcaccaacac ttcgcagtgt aaaaggccaa    37500
gtgccgagag agtatatata ggaataaaaa gtgacgtaaa cgggcaaagt ccaaaaaacg    37560
cccagaaaaa ccgcacgcga acctacgccc cgaaacgaaa gccaaaaaac actagacact    37620
cccttccggc gtcaacttcc gctttcccac gctacgtcac ttccccggt caaacaaact    37680 acatatcccg aacttccaag tcgccacgcc caaaacaccg cctacacctc cccgcccgcc    37740
ggcccgcccc cggacccgcc tcccgccccg cgccgcccat ctcattatca tattggcttc    37800
aatccaaaat aaggtatatt attgatgatg                                    37830

<210> SEQ ID NO 14
<211> LENGTH: 15422
<212> TYPE: DNA
<213> ORGANISM: Pan troglodytes

<400> SEQUENCE: 14
tgcccgcttt ccagtcggga aacctgtcgt gccagctgca ttaatgaatc ggccaacgcg      60
cggggagagg cggtttgcgt attgggcgct agatctccca tcacatatac ctgccgttca     120
ctattattta gtgaaatgag atattatgat attttctgaa ttgtgattaa aaaggcaact     180
ttatgcccat gcaacagaaa ctataaaaaa tacagagaat gaaagaaac agatagattt     240 tttagttctt taggcccgta gtctgcaaat ccttttatga ttttctatca aacaaaagag     300
gaaaatagac cagttgcaat ccaaacgaga gtctaataga atgaggtcga aaagtaaatc     360
gcgcgggttt gttactgata aagcaggcaa gacctaaaat gtgtaaaggg caaagtgtat     420
actttggcgt caccccttac atattttagg tcttttttta ttgtgcgtaa ctaacttgcc     480
atcttcaaac aggagggctg gaagaagcag accgctaaca cagtacataa aaaaggagac     540
atgaacgatg aacatcaaaa agtttgcaaa acaagcaaca gtattaaacct ttactaccgc     600 actgctggca ggaggcgcaa ctcaagcgtt tgcgaaagaa acgaaccaaa agccatataa     660
ggaaacatac ggcatttccc atattacacg ccatgatatg ctgcaaatcc ctgaacagca     720
aaaaaatgaa aaatatcaag ttcctgaatt cgattcgtcc acaattaaaa atatctcttc     780
tgcaaaaggc ctggacgttt gggacagctg gccattacaa aacgctgacg gcactgtcgc     840
aaactatcac ggctaccaca tcgtctttgc attagccgga gatcctaaaa atgcggatga     900
cacatcgatt tacatgttct atcaaaaagt cggcgaaact tctattgaca gctggaaaaa     960
cgctggccgc gtctttaaag acagcgacaa attcgatgca aatgattcta tcctaaaaga    1020
ccaaacacaa gaatggtcag gttcagccac atttacatct gacggaaaaa tccgtttatt    1080
ctacactgat ttctccggta acattacgg caaacaaaca ctgacaactg cacaagttaa    1140
cgtatcagca tcagacagct cttttgaacat caacggtgta gaggattata atcaatctt    1200 tgacggtgac ggaaaaacgt atcaaaatgt acagcagttc atcgatgaag caactacag     1260 ctcaggcgac aaccatacgc tgagagatcc tcactacgta aagataaag gccacaaata    1320 cttagtattt gaagcaaaca ctggaactga agatggctac caaggcgaag aatctttatt    1380
taacaaagca tactatggca aaagcacatc attcttccgt caagaaagtc aaaaacttct    1440
gcaaagcgat aaaaaacgca cggctgagtt agcaaacggc gctctcggta tgattgagct    1500
```

```
aaacgatgat tacacactga aaaaagtgat gaaaccgctg attgcatcta acacagtaac      1560
agatgaaatt gaacgcgcga acgtctttaa aatgaacggc aaatggtacc tgttcactga      1620
ctcccgcgga tcaaaaatga cgattgacgg cattacgtct aacgatattt acatgcttgg      1680
ttatgtttct aattctttaa ctggcccata caagccgctg aacaaaactg gccttgtgtt      1740
aaaaatggat cttgatccta acgatgtaac ctttacttac tcacacttcg ctgtacctca      1800
agcgaaagga aacaatgtcg tgattacaag ctatatgaca aacagaggat tctacgcaga      1860
caaacaatca acgtttgcgc caagcttcct gctgaacatc aaaggcaaga aaacatctgt      1920
tgtcaaagac agcatccttg aacaaggaca attaacagtt aacaaataat agggataaca      1980
gggtaatgct agaagacccg agtcttacca gtaaaagaaa aaagatctct caacgcagca      2040
ccagcaccaa cacttcgcag tgtaaaaggc caagtgccga gagagtatat ataggaataa      2100
aaagtgacgt aaacgggcaa agtccaaaaa acgcccagaa aaaccgcacg cgaacctacg      2160
ccccgaaacg aaagccaaaa aacactagac actcccttcc ggcgtcaact tccgctttcc      2220
cacgctacgt cacttgcccc agtcaaacaa actacatatc ccgaacttcc aagtcgccac      2280
gcccaaaaca ccgcctacac ctccccgccc gccggcccgc ccccaaaccc gcctcccgcc      2340
ccgcgccccg ccccgcgccg cccatctcat tatcatattg gcttcaatcc aaaataaggt      2400
atattattga tgatggttta aacggatcct ctagagtcga cctgcaggca tgcaagcttg      2460
agtattctat agtgtcacct aaatagcttg gcgtaatcat ggtcatagct gtttcctgtg      2520
tgaaattgtt atccgctcac aattccacac aacatacgag ccggaagcat aaagtgtaaa      2580
gcctggggtg cctaatgagt gagctaactc acattaattg cgttgcgctc actgcccgct      2640
ttccagtcgg gaaacctgtc gtgccagctg cattaatgaa tcggccaacg cgaacccctt      2700
gcggccgccc gggccgtcga ccaattctca tgtttgacag cttatcatcg aatttctgcc      2760
attcatccgc ttattatcac ttattcaggc gtagcaacca ggcgtttaag ggcaccaata      2820
actgccttaa aaaaattacg ccccgccctg ccactcatcg cagtactgtt gtaattcatt      2880
aagcattctg ccgacatgga agccatcaca acggcatga tgaacctgaa tcgccagcgg      2940
catcagcacc ttgtcgcctt gcgtataata tttgcccatg gtgaaaacgg gggcgaagaa      3000
gttgtccata ttggccacgt ttaaatcaaa actggtgaaa ctcacccagg gattggctga      3060
gacgaaaaac atattctcaa taaacccttt agggaaatag gccaggtttt caccgtaaca      3120
cgccacatct tgcgaatata tgtgtagaaa ctgccggaaa tcgtcgtggt attcactcca      3180
gagcgatgaa aacgtttcag tttgctcatg gaaaacggtg taacaagggt gaacactatc      3240
ccatatcacc agctcaccgt ctttcattgc catacggaat tccggatgag cattcatcag      3300
gcgggcaaga atgtgaataa aggccggata aaacttgtgc ttattttct ttacggtctt      3360 taaaaaggcc gtaatatcca gctgaacggt ctggttatag gtacattgag caactgactg      3420
aaatgcctca aaatgttctt tacgatgcca ttgggatata tcaacggtgg tatatccagt      3480
gatttttttc tccattttag cttccttagc tcctgaaaat ctcgataact caaaaaatac      3540
gcccggtagt gatcttattt cattatggtg aaagttggaa cctcttacgt gccgatcaac      3600
gtctcatttt cgccaaaagt tggcccaggg cttcccggta tcaacaggga caccaggatt      3660
tatttattct gcgaagtgat cttccgtcac aggtatttat tcgcgataag ctcatggagc      3720
ggcgtaaccg tcgcacagga aggacagaga aagcgcggat ctgggaagtg acggacagaa      3780
cggtcaggac ctggattggg gaggcggttg ccgccgctgc tgctgacggt gtgacgttct      3840
ctgttccggt cacaccacat acgttccgcc attcctatgc gatgcacatg ctgtatgccg      3900
```

-continued

```
gtataccgct gaaagttctg caaagcctga tgggacataa gtccatcagt tcaacggaag   3960
tctacacgaa ggttttgcg ctggatgtgg ctgcccggca ccgggtgcag tttgcgatgc    4020
cggagtctga tgcggttgcg atgctgaaac aattatcctg agaataaatg ccttggcctt   4080
tatatgaaaa tgtggaactg agtggatatg ctgttttgt ctgttaaaca gagaagctgg    4140
ctgttatcca ctgagaagcg aacgaaacag tcgggaaaat ctcccattat cgtagagatc   4200
cgcattatta atctcaggag cctgtgtagc gtttatagga agtagtgttc tgtcatgatg   4260
cctgcaagcg gtaacgaaaa cgatttgaat atgccttcag gaacaataga aatcttcgtg   4320
cggtgttacg ttgaagtgga gcggattatg tcagcaatgg acagaacaac ctaatgaaca   4380
cagaaccatg atgtggtctg tcctttaca gccagtagtg ctcgccgcag tcgagcgaca     4440
gggcgaagcc ctcgagtgag cgaggaagca ccagggaaca gcacttatat attctgctta   4500
cacacgatgc ctgaaaaaac ttcccttggg gttatccact tatccacggg gatatttta    4560 taattatttt ttttatagtt tttagatctt ctttttaga gcgccttgta ggcctttatc    4620
catgctggtt ctagagaagg tgttgtgaca aattgcccct tcagtgtgac aaatcaccct   4680
caaatgacag tcctgtctgt gacaaattgc ccttaaccct gtgacaaatt gccctcagaa   4740
gaagctgttt tttcacaaag ttatccctgc ttattgactc tttttatt agtgtgacaa    4800 tctaaaaact tgtcacactt cacatggatc tgtcatggcg gaaacagcgg ttatcaatca   4860
caagaaacgt aaaaatagcc cgcgaatcgt ccagtcaaac gacctcactg aggcggcata   4920
tagtctctcc cgggatcaaa aacgtatgct gtatctgttc gttgaccaga tcagaaaatc   4980
tgatggcacc ctacaggaac atgacggtat ctgcgagatc catgttgcta aatatgctga   5040
aatattcgga ttgacctctg cggaagccag taaggatata cggcaggcat tgaagagttt   5100
cgcggggaag gaagtggttt tttatcgccc tgaagaggat gccggcgatg aaaaaggcta   5160
tgaatctttt ccttggttta tcaaacgtgc gcacagtcca tccagagggc tttacagtgt   5220
acatatcaac ccatatctca ttcccttctt tatcgggtta cagaaccggt ttacgcagtt   5280
tcggcttagt gaaacaaaag aaatcaccaa tccgtatgcc atgcgtttat acgaatccct   5340
gtgtcagtat cgtaagccgg atggctcagg catcgtctct ctgaaaatcg actggatcat   5400
agagcgttac cagctgcctc aaagttacca gcgtatgcct gacttccgcc gccgcttcct   5460
gcaggtctgt gttaatgaga tcaacagcag aactccaatg cgcctctcat acattgagaa   5520
aaagaaaggc cgccagacga ctcatatcgt attttccttc cgcgatatca cttccatgac   5580
gacaggatag tctgagggtt atctgtcaca gatttgaggg tggttcgtca catttgttct   5640
gacctactga gggtaatttg tcacagtttt gctgtttcct tcagcctgca tggattttct   5700
catacttttt gaactgtaat ttttaaggaa gccaaatttg agggcagttt gtcacagttg   5760
atttccttct ctttcccttc gtcatgtgac ctgatatcgg gggttagttc gtcatcattg   5820
atgagggttg attatcacag tttattactc tgaattggct atccgcgtgt gtacctctac   5880
ctggagtttt tcccacggtg gatatttctt cttgcgctga gcgtaagagc tatctgacag   5940
aacagttctt ctttgcttcc tcgccagttc gctcgctatg ctcggttaca cggctgcggc   6000
gagcgctagt gataataagt gactgaggta tgtgctcttc ttatctcctt ttgtagtgtt   6060
gctcttattt taaacaactt tgcggttttt tgatgacttt gcgatttgt tgttgctttg    6120 cagtaaattg caagatttaa taaaaaaacg caaagcaatg attaaggat gttcagaatg    6180 aaactcatgg aaacacttaa ccagtgcata acgctggtc atgaaatgac gaaggctatc    6240
```

```
gccattgcac agtttaatga tgacagcccg gaagcgagga aaataacccg gcgctggaga       6300
ataggtgaag cagcggattt agttggggtt tcttctcagg ctatcagaga tgccgagaaa       6360
gcagggcgac taccgcaccc ggatatggaa attcgaggac gggttgagca acgtgttggt       6420
tatacaattg aacaaattaa tcatatgcgt gatgtgtttg gtacgcgatt gcgacgtgct       6480
gaagacgtat ttccaccggt gatcggggtt gctgcccata aaggtggcgt ttacaaaacc       6540
tcagtttctg ttcatcttgc tcaggatctg gctctgaagg ggctacgtgt tttgctcgtg       6600
gaaggtaacg accccaggg aacagcctca atgtatcacg gatgggtacc agatcttcat       6660
attcatgcag aagacactct cctgcctttc tatcttgggg aaaaggacga tgtcacttat       6720
gcaataaagc ccacttgctg gccggggctt gacattattc cttcctgtct ggctctgcac       6780
cgtattgaaa ctgagttaat gggcaaattt gatgaaggta aactgcccac cgatccacac       6840
ctgatgctcc gactggccat tgaaactgtt gctcatgact atgatgtcat agttattgac       6900
agcgcgccta acctgggtat cggcacgatt aatgtcgtat gtgctgctga tgtgctgatt       6960
gttcccacgc ctgctgagtt gtttgactac acctccgcac tgcagttttt cgatatgctt       7020
cgtgatctgc tcaagaacgt tgatcttaaa gggttcgagc ctgatgtacg tattttgctt       7080
accaaataca gcaatagtaa tggctctcag tccccgtgga tggaggagca aattcgggat       7140
gcctggggaa gcatggttct aaaaaatgtt gtacgtgaaa cggatgaagt tggtaaaggt       7200
cagatccgga tgagaactgt ttttgaacag gccattgatc aacgctcttc aactggtgcc       7260
tggagaaatg ctctttctat ttgggaacct gtctgcaatg aaattttcga tcgtctgatt       7320
aaaccacgct gggagattag ataatgaagc gtgcgcctgt tattccaaaa catacgctca       7380
atactcaacc ggttgaagat acttcgttat cgacaccagc tgccccgatg gtggattcgt       7440
taattgcgcg cgtaggagta atggctcgcg gtaatgccat tactttgcct gtatgtggtc       7500
gggatgtgaa gtttactctt gaagtgctcc ggggtgatag tgttgagaag acctctcggg       7560
tatggtcagg taatgaacgt gaccaggagc tgcttactga ggacgcactg gatgatctca       7620
tcccttcttt tctactgact ggtcaacaga caccggcgtt cggtcgaaga gtatctggtg       7680
tcatagaaat tgccgatggg agtcgccgtc gtaaagctgc tgcacttacc gaaagtgatt       7740
atcgtgttct ggttggcgag ctggatgatg agcagatggc tgcattatcc agattgggta       7800
acgattatcg cccaacaagt gcttatgaac gtggtcagcg ttatgcaagc cgattgcaga       7860
atgaatttgc tggaaatatt tctgcgctgg ctgatgcgga aaatatttca cgtaagatta       7920
ttacccgctg tatcaacacc gccaaattgc ctaaatcagt tgttgctctt ttttctcacc       7980
ccggtgaact atctgcccgg tcaggtgatg cacttcaaaa agcctttaca gataaagagg       8040
aattacttaa gcagcaggca tctaaccttc atgagcagaa aaaagctggg gtgatatttg       8100
aagctgaaga agttatcact cttttaactt ctgtgcttaa aacgtcatct gcatcaagaa       8160
ctagtttaag ctcacgacat cagtttgctc ctggagcgac agtattgtat aagggcgata       8220
aaatggtgct taacctggac aggtctcgtg ttccaactga gtgtatagag aaaattgagg       8280
ccattcttaa ggaacttgaa aagccagcac cctgatgcga ccacgtttta gtctacgttt       8340
atctgtcttt acttaatgtc ctttgttaca ggccagaaag cataactggc tgaatattc       8400 tctctgggcc cactgttcca cttgtatcgt cggtctgata atcagactgg gaccacggtc       8460
ccactcgtat cgtcggtctg attattagtc tgggaccacg gtcccactcg tatcgtcggt       8520
ctgattatta gtctgggacc acggtcccac tcgtatcgtc ggtctgataa tcagactggg       8580
accacggtcc cactcgtatc gtcggtctga ttattagtct gggaccatgg tcccactcgt       8640
```

```
atcgtcggtc tgattattag tctgggacca cggtcccact cgtatcgtcg gtctgattat   8700
tagtctggaa ccacggtccc actcgtatcg tcggtctgat tattagtctg ggaccacggt   8760
cccactcgta tcgtcggtct gattattagt ctgggaccac gatcccactc gtgttgtcgg   8820
tctgattatc ggtctgggac cacggtccca cttgtattgt cgatcagact atcagcgtga   8880
gactacgatt ccatcaatgc ctgtcaaggg caagtattga catgtcgtcg taacctgtag   8940
aacggagtaa cctcggtgtg cggttgtatg cctgctgtgg attgctgctg tgtcctgctt   9000
atccacaaca ttttgcgcac ggttatgtgg acaaaatacc tggttaccca ggccgtgccg   9060
gcacgttaac cgggctgcat ccgatgcaag tgtgtcgctg tcgacgagct cgcgagctcg   9120
gacatgaggt tgccccgtat tcagtgtcgc tgatttgtat tgtctgaagt tgttttacg    9180
ttaagttgat gcagatcaat taatacgata cctgcgtcat aattgattat ttgacgtggt   9240
ttgatggcct ccacgcacgt tgtgatatgt agatgataat cattatcact ttacgggtcc   9300
tttccggtga tccgacaggt tacggggcgg cgacctcgcg ggttttcgct atttatgaaa   9360
attttccggt ttaaggcgtt tccgttcttc ttcgtcataa cttaatgttt ttatttaaaa   9420
taccctctga aaagaaagga aacgacaggt gctgaaagcg agcttttttgg cctctgtcgt  9480
ttcctttctc tgttttttgtc cgtggaatga acaatggaag tccgagctca tcgctaataa   9540
cttcgtatag catacattat acgaagttat attcgatgcg gccgcaaggg gttcgcgtca   9600
gcgggtgttg gcgggtgtcg gggctggctt aactatgcgg catcagagca gattgtactg   9660
agagtgcacc atatgcggtg tgaaataccg cacagatgcg taaggagaaa ataccgcatc   9720
aggcgccatt cgccattcag gctgcgcaac tgttgggaag ggcgatcggt gcgggcctct   9780
tcgctattac gccagctggc gaaagggggga tgtgctgcaa ggcgattaag ttgggtaacg   9840
ccagggtttt cccagtcacg acgttgtaaa acgacggcca gtgaattgta atacgactca   9900
ctatagggcg aattcgagct cggtacccgg ggatcctcgt ttaaaccatc atcaataata   9960
taccttattt tggattgaag ccaatatgat aatgagatgg gcggcgcggg gcggggcgcg  10020
gggcgggagg cgggtttggg ggcgggccgg cgggcggggc ggtgtggcgg aagtggactt  10080
tgtaagtgtg gcggatgtga cttgctagtg ccgggcgcgg taaaagtgac gttttccgtg  10140
cgcgacaacg cccccgggaa gtgacatttt tcccgcggtt tttaccggat gttgtagtga  10200
atttgggcgt aaccaagtaa gatttggcca ttttcgcggg aaaactgaaa cggggaagtg  10260
aaatctgatt aattttgcgt tagtcatacc gcgtaatatt tgtctagggc cgagggactt  10320
tggccgatta cgtggaggac tcgcccaggt gttttttgag gtgaatttcc gcgttccggg  10380
tcaaagtctg cgttttatta ttataggata tcccattgca tacgttgtat ccatatcata  10440
atatgtacat ttatattggc tcatgtccaa cattaccgcc atgttgacat tgattattga  10500
ctagttatta atagtaatca attacgggt cattagttca tagcccatat atggagttcc    10560
gcgttacata acttacggta aatggcccgc ctggctgacc gcccaacgac ccccgcccat  10620
tgacgtcaat aatgacgtat gttcccatag taacgccaat agggactttc cattgacgtc  10680
aatgggtgga gtatttacgg taaactgccc acttggcagt acatcaagtg tatcatatgc  10740
caagtacgcc ccctattgac gtcaatgacg gtaaatggcc cgcctggcat tatgcccagt  10800
acatgacctt atgggacttt cctacttggc agtacatcta cgtattagtc atcgctatta  10860
ccatggtgat gcggttttgg cagtacatca atgggcgtgg atagcggttt gactcacggg  10920
gatttccaag tctccacccc attgacgtca atgggagttt gttttggcac caaaatcaac  10980
```

```
gggactttcc aaaatgtcgt aacaactccg ccccattgac gcaaatgggc ggtaggcgtg    11040
tacggtggga ggtctatata agcagagctc tccctatcag tgatagagat ctccctatca    11100
gtgatagaga tcgtcgacga gctcgtttag tgaaccgtca gatcgcctgg agacgccatc    11160
cacgctgttt tgacctccat agaagacacc gggaccgatc cagcctccgc ggccgggaac    11220
ggtgcattgg aacgcggatt ccccgtgcca agagtgagat cttccgttta tctaggtacc    11280
gggccccccc tcgaggtcga cggtatcgat aagcttcacg ctgccgcaag cactcagggc    11340
gcaagggctg ctaaaggaag cggaacacgt agaaagccag tccgcagaaa cggtgctgac    11400
cccggatgaa tgtcagctac tgggctatct ggacaaggga aaacgcaagc gcaaagagaa    11460
agcaggtagc ttgcagtggg cttacatggc gatagctaga ctgggcggtt ttatggacag    11520
caagcgaacc ggaattgcca gctggggcgc cctctggtaa ggttgggaag ccctgcaaag    11580
taaactggat ggctttcttg ccgccaagga tctgatggcg caggggatca agatctaacc    11640
aggagctatt taatggcaac agttaaccag ctggtacgca aaccacgtgc tcgcaaagtt    11700
gcgaaaagca acgtgcctgc gctggaagca tgcccgcaaa aacgtggcgt atgtactcgt    11760
gtatatacta ccactcctaa aaaccgaac tccgcgctgc gtaaagtatg ccgtgttcgt    11820
ctgactaacg gtttcgaagt gacttcctac atcggtggtg aaggtcacaa cctgcaggag    11880
cactccgtga tcctgatccg tggcggtcgt gttaaagacc tcccgggtgt tcgttaccac    11940
accgtacgtg gtgcgcttga ctgctccggc gttaaagacc gtaagcaggc tcgttccaag    12000
tatggcgtga agcgtcctaa ggcttaatgg tagatctgat caagagacag gatgacggtc    12060
gtttcgcatg cttgaacaag atggattgca cgcaggttct ccggccgctt gggtggagag    12120
gctattcggc tatgactggg cacaacagac aatcggctgc tctgatgccg ccgtgttccg    12180
gctgtcagcg caggggcgcc cggttctttt tgtcaagacc gacctgtccg gtgccctgaa    12240
tgaactgcag gacgaggcag cgcggctatc gtggctggcc acgacgggcg ttccttgcgc    12300
agctgtgctc gacgttgtca ctgaagcggg aagggactgg ctgctattgg gcgaagtgcc    12360
ggggcaggat ctcctgtcat ctcaccttgc tcctgccgag aaagtatcca tcatggctga    12420
tgcaatgcgg cggctgcata cgcttgatcc ggctacctgc ccattcgacc accaagcgaa    12480
acatcgcatc gagcgagcac gtactcggat ggaagccggt cttgtcgatc aggatgatct    12540
ggacgaagag catcagggc tcgcgccagc cgaactgttc gccaggctca aggcgcgcat    12600
gcccgacggc gaggatctcg tcgtgaccca tggcgatgcc tgcttgccga atatcatggt    12660
ggaaaatggc cgcttttctg gattcatcga ctgtggccgg ctgggtgtgg cggaccgcta    12720
tcaggacata gcgttggcta cccgtgatat tgctgaagag cttggcggcg aatgggctga    12780
ccgcttcctc gtgctttacg gtatcgccgc tcccgattcg cagcgcatcg ccttctatcg    12840
ccttcttgac gagttcttct gagcgggact ctggggttcg aaatgaccga ccaagcgacg    12900
cccaacctgc catcacgaga tttcgattcc accgccgcct tctatgaaag gttgggcttc    12960
ggaatcgttt tccgggacgc cggctggatg atcctccagc gcgggatct catgctggag    13020 ttcttcgccc accccgggct cgatcccctc gggggaatc agaattcagt cgacagcggc    13080
cgcgatctgc tgtgccttct agttgccagc catctgttgt ttgcccctcc ccgtgcctt    13140 ccttgaccct ggaaggtgcc actcccactg tcctttccta ataaaatgag gaaattgcat    13200
cgcattgtct gagtaggtgt cattctattc tggggggtgg ggtggggcag gacagcaagg    13260
gggaggattg ggaagacaat agcaggcatg ctggggatgc ggtgggctct atggccgatc    13320
agcgatcgct gaggtgggtg agtgggcgtg gcctggggtg gtcatgaaaa tatataagtt    13380
```

```
ggggtctta gggtctcttt atttgtgttg cagagaccgc cggagccatg agcgggagca    13440
gcagcagcag cagtagcagc agcgccttgg atggcagcat cgtgagccct tatttgacga    13500
cgcggatgcc ccactgggcc ggggtgcgtc agaatgtgat gggctccagc atcgacggcc    13560
gacccgtcct gcccgcaaat tccgccacgc tgacctatgc gaccgtcgcg gggacgccgt    13620
tggacgccac cgccgccgcc gccgccaccg cagccgcctc ggccgtgcgc agcctggcca    13680
cggactttgc attcctggga ccactggcga caggggctac ttctcgggcc gctgctgccg    13740
ccgttcgcga tgacaagctg accgccctgc tggcgcagtt ggatgcgctt actcgggaac    13800
tgggtgacct ttctcagcag gtcatggccc tgcgccagca ggtctcctcc ctgcaagctg    13860
gcgggaatgc ttctcccaca aatgccgttt aagggcgcgc ctagggataa cagggtaata    13920
cccctatttg tttattttc taaatacatt caaatatgta tccgctcatg agacaataac    13980
cctgataaat gcttcaataa tattgaaaaa ggaagagtat gagtattcaa catttccgtg    14040
tcgcccttat tccctttttt gcggcatttt gccttcctgt ttttgctcac ccagaaacgc    14100
tggtgaaagt aaaagatgct gaagatcagt tgggtgcacg agtgggttac atcgaactgg    14160
atctcaacag cggtaagatc cttgagagtt ttcgccccga agaacgtttt ccaatgatga    14220
gcacttttaa agttctgcta tgtggcgcgg tattatcccg tattgacgcc gggcaagagc    14280
aactcggtcg ccgcatacac tattctcaga atgacttggt tgagtactca ccagtcacag    14340
aaaagcatct tacggatggc atgacagtaa gagaattatg cagtgctgcc ataaccatga    14400
gtgataacac tgcggccaac ttacttctga caacgatcgg aggaccgaag gagctaaccg    14460
cttttttgca caacatgggg gatcatgtaa ctcgccttga tcgttgggaa ccggagctga    14520
atgaagccat accaaacgac gagcgtgaca ccacgatgcc tgtagcaatg gcaacaacgt    14580
tgcgcaaact attaactggc gaactactta ctctagcttc ccggcaacaa ttaatagact    14640
ggatggaggc ggataaagtt gcaggaccac ttctgcgctc ggcccttccg gctggctggt    14700
ttattgctga taaatctgga gccggtgagc gtgggtctcg cggtatcatt gcagcactgg    14760
ggccagatgg taagccctcc cgtatcgtag ttatctacac gacggggagt caggcaacta    14820
tggatgaacg aaatagacag atcgctgaga taggtgcctc actgattaag cattggtaac    14880
tgtcagacca gtttactca tatatacttt agattgattt aaaatacgta tatgtatt      14940
agtcatcgct attaccatgg ttaatgcgcc gctacagggc gcgtccattc gccattcagg    15000
ctgcgcaact gttgggaagg gcgatcggtg cgggcctctt cgctattacg ccagctggcg    15060
aaagggggat gtgctgcaag gcgattaagt tgggtaacgc cagggttttc ccagtcacga    15120
cgttgtaaaa cgacggccag tgaattgtaa tacgactcac tatagggcga attgggccct    15180
ctagatgcat gctcgagcgg ccgccagtgt gatggatatc tgcagaattc agcacactg    15240
gcggccgtta ctagtggatc cgagctcggt accaagcttg gcgtaatcat ggtcatagct    15300
gtttcctgtg tgaaattgtt atccgctcac aattccacac aacatacgag ccggaagcat    15360
aaagtgtaaa gcctggggtg cctaatgagt gagctaactc acattaattg cgttgcgctc    15420
ac                                                                   15422
```

```
<210> SEQ ID NO 15
<211> LENGTH: 39535
<212> TYPE: DNA
<213> ORGANISM: Pan troglodytes
<220> FEATURE:
<221> NAME/KEY: misc_feature
<222> LOCATION: (24391)..(24393)
```

<223> OTHER INFORMATION: n is a, c, g, or t

<400> SEQUENCE: 15

```
catcatcaat aatatacctt attttggatt gaagccaata tgataatgag atgggcggcg      60
cggggcgggg cgcggggcgg gaggcgggtt tggggcggg ccggcgggcg gggcggtgtg     120
gcggaagtgg actttgtaag tgtggcggat gtgacttgct agtgccgggc gcggtaaaag     180
tgacgttttc cgtgcgcgac aacgcccccg ggaagtgaca ttttttcccgc ggttttttacc   240
ggatgttgta gtgaatttgg gcgtaaccaa gtaagatttg gccattttcg cgggaaaact    300
gaaacgggga agtgaaatct gattaatttt gcgttagtca taccgcgtaa tatttgtcta    360
gggccgaggg actttggccg attacgtgga ggactcgccc aggtgttttt tgaggtgaat    420
ttccgcgttc cgggtcaaag tctgcgtttt attattatag gatatcccat tgcatacgtt    480
gtatccatat cataatatgt acatttatat tggctcatgt ccaacattac cgccatgttg    540
acattgatta ttgactagtt attaatagta atcaattacg gggtcattag ttcatagccc    600
atatatggag ttccgcgtta cataacttac ggtaaatggc ccgcctggct gaccgcccaa    660
cgacccccgc ccattgacgt caataatgac gtatgttccc atagtaacgc caatagggac    720
tttccattga cgtcaatggg tggagtattt acggtaaact gcccacttgg cagtacatca    780
agtgtatcat atgccaagta cgccccctat tgacgtcaat gacggtaaat ggcccgcctg    840
gcattatgcc cagtacatga ccttatggga ctttcctact tggcagtaca tctacgtatt    900
agtcatcgct attaccatgg tgatgcggtt ttggcagtac atcaatgggc gtggatagcg    960
gtttgactca cggggatttc caagtctcca ccccattgac gtcaatggga gtttgttttg   1020
gcaccaaaat caacgggact ttccaaaatg tcgtaacaac tccgccccat tgacgcaaat   1080
gggcggtagg cgtgtacggt gggaggtcta tataagcaga gctctcccta tcagtgatag   1140
agatctccct atcagtgata gagatcgtcg acgagctcgt ttagtgaacc gtcagatcgc   1200
ctggagacgc catccacgct gttttgacct ccatagaaga caccgggacc gatccagcct   1260
ccgcggccgg gaacggtgca ttggaacgcg gattccccgt gccaagagtg agatcttccg   1320
tttatctagg taccgggccc cccctcgagg tcgacggtat cgataagctt cacgctgccg   1380
caagcactca gggcgcaagg gctgctaaag gaagcggaac acgtagaaag ccagtccgca   1440
gaaacggtgc tgaccccgga tgaatgtcag ctactgggct atctggacaa gggaaaacgc   1500
aagcgcaaag agaaagcagg tagcttgcag tgggcttaca tggcgatagc tagactgggc   1560
ggttttatgg acagcaagcg aaccggaatt gccagctggg gcgccctctg gtaaggttgg   1620
gaagccctgc aaagtaaact ggatggcttt cttgccgcca aggatctgat ggcgcagggg   1680
atcaagatct aaccaggagc tatttaatgg caacagttaa ccagctggta cgcaaaccac   1740
gtgctcgcaa agttgcgaaa agcaacgtgc ctgcgctgga agcatgcccg caaaaacgtg   1800
gcgtatgtac tcgtgtatat actaccactc ctaaaaaacc gaactccgcg ctgcgtaaag   1860
tatgccgtgt tcgtctgact aacggtttcg aagtgacttc ctacatcggt ggtgaaggtc   1920
acaacctgca ggagcactcc gtgatcctga tccgtggcgg tcgtgttaaa gacctcccgg   1980
gtgttcgtta ccacaccgta cgtggtgcgc ttgactgctc cggcgttaaa gaccgtaagc   2040
aggctcgttc caagtatggc gtgaagcgtc ctaaggctta atggtagatc tgatcaagag   2100
acaggatgac ggtcgtttcg catgcttgaa caagatggat tgcacgcagg ttctccggcc   2160
gcttgggtga gaggctatt cggctatgac tgggcacaac agacaatcgg ctgctctgat   2220
gccgccgtgt tccggctgtc agcgcagggg cgcccggttc ttttttgtcaa gaccgacctg   2280
```

```
tccggtgccc tgaatgaact gcaggacgag gcagcgcggc tatcgtggct ggccacgacg   2340
ggcgttcctt gcgcagctgt gctcgacgtt gtcactgaag cgggaaggga ctggctgcta   2400
ttgggcgaag tgccggggca ggatctcctg tcatctcacc ttgctcctgc cgagaaagta   2460
tccatcatgg ctgatgcaat gcggcggctg catacgcttg atccggctac ctgcccattc   2520
gaccaccaag cgaaacatcg catcgagcga gcacgtactc ggatggaagc cggtcttgtc   2580
gatcaggatg atctggacga agagcatcag gggctcgcgc cagccgaact gttcgccagg   2640
ctcaaggcgc gcatgcccga cggcgaggat ctcgtcgtga cccatggcga tgcctgcttg   2700
ccgaatatca tggtggaaaa tggccgcttt tctggattca tcgactgtgg ccggctgggt   2760
gtggcggacc gctatcagga catagcgttg gctacccgtg atattgctga agagcttggc   2820
ggcgaatggg ctgaccgctt cctcgtgctt tacggtatcg ccgctcccga ttcgcagcgc   2880
atcgccttct atcgccttct tgacgagttc ttctgagcgg gactctgggg ttcgaaatga   2940
ccgaccaagc gacgcccaac ctgccatcac gagatttcga ttccaccgcc gccttctatg   3000
aaaggttggg cttcggaatc gttttccggg acgccggctg atgatcctc cagcgcgggg    3060 atctcatgct ggagttcttc gcccaccccg ggctcgatcc cctcgggggg aatcagaatt   3120
cagtcgacag cggccgcgat ctgctgtgcc ttctagttgc cagccatctg ttgtttgccc   3180
ctcccccgtg ccttccttga ccctggaagg tgccactccc actgtccttt cctaataaaa   3240
tgaggaaatt gcatcgcatt gtctgagtag gtgtcattct attctggggg gtgggtggg    3300 gcaggacagc aaggggagg attgggaaga caatagcagg catgctgggg atgcggtggg    3360
ctctatggcc gatcagcgat cgctgaggtg ggtgagtggg cgtggcctgg ggtggtcatg   3420
aaaatatata agttggggt cttagggtct ctttatttgt gttgcagaga ccgccggagc    3480
catgagcggg agcagcagca gcagcagtag cagcagcgcc ttggatggca gcatcgtgag   3540
cccttatttg acgacgcgga tgccccactg ggccggggtg cgtcagaatg tgatgggctc   3600
cagcatcgac ggccgacccg tcctgcccgc aaattccgcc acgctgacct atgcgaccgt   3660
cgcggggacg ccgttggacg ccaccgccgc cgccgccgcc accgcagccg cctcggccgt   3720
gcgcagcctg gccacggact ttgcattcct gggaccactg gcgacagggg ctacttctcg   3780
ggccgctgct gccgccgttc gcgatgacaa gctgaccgcc ctgctggcgc agttggatgc   3840
gcttactcgg gaactgggtg accttttctca gcaggtcatg gccctgcgcc agcaggtctc   3900
ctccctgcaa gctggcggga atgcttctcc cacaaatgcc gtttaagata aataaaacca   3960
gactctgttt ggattaaaga aaagtagcaa gtgcattgct ctctttattt cataattttc   4020
cgcgcgcgat aggccctaga ccagcgttct cggtcgttga gggtgcggtg tatcttctcc   4080
aggacgtggt agaggtggct ctggacgttg agatacatgg gcatgagccc gtcccggggg   4140
tggaggtagc accactgcag agcttcatgc tccggggtgg tgttgtagat gatccagtcg   4200
tagcaggagc gctgggcatg gtgcctaaaa atgtccttca gcagcaggcc gatggccagg   4260
gggaggccct tggtgtaagt gtttacaaaa cggttaagtt gggaagggtg cattcgggga   4320
gagatgatgt gcatcttgga ctgtattttt agattggcga tgtttccgcc cagatccctt   4380
ctgggattca tgttgtgcag gaccaccagt acagtgtatc cggtgcactt ggggaatttg   4440
tcatgcagct tagagggaaa agcgtggaag aacttggaga cgcccttgtg gcctcccaga   4500
ttttccatgc attcgtccat gatgatgcaa atgggcccgc gggaggcagc ttgggcaaag   4560
atatttctgg ggtcgctgac gtcgtagttg tgttccaggg tgaggtcgtc ataggccatt   4620
```

```
tttacaaagc gcgggcggag ggtgcccgac tgggggatga tggtcccctc tggccccggg    4680
gcgtagttgc cctcgcagat ctgcatttcc caggccttaa tctcggaggg gggaatcata    4740
tccacctgcg gggcgatgaa gaaaacggtt ccggagccg  ggagattaa  ctgggatgag    4800
agcaggtttc taagcagctg tgattttcca caaccggtgg gcccataaat aacacctata    4860
accggttgca gctggtagtt tagagagctg cagctgccgt cgtcccggag agggggggcc    4920
acctcgttga gcatgtccct gacgcgcatg ttctccccga ccagatccgc cagaaggcgc    4980
tcgccgccca gggacagcag ctcttgcaag gaagcaaagt ttttcagcgg cttgaggccg    5040
tccgccgtgg gcatgttttt cagggtctgg ctcagcagct ccaggcggtc ccagagctcg    5100
gtgacgtgct ctacggcatc tctatccagc atatctcctc gtttcgcggg ttggggcgac    5160
tttcgctgta gggcaccaag cggtggtcgt ccagcggggc cagagtcatg tccttccatg    5220
ggcgcagggt cctcgtcagg gtggtctggg tcacggtgaa ggggtgcgct ccgggctgag    5280
cgcttgccaa ggtgcgcttg aggctggttc tgctggtgct gaagcgctgc cggtcttcgc    5340
cctgcgcgtc ggccaggtag catttgacca tggtgtcata gtccagcccc tccgcggcgt    5400
gtcccttggc gcgcagcttg cccttggagg tggcgccgca cgaggggcag agcaggctct    5460
tgagcgcgta gagcttgggg gcgaggaaga ccgattcggg ggagtaggcg tccgcgccgc    5520
agacccccgca cacggtctcg cactccacca gccaggtgag ctcggggcgc gccgggtcaa    5580
aaaccaggtt tcccccatgc ttttttgatgc gtttcttacc tcgggtctcc atgaggtggt    5640
gtccccgctc ggtgacgaag aggctgtccg tgtctccgta gaccgacttg aggggtcttt    5700
tctccagggg ggtccctcgg tcttcctcgt agaggaactc ggaccactct gagacgaagg    5760
cccgcgtcca ggccaggacg aaggaggcta tgtgggaggg gtagcggtcg ttgtccacta    5820
gggggtccac cttctccaag gtgtgaagac acatgtcgcc ttcctcggcg tccaggaagg    5880
tgattggctt gtaggtgtag gccacgtgac cgggggttcc tgacgggggg gtataaaagg    5940
gggtgggggc gcgctcgtcg tcactctctt ccgcatcgct gtctgcgagg ccagctgct    6000
ggggtgagta ttccctctcg aaggcgggca tgacctccgc gctgaggttg tcagtttcca    6060
aaaacgagga ggatttgatg ttcacctgtc ccgaggtgat acctttgagg gtacccgcgt    6120
ccatctggtc agaaaacacg atctttttat tgtccagctt ggtggcgaac gacccgtaga    6180
gggcgttgga gagcagcttg gcgatggagc gcagggtctg gttcttgtcc ctgtcggcgc    6240
gctccttggc cgcgatgttg agctgcacgt actcgcgcgc gacgcagcgc cactcgggga    6300
agacggtggt gcgctcgtcg ggcaccaggc gcacgcgcca gccgcggttg tgcagggtga    6360
ccaggtccac gctggtggcg acctcgccgc gcaggcgctc gttggtccag cagagacggc    6420
cgcccttgcg cgagcagaag gggggcaggg ggtcgagctg ggtctcgtcc gggggggtccg    6480
cgtccacggt gaaaaccccg gggcgcaggc gcgcgtcgaa gtagtctatc ttgcaacctt    6540
gcatgtccag cgcctgctgc cagtcgcggg cggcgagcgc gcgctcgtag gggttgagcg    6600
gcgggcccca gggcatgggg tgggtgagtg cggaggcgta catgccgcag atgtcataga    6660
cgtagagggg ctcccgcagg accccgatgt aggtggggta gcagcggccg ccgcggatgc    6720
tggcgcgcac gtagtcatac agctcgtgcg aggggggcgag gaggtcgggg cccaggttgg    6780
tgcgggcggg gcgctccgtg cggaagacga tctgcctgaa gatggcatgc gagttggaag    6840
agatggtggg gcgctggaag acgttgaagc tggcgtcctg caggccgacg cgtcgcgca    6900
cgaaggaggc gtaggagtcg cgcagcttgt gtaccagctc ggcggtgacc tgcacgtcga    6960
gcgcgcagta gtcgagggtc tcgcggatga tgtcatattt agcctgcccc ttcttttttcc    7020
```

| | |
|---|---|
| acagctcgcg gttgaggaca aactcttcgc ggtctttcca gtactcttgg atcgggaaac | 7080 |
| cgtccggttc cgaacggtaa gagcctagca tgtagaactg gttgacggcc tggtaggcgc | 7140 |
| agcagcccct ctccacgggg agggcgtagg cctgcgcggc cttgcggagc gaggtgtggg | 7200 |
| tcagggcgaa ggtgtccctg accatgactt gaggtactg gtgcttgaag tcggagtcgt | 7260 |
| cgcagccgcc ccgctcccag agcgagaagt cggtgcgctt cttggagcgg gggttgggca | 7320 |
| gagcgaaggt gacatcgttg aagaggattt tgcccgcgcg gggcatgaag ttgcgggtga | 7380 |
| tgcggaaggg ccccggcact tcagagcggt tgttgatgac ctgggcggcg agcacgatct | 7440 |
| cgtcgaagcc gttgatgttg tggcccacga tgtagagttc caggaagcgg ggccggccct | 7500 |
| ttacggtggg cagcttcttt agctcttcgt aggtgagctc ctcgggcgag gcgaggccgt | 7560 |
| gctcggccag ggcccagtcc gcgaggtgcg ggttgtctct gaggaaggac tcccagaggt | 7620 |
| cgcgggccag gagggtctgc aggcggtccc tgaaggtcct gaactggcgg cccacggcca | 7680 |
| tttttccggg ggtgatgcag tagaaggtga ggggtcttg ctgccagcgg tcccagtcga | 7740 |
| gctgcagggc gaggtcgcgc cggcggtga ccaggcgctc gtcgcccccg aatttcatga | 7800 |
| ccagcatgaa gggcacgagc tgcttccga aggcccccat ccaagtgtag gtctctacat | 7860 |
| cgtaggtgac aaagaggcgc tccgtgcgag gatgcgagcc gatcgggaag aactggatct | 7920 |
| cccgccacca gttggaggag tggctgttga tgtggtggaa gtagaagtcc cgtcgccggg | 7980 |
| ccgaacactc gtgctggctt ttgtaaaagc gagcgcagta ctggcagcgc tgcacgggct | 8040 |
| gtacctcatg cacgagatgc acctttcgcc cgcgcacgag gaagccgagg ggaaatctga | 8100 |
| gccccccgcc tggctcgcgg catggctggt gctcttctac tttggatgcg tgtccgtctc | 8160 |
| cgtctggctc ctcgaggggt gttacggtgg agcggaccac cacgccgcgc gagccgcagg | 8220 |
| tccagatatc ggcgcgcggc ggtcggagtt tgatgacgac atcgcgcagc tgggagctgt | 8280 |
| ccatggtctg gagctcccgc ggcggcggca ggtcagccgg gagttcttgc aggttcacct | 8340 |
| cgcagagtcg ggccagggcg cggggcaggt ctaggtggta cctgatctct aggggcgtgt | 8400 |
| tggtggcggc gtcgatggct tgcaggagcc cgcagccccg gggggcgacg acggtgcccc | 8460 |
| gcggggtggt ggtggtggtg gcggtgcagc tcagaagcgg tgccgcgggc gggccccgg | 8520 |
| aggtaggggg ggctccggtc ccgcgggcag gggcggcagc ggcacgtcgg cgtggagcgc | 8580 |
| gggcaggagt tggtgctgtg cccggaggtt gctggcgaag gcgacgacgc ggcggttgat | 8640 |
| ctcctggatc tggcgcctct gcgtgaagac gacgggcccg gtgagcttga acctgaaaga | 8700 |
| gagttcgaca gaatcaatct cggtgtcatt gaccgcggcc tggcgcagga tctcctgcac | 8760 |
| gtctcccgag ttgtcttggt aggcgatctc ggccatgaac tgctcgatct cttcctcctg | 8820 |
| gaggtctccg cgtccggcgc gttccacggt ggccgccagg tcgttggaga tgcgcccat | 8880 |
| gagctgcgag aaggcgttga gtccgccctc gttccagact cggctgtaga ccacgccccc | 8940 |
| ctggtcatcg cgggcgcgca tgaccacctg cgcgaggttg agctccacgt gccgcgcgaa | 9000 |
| gacggcgtag ttgcgcagac gctggaagag gtagttgagg gtggtggcgg tgtgctcggc | 9060 |
| cacgaagaag ttcatgaccc agcggcgcaa cgtggattcg ttgatgtccc ccaaggcctc | 9120 |
| cagccgttcc atggcctcgt agaagtccac ggcgaagttg aaaaactggg agttgcgcgc | 9180 |
| cgacacggtc aactcctcct ccagaagacg gatgagctcg gcgacggtgt cgcgcacctc | 9240 |
| gcgctcgaag gctatgggga tctcttcctc cgctagcatc accacctcct cctcttcctc | 9300 |
| ctcttctggc acttccatga tggcttcctc ctcttcgggg ggtggcggcg gcggcggtgg | 9360 |

```
gggaggggc   gctctgcgcc   ggcggcggcg   caccgggagg   cggtccacga   agcgcgcgat      9420
catctccccg   cggcggcggc   gcatggtctc   ggtgacggcg   cggccgttct   cccggggggcg    9480
cagttggaag   acgccgccgg   acatctggtg   ctggggcggg   tggccgtgag   gcagcgagac    9540
ggcgctgacg   atgcatctca   acaattgctg   cgtaggtacg   ccgccgaggg   acctgaggga    9600
gtccatatcc   accggatccg   aaaacctttc   gaggaaggcg   tctaaccagt   cgcagtcgca    9660
aggtaggctg   agcaccgtgg   cgggcggcgg   ggggtggggg   gagtgtctgg   cggaggtgct    9720
gctgatgatg   taattgaagt   aggcggactt   gacacggcgg   atggtcgaca   ggagcaccat    9780
gtccttgggt   ccggcctgct   ggatgcggag   gcggtcggct   atgccccagg   cttcgttctg    9840
gcatcggcgc   aggtccttgt   agtagtcttg   catgagcctt   tccaccggca   cctcttctcc    9900
ttcctcttct   gcttcttcca   tgtctgcttc   ggccctgggg   cggcgccgcg   ccccctgcc    9960
ccccatgcgc   gtgaccccga   accccctgag   cggttggagc   agggccaggt   cggcgacgac    10020
gcgctcggcc   aggatggcct   gctgcacctg   cgtgagggtg   gtttggaagt   catccaagtc    10080
cacgaagcgg   tggtaggcgc   ccgtgttgat   ggtgtaggtg   cagttggcca   tgacggacca    10140
gttgacggtc   tggtggcccg   gttgcgacat   ctcggtgtac   ctgagtcgcg   agtaggcgcg    10200
ggagtcgaag   acgtagtcgt   tgcaagtccg   caccaggtac   tggtagccca   ccaggaagtg    10260
cggcggcggc   tggcggtaga   ggggccagcg   cagggtggcg   ggggctccgg   gggccaggtc    10320
ttccagcatg   aggcggtggt   aggcgtagat   gtacctggac   atccaggtga   tacccgcggc    10380
ggtggtggag   gcgcgcggga   agtcgcgcac   ccggttccag   atgttgcgca   ggggcagaaa    10440
gtgctccatg   gtaggcgtgc   tctgtccagt   cagacgcgcg   cagtcgttga   tactctagac    10500
cagggaaaac   gaaagccggt   cagcgggcac   tcttccgtgg   tctggtgaat   agatcgcaag    10560
ggtatcatgg   cggagggcct   cggttcgagc   ccgggtccg    ggccgacgg    tccgccatga    10620
tccacgcggt   taccgcccgc   gtgtcgaacc   caggtgtgcg   acgtcagaca   acggtggagt    10680
gttcctttg    gcgttttcct   ggccgggcgc   cggcgccgcg   taagagacta   agccgcgaaa    10740
gcgaaagcag   taagtggctc   gctccccgta   gccggaggga   tccttgctaa   gggttgcgtt    10800
gcggcgaacc   ccggttcgaa   tcccgtactc   gggccggccg   gacccgcggc   taaggtgttg    10860
gattggcctc   cccctcgtat   aaagaccccg   cttgcggatt   gactccggac   acggggacga    10920
gccccttta    tttttgcttt   ccccagatgc   atccggtgtt   gcgacagatg   cgccccccgc    10980
cccagcagca   gcaacaacac   cagcaagagc   ggcagcaaca   gcagcgggag   tcatgcaggg    11040
cccctcacc    caccctcggc   ggcccggcca   cctcggcgtc   cgcggccgtg   tctggcgcct    11100
gcggcggcgg   cggcgggggg   ccggctgacg   acccgagga   gccccgcgg    cgcagggcca    11160
gacactacct   ggacctggag   gagggcgagg   gcctggcgcg   gctggggcg    ccgtctcccg    11220
agcgccaccc   gcgggtgcag   ctaaagcgcg   actcgcgcga   ggcgtacgtg   cctcggcaga    11280
acctgttcag   ggaccgcgcg   ggcgaggagc   ccgaggagat   gcgggacagg   aggttcagcg    11340
cggggcggga   gctgcggcag   gggctgaacc   gcgagcggct   gctgcgcgag   gaggactttg    11400
agcccgacgc   gcggacgggg   atcagccccg   cgcgcgcgca   cgtggcggcc   gccgacctgg    11460
tgacggcgta   cgagcagacg   gtgaaccagg   agatcaactt   ccaaaagagt   ttcaacaacc    11520
acgtgcgcac   gctggtggcg   cgcgaggagg   tgaccatcgg   gctgatgcac   ctgtgggact    11580
ttgtgagcgc   gctggtgcag   aaccccaata   gcaagcctct   gacggcgcag   ctgttcctga    11640
tagtgcagca   cagcagggac   aacgaggcgt   ttagggacgc   gctgctgaac   atcaccgagc    11700
ccgagggccg   gtggctgctg   gacctgatta   acatcctgca   gagcatagtg   gtgcaggagc    11760
```

```
gcagcctgag cctggccgac aaggtggcgg ccatcaacta ctcgatgctg agcctgggca    11820
agttttacgc gcgcaagatc taccagacgc cgtacgtgcc catagacaag gaggtgaaga    11880
tcgacggttt ttacatgcgc atggcgctga aggtgctcac cctaagcgac gacctgggcg    11940
tgtaccgcaa cgagcgcatc cacaaggccg tgagcgtgag ccggcggcgc gagctgagcg    12000
accgcgagct gatgcatagc ctgcagcggg cgctggcggg cgccggcagc ggcgacaggg    12060
aggcggagtc ctacttcgat gcggggcgg acctgcgctg ggcgcccagc cggcgggccc    12120
tggaggccgc gggggtccgc gaggactatg acgaggacgg cgaggaggat gaggagtacg    12180
agctagagga gggcgagtac ctggactaaa ccgcgggtgg tgtttccggt agatgcaaga    12240
cccgaacgtg gtggacccgg cgctgcgggc ggctctgcag agccagccgt ccggccttaa    12300
ctcctcagac gactggcgac aggtcatgga ccgcatcatg tcgctgacgg cgcgtaaccc    12360
ggacgcgttc cggcagcagc cgcaggccaa caggctctcc gccatcctgg aggcggtggt    12420
gcctgcgcgc tcgaacccca cgcacgagaa ggtgctggcc atagtgaacg cgctggccga    12480
gaacagggcc atccgcccgg acgaggccgg gctggtgtac gacgcgctgc tgcagcgcgt    12540
ggcccgctac aacagcggca acgtgcagac caacctggac cggctggtgg gggacgtgcg    12600
cgaggcggtg gcgcagcgcg agcgcgcgga tcggcagggc aacctgggct ccatggtggc    12660
gctgaatgcc ttcctgagca cgcagccggc caacgtgccg cggggcagg aagactacac    12720 caactttgtg agcgcgctgc ggctgatggt gaccgagacc ccccagagcg aggtgtacca    12780
gtcgggtccg gactacttct tccagaccag cagacagggc ctgcagacgg tgaacctgag    12840
ccaggctttc aagaacctgc ggggctgtg gggcgtgaag gcgcccaccg cgaccgggc    12900 gacggtgtcc agcctgctga cgcccaactc gcgcctgctg ctgctgctga tcgcgccgtt    12960
cacggacagc ggcagcgtgt cccgggacac ctacctgggg cacctgctga ccctgtaccg    13020
cgaggccatc gggcaggcgc aggtggacga gcacaccttc caggagatca ccagcgttag    13080
ccgcgcgctg gggcaggagg acacgagcag cctggaggcg actctgaact acctgctgac    13140
caaccggcgg cagaagattc cctcgctgca cagcctgacc tccgaggagg agcgcatctt    13200
gcgctacgtg cagcagagcg tgagcctgaa cctgatgcgc gacggggtga cgcccagtgt    13260
ggcgctggac atgaccgcgc gcaacatgga accgggcatg tacgccgcgc accggcctta    13320
catcaaccgc ctgatggact acctgcatcg cgcggcggcc gtgaacccg agtactttac    13380 caacgccatc ctgaacccgc actggctccc gccgccgggg ttctacagcg ggggcttcga    13440
ggtcccggag gccaacgatg gcttcctgtg ggacgacatg gacgacagcg tgttctcccc    13500
gcggccgcag gcgctggcgg aagcgtccct gctgcgtccc aagaaggagg aggaggcgag    13560
tcgccgccgc ggcagcagcg gcgtggcttc tctgtccgag ctgggggcgg cagccgcgc    13620 gcgccccggg tccctgggcg gcagcccctt tccgagcctg gtggggtctc tgcacagcga    13680
gcgcaccacc cgcccctcgg ctgctgggcga ggacgagtac ctgaataact ccctgctgca    13740
gccggtgcgg gagaaaaacc tgcctcccgc cttccccaac aacgggatag agagcctggt    13800
ggacaagatg agcagatgga agacctatgc gcaggagcac agggacgcgc ccgcgctccg    13860
gccgcccacg cggcgccagc gccacgaccg gcagcggggg ctggtgtggg atgacgagga    13920
ctccgcggac gatagcagcg tgctggacct gggagggagc ggcaacccgt tcgcgcacct    13980
gcgcccccgc ctggggagga tgttttaaaa aaaaaaaaaa gcaagaagca tgatgcaaaa    14040
attaaataaa actcaccaag gccatggcga ccgagcgttg gtttcttgtg ttcccttcag    14100
```

```
tatgcggcgc gcggcgatgt accaggaggg acctcctccc tcttacgaga gcgtggtggg   14160
cgcggcggcg gcgcgcccct cttctccctt tgcgtcgcag ctgctggagc cgccgtacgt   14220
gcctccgcgc tacctgcggc ctacgggggg gagaaacagc atccgttact cggagctggc   14280
gcccctgttc gacaccaccc gggtgtacct ggtggacaac aagtcggcgg acgtggcctc   14340
cctgaactac cagaacgacc acagcaattt tttgaccacg gtcatccaga acaatgacta   14400
cagcccgagc gaggccagca cccagaccat caatctggat gaccggtcgc actgggcgg   14460 cgacctgaaa accatcctgc acaccaacat gcccaacgtg aacgagttca tgttcaccaa   14520
taagttcaag gcgcgggtga tggtgtcgcg ctcgcacacc aaggaagacc gggtggagct   14580
gaagtacgag tgggtggagt tcgagctgcc agagggcaac tactccgaga ccatgaccat   14640
tgacctgatg aacaacgcga tcgtggagca ctatctgaaa gtgggcaggc agaacggggt   14700
cctggagagc gacatcgggg tcaagttcga caccaggaac ttccgcctgg ggctggaccc   14760
cgtgaccggg ctggttatgc ccggggtgta caccaacgag gccttccatc ccgacatcat   14820
cctgctgccc ggctgcgggg tggacttcac ttacagccgc ctgagcaacc tcctgggcat   14880
ccgcaagcgg cagcccttcc aggagggctt caggatcacc tacgaggacc tggaggggg   14940 caacatcccc gcgctcctcg atgtggaggc ctaccaggat agcttgaagg aaaatgaggc   15000
gggacaggag gataccgccc ccgccgcctc cgccgccgcc gagcagggcg aggatgctgc   15060
tgacaccgcg gccgcggacg gggcggaggc cgaccccgct atggtggtgg aggctgccga   15120
gcaggaggag gacatgaatg acagtgcggt gcgcggagac accttcgtca cccgggggga   15180
ggaaaagcaa gcgggggccg aggccgcggc cgaggaaaag caactggcgg cagcagcggc   15240
ggcggcggcg ttggccgcgg cggaggctga gtctgagggg accaagcccg ccaaggagcc   15300
cgtgattaag cccctgaccg aagatagcaa gaagcgcagt tacaacctgc tcaaggacag   15360
caccaacacc gcgtaccgca gctggtacct ggcctacaac tacggcgacc cgtcgacggg   15420
ggtgcgctcc tggaccctgc tgtgcacgcc ggacgtgacc tgcggctcgg agcaggtgta   15480
ctggtcgctg cccgacatga tgcaagaccc cgtgaccttc cgctccacgc ggcaggtcag   15540
caacttcccg gtggtgggcg ccgagctgct gcccgtgcac tccaagagct tctacaacga   15600
ccaggccgtc tactcccagc tcatccgcca gttcacctct ctgacccacg tgttcaatcg   15660 cttttcctgag aaccagattc tggcgcgccc gcccgcccc accatcacca ccgtcagtga   15720
aaacgttcct gctctcacag atcacgggac gctaccgctg cgcaacagca tcggaggagt   15780
ccagcgagtg accgttactg acgccagacg ccgcacctgc ccctacgttt acaaggcctt   15840
gggcatagtc tcgccgcgcg tcctttccag ccgcactttt tgagcaacac caccatcatg   15900
tccatcctga tctcacccag caataactcc ggctggggac tgctgcgcgc gcccagcaag   15960
atgttcggag gggcgaggaa gcgttccgag cagcaccccg tgcgcgtgcg cgggcacttc   16020 cgcgcccct ggggagcgca caaacgcggc cgcgcggggc gcaccaccgt ggacgacgcc   16080
atcgactcgg tggtggagca ggcgcgcaac tacaggcccg cggtctctac cgtggacgcg   16140
gccatccaga ccgtggtgcg gggcgcgcgg cggtacgcca agctgaagag ccgccggaag   16200
cgcgtggccc gccgccaccg ccgccgaccc ggggccgccc caaacgcgc cgccgcggcc   16260 ctgcttcgcc gggccaagcg cacgggccgc cgccgccgca tgagggccgc gcgccgcttg   16320
gccgccggca tcaccgccgc caccatggcc cccgtaccc gaagacgcgc ggccgccgcc   16380 gccgccgcc ccatcagtga catggccagc aggcgccggg gcaacgtgta ctgggtgcgc   16440
gactcggtga ccggcacgcg cgtgcccgtg cgcttccgcc ccccgcggac ttgagatgat   16500
```

```
gtgaaaaaac aacactgagt ctcctgctgt tgtgtgtatc ccagcggcgg cggcggcgcg   16560
cgcagcgtca tgtccaagcg caaaatcaaa gaagagatgc tccaggtcgt cgcgccggag   16620
atctatgggc ccccgaagaa ggaagagcag gattcgaagc cccgcaagat aaagcgggtc   16680
aaaaagaaaa agaaagatga tggcgatgcc gatggggagg tggagttcct gcgcgccacg   16740
gcgcccaggc gcccggtgca gtggaagggc cggcgcgtaa agcgcgtcct gcgccccggc   16800
accgcggtgg tcttcacgcc cggcgagcgc tccacccgga cttttcaagcg cgtctatgac   16860 gaggtgtacg gcgacgaaga cctgctggag caggccaacg agcgcttcgg agagtttgct   16920
tacgggaagc gtcagcggcc gctggggaag gaggacctgc tggcgctgcc gctggaccag   16980 ggcaaccccca cccccagtct gaagcccgtg accctgcagc aggtgctgcc gagcagcgca   17040
ccctccgagg cgaagcgggg tctgaagcgc gagggcggcg acctggcgcc caccgtgcag   17100
ctcatggtgc ccaagcggca gaggctggag gatgtgctgg agaaaatgaa agtagacccc   17160
ggtctgcagc cggacatcag ggtccgtccc atcaagcagg tggcgccggg cctcggcgtg   17220
cagaccgtgg acgtggtcat ccccaccggc aactccccccg ccgccaccac cactaccgct   17280
gcctccacgg acatggagac acagaccgat cccgccgcag ccgccgccac cgccgccgcc   17340
gcgacctcct cggcggaggt gcagacggac ccctggctgc cgccggcgat gtcagctccc   17400
cgcgcgcgtc gcgggcgcag gaagtacggc gccgccaacg cgctcctgcc cgagtacgcc   17460
ttgcatcctt ccatcgcgcc cacccccggc taccgaggct atacctaccg cccgcgaaga   17520
gccaagggtt ccaccccgcc tccccgccga cgcgccgccg ccaccacccg ccgccgccgc   17580
cgcagacgcc agcccgcact ggctccagtc tccgtgagga gagtggcgcg cgacggacac   17640
accctggtgc tgcccagggc gcgctaccac cccagcatcg tttaaaagcc tgttgtggtt   17700
cttgcagata tggccctcac ttgccgcctc cgtttcccgg tgccgggata ccgaggagga   17760
agatcgcgcc gcaggagggg tctggccggc cgcggcctga gcggaggcag ccgccgcgcg   17820
caccggcggc gacgcgccac cagccgacgc atgcgcggcg gggtgctgcc cctgttaatc   17880
cccctgatcg ccgcggcgat cggcgccgtg cccgggatcg cctccgtggc cttgcaggcg   17940
tcccagaggc attgacagac ttgcaaactt gcaaatatgg aaaaaaaccc caataaaaaa   18000
gtctagactc tcacgctcgc ttggtcctgt gactattttg tagaatggaa gacatcaact   18060
ttgcgtcgct ggccccgcgt cacggctcgc gcccgttcct gggacactgg aacgatatcg   18120
gcaccagcaa catgagcggt ggcgccttca gttgggctc tctgtggagc ggcattaaaa   18180
gtatcgggtc tgccgttaaa aattacggct cccgggcctg gaacagcagc acgggccaga   18240
tgttgagaga caagttgaaa gagcagaact tccagcagaa ggtggtggag ggcctggcct   18300
ccggcatcaa cggggtggtg gacctggcca accaggccgt gcagaataag atcaacagca   18360
gactggaccc ccggccgccg gtggaggagg tgccgccggc gctggagacg gtgtcccccg   18420
atgggcgtgg cgagaagcgc ccgcggcccg ataggggaaga gaccactctg gtcacgcaga   18480
ccgatgagcc gccccccgtat gaggaggccc tgaagcaagg tctgcccacc acgcggccca   18540
tcgcgcccat ggccaccggg gtggtgggcc gccacacccc cgccacgctg gacttgcctc   18600
cgcccgccga tgtgccgcag cagcagcaga aggcggcaca gccgggcccg cccgtgaccg   18660
cctcccgttc ctccgccggt cctctgcgcc gcgcggccag cggccccgc ggggggtcg   18720 cgaggcacgg caactggcag agcacgctga acagcatcgt gggtctgggg gtgcggtccg   18780
tgaagcgccg ccgatgctac tgaatagctt agctaacgtg ttgtatgtgt gtatgcgccc   18840
```

```
tatgtcgccg ccagaggagc tgctgagtcg ccgccgttcg cgcgcccacc accaccaccg   18900
ccactccgcc cctcaagatg gcgacccat cgatgatgcc gcagtggtcg tacatgcaca    18960
tctcgggcca ggacgcctcg gagtacctga gccccgggct ggtgcagttc gcccgcgcca   19020
ccgagagcta cttcagcctg agtaacaagt ttaggaaccc cacggtggcg cccacgcacg   19080
atgtgaccac cgaccggtct cagcgcctga cgctgcggtt cattcccgtg gaccgcgagg   19140
acaccgcgta ctcgtacaag gcgcggttca ccctggccgt gggcgacaac cgcgtgctgg   19200
acatggcctc cacctacttt gacatccgcg gggtgctgga ccggggcccc actttcaagc   19260
cttactctgg caccgcctac aactccctgg ccccaaggg cgctcccaac tcctgcgagt    19320
gggagcaatt agaagaagcc caggccgctg tggaagacga agaattagaa gatgaagacg   19380
aggaaccaca ggatgaggca cctgtgaaaa aacccatgt atacgctcag gctccccttt    19440
ctggagaaga aattactaaa aacggtttgc aaatagggtc agataacaca gaagcccagt   19500
ctaagcccat atatgcagat cctacattcc agcctgaacc ccaaatcggg gaatcccagt   19560
ggaatgaggc agatgctaca gttgccggcg gtagagtgct aaagaaatcc actcccatga   19620
agccatgcta tggttcctat gcaagaccca caaactccaa tggaggtcaa ggtgtgctgg   19680
tggctgatga taagggggtt cttcaatcta agttgaatt gcaattttttt tcaaatacta   19740 ctactcttaa tcagcgggag ggtaacgata caaaaccaaa agtggtgctg tatagcgaag   19800
atgtgcacat ggaaactcca gacacccaca tttcttacaa gcccacaaaa agcgatgaca   19860
attcaaaaat catgctgggt cagcagtcca tgcccaacag acctaattac atcggcttca   19920
gagacaactt tatcggcctc atgtattaca atagcactgg caacatggga gtgcttgcag   19980
gtcaggcctc tcagttgaat gcagtggtgg acttgcaaga cagaaacaca gaactgtcct   20040
accagctctt gcttgattcc atgggtgaca gaaccagata cttttccatg tggaatcagg   20100
cagtggacag ttatgaccca gatgtcagaa ttattgaaaa tcatggaact gaagacgagc   20160
tccccaacta ttgtttccct ctgggcggca taggggtaac tgacacttac caggccatta   20220 aaccaatgg caatggtcaa gaaaacccaa cctgggaaaa agatacagag tttgcagacc   20280
gcaatgaaat agggtggga aacaatttcg ctatggagat caacctcagt gccaacctgt   20340
ggagaaactt cctgtactcc aacgtggcgc tgtacctgcc agacaagctt aagtacaacc   20400
cctccaatgt ggacatctct gacaaccca acacctacga ttacatgaac aagcgagtgg   20460
tggccccggg gctggtggac tgctacatca acctgggcgc gcgctggtcg ctggactaca   20520
tggacaacgt caacccccttc aaccaccacc gcaatgcggg cctgcgctac cgctccatgc   20580
tcctgggcaa cgggcgctac gtgcccttcc acatccaggt gccccagaag ttctttgcca   20640
tcaagaacct cctcctcctg ccgggctcct acacctacga gtggaacttc aggaaggatg   20700
tcaacatggt cctccagagc tctctgggta cgatctcag ggtggacggg ccagcatca    20760 agttcgagag catctgcctc tacgccacct tcttccccat ggcccacaac acggcctcca   20820
cgctcgaggc catgctcagg aacgacacca acgaccagtc cttcaatgac tacctctccg   20880
ccgccaacat gctctacccc ataccgccca acgccaccaa cgtccccatc tccatcccct   20940
cgcgcaactg gcggccttc cgcggctggg ccttcacccg cctcaagacc aaggagaccc    21000
cctccctggg ctcgggattc gacccctact acacctactc gggctccatt ccctacctgg   21060
acggcacctt ctacctcaac cacactttca gaaggtctc ggtcaccttc gactcctcgg    21120
tcagctggcc gggcaacgac cgtctgctca ccccccaacga gttcgaaatc aagcgctcgg   21180
tcgacgggga gggctacaac gtggcccagt gcaacatgac caaggactgg ttcctggtcc   21240
```

```
agatgctggc caactacaac atcggctacc agggcttcta catcccagag agctacaagg    21300
acaggatgta ctccttcttc aggaacttcc agcccatgag ccggcaggtg gtggaccaga    21360
ccaagtacaa ggactaccag gaggtgggca tcatccacca gcacaacaac tcgggcttcg    21420
tgggctacct cgcccccacc atgcgcgagg acaggcctac cccgccaac ttcccctacc     21480
cgctcatagg caagaccgcg gtcgacagca tcacccagaa aaagttcctc tgcgatcgca    21540
ccctctggcg catcccttc tccagcaact tcatgtccat gggtgcgctc tcggacctgg    21600
gccagaactt gctctacgcc aactccgccc acgccctcga catgaccttc gaggtcgacc    21660
ccatggacga gcccacccct ctctatgttc tgttcgaagt ctttgacgtg gtccgggtcc    21720
accagccgca ccgcggcgtc atcgagaccg tgtacctgcg tacgcccttc tcggccggca    21780
acgccaccac ctaaagaagc aagccgcagt catcgccgcc tgcatgccgt cgggttccac    21840
cgagcaagag ctcagggcca tcgtcagaga cctgggatgc gggccctatt ttttgggcac    21900
tttcgacaag cgcttccctg gctttgtctc cccacacaag ctggcctgcg ccatcgtcaa    21960
cacggccggc cgcgagaccg ggggcgtgca ctggctggcc ttcgcctgga cccgcgctc    22020
caaaacatgc ttcctctttg acccctttcgg cttttcggac cagcggctca gcaaatcta   22080
cgagttcgag tacgagggct gctgcgtcg cagcgccatc gcctcctcgc ccgaccgctg    22140
cgtcaccctc gaaaagtcca cccagaccgt gcaggggccc gactcggccg cctgcggtct    22200
cttctgctgc atgtttctgc acgcctttgt gcactggcct cagagtccca tggaccgcaa    22260
ccccaccatg aacttgctga cggggtgcc caactccatg ctccagagcc ccaggtcga     22320
gcccaccctg cgccgcaacc aggagcagct ctacagcttc ctggagcgcc actcgcccta    22380
cttccgccgc cacagcgcac agatcaggag ggccacctcc ttctgccact tgcaagagat    22440
gcaagaaggg taataacgat gtacacactt ttttctcaat aaatggcatt tttttattta    22500
tacaagctct ctggggtatt catttcccac caccaccacc acccgccgtt gtcgccatct    22560
ggctctattt agaaatcgaa agggttctgc cgggagtcgc cgtgcgccac gggcagggac    22620
acgttgcgat actggtagcg ggtgccccac ttgaactcgg gcaccaccag gcgaggcagc    22680
tcggggaagt tttcgctcca caggctgcgg gtcagcacca gcgcgttcat caggtcgggc    22740
gccgagatct tgaagtcgca gttggggccg ccgccctgcg cgcgcgagtt gcggtacacc    22800
gggttgcagc actggaacac caacagcgcc gggtgcttca cgctagccag cacgctgcgg    22860
tcggagatca gctcggcgtc caggtcctcc gcgttgctca gcgcgaacgg ggtcatcttg    22920
ggcacttgcc tccccaggaa gggcgcgtgc cccggtttcg agttgcagtc gcagcgcagc    22980
gggatcagca ggtgcccatg cccggactcg gcgttgggt acagcgcgcg catgaaggcc     23040
tgcatctggc ggaaggccat ctgggccttg gcgccctccg agaagaacat gccgcaggac    23100
ttgcccgaga actggtttgc ggggcagctg gcgtcgtgca ggcagcagcg cgcgtcggtg    23160
ttggcgatct gcaccacgtt gcgccccac cggttcttca cgatcttggc cttggacgat    23220
tgctccttca gcgcgcgctg cccgttctcg ctggtcacat ccatctcgat cacatgttcc    23280
ttgttcacca tgctgctgcc gtgcaggcac ttcagctcgc cctccgtctc ggtgcagcgg    23340
tgctgccaca gcgcgcagcc cgtgggctcg aaagacttgt aggtcacctc cgcgaaggac    23400
tgcaggtacc cctgcaaaaa gcggcccatc atggtcacga aggtcttgtt gctgctgaag    23460
gtcagctgca gcccgcggtg ctcctcgttc agccaggtct tgcacacggc cgccagcgcc    23520
tccacctggt cgggcagcat cttgaagttc accttcagct cattctccac gtggtacttg    23580
```

```
tccatcagcg tgcgcgccgc ctccatgccc ttctcccagg ccgacaccag cggcaggctc    23640
acggggttct tcaccatcac cgtggccgcc gcctccgccg cgctttcgct ttccgccccg    23700
ctgttctctt cctcttcctc ctcttcctcg ccgccgccca ctcgcagccc ccgcaccacg    23760
gggtcgtctt cctgcaggcg ctgcaccttg cgcttgccgt tgcgcccctg cttgatgcgc    23820
acgggcgggt tgctgaagcc caccatcacc agcgcggcct cttcttgctc gtcctcgctg    23880
tccagaatga cctccgggga ggggggttg gtcatcctca gtaccgaggc acgcttcttt    23940
ttcttcctgg gggcgttcgc cagctccgcg gctgcgccg ctgccgaggt cgaaggccga    24000
gggctgggcg tgcgcggcac cagcgcgtcc tgcgagccgt cctcgtcctc ctcggactcg    24060
agacggaggc gggcccgctt cttcggggc gcgcggggcg gcggaggcgg cggcggcgac    24120
ggagacgggg acgagacatc gtccagggtg ggtggacggc gggccgcgcc gcgtccgcgc    24180
tcggggtgg tctcgcgctg gtcctcttcc cgactggcca tctcccactg ctccttctcc    24240
tataggcaga aagagatcat ggagtctctc atgcgagtcg agaaggagga ggacagccta    24300
accgccccct ctgagccctc caccaccgcc gccaccaccg ccaatgccgc cgcggacgac    24360
gcgcccaccg agaccaccgc cagtaccacc nnnctcccca gcgacgcacc cccgctcgag    24420
aatgaagtgc tgatcgagca ggacccgggt tttgtgagcg agaggagga tgaggtggat    24480
gagaaggaga aggaggaggt cgccgcctca gtgccaaaag aggataaaaa gcaagaccag    24540
gacgacgcag ataaggatga cagcagtc gggcgggga acgaagcca tgatgctgat    24600
gacggctacc tagacgtggg agacgacgtg ctgcttaagc acctgcaccg ccagtgcgtc    24660
atcgtctgcg acgcgctgca ggagcggtgc gaagtgcccc tggacgtggc ggaggtcagc    24720
cgcgcctacg agcggcacct cttcgcgccg cacgtgcccc ccaagcgccg ggagaacggc    24780
acctgcgagc ccaacccgcg tctcaacttc tacccggtct tcgcggtacc cgaggtgctg    24840
gccacctacc acatcttttt ccaaaactgc aagatccccc tctcctgccg cgctaaccgc    24900
acccgcgccc acaaaaccct gaccctgcgg cagggcgccc acatacctga tattgcctct    24960
ctggaggaag tgcccaagat cttcgagggt ctcggtcgcg acgagaaacg ggcggcgaac    25020
gctctgcacg gagacagcga aaacgagagt cactcggggg tgctggtgga gctcgagggc    25080
gacaacgcgc gcctggccgt actcaagcgc agcatagagg tcacccactt tgcctacccg    25140
gcgctcaacc tgcccccaa ggtcatgagt gtggtcatgg gcgagctcat catgcgccgc    25200
gcccagcccc tggccgcgga tgcaaacttg caagagtcct cagaggaagg cctgcccgcg    25260
gtcagcgacg agcagctggc gcgctggctg gagacccgcg accccgcgca gctggaggag    25320
cggcgcaagc tcatgatggc cgcggtgctg gtcaccgtgg agctcgagtg tctgcagcgc    25380
ttcttcgcgg accccgagat gcagcgcaag ctcgaggaga ccctgcacta caccttccgc    25440
cagggctacg tgcgccaggc ctgcaagatc tccaacgtgg agctctgcaa cctggtctcc    25500
tacctgggca tcctgcacga gaaccgcctc gggcagaacg tcctgcactc caccctcaaa    25560
ggggaggcgc gccgcgacta catccgcgac tgcgcctacc tcttcctctg ctacacctgg    25620
cagacggcca tgggggtctg gcagcagtgc ctggaggagc gcaacctcaa ggagctggaa    25680
aagtccctca gcgcgcaccct cagggacctc tggacgggct tcaacgagcg ctcggtggcc    25740
gccgcgctgg cggacatcat cttccccgag cgcctgctca gaccctgca gcagggcctg    25800
cccgacttca ccagccagag catgctgcag aacttcagga cttttcatcct ggagcgctcg    25860
ggcatcctgc cggccacttg ctgcgcgctg cccagcgact tcgtgcccat caagtacagg    25920
gagtgcccgc cgccgctctg ggccactgc tacctcttcc agctggccaa ctacctcgcc    25980
```

```
taccactcgg acctcatgga agacgtgagc ggcgagggcc tgctcgagtg ccactgccgc   26040
tgcaacctct gcacgcccca ccgctctcta gtctgcaacc cgcagctgct cagcgagagt   26100
cagattatcg gtaccttcga gctgcagggt ccctcgcctg acgagaagtc cgcggctccg   26160
gggctgaaac tcactccggg gctgtggact tccgcctacc tacgcaaatt tgtacctgag   26220
gactaccacg cccacgagat caggttctac gaagaccaat cccgcccgcc caaggcggag   26280
ctcaccgcct gcgtcatcac ccaggggcac atcctgggcc aattgcaagc catcaacaaa   26340
gcccgccgag agttcttgct gaaaaagggt cgggggggtgt acctggaccc ccagtccggc   26400
gaggagctaa acccgctacc cccgccgccg cccccagcag gggaccttgc ttcccaggat   26460
ggcacccaga agaagcagc agccgccgcc gcagccatac atgcttctgg aggaagagga   26520
ggaggactgg gacagtcagg cagaggagat gatggaagac tgggaggagg acagcagcct   26580
agacgaggaa gcttcagagg ccgaagaggt ggcagacgca acaccatcac cctcggtcgc   26640 agcccctcg ccggggcccc tgaaatcctc cgaacccagc accagcgcta taacctccgc   26700
tcctccggcg ccggcgccac ccgcccgcag acccaaccgt agatgggaca ccacaggaac   26760
cggggtcggt aagtccaagt gcccgccgcc gccaccgcag cagcagcagc agcagccca   26820 gggctaccgc tcgtggcgcg ggcacaagaa cgccatagtc gcctgcttgc aagactgcgg   26880
gggcaacatc tctttcgccc gccgcttcct gctattccac cacggggtcg cctttccccg   26940
caatgtcctg cattactacc gtcatctcta cagcccctac tgcagcggcg acccagaggc   27000
ggcagcggca gccacagcgg cgaccaccac ctaggaagat atcctccgcg ggcaagacag   27060
cggcagcagc ggccaggaga cccgcggcag cagcggcggg agcggtgggc gcactgcgcc   27120
tctcgcccaa cgaaccccctc tcgacccggg agctcagaca caggatcttc cccactttgt   27180
atgccatctt ccaacagagc agaggccagg agcaggagct gaaaataaaa aacagatctc   27240
tgcgctccct cacccgcagc tgtctgtatc acaaaagcga agatcagctt cggcgcacgc   27300
tggaggacgc ggaggcactc ttcagcaaat actgcgcgct cactcttaaa gactagctcc   27360
gcgcccttct cgaatttagg cgggagaaaa ctacgtcatc gccggccgcc gcccagcccg   27420
cccagccgag atgagcaaag agattcccac gccatacatg tggagctacc agccgcagat   27480
gggactcgcg gcgggagcgg cccaggacta ctccacccgc atgaactaca tgagcgcggg   27540
accccacatg atctcacagg tcaacgggat ccgcgcccag cgaaaccaaa tactgctgga   27600
acaggcggcc atcaccgcca cgccccgcca taatctcaac ccccgaaatt ggcccgccgc   27660
cctagtgtac caggaaaccc cctccgccac caccgtacta cttccgcgtg acgcccaggc   27720
cgaagtccag atgactaact cagggggcgca gctcgcgggc ggctttcgtc acggggcgcg   27780
gccgctccga ccaggtataa gacacctgat gatcagaggc cgaggtatcc agctcaacga   27840
cgagtcggtg agctcttcgc tcggtctccg tccggacgga actttccagc tcgccggatc   27900
cggtcgctct tcgttcacgc cccgccaggc gtacctgact ctgcagacct cgtcctcgga   27960
gccccgctcc ggcggcatcg gaaccctcca gttcgtggag gagttcgtgc cctcggtcta   28020
cttcaacccc ttctcgggac ctcctccggacg ctacccccgac cagttcattc cgaactttga   28080
cgcggtgaag gactcggcgg acggctacga ctgaatgtca ggtgccgagg cagagcagct   28140
tcgcctgaga cacctcgagc actgccgccg ccacaagtgc ttcgcccgcg gttccggtga   28200
gttctgctac tttcagctac ccgaggagca taccgagggg ccggcgcacg gcgtccgcct   28260
gaccacccag ggcgaggtta cctgttccct catccgggag ttcaccctcc gtcccctgct   28320
```

```
agtggagcgg gagcggggtc cctgtgtcct aactatcgcc tgcaactgcc ctaaccctgg    28380
attacatcaa gatctttgct gtcatctctg tgctgagttt aataaacgct gagatcagaa    28440
tctactgggg ctcctgtcgc catcctgtga acgccaccgt cttcacccac cccgaccagg    28500
cccaggcgaa cctcacctgc ggtctgcatc ggaggtccaa gaagtacctc acctggtact    28560
tcaacggcac cccctttgtg gtttacaaca gcttcgacgg ggacggagtc tccctgaaag    28620
accagctctc cggtctcagc tactccatcc acaagaacac caccctccaa ctcttccctc    28680
cctacctgcc gggaacctac gagtgcgtca ccggccgctg cacccacctc acccgcctga    28740
tcgtaaacca gagctttccg ggaacagata actccctctt ccccagaaca ggaggtgagc    28800
tcaggaaact ccccggggac cagggcggag acgtaccttc gacccttgtg gggttaggat    28860 ttttttattac cggggttgctg gctcttttaa tcaaagcttc cttgagattt gttctttcct    28920
tctacgtgta tgaacacctc agcctccaat aactctaccc tttcttcggg atcaggtgac    28980
ttttctgaaa tcgggcttgg tgtgctgctt actctgttga ttttttttcct tatcatactc    29040 agccttctgt gcctcaggct cgccgcctgc tgcgcacaca tctatatcta ctgctggttg    29100
ctcaagtgca ggggtcgcca cccaagatga acaggtacat ggtcctatcg atcctaggcc    29160
tgctggccct ggcggcctgc agcgccgcca aaaagagat tacctttgag gagcccgctt    29220
gcaatgtaac tttcaagccc gagggtgacc aatgcaccac cctcgtcaaa tgcgttacca    29280
atcatgagaa gctgcgcatc gactacaaaa acaaaactgg ccggtttgcg gtctatagtg    29340
tgtttacgcc cggagacccc tctaactact ctgtcaccgt cttccagggc ggacagtcta    29400
agatattcaa ttcacttttc cctttttatg agttgtgcga tgcggtcatg tacatgtcaa    29460
aacagtacaa cctgtggcct ccctctcccc aggcgtgtgt ggaaaatact gggtcttact    29520
gctgtatggc tttggcaatc actacgctcg ctctaatctg cacggtgcta tatataaat    29580 tcaggcagag gcgaatcttt atcgatgaaa agaaaatgcc ttgatcgcta acaccggctt    29640
tctatctgca gaatgaatgc aatcacctcc ctactaatca ccaccaccct ccttgcgatt    29700
gcccatgggt tgacacgaat cgaagtgcca gtggggtcca atgtcaccat ggtgggcccc    29760
gccggcaatt ccaccctcat gtgggaaaaa tttgtccgca atcaatgggt tcatttctgc    29820
tctaaccgaa tcagtatcaa gcccagagcc atctgcgatg ggcaaaatct aactctgatc    29880
aatgtgcaaa tgatggatgc tgggtactat tacgggcagc ggggagaaat cattaattac    29940
tggcgacccc acaaggacta catgctgcat gtagtcgagg cacttcccac taccaccccc    30000
actaccacct ctcccaccac cactaccact actactacta ctactaccac taccgctgcc    30060 cgccatacccc gcaaaagcac catgattagc acaaagcccc ctcgtgctca ctcccacgcc    30120
ggcgggccca tcggtgcgac ctcagaaacc accgagcttt gcttctgcca atgcactaac    30180
gccagcgctc atgaactgtt cgacctggag aatgaggatg cccagcagag ctccgcttgc    30240
ctgacccagg aggctgtgga gcccgttgcc ctgaagcaga tcggtgattc aataattgac    30300
tcttcttctt ttgccactcc cgaatacct cccgattcta ctttccacat cacgggtacc    30360
aaagacccta acctctcttt ctacctgatg ctgctgctct gtatctctgt ggtctcttcc    30420
gcgctgatgt tactggggat gttctgctgc ctgatctgcc gcagaaagag aaaagctcgc    30480
tctcagggcc aaccactgat gcccttcccc tacccccggg attttgcaga taacaagata    30540
tgagctcgct gctgacacta accgcttac tagcctgcgc tctaacccct gtcgcttgcg    30600
actcgagatt ccacaatgtc acagctgtgg caggagaaaa tgttactttc aactccacgg    30660
ccgataccca gtggtcgtgg agtggctcag gtagctactt aactatctgc aatagctcca    30720
```

```
cttcccccag catatcccca accaagtacc aatgcaatgc cagcctgttc accctcatca   30780
acgcttccac cctggacaat ggactctatg taggctatgt acccttttggt gggcaaggaa   30840
agacccacgc ttacaacctg gaagttcgcc agcccagaac cactacccaa gctwcymcca   30900
ycaccagcac cagcagcagc agccacagca gcagcagcag attattgact ttggttttgg   30960
ccagctcatc tgccgctacc caggccatct acagctctgt gcccgaaacc actcagaccc   31020
accgcccaga aacgaccacc gccaccaccc tacacacctc cagcgatcag atgccgacca   31080
acatcacccc cttggctctt caaatgggac ttacaagccc cactccaaaa ccagtggatg   31140
cggccgaggt ctccgccctc gtcaatgact gggcggggct gggaatgtgg tggttcgcca   31200
taggcatgat ggcgctctgc ctgcttctgc tctggctcat ctgctgcctc caccgcaggc   31260
gagccagacc ccccatctat agacccatca ttgtcctgaa cccgataat gatgggatcc   31320
atagattgga tggcctgaaa aacctacttt tttcttttac agtatgataa attgagacat   31380
gcctcgcatt ttcttgtaca tgttccttct cccacctttt ctggggtgtt ctacgctggc   31440
cgctgtgtct cacctggagg tagactgcct ctcacccttc actgtctacc tgctttacgg   31500
attggtcacc ctcactctca tctgcagcct aatcacagta atcatcgcct tcatccagtg   31560
cattgattac atctgtgtgc gcctcgcata cttcagacac caccccgcagt accgagacag   31620
gaacattgcc caacttctaa gactgctcta atcatgcata agactgtgat ctgccttctg   31680
atcctctgca tcctgcccac cctcacctcc tgccagtaca ccacaaaatc tccgcgcaaa   31740
agacatgcct cctgccgctt cacccaactg tggaatatac ccaaatgcta caacgaaaag   31800
agcgagctct ccgaagcttg gctgtatggg gtcatctgtg tcttagtttt ctgcagcact   31860
gtctttgccc tcatgatcta cccctacttt gatttgggat ggaacgcgat cgatgccatg   31920
aattacccca ccttccccgc acccgagata attccactgc gacaagttgt acccgttgtc   31980
gttaatcaac gccccccatc ccctacgccc actgaaatca gctactttaa cctaacaggc   32040
ggagatgact gacgccctag atctagaaat ggacggcatc agtaccgagc agcgtctcct   32100
agagaggcgc aggcaggcgg ctgagcaaga gcgcctcaat caggagctcc gagatctcgt   32160
taacctgcac cagtgcaaaa gaggcatctt ttgtctggta aagcaggcca aagtcaccta   32220
cgagaagacc ggcaacagcc accgcctcag ttacaaattg cccacccagc gccagaagct   32280
ggtgctcatg gtgggtgaga atcccatcac cgtcacccag cactcggtag agaccgaggg   32340
gtgtctgcac tcccctgtc ggggtccaga agacctctgc accctggtaa agaccctgtg   32400
cggtctcaga gatttagtcc cctttaacta atcaaacact ggaatcaata aaagaatca   32460
cttacttaaa atcagacagc aggtctctgt ccagtttatt cagcagcacc tccttcccct   32520
cctcccaact ctggtactcc aaacgccttc tggcggcaaa cttcctccac accctgaagg   32580
gaatgtcaga ttcttgctcc tgtccctccg cacccactat cttcatgttg ttgcagatga   32640
agcgcaccaa aacgtctgac gagagcttca acccgtgta cccctatgac acggaaagcg   32700
gccctccctc cgtcccttc ctcaccccctc ccttcgtgtc tcccgatgga ttccaagaaa   32760
gtccccccgg ggtcctgtct ctgaacctgg ccgagcccct ggtcacttcc cacggcatgc   32820
tcgccctgaa aatgggaagt ggcctctccc tggacgacgc tggcaacctc acctctcaag   32880
atatcaccac cgctagccct cccctcaaaa aaaccaagac caacctcagc ctagaaacct   32940
catcccccct aactgtgagc acctcaggcg ccctcaccgt agcagccgcc gctcccctgg   33000
cggtggccgg cacctccctc accatgcaat cagaggcccc cctgacagta caggatgcaa   33060
```

```
aactcaccct ggccaccaaa ggcccctga ccgtgtctga aggcaaactg gccttgcaaa    33120
catcggcccc gctgacggcc gctgacagca gcaccctcac cgttagcgcc acaccaccaa    33180
ttaatgtaag cagtggaagt ttaggcttag acatggaaga ccctatgtat actcacaatg    33240
gaaaactggg aataagaatt gggggtccac taagagtagt agacagcttg catacactca    33300
ctgtagttac cggaaatgga ctaactgtag ataacaatgc cctccaaact aaagttacgg    33360
gcgccctagg ttatgacaca tcaggaaatc tacaattaag agctgcagga ggtatgcgaa    33420
ttgacgcaaa tggccaactt atccttaatg tggcataccc atttgatgct cagaacaatc    33480
tcagccttag acttggtcag ggaccctgt atataaacac agaccacaac ctggatttga    33540
attgcaacag aggtctaacc acaactacca ccaacaacac aaaaaaactt gagactaaaa    33600
ttagctcagg cttagactat gacaccaatg gtgctgtcat tattaaactt ggcactggtc    33660
taagcttcga caacacaggc gccctaactg tgggaaacac tggtgatgat aaactgactc    33720
tgtggacgac cccagaccca tctccaaatt gcagaattca ctcagacaaa gactgcaagt    33780
ttactctagt cctaactaag tgtggaagcc aaatcctggc ctctgtcgcc gccctagcgg    33840
tatcaggaaa tctggcttcg ataacaggca ccgttgccag cgttaccatc tttctcagat    33900
ttgatcagaa tggagtgctt atggaaaact cctcgctaga caggcagtac tggaacttca    33960
gaaatggcaa ctcaactaac gctgcccct acaccaatgc agttgggttc atgccaaacc    34020
tcgcagcata ccccaaaacg caaagccaga ctgctaaaaa caacattgta agtcaggttt    34080
acttgaatgg agacaaatcc aaacccatga cccttaccat caccctcaat ggaactaatg    34140
aatccagtga aactagccag gtgagtcact actccatgtc atttacatgg gcttgggaaa    34200
gtgggcaata tgccactgaa acctttgcca ccaactcctt caccttttct tacattgctg    34260
aacaataaaa agcatgacac tgatgttcat ttctgattct tatttatta ttttcaaaca    34320
caacaaaatc attcaagtca ttcttccatc ttagcttaat agacacagta gcttaataga    34380
cccagtagtg caaagcccca ttctagctta tagatcagac agtgataatt aaccaccacc    34440
accaccatac cttttgattc aggaaatcat gatcatcaca ggatcctagt cttcaggccg    34500
ccccctccct cccaagacac agaatacaca gtcctctccc cccgactggc tttaaataac    34560
accatctggt tggtcacaga catgttctta ggggttatat tccacacggt ctcctgccgc    34620
gccaggcgct cgtcggtgat gttgataaac tctcccggca gctcgctcaa gttcacgtcg    34680
ctgtccagcg gctgaacctc cggctgacgc gataactgtg cgaccggctg ctggacaaac    34740
ggaggccgcg cctacaaggg ggtagagtca taatcctcgg tcaggatagg gcggtgatgc    34800
agcagcagcg agcgaaacat ctgctgccgc cgccgctccg tccggcagga aaacaacacg    34860
ccggtggtct cctccgcgat aatccgcacc gcccgcagca tcagcttcct cgttctccgc    34920
gcgcagcacc tcaccctgat ctcgctcaag tcggcgcagt aggtacagca cagcaccacg    34980
atgttattca tgatcccaca gtgcagggcg ctgtatccaa agctcatgcc gggaaccacc    35040
gccccacgt ggccatcgta ccacaagcgc acgtaaatta agtgtcgacc cctcatgaac    35100
gtgctggaca caaacattac ttccttgggc atgttgtaat tcaccacctc ccggtaccag    35160
ataaacctct ggttaaacag ggcaccttcc accaccatcc tgaaccaaga ggccagaacc    35220
tgcccaccgg ctatgcactg cagggaaccc gggttggaac aatgacaatg cagactccaa    35280
ggctcgtaac cgtggatcat ccggctgctg aaggcatcga tgttggcaca acacagacac    35340
acgtgcatgc actttctcat gattagcagc tcttccctcg tcaggatcat atcccaagga    35400
ataacccatt cttgaatcaa cgtaaaaccc acacagcagg gaaggcctcg cacataactc    35460
```

```
acgttgtgca tggtcagcgt gttgcattcc ggaaacagcg gatgatcctc cagtatcgag    35520
gcgcgggtct ccttctcaca gggaggtaaa gggtccctgc tgtacggact gcgccgggac    35580
gaccgagatc gtgttgagcg tagtgtcatg gaaaagggaa cgccggacgt ggtcatactt    35640
cttgaagcag aaccaggttc gcgcgtggca ggcctccttg cgtctgcggt ctcgccgtct    35700
agctcgctcc gtgtgatagt tgtagtacag ccactcccgc agagcgtcga ggcgcaccct    35760
ggcttccgga tctatgtaga ctccgtcttg caccgcggcc ctgataatat ccaccaccgt    35820
agaataagca cacccagcc aagcaataca ctcgctctgc gagcggcaga caggaggagc     35880
gggcagagat gggagaacca tgataaaaaa cttttttaa agaatatttt ccaattcttc     35940
gaaagtaaga tctatcaagt ggcagcgctc ccctccactg gcgcggtcaa actctacggc    36000
caaagcacag acaacggcat ttctaagatg ttccttaatg gcgtccaaaa gacacaccgg    36060
tctcaagtcg cagtaaacta tgaatgaaaa cccatccggc tgattttcca atatagacgc    36120
gccggcggcg tccaccaaac ccagataatt ttcttctctc cagcggttta gaatctgtct    36180
aagcaaatcc cttatatcaa gtccggccat gccaaaaatc tgctcaagag cgccctccac    36240
cttcatgacc aagcagcgca tcatgattgc aaaaattcag gttcttcaga gacctgtata    36300
agattcaaaa tgggaacatt aacaaaaatt cctctgtcgc gcagatccct tcgcagggca    36360
agctgaacat aatcagacag gtctgaacgg accagtgagg ccaaatcccc accaggaacc    36420
agatccagag accctatact gattatgacg cgcatactcg gggctatgct gaccagcgta    36480
gcgccgatgt aggcgtgctg catgggcggc gagataaaat gcaaagtgct ggttaaaaaa    36540
tcaggcaaag cctcgcgcaa aaaagctaac acatcataat catgctcatg caggtagttg    36600
caggtaagct caggaaccaa aacggaataa cacacgattt tcctctcaaa catgacttcg    36660
cggatactgc gtaaaacaaa aattataaat aaaaaattaa ttaacttaaa cattggaagc    36720
ctgtctcaca acaggaaaaa ccactttaat caacataaga cgggccacgg gcatgccggc    36780
atagccgtaa aaaaattggt ccccgtgatt aacaagtacc acagacagct ccccggtcat    36840
gtcgggggtc atcatgtgag actctgtata cacgtctgga ttgtgaacat cagacaaaca    36900
aagaaatcga gccacgtagc ccggaggtat aatcacccgc aggcggaggt acagcaaaac    36960
gacccccata ggaggaatca caaaattagt aggagaaaaa aatacataaa caccagaaaa    37020
accctgttgc tgaggcaaaa tagcgccctc ccgatccaaa acaacataaa gcgcttccac    37080
aggagcagcc ataacaaaga cccgagtctt accagtaaaa agaaaaaaga tctctcaacg    37140
cagcaccagc accaacactt cgcagtgtaa aaggccaagt gccgagagag tatatatagg    37200
aataaaaagt gacgtaaacg ggcaaagtcc aaaaaacgcc cagaaaaacc gcacgcgaac    37260
ctacgccccg aaacgaaagc caaaaaacac tagacactcc cttccggcgt caacttccgc    37320
tttcccacgc tacgtcactt gccccagtca aacaaactac atatcccgaa cttccaagtc    37380
gccacgccca aaacaccgcc tacacctccc gcccgccgg cccgccccca aacccgcctc     37440
ccgccccgcg ccccgccccg cgccgcccat ctcattatca tattggcttc aatccaaaat    37500
aaggtatatt attgatgatg gtttaaacgg atccaattct tgaagacgaa agggcctcgt    37560
gatacgccta ttttttatagg ttaatgtcat gataataatg gtttcttaga cgtcaggtgg    37620
cacttttcgg ggaaatgtgc gcggaacccc tatttgttta ttttctaaa tacattcaaa     37680
tatgtatccg ctcatgagac aataaccctg ataaatgctt caataatatt gaaaaggaa     37740
gagtatgagt attcaacatt tccgtgtcgc ccttattccc ttttttgcgg catttttgcct   37800
```

```
tcctgttttt gctcacccag aaacgctggt gaaagtaaaa gatgctgaag atcagttggg   37860
tgcacgagtg ggttacatcg aactggatct caacagcggt aagatccttg agagttttcg   37920
ccccgaagaa cgttttccaa tgatgagcac ttttaaagtt ctgctatgtg gcgcggtatt   37980
atcccgtgtt gacgccgggc aagagcaact cggtcgccgc atacactatt ctcagaatga   38040
cttggttgag tactcaccag tcacagaaaa gcatcttacg gatggcatga cagtaagaga   38100
attatgcagt gctgccataa ccatgagtga taacactgcg gccaacttac ttctgacaac   38160
gatcggagga ccgaaggagc taaccgcttt tttgcacaac atgggggatc atgtaactcg   38220
ccttgatcgt tgggaaccgg agctgaatga agccatacca aacgacgagc gtgacaccac   38280
gatgcctgta gcaatggcaa caacgttgcg caaactatta actggcgaac tacttactct   38340
agcttcccgg caacaattaa tagactggat ggaggcggat aaagttgcag gaccacttct   38400
gcgctcggcc cttccggctg gctggtttat tgctgataaa tctggagccg gtgagcgtgg   38460
gtctcgcggt atcattgcag cactggggcc agatggtaag ccctcccgta tcgtagttat   38520
ctacacgacg gggagtcagg caactatgga tgaacgaaat agacagatcg ctgagatagg   38580
tgcctcactg attaagcatt ggtaactgtc agaccaagtt tactcatata ctttagat    38640 tgatttaaaa ggatctaggt gaagatcctt tttgataatc tcatgaccaa aatcccttaa   38700
cgtgagtttt cgttccactg agcgtcagac cccgtagaaa agatcaaagg atcttcttga   38760 gatcctttt tctgcgcgt aatctgctgc ttgcaaacaa aaaaaccacc gctaccagcg    38820
gtggtttgtt tgccggatca agagctacca actcttttc cgaaggtaac tggcttcagc    38880
agagcgcaga taccaaatac tgtccttcta gtgtagccgt agttaggcca ccacttcaag   38940
aactctgtag caccgcctac atacctcgct ctgctaatcc tgttaccagt ggctgctgcc   39000
agtggcgata agtcgtgtct taccgggttg gactcaagac gatagttacc ggataaggcg   39060
cagcggtcgg gctgaacggg gggttcgtgc acacagccca gcttggagcg aacgacctac   39120
accgaactga gatacctaca gcgtgagcta tgagaaagcg ccacgcttcc cgaagggaga   39180
aaggcggaca ggtatccggt aagcggcagg gtcggaacag gagagcgcac gagggagctt   39240
ccagggggaa acgcctggta tctttatagt cctgtcgggt ttcgccacct ctgacttgag   39300
cgtcgatttt tgtgatgctc gtcaggggg cggagcctat ggaaaaacgc cagcaacgcg    39360 gccttttac ggttcctggc cttttgctgg ccttgaagct gtccctgatg gtcgtcatct    39420
acctgcctgg acagcatggc ctgcaacgcg ggcatcccga tgccgccgga agcgagaaga   39480
atcataatgg ggaaggccat ccagcctcgc gtcgcagatc cgaattcgtt taaac         39535
```

<210> SEQ ID NO 16
<211> LENGTH: 1500
<212> TYPE: DNA
<213> ORGANISM: Human immunodeficiency virus

<400> SEQUENCE: 16

```
atgggtgcta gggcttctgt gctgtctggt ggtgagctgg acaagtggga gaagatcagg    60
ctgaggcctg gtggcaagaa gaagtacaag ctaaagcaca ttgtgtgggc ctccagggag   120
ctggagaggt tgctgtgaa ccctggcctg ctggagacct tgaggggtg caggcagatc    180 ctgggccagc tccagccctc cctgcaaaca ggctctgagg agctgaggtc cctgtacaac   240
acagtggcta ccctgtactg tgtgcaccag aagattgatg tgaaggacac caaggaggcc   300
ctggagaaga ttgaggagga gcagaacaag tccaagaaga ggcccagca ggctgctgct   360 ggcacaggca actccagcca ggtgtcccag aactacccca ttgtgcagaa cctccagggc   420
```

| | | | |
|---|---|---|---|
| cagatggtgc | accaggccat | ctccccccgg | accctgaatg cctgggtgaa ggtggtggag | 480 |
| gagaaggcct | tctcccctga | ggtgatcccc | atgttctctg ccctgtctga gggtgccacc | 540 |
| ccccaggacc | tgaacaccat | gctgaacaca | gtgggggggcc atcaggctgc catgcagatg | 600 |
| ctgaaggaga | ccatcaatga | ggaggctgct | gagtgggaca ggctgcatcc tgtgcacgct | 660 |
| ggccccattg | cccccggcca | gatgagggag | cccaggggct ctgacattgc tggcaccacc | 720 |
| tccaccctcc | aggagcagat | tggctggatg | accaacaacc cccccatccc tgtggggggaa | 780 |
| atctacaaga | ggtggatcat | cctgggcctg | aacaagattg tgaggatgta ctcccccacc | 840 |
| tccatcctgg | acatcaggca | gggccccaag | gagcccttca gggactatgt ggacaggttc | 900 |
| tacaagaccc | tgagggctga | gcaggcctcc | caggaggtga agaactggat gacagagacc | 960 |
| ctgctggtgc | agaatgccaa | ccctgactgc | aagaccatcc tgaaggccct gggccctgct | 1020 |
| gccaccctgg | aggagatgat | gacagcctgc | caggggggtgg ggggccctgg tcacaaggcc | 1080 |
| agggtgctgc | tgaggccat | gtcccaggtg | accaactccg ccaccatcat gatgcagagg | 1140 |
| ggcaacttca | ggaaccagag | gaagacagtg | aagtgcttca actgtggcaa ggtgggccac | 1200 |
| attgccaaga | actgtagggc | ccccaggaag | aagggctgct ggaagtgtgg caaggagggc | 1260 |
| caccagatga | aggactgcaa | tgagaggcag | gccaacttcc tgggcaaaat ctggccctcc | 1320 |
| cacaagggca | ggcctggcaa | cttcctccag | tccaggcctg agcccacagc ccctcccgag | 1380 |
| gagtccttca | ggtttgggga | ggagaagacc | accccccagcc agaagcagga gcccattgac | 1440 |
| aaggagctgt | accccctggc | ctccctgagg | tccctgtttg gcaacgaccc ctcctcccag | 1500 |

<210> SEQ ID NO 17
<211> LENGTH: 39240
<212> TYPE: DNA
<213> ORGANISM: Pan troglodytes
<220> FEATURE:
<221> NAME/KEY: misc_feature
<222> LOCATION: (24096)..(24098)
<223> OTHER INFORMATION: n is a, c, g, or t

<400> SEQUENCE: 17

| | | | |
|---|---|---|---|
| catcatcaat | aatataccct | attttggatt | gaagccaata tgataatgag atgggcggcg | 60 |
| cggggcgggg | cgcggggcgg | gaggcgggtt | tgggggcggg ccggcgggcg ggcggtgtg | 120 |
| gcggaagtgg | actttgtaag | tgtggcggat | gtgacttgct agtgccgggc gcggtaaaag | 180 |
| tgacgttttc | cgtgcgcgac | aacgcccccg | ggaagtgaca tttttcccgc ggttttacc | 240 |
| ggatgttgta | gtgaatttgg | gcgtaaccaa | gtaagatttg gccattttcg cgggaaaact | 300 |
| gaaacgggga | agtgaaatct | gattaatttt | gcgttagtca taccgcgtaa tatttgtcta | 360 |
| gggccgaggg | actttggccg | attacgtgga | ggactcgccc agtgtgttttt tgaggtgaat | 420 |
| ttccgcgttc | cgggtcaaag | tctgcgtttt | attattatag gatatcccat tgcatacgtt | 480 |
| gtatccatat | cataatatgt | acatttatat | tggctcatgt ccaacattac cgccatgttg | 540 |
| acattgatta | ttgactagtt | attaatagta | atcaattacg gggtcattag ttcatagccc | 600 |
| atatatggag | ttccgcgtta | cataacttac | ggtaaatggc ccgcctggct gaccgcccaa | 660 |
| cgaccccgc | ccattgacgt | caataatgac | gtatgttccc atagtaacgc caatagggac | 720 |
| tttccattga | cgtcaatggg | tggagtattt | acggtaaact gcccacttgg cagtacatca | 780 |
| agtgtatcat | atgccaagta | cgccccctat | tgacgtcaat gacggtaaat ggcccgcctg | 840 |
| gcattatgcc | cagtacatga | ccttatggga | ctttcctact tggcagtaca tctacgtatt | 900 |

```
agtcatcgct attaccatgg tgatgcggtt ttggcagtac atcaatgggc gtggatagcg    960
gtttgactca cggggatttc caagtctcca ccccattgac gtcaatggga gtttgttttg   1020
gcaccaaaat caacgggact ttccaaaatg tcgtaacaac tccgccccat tgacgcaaat   1080
gggcggtagg cgtgtacggt gggaggtcta tataagcaga gctctcccta tcagtgatag   1140
agatctccct atcagtgata gagatcgtcg acgagctcgt ttagtgaacc gtcagatcgc   1200
ctggagacgc catccacgct gttttgacct ccatagaaga caccgggacc gatccagcct   1260
ccgcggccgg aacggtgca ttggaacgcg gattccccgt gccaagagtg agatctacca   1320
tgggtgctag gcttctgtg ctgtctggtg gtgagctgga caagtgggag aagatcaggc   1380
tgaggcctgg tggcaagaag aagtacaagc taaagcacat tgtgtgggcc tccagggagc   1440
tggagaggtt tgctgtgaac cctggcctgc tggagacctc tgaggggtgc aggcagatcc   1500
tgggccagct ccagccctcc ctgcaaacag gctctgagga gctgaggtcc ctgtacaaca   1560
cagtggctac cctgtactgt gtgcaccaga agattgatgt gaaggacacc aaggaggccc   1620
tggagaagat tgaggaggag cagaacaagt ccaagaagaa ggcccagcag ctgctgctg    1680
gcacaggcaa ctccagccag gtgtcccaga actaccccat tgtgcagaac ctccagggcc   1740
agatggtgca ccaggccatc tccccccgga ccctgaatgc ctgggtgaag gtggtggagg   1800
agaaggcctt ctcccctgag gtgatcccca tgttctctgc cctgtctgag ggtgccaccc   1860
cccaggacct gaacaccatg ctgaacacag tgggggcca tcaggctgcc atgcagatgc   1920
tgaaggagac catcaatgag gaggctgctg agtgggacag gctgcatcct gtgcacgctg   1980
gccccattgc ccccggccag atgagggagc caggggctc tgacattgct ggcaccacct   2040
ccaccctcca ggagcagatt ggctggatga ccaacaaccc cccatccct gtggggaaa    2100
tctacaagag gtggatcatc ctgggcctga caagattgt gaggatgtac tcccccacct   2160
ccatcctgga catcaggcag ggccccaagg agcccttcag ggactatgtg acaggttct   2220
acaagaccct gagggctgag caggcctccc aggaggtgaa gaactggatg acagagaccc   2280
tgctggtgca gaatgccaac cctgactgca agaccatcct gaaggccctg gccctgctg    2340
ccaccctgga ggagatgatg acagcctgcc agggggtggg gggccctggt cacaaggcca   2400
gggtgctggc tgaggccatg tcccaggtga ccaactccgc caccatcatg atgcagaggg   2460
gcaacttcag gaaccagagg aagacagtga agtgcttcaa ctgtggcaag gtgggccaca   2520
ttgccaagaa ctgtagggcc cccaggaaga agggctgctg gaagtgtggc aaggagggcc   2580
accagatgaa ggactgcaat gagaggcagg ccaacttcct gggcaaaatc tggccctccc   2640
acaagggcag gcctggcaac ttcctccagt ccaggcctga gcccacagcc cctcccgagg   2700
agtccttcag gtttggggag gagaagacca ccccagcca gaagcaggag cccattgaca   2760
aggagctgta ccccctggcc tccctgaggt ccctgtttgg caacgacccc tcctcccagt   2820
aaaataaagc ccgggcagat ctgatctgct gtgccttcta gttgccagcc atctgttgtt   2880
tgcccctccc ccgtgccttc cttgaccctg gaaggtgcca ctcccactgt cctttcctaa   2940
taaaatgagg aaattgcatc gcattgtctg agtaggtgtc attctattct ggggggtggg   3000
gtggggcagc acagcaaggg ggaggattgg gaagacaata gcaggcatgc tggggatgcg   3060
gtgggctcta tggccgatca gcgatcgctg aggtgggtga gtgggcgtgg cctggggtgg   3120
tcatgaaaat atataagttg ggggtcttag ggtctctta tttgtgttgc agagaccgcc   3180
ggagccatga gcgggagcag cagcagcagc agtagcagca gcgccttgga tggcagcatc   3240
gtgagccctt atttgacgac gcggatgccc cactgggccg gggtgcgtca gaatgtgatg   3300
```

```
ggctccagca tcgacggccg acccgtcctg cccgcaaatt ccgccacgct gacctatgcg   3360
accgtcgcgg ggacgccgtt ggacgccacc gccgccgccg ccgccaccgc agccgcctcg   3420
gccgtgcgca gcctggccac ggactttgca ttcctgggac cactggcgac aggggctact   3480
tctcgggccg ctgctgccgc cgttcgcgat gacaagctga ccgccctgct ggcgcagttg   3540
gatgcgctta ctcgggaact gggtgacctt tctcagcagg tcatggccct cgccagcag   3600 gtctcctccc tgcaagctgg cgggaatgct tctcccacaa atgccgttta agataaataa   3660
aaccagactc tgtttggatt aaagaaaagt agcaagtgca ttgctctctt tatttcataa   3720
ttttccgcgc gcgataggcc ctagaccagc gttctcggtc gttgagggtg cggtgtatct   3780
tctccaggac gtggtagagg tggctctgga cgttgagata catgggcatg agcccgtccc   3840
gggggtggag gtagcaccac tgcagagctt catgctccgg ggtggtgttg tagatgatcc   3900
agtcgtagca ggagcgctgg gcatggtgcc taaaaatgtc cttcagcagc aggccgatgg   3960 ccaggggag gcccttggtg taagtgttta caaaacggtt aagttgggaa gggtgcattc   4020
ggggagagat gatgtgcatc ttggactgta tttttagatt ggcgatgttt ccgcccagat   4080
cccttctggg attcatgttg tgcaggacca ccagtacagt gtatccggtg cacttgggga   4140
atttgtcatg cagcttagag ggaaaagcgt ggaagaactt ggagacgccc ttgtggcctc   4200
ccagattttc catgcattcg tccatgatga tggcaatggg cccgcgggag gcagcttggg   4260
caaagatatt tctggggtcg ctgacgtcgt agttgtgttc cagggtgagg tcgtcatagg   4320
ccatttttac aaagcgcggg cggagggtgc ccgactgggg gatgatggtc ccctctggcc   4380
ccggggcgta gttgccctcg cagatctgca tttcccaggc cttaatctcg gagggggaa   4440 tcatatccac ctgcggggcg atgaagaaaa cggtttccgg agccggggag attaactggg   4500
atgagagcag gtttctaagc agctgtgatt ttccacaacc ggtgggccca taaataacac   4560
ctataaccgg ttgcagctgg tagtttagag agctgcagct gccgtcgtcc cggaggaggg   4620
gggccacctc gttgagcatg tccctgacgc gcatgttctc cccgaccaga tccgccagaa   4680
ggcgctcgcc gcccagggac agcagctctt gcaaggaagc aaagttttc agcggcttga   4740 ggccgtccgc cgtgggcatg ttttcaggg tctggctcag cagctccagg cggtcccaga   4800
gctcggtgac gtgctctacg gcatctctat ccagcatatc tcctcgtttc gcgggttggg   4860
gcgactttcg ctgtagggca ccaagcgtg tcgtccagc ggggcagag tcatgtcctt   4920 ccatgggcgc agggtcctcg tcagggtggt ctgggtcacg gtgaagggt gcgctccggg   4980 ctgagcgctt gccaaggtgc gcttgaggct ggttctgctg tgctgaagc gctgccggtc   5040 ttcgccctgc gcgtcggcca ggtagcattt gaccatggtg tcatagtcca gccccctccgc   5100 ggcgtgtccc ttggcgcgca gcttgccctt ggaggtggcg ccgcacgagg ggcagagcag   5160
gctcttgagc gcgtagagct tggggcgag gaagaccgat tcggggagt aggcgtccgc   5220 gccgcagacc ccgcacacgg tctcgcactc caccagccag gtgagctcgg ggcgcgccgg   5280
gtcaaaaacc aggtttcccc catgcttttt gatgcgtttc ttacctcggg tctccatgag   5340
gtggtgtccc cgctcggtga cgaagaggct gtccgtgtct ccgtagaccg acttgagggg   5400
tcttttctcc agggggtcc ctcggtcttc ctcgtagagg aactcggacc actctgagac   5460 gaaggccgc gtccaggcca ggacgaagga ggctatgtgg gaggggtagc ggtcgttgtc   5520
cactaggggg tccaccttct ccaaggtgtg aagacacatg tcgccttcct cggcgtccag   5580
gaaggtgatt ggcttgtagg tgtaggccac gtgaccgggg gttcctgacg gggggtata   5640
```

```
aaaggggggtg ggggcgcgct cgtcgtcact ctcttccgca tcgctgtctg cgagggccag    5700
ctgctggggt gagtattccc tctcgaaggc gggcatgacc tccgcgctga ggttgtcagt    5760
ttccaaaaac gaggaggatt tgatgttcac ctgtcccgag gtgataccct tgagggtacc    5820
cgcgtccatc tggtcagaaa acacgatctt tttattgtcc agcttggtgg cgaacgaccc    5880
gtagagggcg ttggagagca gcttggcgat ggagcgcagg gtctggttct tgtccctgtc    5940
ggcgcgctcc ttggccgcga tgttgagctg cacgtactcg cgcgcgacgc agcgccactc    6000
ggggaagacg gtggtgcgct cgtcgggcac caggcgcacg cgccagccgc ggttgtgcag    6060
ggtgaccagg tccacgctgg tggcgacctc gccgcgcagg cgctcgttgg tccagcagag    6120
acggccgccc ttgcgcgagc agaaggggggg caggggggtcg agctgggtct cgtccggggg    6180
gtccgcgtcc acggtgaaaa ccccgggggcg caggcgcgcg tcgaagtagt ctatcttgca    6240
accttgcatg tccagcgcct gctgccagtc gcgggcggcg agcgcgcgct cgtagggggtt    6300 gagcggcggg ccccagggca tgggggtgggt gagtgcggag gcgtacatgc cgcagatgtc    6360
atagacgtag aggggctccc gcaggacccc gatgtaggtg gggtagcagc ggccgccgcg    6420
gatgctggcg cgcacgtagt catacagctc gtgcgagggg gcgaggaggt cggggcccag    6480
gttggtgcgg gcggggcgct ccgtgcgaaa gacgatctgc ctgaagatgg catgcgagtt    6540
ggaagagatg gtggggcgct ggaagacgtt gaagctggcg tcctgcaggc cgacggcgtc    6600
gcgcacgaag gaggcgtagg agtcgcgcag cttgtgtacc agctcggcgg tgacctgcac    6660
gtcgagcgcg cagtagtcga gggtctcgcg gatgatgtca tatttagcct gcccccttctt    6720 tttccacagc tcgcggttga ggacaaactc ttcgcggtct ttccagtact cttggatcgg    6780
gaaaccgtcc ggttccgaac ggtaagagcc tagcatgtag aactggttga cggcctggta    6840
ggcgcagcag cccttctcca cggggggagggc gtaggcctgc cgggccttgc ggagcgaggt    6900
gtgggtcagg gcgaaggtgt ccctgaccat gactttgagg tactggtgct tgaagtcgga    6960
gtcgtcgcag ccgccccgct cccagagcga gaagtcggtg cgcttcttgg agcggggggtt    7020 gggcagagcg aaggtgacat cgttgaagag gattttgccc gcgcggggca tgaagttgcg    7080
ggtgatgcgc aagggccccg gcacttcaga gcggttgttg atgacctggg cggcgagcac    7140
gatctcgtcg aagccgttga tgttgtggcc cacgatgtag agttccagga agcggggccg    7200
gccctttacg gtgggcagct tctttagctc ttcgtaggtg agctcctcgg gcgaggcgag    7260
gccgtgctcg gccagggccc agtccgcgag gtgcgggttg tctctgagga aggactccca    7320
gaggtcgcgg gccaggaggg tctgcaggcg gtccctgaag gtcctgaact ggcggcccac    7380
ggccattttt tcgggggtga tgcagtagaa ggtgaggggg tcttgctgcc agcggtccca    7440
gtcgagctgc agggcgaggt cgcgcgcggc ggtgaccagg cgctcgtcgc ccccgaattt    7500
catgaccagc atgaagggca cgagctgctt tccgaaggcc cccatccaag tgtaggtctc    7560
tacatcgtag gtgacaaaga ggcgctccgt gcgaggatgc gagccgatcg ggaagaactg    7620
gatctcccgc caccagttgg aggagtggct gttgatgtgg tggaagtaga agtcccgtcg    7680
ccgggccgaa cactcgtgct ggcttttgta aaagcgagcg cagtactggc agcgctgcac    7740
gggctgtacc tcatgcacga gatgcacctt tcgcccgcgc acgaggaagc cgagggggaaa    7800 tctgagcccc ccgcctggct cgcggcatgg ctggtgctct tctactttgg atgcgtgtcc    7860
gtctccgtct ggctcctcga ggggtgttac ggtggagcgg accaccacgc gcgcgcgagcc    7920 gcaggtccag atatcggcgc gcggcggtcg gagtttgatg acgacatcgc gcagctggga    7980
gctgtccatg gtctggagct cccgcggcgg cggcaggtca gccgggagtt cttgcaggtt    8040
```

```
cacctcgcag agtcgggcca gggcgcgggg caggtctagg tggtacctga tctctagggg    8100
cgtgttggtg gcggcgtcga tggcttgcag gagcccgcag ccccggggg cgacgacggt     8160 gccccgcggg gtggtggtgg tggtggcggt gcagctcaga agcggtgccg cgggcgggcc    8220
cccggaggta ggggggctc cggtcccgcg ggcaggggcg gcagcggcac gtcggcgtgg     8280
agcgcgggca ggagttggtg ctgtgcccgg aggttgctgg cgaaggcgac gacgcggcgg    8340
ttgatctcct ggatctggcg cctctgcgtg aagacgacgg gcccggtgag cttgaacctg    8400
aaagagagtt cgacagaatc aatctcggtg tcattgaccg cggcctggcg caggatctcc    8460
tgcacgtctc ccgagttgtc ttggtaggcg atctcggcca tgaactgctc gatctcttcc    8520
tcctggaggt ctccgcgtcc ggcgcgttcc acggtggccg ccaggtcgtt ggagatgcgc    8580
cccatgagct gcgagaaggc gttgagtccg ccctcgttcc agactcggct gtagaccacg    8640
cccccctggt catcgcgggc gcgcatgacc acctgcgcga ggttgagctc cacgtgccgc    8700
gcgaagacgg cgtagttgcg cagacgctgg aagaggtagt tgagggtggt ggcggtgtgc    8760
tcggccacga agaagttcat gacccagcgg cgcaacgtgg attcgttgat gtcccccaag    8820
gcctccagcc gttccatggc ctcgtagaag tccacggcga agttgaaaaa ctgggagttg    8880
cgcgccgaca cggtcaactc ctcctccaga agacggatga gctcggcgac ggtgtcgcgc    8940
acctcgcgct cgaaggctat ggggatctct tcctccgcta gcatcaccac ctcctcctct    9000
tcctcctctt ctggcacttc catgatggct tcctcctctt cggggggtgg cggcggcgg    9060 ggtgggggag gggcgctct gcgccggcgg cggcgcaccg ggaggcggtc cacgaagcgc    9120
gcgatcatct ccccgcggcg gcggcgcatg gtctcggtga cggcgcggcc gttctcccgg    9180
gggcgcagtt ggaagacgcc gccggacatc tggtgctggg gcgggtggcc gtgaggcagc    9240
gagacggcgc tgacgatgca tctcaacaat tgctgcgtag gtacgccgcc gagggacctg    9300
agggagtcca tatccaccgg atccgaaaac ctttcgagga aggcgtctaa ccagtcgcag    9360
tcgcaaggta ggctgagcac cgtggcgggc ggcgggggt gggggagtg tctggcggag      9420 gtgctgctga tgatgtaatt gaagtaggcg gacttgacac ggcggatggt cgacaggagc    9480
accatgtcct tgggtccggc ctgctggatg cggaggcggt cggctatgcc ccaggcttcg    9540
ttctggcatc ggcgcaggtc cttgtagtag tcttgcatga gcctttccac cggcacctct    9600
tctccttcct cttctgcttc ttccatgtct gcttcggccc tggggcggcg ccgcgccccc    9660
ctgcccccca tgcgcgtgac cccgaacccc ctgagcggtt ggagcagggc caggtcggcg    9720
acgacgcgct cggccaggat ggcctgctgc acctgcgtga gggtggtttg gaagtcatcc    9780
aagtccacga agcggtggta ggcgcccgtg ttgatggtgt aggtgcagtt ggccatgacg    9840
gaccagttga cggtctggtg gcccggttgc gacatctcgg tgtacctgag tcgcgagtag    9900
gcgcgggagt cgaagacgta gtcgttgcaa gtccgcacca ggtactggta gcccaccagg    9960
aagtgcggcg gcgctggcg gtagaggggc cagcgcaggg tggcggggc tccggggcc     10020 aggtcttcca gcatgaggcg gtggtaggcg tagatgtacc tggacatcca ggtgatacccc   10080 gcggcggtgg tggaggcgcg cgggaagtcg cgcacccggt tccagatgtt gcgcagggg    10140 agaaagtgct ccatggtagg cgtgctctgt ccagtcagac gcgcgcagtc gttgatactc    10200
tagaccaggg aaaacgaaag ccggtcagcg ggcactcttc cgtggtctgg tgaatagatc    10260
gcaagggtat catggcggag ggcctcggtt cgagccccgg gtccgggccg gacgtccgc    10320 catgatccac gcggttaccg cccgcgtgtc gaacccaggt gtgcgacgtc agacaacggt    10380
```

```
ggagtgttcc ttttggcgtt tttctggccg ggcgccggcg ccgcgtaaga gactaagccg   10440
cgaaagcgaa agcagtaagt ggctcgctcc ccgtagccgg agggatcctt gctaagggtt   10500
gcgttgcggc gaaccccggt tcgaatcccg tactcgggcc ggccggaccc gcggctaagg   10560
tgttggattg gcctcccect cgtataaaga ccccgcttgc ggattgactc cggacacggg   10620
gacgagcccc ttttattttt gctttcccca gatgcatccg gtgttgcgac agatgcgccc   10680
cccgccccag cagcagcaac aacaccagca agagcggcag caacagcagc gggagtcatg   10740 cagggcccc tcacccaccc tcggcggccc ggccacctcg gcgtccgcgg ccgtgtctgg   10800
cgcctgcggc ggcggcggcg gggggccggc tgacgacccc gaggagcccc cgcggcgcag   10860
ggccagacac tacctggacc tggaggaggg cgagggcctg gcgcggctgg gggcgccgtc   10920
tcccgagcgc cacccgcggg tgcagctaaa gcgcgactcg cgcgaggcgt acgtgcctcg   10980
gcagaacctg ttcagggacc gcgcgggcga ggagcccgag gagatgcggg acaggaggtt   11040
cagcgcgggg cggagctgc ggcaggggct gaaccgcgag cggctgctgc gcgaggagga   11100 cttttgagccc gacgcgcgga cggggatcag ccccgcgcgc gcgcacgtgg cggccgccga   11160
cctggtgacg gcgtacgagc agacggtgaa ccaggagatc aacttccaaa agagtttcaa   11220
caaccacgtg cgcacgctgg tggcgcgcga ggaggtgacc atcgggctga tgcacctgtg   11280
ggactttgtg agcgcgctgg tgcagaaccc caatagcaag cctctgacgg cgcagctgtt   11340
cctgatagtg cagcacagca gggacaacga ggcgttaggg gacgcgctgc tgaacatcac   11400
cgagcccgag ggccggtggc tgctggaccc tgattaacatc ctgcagagca tagtggtgca   11460
ggagcgcagc ctgagcctgg ccgacaaggt ggcggccatc aactactcga tgctgagcct   11520
gggcaagttt tacgcgcgca agatctacca gacgccgtac gtgcccatag acaaggaggt   11580
gaagatcgac ggtttttaca tgcgcatggc gctgaaggtg ctcaccctaa gcgacgacct   11640
gggcgtgtac cgcaacgagc gcatccacaa ggccgtgagc gtgagccggc ggcgcgagct   11700
gagcgaccgc gagctgatgc atagcctgca gcgggcgctg gcgggcgccg gcagcggcga   11760
cagggaggcg gagtcctact tcgatgcggg ggcggacctg cgctgggcgc ccagccggcg   11820
ggccctggag gccgcggggg tccgcgagga ctatgacgag gacggcgagg aggatgagga   11880
gtacgagcta gaggagggcg agtacctgga ctaaaccgcg ggtggtgttt ccggtagatg   11940
caagacccga acgtggtgga cccggcgctg cgggcggctc tgcagagcca gccgtccggc   12000
cttaactcct cagacgactg gcgacaggtc atggaccgca tcatgtcgct gacggcgcgt   12060
aacccggacg cgttccggca gcagccgcag gccaacaggc tctccgccat cctggaggcg   12120
gtggtgcctg cgcgctcgaa ccccacgcac gagaaggtgc tggccatagt gaacgcgctg   12180
gccgagaaca gggccatccg cccggacgag gccgggctgg tgtacgacgc gctgctgcag   12240
cgcgtggccc gctacaacag cggcaacgtg cagaccaacc tggaccggct ggtgggggac   12300
gtgcgcgagg cggtggcgca gcgcgagcgc gcggatcggc agggcaacct gggctccatg   12360
gtggcgctga atgccttcct gagcacgcag ccggccaacg tgccgcgggg gcaggaagac   12420
tacaccaact ttgtgagcgc gctgcggctg atggtgaccg agaccccca gagcgaggtg   12480 taccagtcgg gtccggacta cttcttccag accagcagac agggcctgca gacggtgaac   12540
ctgagccagg cttttcaagaa cctgcggggg ctgtggggcg tgaaggcgcc caccggcgac   12600
cgggcgacgg tgtccagcct gctgacgccc aactcgcgcc tgctgctgct gctgatcgcg   12660
ccgttcacgg acagcggcag cgtgtccgg gacacctacc tggggcacct gctgaccctg   12720
taccgcgagg ccatcgggca ggcgcaggtg gacgagcaca ccttccagga gatcaccagc   12780
```

```
gttagccgcg cgctggggca ggaggacacg agcagcctgg aggcgactct gaactacctg   12840
ctgaccaacc ggcggcagaa gattccctcg ctgcacagcc tgacctccga ggaggagcgc   12900
atcttgcgct acgtgcagca gagcgtgagc ctgaacctga tgcgcgacgg ggtgacgccc   12960
agtgtggcgc tggacatgac cgcgcgcaac atggaaccgg gcatgtacgc cgcgcaccgg   13020
ccttacatca accgcctgat ggactacctg catcgcgcgg cggccgtgaa ccccgagtac   13080
tttaccaacg ccatcctgaa cccgcactgg ctcccgccgc ccgggttcta cagcggggggc   13140 ttcgaggtcc cggaggccaa cgatggcttc ctgtgggacg acatggacga cagcgtgttc   13200
tccccgcggc cgcaggcgct ggcggaagcg tccctgctgc gtcccaagaa ggaggaggag   13260
gcgagtcgcc gccgcggcag cagcggcgtg gcttctctgt ccgagctggg ggcggcagcc   13320
gccgcgcgcc ccgggtccct gggcggcagc ccctttccga gcctggtggg gtctctgcac   13380
agcgagcgca ccacccgccc tcggctgctg ggcgaggacg agtacctgaa taactccctg   13440
ctgcagccgt gcgggagaa aaacctgcct cccgccttcc ccaacaacgg gatagagagc   13500
ctggtggaca agatgagcag atggaagacc tatgcgcagc agcacaggga cgcgcccgcg   13560
ctccggccgc ccacgcggcg ccagcgccac gaccggcagc gggggctggt gtgggatgac   13620
gaggactccg cggacgatag cagcgtgctg gacctgggag ggagcggcaa cccgttcgcg   13680
cacctgcgcc ccgcctggg gaggatgttt taaaaaaaaa aaaaagcaag aagcatgatg   13740
caaaaattaa ataaaactca ccaaggccat ggcgaccgag cgttggtttc ttgtgttccc   13800
ttcagtatgc ggcgcgcggc gatgtaccag gagggacctc ctccctctta cgagagcgtg   13860
gtgggcgcgg cggcggcggc gccctcttct ccctttgcgt cgcagctgct ggagccgccg   13920
tacgtgcctc cgcgctacct gcggcctacg ggggggagaa acagcatccg ttactcggag   13980
ctggcgcccc tgttcgacac caccgggtg tacctggtgg acaacaagtc ggcggacgtg   14040
gcctccctga actaccagaa cgaccacagc aatttttga ccacggtcat ccagaacaat   14100
gactacagcc cgagcgaggc cagcacccag accatcaatc tggatgaccg gtcgcactgg   14160
ggcggcgacc tgaaaaccat cctgcacacc aacatgccca acgtgaacga gttcatgttc   14220
accaataagt tcaaggcgcg ggtgatggtg tcgcgctcgc acaccaagga agaccgggtg   14280
gagctgaagt acgagtgggt ggagttcgag ctgccagagg gcaactactc cgagaccatg   14340
accattgacc tgatgaacaa cgcgatcgtg gagcactatc tgaaagtggg caggcagaac   14400
ggggtcctgg agagcgacat cggggtcaag ttcgacacca ggaacttccg cctggggctg   14460
gaccccgtga ccgggctggt tatgcccggg gtgtacacca cgaggccctt ccatcccgac   14520
atcatcctgc tgcccggctg cggggtggac ttcacttaca gccgcctgag caacctcctg   14580
ggcatccgca agcggcagcc cttccaggag ggcttcagga tcacctacga ggacctggag   14640
gggggcaaca tccccgcgct cctcgatgtg gaggcctacc aggatagctt gaaggaaaat   14700
gaggcgggac aggaggatac cgcccccgcc gcctccgccg ccgccgagca gggcgaggat   14760
gctgctgaca ccgcggccgc ggacgggggcg gaggccgacc ccgctatggt ggtggaggct   14820
gccgagcagg aggaggacat gaatgacagt gcggtgcgcg agacaccttc gtcacccgg   14880 ggggaggaaa agcaagcgga ggccgaggcc gcggccgagg aaaagcaact ggcggcagca   14940
gcggcggcgg cggcgttggc cgcggcggag gctgagtctg aggggaccaa gcccgccaag   15000
gagcccgtga ttaagcccct gaccgaagat agcaagaagc gcagttacaa cctgctcaag   15060
gacagcacca acaccgcgta ccgcagctgg tacctggcct acaactacgg cgacccgtcg   15120
```

```
acggggtgc gctcctggac cctgctgtgc acgccggacg tgacctgcgg ctcggagcag     15180
gtgtactggt cgctgcccga catgatgcaa gacccgtga ccttccgctc cacgcggcag     15240
gtcagcaact tcccggtggt gggcgccgag ctgctgcccg tgcactccaa gagcttctac     15300
aacgaccagg ccgtctactc ccagctcatc cgccagttca cctctctgac ccacgtgttc     15360
aatcgctttc ctgagaacca gattctggcg cgcccgcccg ccccaccat caccaccgtc     15420 agtgaaaacg ttcctgctct cacagatcac gggacgctac cgctgcgcaa cagcatcgga     15480
ggagtccagc gagtgaccgt tactgacgcc agacgccgca cctgcccta cgtttacaag     15540 gccttgggca tagtctcgcc gcgcgtcctt tccagccgca cttttgagc aacaccacca     15600 tcatgtccat cctgatctca cccagcaata actccggctg gggactgctg cgcgcgccca     15660
gcaagatgtt cggaggggcg aggaagcgtt ccgagcagca ccccgtgcgc gtgcgcgggc     15720
acttccgcgc ccctggga gcgcacaaac gcggccgcgc ggggcgcacc accgtggacg     15780
acgccatcga ctcggtggtg gagcaggcgc gcaactacag gcccgcggtc tctaccgtgg     15840
acgcggccat ccagaccgtg gtgcggggcg cgcggcggta cgccaagctg aagagccgcc     15900
ggaagcgcgt ggcccgccgc caccgccgcc gacccggggc cgccgccaaa cgcgccgccg     15960
cggccctgct tcgccgggcc aagcgcacgg ccgccgcgc cgccatgagg gccgcgcgcc     16020
gcttggccgc cggcatcacc gccgccacca tggcccccg tacccgaaga cgcgcggccg     16080
ccgccgccgc cgccgccatc agtgacatgg ccagcaggcg ccggggcaac gtgtactggg     16140
tgcgcgactc ggtgaccggc acgcgcgtgc ccgtgcgctt ccgcccccg cggacttgag     16200 atgatgtgaa aaacaacac tgagtctcct gctgttgtgt gtatcccagc ggcggcggc     16260 gcgcgcgcag cgtcatgtcc aagcgcaaaa tcaaagaaga gatgctccag gtcgtcgcgc     16320
cggagatcta tgggcccccg aagaaggaag agcaggattc gaagcccgc aagataaagc     16380 gggtcaaaaa gaaaagaaa gatgatggcg atgccgatgg ggaggtggag ttcctgcgcg     16440
ccacggcgcc caggcgcccg gtgcagtgga agggccggcg cgtaaagcgc gtcctgcgcc     16500
ccggcaccgc ggtggtcttc acgcccggcg agcgctccac ccggactttc aagcgcgtct     16560
atgacgaggt gtacgcgac gaagacctgc tggagcaggc caacgagcgc ttcggagagt     16620
ttgcttacgg gaagcgtcag cggccgctgg ggaaggagga cctgctggcg ctgccgctgg     16680
accagggcaa cccccacccc agtctgaagc ccgtgaccct gcagcaggtg ctgccgagca     16740
gcgcaccctc cgaggcgaag cggggtctga agcgcgaggg cggcgacctg cgcccaccg     16800 tgcagctcat ggtgcccaag cggcagaggc tggaggatgt gctggagaaa atgaaagtag     16860
accccggtct gcagccggac atcagggtcc gtcccatcaa gcaggtggcg ccgggcctcg     16920
gcgtgcagac cgtggacgtg gtcatcccca ccggcaactc ccccgccgcc accaccacta     16980
ccgctgcctc cacggacatg gagacacaga ccgatcccgc cgcagccgcc gccaccgccg     17040
ccgccgcgac ctcctcggcg gaggtgcaga cggacccctg gctgccgccg gcgatgtcag     17100
ctcccccgcg cgcgtcgcggg cgcaggaagt acggcgccgc caacgcgctc ctgcccgagt     17160
acgccttgca tccttccatc gcgcccaccc ccggctaccg aggctatacc taccgcccgc     17220
gaagagccaa gggttccacc cgccgtcccc gccgacgcgc cgccgccacc acccgccgcc     17280
gccgccgcag acgccagccc gcactggctc cagtctccgt gaggagagtg gcgcgcgacg     17340
gacacaccct ggtgctgccc agggcgcgct accacccag catcgtttaa aagcctgttg     17400
tggttcttgc agatatggcc ctcacttgcc gcctccgttt cccggtgccg ggataccgag     17460
gaggaagatc gcgccgcagg aggggtctgg ccggccgcgg cctgagcgga ggcagccgcc     17520
```

```
gcgcgcaccg gcggcgacgc gccaccagcc gacgcatgcg cggcggggtg ctgcccctgt   17580 taatcccct  gatcgccgcg gcgatcggcg ccgtgcccgg gatcgcctcc gtggccttgc   17640
aggcgtccca gaggcattga cagacttgca aacttgcaaa tatggaaaaa aaccccaata   17700
aaaaagtcta gactctcacg ctcgcttggt cctgtgacta ttttgtagaa tggaagacat   17760
caactttgcg tcgctggccc cgcgtcacgg ctcgcgcccg ttcctgggac actggaacga   17820
tatcggcacc agcaacatga gcggtggcgc cttcagttgg ggctctctgt ggagcggcat   17880
taaaagtatc gggtctgccg ttaaaaatta cggctcccgg gcctggaaca gcagcacggg   17940
ccagatgttg agagacaagt tgaaagagca gaacttccag cagaaggtgg tggagggcct   18000
ggcctccggc atcaacgggg tggtggacct ggccaaccag gccgtgcaga taagatcaa   18060 cagcagactg gaccccggc cgccggtgga ggaggtgccg ccggcgctgg agacggtgtc   18120
ccccgatggg cgtggcgaga agcgcccgcg gcccgatagg aagagacca ctctggtcac   18180 gcagaccgat gagccgcccc cgtatgagga ggccctgaag caaggtctgc ccaccacgcg   18240
gcccatcgcg cccatggcca ccggggtggt gggccgccac accccgcca cgctggactt   18300 gcctccgccc gccgatgtgc cgcagcagca gcagaaggcg gcacagccgg gcccgcccgt   18360
gaccgcctcc cgttcctccg ccggtcctct gcgccgcgcg gccagcggcc ccgcgggggg   18420
ggtcgcgagg cacggcaact ggcagagcac gctgaacagc atcgtgggtc tgggggtgcg   18480
gtccgtgaag cgccgccgat gctactgaat agcttagcta acgtgttgta tgtgtgtatg   18540
cgccctatgt cgccgccaga ggagctgctg agtcgccgcc gttcgcgcgc ccaccaccac   18600
caccgccact ccgcccctca agatggcgac cccatcgatg atgccgcagt ggtcgtacat   18660
gcacatctcg ggccaggacg cctcggagta cctgagcccc gggctggtgc agttcgcccg   18720
cgccaccgag agctacttca gcctgagtaa caagtttagg aaccccacgg tggcgcccac   18780
gcacgatgtg accaccgacc ggtctcagcg cctgacgctg cggttcattc ccgtggaccg   18840
cgaggacacc gcgtactcgt acaaggcgcg gttcaccctg gccgtgggcg acaaccgcgt   18900
gctggacatg gcctccacct actttgacat ccgcggggtg ctggaccggg gccccacttt   18960
caagccttac tctggcaccg cctacaactc cctggccccc aagggcgctc ccaactcctg   19020
cgagtgggag caattagaag aagcccaggc cgctgtggaa gacgaagaat tagaagatga   19080
agacgaggaa ccacaggatg aggcacctgt gaaaaaaacc catgtatacg ctcaggctcc   19140
cctttctgga gaagaaatta ctaaaaacgg tttgcaaata gggtcagata cacagaagc   19200 ccagtctaag cccatatatg cagatcctac attccagcct gaaccccaaa tcggggaatc   19260
ccagtggaat gaggcagatg ctacagttgc cggcggtaga gtgctaaaga aatccactcc   19320
catgaagcca tgctatggtt cctatgcaag acccacaaac tccaatggag tcaaggtgt   19380 gctggtggct gatgataagg gggttcttca atctaaagtt gaattgcaat tttttttcaaa   19440 tactactact cttaatcagc gggagggtaa cgatacaaaa ccaaaagtgg tgctgtatag   19500
cgaagatgtg cacatggaaa ctccagacac ccacatttct tacaagccca caaaaagcga   19560
tgacaattca aaaatcatgc tgggtcagca gtccatgccc aacagaccta attacatcgg   19620
cttcagagac aactttatcg gcctcatgta ttacaatagc actggcaaca tgggagtgct   19680
tgcaggtcag gcctctcagt tgaatgcagt ggtggacttg caagacagaa acacagaact   19740
gtcctaccag ctcttgcttg attccatggg tgacagaacc agatacttt ccatgtggaa   19800 tcaggcagtg gacagttatg acccagatgt cagaattatt gaaaatcatg gaactgaaga   19860
```

-continued

```
cgagctcccc aactattgtt tccctctggg cggcataggg gtaactgaca cttaccaggc    19920
cattaaaacc aatggcaatg gtcaagaaaa cccaacctgg gaaaagata cagagtttgc    19980
agaccgcaat gaaatagggg tgggaaacaa tttcgctatg gagatcaacc tcagtgccaa    20040
cctgtggaga aacttcctgt actccaacgt ggcgctgtac ctgccagaca agcttaagta    20100
caacccctcc aatgtggaca tctctgacaa ccccaacacc tacgattaca tgaacaagcg    20160
agtggtggcc ccggggctgg tggactgcta catcaacctg ggcgcgcgct ggtcgctgga    20220
ctacatggac aacgtcaacc ccttcaacca ccaccgcaat gcgggcctgc gctaccgctc    20280
catgctcctg gcaacgggc gctacgtgcc cttccacatc caggtgcccc agaagttctt    20340
tgccatcaag aacctcctcc tcctgccggg ctcctacacc tacgagtgga acttcaggaa    20400
ggatgtcaac atggtcctcc agagctctct gggtaacgat ctcagggtgg acggggccag    20460
catcaagttc gagagcatct gcctctacgc caccttcttc cccatggccc acaacacggc    20520
ctccacgctc gaggccatgc tcaggaacga caccaacgac cagtccttca atgactacct    20580
ctccgccgcc aacatgctct accccatacc cgccaacgcc accaacgtcc ccatctccat    20640
cccctcgcgc aactgggcgg ccttccgcgg ctgggccttc acccgcctca agaccaagga    20700
gacccctcc ctgggctcgg gattcgaccc ctactacacc tactcgggct ccattcccta    20760
cctggacggc accttctacc tcaaccacac tttcaagaag gtctcggtca ccttcgactc    20820
ctcggtcagc tggccgggca acgaccgtct gctcaccccc aacgagttcg aaatcaagcg    20880
ctcggtcgac ggggagggct acaacgtggc ccagtgcaac atgaccaagg actggttcct    20940
ggtccagatg ctggccaact acaacatcgg ctaccagggc ttctacatcc cagagagcta    21000
caaggacagg atgtactcct tcttcaggaa cttccagccc atgagccggc aggtggtgga    21060
ccagaccaag tacaaggact accaggaggt gggcatcatc caccagcaca caactcggg    21120
cttcgtgggc tacctcgccc ccaccatgcg cgagggacag gcctaccccg ccaacttccc    21180
ctacccgctc ataggcaaga ccgcggtcga cagcatcacc cagaaaaagt tcctctgcga    21240
tcgcacccct tggcgcatcc ccttctccag caacttcatg tccatgggtg cgctctcgga    21300
cctgggccag aacttgctct acgccaactc cgcccacgcc ctcgacatga ccttcgaggt    21360
cgaccccatg gacgagccca cccttctcta tgttctgttc gaagtctttg acgtggtccg    21420
ggtccaccag ccgcaccgcg cgtcatcga gaccgtgtac ctgcgtacgc ccttctcggc    21480
cggcaacgcc accacctaaa gaagcaagcc gcagtcatcg ccgcctgcat gccgtcgggt    21540
tccaccgagc aagagctcag ggccatcgtc agagacctgg gatgcgggcc ctatttttg    21600
ggcactttcg acaagcgctt ccctggcttt gtctccccac acaagctggc ctgcgccatc    21660
gtcaacacgg ccggccgcga gaccgggggc gtgcactggc tggccttcgc ctggaacccg    21720
cgctccaaaa catgcttcct ctttgacccc ttcggctttt cggaccagcg gctcaagcaa    21780
atctacgagt tcgagtacga gggcttgctg cgtcgcagcg ccatcgcctc ctcgcccgac    21840
cgctgcgtca ccctcgaaaa gtccacccag accgtgcagg ggcccgactc ggccgcctgc    21900
ggtctcttct gctgcatgtt tctgcacgcc tttgtgcact ggcctcagag tcccatggac    21960
cgcaacccca ccatgaactt gctgacgggg gtgcccaact ccatgctcca gagccccag    22020
gtcgagccca ccctgcgccg caaccaggag cagctctaca gcttcctgga gcgccactcg    22080
ccctacttcc gccgccacag cgcacagatc aggagggcca cctccttctg ccacttgcaa    22140
gagatgcaag aagggtaata acgatgtaca cactttttc tcaataaatg gcatttttt    22200
atttatacaa gctctctggg gtattcattt cccaccacca ccaccaccg ccgttgtcgc    22260
```

```
catctggctc tatttagaaa tcgaaagggt tctgccggga gtcgccgtgc gccacgggca    22320
gggacacgtt gcgatactgg tagcgggtgc cccacttgaa ctcgggcacc accaggcgag    22380
gcagctcggg gaagttttcg ctccacaggc tgcgggtcag caccagcgcg ttcatcaggt    22440
cgggcgccga gatcttgaag tcgcagttgg ggccgccgcc ctgcgcgcgc gagttgcggt    22500
acaccgggtt gcagcactgg aacaccaaca gcgccgggtg cttcacgcta gccagcacgc    22560
tgcggtcgga gatcagctcg gcgtccaggt cctccgcgtt gctcagcgcg aacgggtca    22620
tcttgggcac ttgcctcccc aggaagggcg cgtgccccgg tttcgagttg cagtcgcagc    22680
gcagcgggat cagcaggtgc ccatgccgg actcggcgtt ggggtacagc gcgcgcatga    22740
aggcctgcat ctggcggaag gccatctggg ccttggcgcc ctccgagaag aacatgccgc    22800
aggacttgcc cgagaactgg tttgcggggc agctggcgtc gtgcaggcag cagcgcgcgt    22860
cggtgttggc gatctgcacc acgttgcgcc cccaccggtt cttcacgatc ttggccttgg    22920
acgattgctc cttcagcgcg cgctgcccgt tctcgctggt cacatccatc tcgatcacat    22980
gttccttgtt caccatgctg ctgccgtgca ggcacttcag ctcgccctcc gtctcggtgc    23040
agcggtgctg ccacagcgcg cagcccgtgg gctcgaaaga cttgtaggtc acctccgcga    23100
aggactgcag gtacccctgc aaaaagcggc ccatcatggt cacgaaggtc ttgttgctgc    23160
tgaaggtcag ctgcagcccg cggtgctcct cgttcagcca ggtcttgcac acggccgcca    23220
gcgcctccac ctggtcgggc agcatcttga agttcacctt cagctcattc tccacgtggt    23280
acttgtccat cagcgtgcgc gccgcctcca tgcccttctc ccaggccgac accagcggca    23340
ggctcacggg gttcttcacc atcaccgtgg ccgccgcctc cgccgcgctt tcgctttccg    23400
ccccgctgtt ctcttcctct tcctcctctt cctcgccgcc gcccactcgc agccccgca    23460
ccacggggtc gtcttcctgc aggcgctgca ccttgcgctt gccgttgcgc ccctgcttga    23520
tgcgcacggg cgggttgctg aagcccacca tcaccagcgc ggcctcttct tgctcgtcct    23580
cgctgtccag aatgacctcc ggggaggggg ggttggtcat cctcagtacc gaggcacgct    23640
tctttttctt cctgggggcg ttcgccagct ccgcggctgc ggccgctgcc gaggtcgaag    23700
gccgagggct gggcgtgcgc ggcaccagcg cgtcctgcga gccgtcctcg tcctcctcgg    23760
actcgagacg gaggcgggcc cgcttcttcg ggggcgcgcg gggcggcgga ggcggcggcg    23820
gcgacggaga cggggacgag acatcgtcca gggtgggtgg acggcgggcc gcgccgcgtc    23880
cgcgctcggg ggtggtctcg cgctggtcct cttcccgact ggccatctcc cactgctcct    23940
tctcctatag gcagaaagag atcatggagt ctctcatgcg agtcgagaag gaggaggaca    24000
gcctaaccgc cccctctgag ccctccacca ccgccgccac caccgccaat gccgccgcgg    24060
acgacgcgcc caccgagacc accgccagta ccaccnnnct ccccagcgac gcaccccgc    24120
tcgagaatga agtgctgatc gagcaggacc cgggttttgt gagcggagag gaggatgagg    24180
tggatgagaa ggagaaggag gaggtcgccg cctcagtgcc aaaagaggat aaaaagcaag    24240
accaggacga cgcagataag gatgagacag cagtcgggcg ggggaacgga agccatgatg    24300
ctgatgacgg ctacctagac gtgggagacg acgtgctgct taagcacctg caccgccagt    24360
gcgtcatcgt ctgcgacgcg ctgcaggagc ggtgcgaagt gccctggac gtggcggagg    24420
tcagccgcgc ctacgagcgg cacctcttcg cgccgcacgt gccccccaag cgccgggaga    24480
acggcacctg cgagcccaac ccgcgtctca acttctaccc ggtcttcgcg gtacccgagg    24540
tgctggccac ctaccacatc ttttttccaaa actgcaagat ccccctctcc tgccgcgcta    24600
```

-continued

```
accgcacccg cgccgacaaa accctgaccc tgcggcaggg cgcccacata cctgatattg   24660
cctctctgga ggaagtgccc aagatcttcg agggtctcgg tcgcgacgag aaacgggcgg   24720
cgaacgctct gcacggagac agcgaaaacg agagtcactc gggggtgctg gtggagctcg   24780
agggcgacaa cgcgcgcctg gccgtactca agcgcagcat agaggtcacc cactttgcct   24840
acccggcgct caacctgccc cccaaggtca tgagtgtggt catgggcgag ctcatcatgc   24900
gccgcgccca gccctggcc gcggatgcaa acttgcaaga gtcctcagag gaaggcctgc   24960
ccgcggtcag cgacgagcag ctggcgcgct ggctggagac ccgcgacccc gcgcagctgg   25020
aggagcggcg caagctcatg atggccgcgg tgctggtcac cgtggagctc gagtgtctgc   25080
agcgcttctt cgcggacccc gagatgcagc gcaagctcga ggagaccctg cactacacct   25140
tccgccaggg ctacgtgcgc caggcctgca agatctccaa cgtggagctc tgcaacctgg   25200
tctcctacct gggcatcctg cacgagaacc gcctcgggca gaacgtcctg cactccaccc   25260
tcaaagggga ggcgcgccgc gactacatcc gcgactgcgc ctacctcttc ctctgctaca   25320
cctggcagac ggccatgggg gtctggcagc agtgcctgga ggagcgcaac ctcaaggagc   25380
tggaaaagct cctcaagcgc accctcaggg acctctggac gggcttcaac gagcgctcgg   25440
tggccgccgc gctggcggac atcatcttcc ccgagcgcct gctcaagacc ctgcagcagg   25500
gcctgcccga cttcaccagc cagagcatgc tgcagaactt caggactttc atcctggagc   25560
gctcgggcat cctgccggcc acttgctgcg cgctgcccag cgacttcgtg cccatcaagt   25620
acagggagtg cccgccgccg ctctggggcc actgctacct cttccagctg gccaactacc   25680
tcgcctacca ctcggacctc atggaagacg tgagcggcga gggcctgctc gagtgccact   25740
gccgctgcaa cctctgcacg ccccaccgct ctctagtctg caacccgcag ctgctcagcg   25800
agagtcagat tatcggtacc ttcgagctgc agggtccctc gcctgacgag aagtccgcgg   25860
ctccggggct gaaactcact ccggggctgt ggacttccgc ctacctacgc aaatttgtac   25920
ctgaggacta ccacgcccac gagatcaggt tctacgaaga ccaatcccgc cgcccaagg   25980 cggagctcac cgcctgcgtc atcacccagg ggcacatcct gggccaattg caagccatca   26040
acaaagcccg ccgagagttc ttgctgaaaa agggtcgggg ggtgtacctg gaccccagt   26100 ccggcgagga gctaaacccg ctaccccgc cgccgcccca gcagcgggac cttgcttccc   26160
aggatggcac ccagaaagaa gcagcagccg ccgccgcagc catacatgct tctggaggaa   26220
gaggaggagg actgggacag tcaggcagag gagatgatgg aagactggga ggaggacagc   26280
agcctagacg aggaagcttc agaggccgaa gaggtggcag acgcaacacc atcaccctcg   26340
gtcgcagccc cctcgccggg gcccctgaaa tcctccgaac ccagcaccag cgctataacc   26400
tccgctcctc cggcgccggc gccacccgcc gcagaccca accgtagatg ggacaccaca   26460
ggaaccgggg tcggtaagtc caagtgcccg ccgccgccac cgcagcagca gcagcagcag   26520
cgccagggct accgctcgtg gcgcgggcac aagaacgcca tagtcgcctg cttgcaagac   26580 tgcggggca acatctcttt cgcccgccgc ttcctgctat tccaccacgg ggtcgccttt   26640
ccccgcaatg tcctgcatta ctaccgtcat ctctacagcc cctactgcag cggcgaccca   26700
gaggcggcag cggcagccac agcggcgacc accacctagg aagatatcct ccgcgggcaa   26760
gacagcggca gcagcggcca ggagacccgc ggcagcagcc gcgggagcgg tgggcgcact   26820
gcgcctctcg cccaacgaac ccctctcgac ccgggagctc agacacagga tcttccccac   26880
tttgtatgcc atcttccaac agagcagagg ccaggagcag gagctgaaaa taaaaaacag   26940
atctctgcgc tccctcaccc gcagctgtct gtatcacaaa agcgaagatc agcttcggcg   27000
```

```
cacgctggag gacgcggagg cactcttcag caaatactgc gcgctcactc ttaaagacta   27060
gctccgcgcc cttctcgaat ttaggcggga gaaaactacg tcatcgccgg ccgccgccca   27120
gcccgcccag ccgagatgag caaagagatt cccacgccat acatgtggag ctaccagccg   27180
cagatgggac tcgcggcggg agcggcccag gactactcca cccgcatgaa ctacatgagc   27240
gcgggacccc acatgatctc acaggtcaac gggatccgcg cccagcgaaa ccaaatactg   27300
ctggaacagg cggccatcac cgccacgccc cgccataatc tcaaccccg aaattggccc    27360 gccgccctag tgtaccagga aaccccctcc gccaccaccg tactacttcc gcgtgacgcc   27420
caggccgaag tccagatgac taactcaggg gcgcagctcg cgggcggctt tcgtcacggg   27480
gcgcggccgc tccgaccagg tataagacac ctgatgatca gaggccgagg tatccagctc   27540
aacgacgagt cggtgagctc ttcgctcggt ctccgtccgg acggaactt ccagctcgcc     27600 ggatccggtc gctcttcgtt cacgccccgc caggcgtacc tgactctgca gacctcgtcc   27660
tcggagcccc gctccggcgg catcggaacc ctccagttcg tggaggagtt cgtgccctcg   27720
gtctacttca acccccttctc gggacctccc ggacgctacc ccgaccagtt cattccgaac   27780
tttgacgcgt tgaaggactc ggcggacggc tacgactgaa tgtcaggtgc cgaggcagag   27840
cagcttcgcc tgagacacct cgagcactgc cgccgccaca agtgcttcgc ccgcggttcc   27900
ggtgagttct gctactttca gctacccgag gagcataccg aggggccggc gcacggcgtc   27960
cgcctgacca cccagggcga ggttacctgt tccctcatcc gggagttcac cctccgtccc   28020
ctgctagtgg agcgggagcg gggtccctgt gtcctaacta tcgcctgcaa ctgccctaac   28080
cctggattac atcaagatct ttgctgtcat ctctgtgctg agtttaataa acgctgagat   28140
cagaatctac tggggctcct gtcgccatcc tgtgaacgcc accgtcttca cccacccccga 28200 ccaggcccag gcgaacctca cctgcggtct gcatcggagg tccaagaagt acctcacctg   28260
gtacttcaac ggcacccccct ttgtggttta caacagcttc gacggggacg gagtctccct  28320
gaaagaccag ctctccggtc tcagctactc catccacaag aacaccaccc tccaactctt   28380
ccctccctac ctgccgggaa cctacgagtg cgtcaccggc cgctgcaccc acctcacccg   28440
cctgatcgta aaccagagct ttccgggaac agataactcc ctcttcccca gaacaggagg   28500
tgagctcagg aaactccccg gggaccaggg cggagacgta ccttcgaccc ttgtggggtt   28560
aggatttttt attaccgggt tgctggctct tttaatcaaa gcttccttga gatttgttct   28620
ttccttctac gtgtatgaac acctcagcct ccaataactc tacccctttct tcgggatcag   28680 gtgacttttc tgaaatcggg cttggtgtgc tgcttactct gttgattttt ttccttatca   28740
tactcagcct tctgtgcctc aggctcgccg cctgctgcgc acacatctat atctactgct   28800
ggttgctcaa gtgcaggggt cgccacccaa gatgaacagg tacatggtcc tatcgatcct   28860
aggcctgctg gccctggcgg cctgcagcgc cgccaaaaaa gagattacct tgaggagcc    28920 cgcttgcaat gtaactttca gcccgagggg tgaccaatgc accaccctcg tcaaatgcgt   28980
taccaatcat gagaagctgc gcatcgacta caaaaacaaa actggccggt ttgcggtcta   29040
tagtgtgttt acgcccggag accccctcaa ctactctgtc accgtcttcc agggcggaca   29100
gtctaagata ttcaattaca ctttccctt ttatgagttg tgcgatgcgg tcatgtacat    29160
gtcaaaacag tacaacctgt ggcctccctc tccccaggcg tgtgtggaaa atactgggtc   29220
ttactgctgt atggctttgg caatcactac gctcgctcta atctgcacgg tgctatatat   29280
aaaattcagg cagaggcgaa tctttatcga tgaaaagaaa atgccttgat cgctaacacc   29340
```

```
ggctttctat ctgcagaatg aatgcaatca cctccctact aatcaccacc accctccttg   29400
cgattgccca tgggttgaca cgaatcgaag tgccagtggg gtccaatgtc accatggtgg   29460
gccccgccgg caattccacc ctcatgtggg aaaaatttgt ccgcaatcaa tgggttcatt   29520
tctgctctaa ccgaatcagt atcaagccca gagccatctg cgatgggcaa aatctaactc   29580
tgatcaatgt gcaaatgatg gatgctgggt actattacgg gcagcgggga gaaatcatta   29640
attactggcg accccacaag gactacatgc tgcatgtagt cgaggcactt cccactacca   29700
cccccactac cacctctccc accaccacta ccactactac tactactact accactaccg   29760
ctgcccgcca tacccgcaaa agcaccatga ttagcacaaa gccccctcgt gctcactccc   29820
acgccggcgg gccatcggt gcgacctcag aaaccaccga gctttgcttc tgccaatgca   29880
ctaacgccag cgctcatgaa ctgttcgacc tggagaatga ggatgcccag cagagctccg   29940
cttgcctgac ccaggaggct gtggagcccg ttgccctgaa gcagatcggt gattcaataa   30000
ttgactcttc ttcttttgcc actcccgaat accctcccga ttctactttc cacatcacgg   30060
gtaccaaaga ccctaacctc tctttctacc tgatgctgct gctctgtatc tctgtggtct   30120
cttccgcgct gatgttactg gggatgttct gctgcctgat ctgccgcaga aagagaaaag   30180
ctcgctctca gggccaacca ctgatgccct tcccctaccc cccggatttt gcagataaca   30240
agatatgagc tcgctgctga cactaaccgc tttactagcc tgcgctctaa cccttgtcgc   30300
ttgcgactcg agattccaca atgtcacagc tgtggcagga gaaaatgtta ctttcaactc   30360
cacggccgat acccagtggt cgtggagtgg ctcaggtagc tacttaacta tctgcaatag   30420
ctccacttcc cccagcatat ccccaaccaa gtaccaatgc aatgccagcc tgttcaccct   30480
catcaacgct tccaccctgg acaatggact ctatgtaggc tatgtaccct ttggtgggca   30540
aggaaagacc cacgcttaca acctggaagt tcgccagccc agaaccacta cccaagctwc   30600
ymccaycacc agcaccagca gcagcagcca cagcagcagc agcagattat tgactttggt   30660
tttggccagc tcatctgccg ctacccaggc catctacagc tctgtgcccg aaaccactca   30720
gacccaccgc ccagaaacga ccaccgccac caccctacac acctccagcg atcagatgcc   30780
gaccaacatc ccccccttgg ctcttcaaat gggacttaca agcccactc caaaaccagt   30840
ggatgcggcc gaggtctccg ccctcgtcaa tgactgggcg gggctgggaa tgtggtggtt   30900
cgccataggc atgatggcgc tctgcctgct tctgctctgg ctcatctgct gcctccaccg   30960
caggcgagcc agacccccca tctatagacc catcattgtc ctgaaccccg ataatgatgg   31020
gatccataga ttggatggcc tgaaaaacct acttttttct tttacagtat gataaattga   31080
gacatgcctc gcattttctt gtacatgttc cttctcccac cttttctggg gtgttctacg   31140
ctggccgctg tgtctcacct ggaggtagac tgcctctcac ccttcactgt ctacctgctt   31200
tacggattgg tcaccctcac tctcatctgc agcctaatca cagtaatcat cgccttcatc   31260
cagtgcattg attacatctg tgtgcgcctc gcatacttca gacaccaccc gcagtaccga   31320
gacaggaaca ttgcccaact tctaagactg ctctaatcat gcataagact gtgatctgcc   31380
ttctgatcct ctgcatcctg cccacccctca cctcctgcca gtacaccaca aaatctccgc   31440
gcaaaagaca tgcctcctgc cgcttcaccc aactgtggaa tatacccaaa tgctacaacg   31500
aaaagagcga gctctccgaa gcttggctgt atgggggtcat ctgtgtctta gttttctgca   31560
gcactgtctt tgccctcatg atctacccct actttgattt gggatggaac gcgatcgatg   31620
ccatgaatta ccccaccttt cccgcacccg agataattcc actgcgacaa gttgtacccg   31680
ttgtcgttaa tcaacgcccc ccatcccta cgcccactga aatcagctac tttaacctaa   31740
```

```
caggcggaga tgactgacgc cctagatcta gaaatggacg gcatcagtac cgagcagcgt   31800
ctcctagaga ggcgcaggca ggcggctgag caagagcgcc tcaatcagga gctccgagat   31860
ctcgttaacc tgcaccagtg caaaagaggc atcttttgtc tggtaaagca ggccaaagtc   31920
acctacgaga agaccggcaa cagccaccgc ctcagttaca aattgcccac ccagcgccag   31980
aagctggtgc tcatggtggg tgagaatccc atcaccgtca cccagcactc ggtagagacc   32040 gagggggtgtc tgcactcccc ctgtcggggt ccagaagacc tctgcaccct ggtaaagacc   32100
ctgtgcggtc tcagagattt agtcccctttt aactaatcaa acactggaat caataaaaag   32160
aatcacttac ttaaaatcag acagcaggtc tctgtccagt ttattcagca gcacctcctt   32220
cccctcctcc caactctggt actccaaacg ccttctggcg gcaaacttcc tccacaccct   32280
gaagggaatg tcagattctt gctcctgtcc ctccgcaccc actatcttca tgttgttgca   32340
gatgaagcgc accaaaacgt ctgacgagag cttcaacccc gtgtacccct atgacacgga   32400
aagcggccct ccctccgtcc ctttcctcac ccctccctttc gtgtctcccg atggattcca   32460
agaaagtccc cccggggtcc tgtctctgaa cctggccgag cccctggtca cttcccacgg   32520
catgctcgcc ctgaaaatgg gaagtggcct ctccctggac gacgctggca acctcacctc   32580
tcaagatatc accaccgcta gccctccct caaaaaaacc aagaccaacc tcagcctaga   32640
aacctcatcc cccctaactg tgagcacctc aggcgccctc accgtagcag ccgccgctcc   32700
cctggcggtg gccggcacct ccctcaccat gcaatcagag gcccccctga cagtacagga   32760
tgcaaaactc accctggcca ccaaaggccc cctgaccgtg tctgaaggca aactggcctt   32820
gcaaacatcg gccccgctga cggccgctga cagcagcacc ctcaccgtta gcgccacacc   32880
accaattaat gtaagcagtg gaagttagg cttagacatg gaagaccta tgtatactca   32940 caatggaaaa ctgggaataa gaattggggg tccactaaga gtagtagaca gcttgcatac   33000
actcactgta gttaccggaa atggactaac tgtagataac aatgccctcc aaactaaagt   33060
tacgggcgcc ctaggttatg acacatcagg aaatctacaa ttaagagctg caggaggtat   33120
gcgaattgac gcaaatggcc aacttatcct taatgtggca tacccatttg atgctcagaa   33180
caatctcagc cttagacttg gtcagggacc cctgtatata aacacagacc acaacctgga   33240
tttgaattgc aacagaggtc taaccacaac taccaccaac aacacaaaaa aacttgagac   33300
taaaattagc tcaggcttag actatgacac caatggtgct gtcattatta aacttggcac   33360
tggtctaagc ttcgacaaca caggcgcccct aactgtggga acactggtg atgataaact   33420 gactctgtgg acgaccccag acccatctcc aaattgcaga attcactcag acaaagactg   33480
caagtttact ctagtcctaa ctaagtgtgg aagccaaatc ctggcctctg tcgccgccct   33540
agcggtatca ggaaatctgg cttcgataac aggcaccgtt gccagcgtta ccatctttct   33600
cagatttgat cagaatggag tgcttatgga aaactcctcg ctagacaggc agtactggaa   33660
cttcagaaat ggcaactcaa ctaacgctgc ccctacacc aatgcagttg ggttcatgcc   33720
aaacctcgca gcatacccca aaacgcaaag ccagactgct aaaacaaca ttgtaagtca   33780 ggtttacttg aatggagaca atccaaacc catgacccttt accatcaccc tcaatggaac   33840
taatgaatcc agtgaaacta gccaggtgag tcactactcc atgtcattta catgggcttg   33900
ggaaagtggg caatatgcca ctgaaacctt tgccaccaac tccttcacct tttcttacat   33960
tgctgaacaa taaaaagcat gacactgatg ttcatttctg attcttatttt tattattttc   34020 aaacacaaca aaatcattca agtcattctt ccatcttagc ttaatagaca cagtagctta   34080
```

```
atagacccag tagtgcaaag ccccattcta gcttatagat cagacagtga taattaacca    34140
ccaccaccac catacctttt gattcaggaa atcatgatca tcacaggatc ctagtcttca    34200
ggccgccccc tccctcccaa gacacagaat acacagtcct ctcccccga ctggctttaa     34260 ataacaccat ctggttggtc acagacatgt tcttagggt tatattccac acggtctcct     34320
gccgcgccag gcgctcgtcg gtgatgttga taaactctcc cggcagctcg ctcaagttca    34380
cgtcgctgtc cagcggctga acctccggct gacgcgataa ctgtgcgacc ggctgctgga    34440
caaacggagg ccgcgcctac aaggggtag agtcataatc ctcggtcagg atagggcggt     34500
gatgcagcag cagcgagcga aacatctgct gccgccgccg ctccgtccgg caggaaaaca    34560
acacgccggt ggtctcctcc gcgataatcc gcaccgcccg cagcatcagc ttcctcgttc    34620
tccgcgcgca gcacctcacc ctgatctcgc tcaagtcggc gcagtaggta cagcacagca    34680
ccacgatgtt attcatgatc ccacagtgca gggcgctgta tccaaagctc atgccgggaa    34740
ccaccgcccc cacgtggcca tcgtaccaca agcgcacgta aattaagtgt cgaccctca    34800 tgaacgtgct ggacacaaac attacttcct tgggcatgtt gtaattcacc acctcccggt    34860
accagataaa cctctggtta aacagggcac cttccaccac catcctgaac caagaggcca    34920
gaacctgccc accggctatg cactgcaggg aacccgggtt ggaacaatga caatgcagac    34980
tccaaggctc gtaaccgtgg atcatccggc tgctgaaggc atcgatgttg gcacaacaca    35040
gacacacgtg catgcacttt ctcatgatta gcagctcttc cctcgtcagg atcatatccc    35100
aaggaataac ccattcttga atcaacgtaa acccacaca gcagggaagg cctcgcacat     35160
aactcacgtt gtgcatggtc agcgtgttgc attccgaaaa cagcggatga tcctccagta    35220
tcgaggcgcg ggtctccttc tcacaggag gtaaagggtc cctgctgtac ggactgcgcc     35280
gggacgaccg agatcgtgtt gagcgtagtg tcatggaaaa gggaacgccg gacgtggtca    35340
tacttcttga agcagaacca ggttcgcgcg tggcaggcct ccttgcgtct gcggtctcgc    35400
cgtctagctc gctccgtgtg atagttgtag tacagccact cccgcagagc gtcgaggcgc    35460
accctggctt ccggatctat gtagactccg tcttgcaccg cggccctgat aatatccacc    35520
accgtagaat aagcaacacc cagccaagca atacactcgc tctgcgagcg gcagacagga    35580
ggagcgggca gagatgggag aaccatgata aaaaacttttt tttaaagaat attttccaat    35640
tcttcgaaag taagatctat caagtggcag cgctcccctc cactggcgcg gtcaaactct    35700
acggccaaag cacagacaac ggcatttcta agatgttcct taatggcgtc caaaagacac    35760
accgctctca agtcgcagta aactatgaat gaaaacccat ccggctgatt ttccaatata    35820
gacgcgccgg cggcgtccac caaacccaga taatttttctt ctctccagcg gtttagaatc    35880
tgtctaagca aatcccttat atcaagtccg gccatgccaa aaatctgctc aagagcgccc    35940
tccaccttca tgaccaagca gcgcatcatg attgcaaaaa ttcaggttct tcagagacct    36000
gtataagatt caaaatggga acattaacaa aaattcctct gtcgcgcaga tcccttcgca    36060
gggcaagctg aacataatca gacaggtctg aacggaccag tgaggccaaa tccccaccag    36120
gaaccagatc cagagaccct atactgatta tgacgcgcat actcggggct atgctgacca    36180
gcgtagcgcc gatgtaggcg tgctgcatgg gcggcgagat aaaatgcaaa gtgctggtta    36240
aaaaatcagg caaagcctcg cgcaaaaaag ctaacacatc ataatcatgc tcatgcaggt    36300
agttgcaggt aagctcagga accaaaacgg aataacacac gattttcctc tcaaacatga    36360
cttcgcggat actgcgtaaa acaaaaatta taaataaaaa attaattaac ttaaacattg    36420
gaagcctgtc tcacaacagg aaaaaccact ttaatcaaca taagacgggc cacgggcatg    36480
```

```
ccggcatagc cgtaaaaaaa ttggtccccg tgattaacaa gtaccacaga cagctccccg    36540
gtcatgtcgg gggtcatcat gtgagactct gtatacacgt ctggattgtg aacatcagac    36600
aaacaaagaa atcgagccac gtagcccgga ggtataatca cccgcaggcg gaggtacagc    36660
aaaacgaccc ccataggagg aatcacaaaa ttagtaggaa aaaaaatac ataaacacca     36720 gaaaaccct gttgctgagg caaaatagcg ccctcccgat ccaaaacaac ataaagcgct     36780
tccacaggag cagccataac aaagacccga gtcttaccag taaaaagaaa aaagatctct    36840
caacgcagca ccagcaccaa cacttcgcag tgtaaaaggc caagtgccga gagagtatat    36900
ataggaataa aaagtgacgt aaacgggcaa agtccaaaaa acgcccagaa aaaccgcacg    36960
cgaacctacg ccccgaaacg aaagccaaaa aacactagac actcccttcc ggcgtcaact    37020
tccgctttcc cacgctacgt cacttgcccc agtcaaacaa actacatatc ccgaacttcc    37080
aagtcgccac gcccaaaaca ccgcctacac ctccccgccc gccggcccgc ccccaaaccc    37140
gcctcccgcc ccgcgcccg ccccgcgccg cccatctcat tatcatattg gcttcaatcc     37200
aaaataaggt atattattga tgatggttta aacggatcca attcttgaag acgaaagggc    37260
ctcgtgatac gcctattttt ataggttaat gtcatgataa taatggtttc ttagacgtca    37320
ggtggcactt ttcggggaaa tgtgcgcgga acccctattt gtttattttt ctaaatacat    37380
tcaaatatgt atccgctcat gagacaataa ccctgataaa tgcttcaata atattgaaaa    37440
aggaagagta tgagtattca acatttccgt gtcgccctta ttccctttt tgcggcattt     37500 tgccttcctg tttttgctca cccagaaacg ctggtgaaag taaaagatgc tgaagatcag    37560
ttgggtgcac gagtgggtta catcgaactg gatctcaaca gcggtaagat ccttgagagt    37620
tttcgccccg aagaacgttt tccaatgatg agcacttta aagttctgct atgtggcgcg     37680
gtattatccc gtgttgacgc cgggcaagag caactcggtc ccgcataca ctattctcag     37740 aatgacttgg ttgagtactc accagtcaca gaaaagcatc ttacgatgg catgacagta     37800 agagaattat gcagtgctgc cataaccatg agtgataaca ctgcggccaa cttacttctg    37860
acaacgatcg gaggaccgaa ggagctaacc gcttttttgc acaacatggg ggatcatgta    37920
actcgccttg atcgttggga accggagctg aatgaagcca taccaaacga cgagcgtgac    37980
accacgatgc ctgtagcaat ggcaacaacg ttgcgcaaac tattaactgg cgaactactt    38040
actctagctt cccggcaaca attaatagac tggatggagg cggataaagt tgcaggacca    38100
cttctgcgct cggcccttcc ggctggctgg tttattgctg ataaatctgg agccggtgag    38160
cgtgggtctc gcggtatcat tgcagcactg gggccagatg gtaagccctc ccgtatcgta    38220
gttatctaca cgacggggag tcaggcaact atggatgaac gaaatagaca gatcgctgag    38280
ataggtgcct cactgattaa gcattggtaa ctgtcagacc aagtttactc atatatactt    38340
tagattgatt taaaaggatc taggtgaaga tcctttttga taatctcatg accaaaatcc    38400
cttaacgtga gttttcgttc cactgagcgt cagacccgt agaaaagatc aaaggatctt     38460
cttgagatcc ttttttttctg cgcgtaatct gctgcttgca acaaaaaaa ccaccgctac    38520 cagcggtggt ttgtttgccg gatcaagagc taccaactct ttttccgaag gtaactggct    38580
tcagcagagc gcagatacca aatactgtcc ttctagtgta gccgtagtta ggccaccact    38640
tcaagaactc tgtagcaccg cctacatacc tcgctctgct aatcctgtta ccagtggctg    38700
ctgccagtgg cgataagtcg tgtcttaccg ggttggactc aagacgatag ttaccggata    38760
aggcgcagcg gtcgggctga acggggggtt cgtgcacaca gcccagcttg gagcgaacga    38820
```

```
cctacaccga actgagatac ctacagcgtg agctatgaga aagcgccacg cttcccgaag    38880
ggagaaaggc ggacaggtat ccggtaagcg gcagggtcgg aacaggagag cgcacgaggg    38940
agcttccagg gggaaacgcc tggtatcttt atagtcctgt cgggtttcgc cacctctgac    39000
ttgagcgtcg atttttgtga tgctcgtcag ggggcggag cctatggaaa aacgccagca     39060
acgcggcctt tttacggttc ctggcctttt gctggccttg aagctgtccc tgatggtcgt    39120
catctacctg cctggacagc atggcctgca acgcgggcat cccgatgccg ccggaagcga    39180
gaagaatcat aatgggaag gccatccagc ctcgcgtcgc agatccgaat tcgtttaaac     39240
```

<210> SEQ ID NO 18
<211> LENGTH: 33
<212> TYPE: DNA
<213> ORGANISM: Pan troglodytes

<400> SEQUENCE: 18

```
atacggacta gtggagaagt actcgcctac atg                                      33
```

<210> SEQ ID NO 19
<211> LENGTH: 36
<212> TYPE: DNA
<213> ORGANISM: Pan troglodytes

<400> SEQUENCE: 19

```
atacggaaga tctaagactt caggaaatat gactac                                   36
```

<210> SEQ ID NO 20
<211> LENGTH: 45
<212> TYPE: DNA
<213> ORGANISM: Pan troglodytes

<400> SEQUENCE: 20

```
attcagtgta caggcgcgcc aaagcatgac actgatgttc atttc                         45
```

<210> SEQ ID NO 21
<211> LENGTH: 35
<212> TYPE: DNA
<213> ORGANISM: Pan troglodytes

<400> SEQUENCE: 21

```
actaggacta gttataagct agaatggggc tttgc                                    35
```

<210> SEQ ID NO 22
<211> LENGTH: 37740
<212> TYPE: DNA
<213> ORGANISM: Pan troglodytes
<220> FEATURE:
<221> NAME/KEY: misc_feature
<222> LOCATION: (24391)..(24393)
<223> OTHER INFORMATION: n is a, c, g, or t

<400> SEQUENCE: 22

```
catcatcaat aatataccct attttggatt gaagccaata tgataatgag atgggcggcg      60
cggggcgggg cgcggggcgg gaggcgggtt tgggggcggg ccggcgggcg gggcggtgtg     120
gcggaagtgg actttgtaag tgtggcggat gtgacttgct agtgccgggc gcggtaaaag    180
tgacgttttc cgtgcgcgac aacgcccccg ggaagtgaca ttttcccgc ggttttacc      240 ggatgttgta gtgaatttgg gcgtaaccaa gtaagatttg gccattttcg cgggaaaact    300
gaaacgggga agtgaaatct gattaatttt gcgttagtca taccgcgtaa tatttgtcta    360
gggccgaggg actttggccg attacgtgga ggactcgccc aggtgttttt tgaggtgaat    420
```

```
ttccgcgttc cgggtcaaag tctgcgtttt attattatag gatatcccat tgcatacgtt    480
gtatccatat cataatatgt acatttatat tggctcatgt ccaacattac cgccatgttg    540
acattgatta ttgactagtt attaatagta atcaattacg gggtcattag ttcatagccc    600
atatatggag ttccgcgtta cataacttac ggtaaatggc ccgcctggct gaccgcccaa    660
cgacccccgc ccattgacgt caataatgac gtatgttccc atagtaacgc caatagggac    720
tttccattga cgtcaatggg tggagtattt acggtaaact gcccacttgg cagtacatca    780
agtgtatcat atgccaagta cgccccctat tgacgtcaat gacggtaaat ggcccgcctg    840
gcattatgcc cagtacatga ccttatggga ctttcctact tggcagtaca tctacgtatt    900
agtcatcgct attaccatgg tgatgcggtt ttggcagtac atcaatgggc gtggatagcg    960
gtttgactca cggggatttc caagtctcca ccccattgac gtcaatggga gtttgttttg   1020
gcaccaaaat caacgggact ttccaaaatg tcgtaacaac tccgccccat tgacgcaaat   1080
gggcggtagg cgtgtacggt gggaggtcta tataagcaga gctctcccta tcagtgatag   1140
agatctccct atcagtgata gagatcgtcg acgagctcgt ttagtgaacc gtcagatcgc   1200
ctggagacgc catccacgct gttttgacct ccatagaaga caccgggacc gatccagcct   1260
ccgcggccgg gaacggtgca ttggaacgcg gattccccgt gccaagagtg atcttccg    1320 tttatctagg taccgggccc cccctcgagg tcgacggtat cgataagctt cacgctgccg   1380
caagcactca gggcgcaagg gctgctaaag gaagcggaac acgtagaaag ccagtccgca   1440
gaaacggtgc tgaccccgga tgaatgtcag ctactgggct atctggacaa gggaaaacgc   1500
aagcgcaaag agaaagcagg tagcttgcag tgggcttaca tggcgatagc tagactgggc   1560
ggttttatgg acagcaagcg aaccggaatt gccagctggg gcgccctctg gtaaggttgg   1620
gaagccctgc aaagtaaact ggatggcttt cttgccgcca aggatctgat ggcgcagggg   1680
atcaagatct aaccaggagc tatttaatgg caacagttaa ccagctggta cgcaaaccac   1740
gtgctcgcaa agttgcgaaa agcaacgtgc ctgcgctgga agcatgcccg caaaaacgtg   1800
gcgtatgtac tcgtgtatat actaccactc taaaaaaacc gaactccgcg ctgcgtaaag   1860
tatgccgtgt tcgtctgact aacggtttcg aagtgacttc ctacatcggt ggtgaaggtc   1920
acaacctgca ggagcactcc gtgatcctga tccgtggcgg tcgtgttaaa gacctcccgg   1980
gtgttcgtta ccacaccgta cgtggtgcgc ttgactgctc cggcgttaaa gaccgtaagc   2040
aggctcgttc caagtatggc gtgaagcgtc ctaaggctta atggtagatc tgatcaagag   2100
acaggatgac ggtcgtttcg catgcttgaa caagatggat tgcacgcagg ttctccggcc   2160
gcttgggtgg agaggctatt cggctatgac tgggcacaac agacaatcgg ctgctctgat   2220
gccgccgtgt tccggctgtc agcgcagggg cgcccggttc tttttgtcaa gaccgacctg   2280
tccggtgccc tgaatgaact gcaggacgag gcagcgcggc tatcgtggct ggccacgacg   2340
ggcgttcctt gcgcagctgt gctcgacgtt gtcactgaag cgggaaggga ctggctgcta   2400
ttgggcgaag tgccggggca ggatctcctg tcatctcacc ttgctcctgc cgagaaagta   2460
tccatcatgg ctgatgcaat gcggcggctg catacgcttg atccggctac ctgcccattc   2520
gaccaccaag cgaaacatcg catcgagcga gcacgtactc ggatggaagc cggtcttgtc   2580
gatcaggatg atctggacga agagcatcag gggctcgcgc cagccgaact gttcgccagg   2640
ctcaaggcgc gcatgcccga cggcgaggat ctcgtcgtga cccatggcga tgcctgcttg   2700
ccgaatatca tggtggaaaa tggccgcttt tctggattca tcgactgtgg ccggctgggt   2760
```

```
gtggcggacc gctatcagga catagcgttg gctacccgtg atattgctga agagcttggc    2820
ggcgaatggg ctgaccgctt cctcgtgctt tacggtatcg ccgctcccga ttcgcagcgc    2880
atcgccttct atcgccttct tgacgagttc ttctgagcgg gactctgggg ttcgaaatga    2940
ccgaccaagc gacgcccaac ctgccatcac gagatttcga ttccaccgcc gccttctatg    3000
aaaggttggg cttcggaatc gttttccggg acgccggctg gatgatcctc cagcgcgggg    3060
atctcatgct ggagttcttc gcccaccccg ggctcgatcc cctcgggggg aatcagaatt    3120
cagtcgacag cggccgcgat ctgctgtgcc ttctagttgc cagccatctg ttgtttgccc    3180
ctcccccgtg ccttccttga ccctggaagg tgccactccc actgtccttt cctaataaaa    3240
tgaggaaatt gcatcgcatt gtctgagtag gtgtcattct attctggggg gtggggtggg    3300
gcaggacagc aagggggagg attgggaaga caatagcagg catgctgggg atgcggtggg    3360
ctctatggcc gatcagcgat cgctgaggtg ggtgagtggg cgtggcctgg ggtggtcatg    3420
aaaatatata agttgggggt cttagggtct ctttatttgt gttgcagaga ccgccggagc    3480
catgagcggg agcagcagca gcagcagtag cagcagcgcc ttggatggca gcatcgtgag    3540
cccttatttg acgacgcgga tgccccactg ggccggggtg cgtcagaatg tgatgggctc    3600
cagcatcgac ggccgacccg tcctgcccgc aaattccgcc acgctgacct atgcgaccgt    3660
cgcggggacg ccgttggacg ccaccgccgc cgccgccgcc accgcagccg cctcggccgt    3720
gcgcagcctg gccacggact ttgcattcct gggaccactg cgacagggg ctacttctcg    3780
ggccgctgct gccgccgttc gcgatgacaa gctgaccgcc ctgctggcgc agttggatgc    3840
gcttactcgg gaactgggtg acctttctca gcaggtcatg gccctgcgcc agcaggtctc    3900
ctccctgcaa gctggcggga atgcttctcc cacaaatgcc gtttaagata aataaaacca    3960
gactctgttt ggattaaaga aaagtagcaa gtgcattgct ctctttattt cataattttc    4020
cgcgcgcgat aggccctaga ccagcgttct cggtcgttga gggtgcggtg tatcttctcc    4080
aggacgtggt agaggtggct ctggacgttg agatacatgg gcatgagccc gtcccggggg    4140
tggaggtagc accactgcag agcttcatgc tccggggtgg tgttgtagat gatccagtcg    4200
tagcaggagc gctgggcatg gtgcctaaaa atgtccttca gcagcaggcc gatggccagg    4260
gggaggccct tggtgtaagt gtttacaaaa cggttaagtt gggaagggtg cattcgggga    4320
gagatgatgt gcatcttgga ctgtattttt agattggcga tgtttccgcc cagatccctt    4380
ctgggattca tgttgtgcag gaccaccagt acagtgtatc cggtgcactt ggggaatttg    4440
tcatgcagct tagagggaaa agcgtggaag aacttggaga cgcccttgtg gcctcccaga    4500
ttttccatgc attcgtccat gatgatggca atgggcccgc gggaggcagc ttgggcaaag    4560
atatttctgg ggtcgctgac gtcgtagttg tgttccaggg tgaggtcgtc ataggccatt    4620
tttacaaagc gcgggcggag ggtgcccgac tgggggatga tggtcccctc tggccccggg    4680
gcgtagttgc cctcgcagat ctgcatttcc caggccttaa tctcggaggg gggaatcata    4740
tccacctgcg gggcgatgaa gaaaacggtt tccggagccg gggagattaa ctgggatgag    4800
agcaggtttc taagcagctg tgattttcca caaccggtgg gcccataaat aacacctata    4860
accggttgca gctggtagtt tagagagctg cagctgccgt cgtcccggag gaggggggcc    4920
acctcgttga gcatgtccct gacgcgcatg ttctccccga ccagatccgc cagaaggcgc    4980
tcgccgccca gggacagcag ctcttgcaag gaagcaaagt ttttcagcgg cttgaggccg    5040
tccgccgtgg gcatgttttt cagggtctgg ctcagcagct ccaggcggtc ccagagctcg    5100
gtgacgtgct ctacggcatc tctatccagc atatctcctc gtttcgcggg ttggggcgac    5160
```

```
tttcgctgta gggcaccaag cggtggtcgt ccagcggggc cagagtcatg tccttccatg    5220
ggcgcagggt cctcgtcagg gtggtctggg tcacggtgaa ggggtgcgct ccgggctgag    5280
cgcttgccaa ggtgcgcttg aggctggttc tgctggtgct gaagcgctgc cggtcttcgc    5340
cctgcgcgtc ggccaggtag catttgacca tggtgtcata gtccagcccc tccgcggcgt    5400
gtcccttggc gcgcagcttg cccttggagg tggcgccgca cgaggggcag agcaggctct    5460
tgagcgcgta gagcttgggg gcgaggaaga ccgattcggg ggagtaggcg tccgcgccgc    5520 agacccgca cacggtctcg cactccacca gccaggtgag ctcggggcgc gccgggtcaa    5580
aaaccaggtt tccccatgc tttttgatgc gtttcttacc tcgggtctcc atgaggtggt    5640
gtccccgctc ggtgacgaag aggctgtccg tgtctccgta gaccgacttg agggtctttt   5700
tctccagggg ggtccctcgg tcttcctcgt agaggaactc ggaccactct gagacgaagg    5760
cccgcgtcca ggccaggacg aaggaggcta tgtgggaggg gtagcggtcg ttgtccacta    5820
gggggtccac cttctccaag gtgtgaagac acatgtcgcc ttcctcggcg tccaggaagg    5880
tgattggctt gtaggtgtag gccacgtgac cgggggttcc tgacgggggg gtataaaagg    5940
gggtgggggc gcgctcgtcg tcactctctt ccgcatcgct gtctgcgagg ccagctgct    6000 ggggtgagta ttccctctcg aaggcgggca tgacctccgc gctgaggttg tcagtttcca    6060
aaaacgagga ggatttgatg ttcacctgtc ccgaggtgat acctttgagg gtacccgcgt    6120
ccatctggtc agaaaacacg atcttttat tgtccagctt ggtggcgaac gacccgtaga    6180
gggcgttgga gagcagcttg gcgatggagc gcagggtctg gttcttgtcc ctgtcggcgc    6240
gctccttggc cgcgatgttg agctgcacgt actcgcgcgc gacgcagcgc cactcgggga    6300
agacggtggt gcgctcgtcg ggcaccaggc gcacgcgcca gccgcggttg tgcagggtga    6360
ccaggtccac gctggtggcg acctcgccgc gcaggcgctc gttggtccag cagagacggc    6420
cgcccttgcg cgagcagaag gggggcaggg ggtcgagctg ggtctcgtcc gggggtccg    6480 cgtccacggt gaaaaccccg gggcgcaggc gcgcgtcgaa gtagtctatc ttgcaacctt    6540
gcatgtccag cgcctgctgc cagtcgcggg cggcgagcgc gcgctcgtag gggttgagcg    6600
gcgggcccca gggcatgggg tgggtgagtg cggaggcgta catgccgcag atgtcataga    6660
cgtagagggg ctcccgcagg accccgatgt aggtgggta gcagcggccg ccgcggatgc    6720
tggcgcgcac gtagtcatac agctcgtgcg agggggcgag gaggtcgggg cccaggttgg    6780
tgcgggcggg gcgctccgtg cggaagacga tctgcctgaa gatggcatgc gagttggaag    6840
agatggtggg gcgctggaag acgttgaagc tggcgtcctg caggccgacg cgtcgcgca    6900 cgaaggaggc gtaggagtcg cgcagcttgt gtaccagctc ggcggtgacc tgcacgtcga    6960
gcgcgcagta gtcgagggtc tcgcggatga tgtcatattt agcctgcccc ttctttttcc    7020
acagctcgcg gttgaggaca aactcttcgc ggtctttcca gtactcttgg atcgggaaac    7080
cgtccggttc cgaacggtaa gagcctagca tgtagaactg gttgacggcc tggtaggcgc    7140
agcagccctt ctccacgggg agggcgtagg cctgcgcggc cttgcggagc gaggtgtggg    7200
tcagggcgaa ggtgtccctg accatgactt tgaggtactg gtgcttgaag tcggagtcgt    7260
cgcagccgcc ccgctcccag agcgagaagt cggtgcgctt cttggagcgg ggttgggca    7320 gagcgaaggt gacatcgttg aagaggattt tgcccgcgcg gggcatgaag ttgcgggtga    7380
tgcggaaggg ccccggcact tcagagcggt tgttgatgac ctgggcggcg agcacgatct    7440
cgtcgaagcc gttgatgttg tggcccacga tgtagagttc caggaagcgg ggccggccct    7500
```

```
ttacggtggg cagcttcttt agctcttcgt aggtgagctc ctcgggcgag gcgaggccgt   7560
gctcggccag ggcccagtcc gcgaggtgcg ggttgtctct gaggaaggac tcccagaggt   7620
cgcgggccag gagggtctgc aggcggtccc tgaaggtcct gaactggcgg cccacggcca   7680
tttttcggg ggtgatgcag tagaaggtga gggggtcttg ctgccagcgg tcccagtcga    7740
gctgcagggc gaggtcgcgc gcggcggtga ccaggcgctc gtcgccccg aatttcatga    7800
ccagcatgaa gggcacgagc tgctttccga aggcccccat ccaagtgtag gtctctacat   7860
cgtaggtgac aaagaggcgc tccgtgcgag gatgcgagcc gatcgggaag aactggatct   7920
cccgccacca gttggaggag tggctgttga tgtggtggaa gtagaagtcc cgtcgccggg   7980
ccgaacactc gtgctggctt ttgtaaaagc gagcgcagta ctggcagcgc tgcacgggct   8040
gtacctcatg cacgagatgc acctttcgcc cgcgcacgag gaagccgagg ggaaatctga   8100
gccccccgcc tggctcgcgg catggctggt gctcttctac tttggatgcg tgtccgtctc   8160
cgtctggctc ctcgagggt gttacggtgg agcggaccac cacgccgcgc gagccgcagg    8220
tccagatatc ggcgcgcggc ggtcggagtt tgatgacgac atcgcgcagc tgggagctgt   8280
ccatggtctg gagctcccgc ggcggcggca ggtcagccgg gagttcttgc aggttcacct   8340
cgcagagtcg ggccagggcg cggggcaggt ctaggtggta cctgatctct aggggcgtgt   8400
tggtggcggc gtcgatggct tgcaggagcc gcagccccg gggggcgacg acggtgcccc    8460
gcggggtggt ggtggtggtg gcggtgcagc tcagaagcgg tgccgcgggc gggcccccgg   8520
aggtaggggg ggctccggtc ccgcgggcag gggcggcagc ggcacgtcgg cgtggagcgc   8580
gggcaggagt tggtgctgtg cccggaggtt gctggcgaag gcgacgacgc ggcggttgat   8640
ctcctggatc tggcgcctct gcgtgaagac gacgggcccg gtgagcttga acctgaaaga   8700
gagttcgaca gaatcaatct cggtgtcatt gaccgcggcc tggcgcagga tctcctgcac   8760
gtctcccgag ttgtcttggt aggcgatctc ggccatgaac tgctcgatct cttcctcctg   8820
gaggtctccg cgtccggcgc gttccacggt ggccgccagg tcgttggaga tgcgccccat   8880
gagctgcgag aaggcgttga gtccgccctc gttccagact cggctgtaga ccacgccccc   8940
ctggtcatcg cgggcgcgca tgaccacctg cgcgaggttg agctccacgt gccgcgcgaa   9000
gacggcgtag ttgcgcagac gctggaagag gtagttgagg gtggtggcgg tgtgctcggc   9060
cacgaagaag ttcatgaccc agcggcgcaa cgtggattcg ttgatgtccc caaggcctc    9120
cagccgttcc atggcctcgt agaagtccac ggcgaagttg aaaaactggg agttgcgcgc   9180
cgacacggtc aactcctcct ccagaagacg gatgagctcg gcgacggtgt cgcgcacctc   9240
gcgctcgaag gctatgggga tctcttcctc cgctagcatc accacctcct cctcttcctc   9300
ctcttctggc acttccatga tggcttcctc ctcttcgggg ggtggcggcg gcggcggtgg   9360
gggaggggc gctctgcgcc ggcggcggcg caccgggagg cggtccacga agcgcgcgat   9420
catctccccg cggcggcggc gcatggtctc ggtgacggcg cggccgttct cccgggggcg   9480
cagttggaag acgccgccgg acatctggtg ctggggcggg tggccgtgag gcagcgagac   9540
ggcgctgacg atgcatctca acaattgctg cgtaggtacg ccgccgaggg acctgaggga   9600
gtccatatcc accggatccg aaaaccttc gaggaaggcg tctaaccagt cgcagtcgca    9660
aggtaggctg agcaccgtgg cgggcggcgg ggggtggggg gagtgtctgg cggaggtgct   9720
gctgatgatg taattgaagt aggcggactt gacacggcgg atggtcgaca ggagcaccat   9780
gtccttgggt ccggcctgct ggatgcgag gcggtcggct atgccccagg cttcgttctg    9840
gcatcggcgc aggtccttgt agtagtcttg catgagcctt tccaccggca cctcttctcc   9900
```

```
ttcctcttct gcttcttcca tgtctgcttc ggccctgggg cggcgccgcg ccccctgcc    9960
ccccatgcgc gtgaccccga accccctgag cggttggagc agggccaggt cggcgacgac   10020
gcgctcggcc aggatggcct gctgcacctg cgtgagggtg gtttggaagt catccaagtc   10080
cacgaagcgg tggtaggcgc ccgtgttgat ggtgtaggtg cagttggcca tgacggacca   10140
gttgacggtc tggtggcccg gttgcgacat ctcggtgtac ctgagtcgcg agtaggcgcg   10200
ggagtcgaag acgtagtcgt tgcaagtccg caccaggtac tggtagccca ccaggaagtg   10260
cggcggcggc tggcggtaga ggggccagcg cagggtggcg ggggctccgg gggccaggtc   10320
ttccagcatg aggcggtggt aggcgtagat gtacctggac atccaggtga tacccgcggc   10380
ggtggtggag gcgcgcggga agtcgcgcac ccggttccag atgttgcgca ggggcagaaa   10440
gtgctccatg gtaggcgtgc tctgtccagt cagacgcgcg cagtcgttga tactctagac   10500
cagggaaaac gaaagccggt cagcgggcac tcttccgtgg tctggtgaat agatcgcaag   10560
ggtatcatgg cggagggcct cggttcgagc cccgggtccg ggccgacgg tccgccatga   10620
tccacgcggt taccgcccgc gtgtcgaacc caggtgtgcg acgtcagaca acggtggagt   10680
gttccttttg gcgttttttct ggccgggcgc cggcgccgcg taagagacta agccgcgaaa   10740
gcgaaagcag taagtggctc gctccccgta gccggaggga tccttgctaa gggttgcgtt   10800
gcggcgaacc ccggttcgaa tcccgtactc gggccggccg gacccgcggc taaggtgttg   10860
gattggcctc cccctcgtat aaagaccccg cttgcggatt gactccggac acggggacga   10920
gccccttta ttttgcttt ccccagatgc atccggtgtt gcgacagatg cgccccccgc    10980
cccagcagca gcaacaacac cagcaagagc ggcagcaaca gcagcgggag tcatgcaggg   11040
ccccctcacc cacccctcggc ggccggccgcca cctcggcgtc cgcggccgtg tctggcgcct  11100
gcggcggcgg cggcggggggg ccggctgacg accccgagga gccccgcgg cgcagggcca   11160
gacactacct ggacctggag gagggcgagg gcctggcgcg gctgggggcg ccgtctcccg   11220
agcgccaccc gcgggtgcag ctaaagcgcg actcgcgcga ggcgtacgtg cctcggcaga   11280
acctgttcag ggaccgcgcg ggcgaggagc ccgaggagat gcgggacagg aggttcagcg   11340
cggggcggga gctgcggcag gggctgaacc gcagcggct gctgcgcgag gaggactttg   11400
agcccgacgc gcggacgggg atcagccccg cgcgcgcgca cgtggcggcc gccgacctgg   11460
tgacggcgta cgagcagacg gtgaaccagg agatcaactt ccaaaagagt ttcaacaacc   11520
acgtgcgcac gctggtggcg cgcgaggagg tgaccatcgg gctgatgcac ctgtgggact   11580
ttgtgagcgc gctggtgcag aaccccaata gcaagcctct gacggcgcag ctgttcctga   11640
tagtgcagca cagcagggac aacgaggcgt ttagggacgc gctgctgaac atcaccgagc   11700
ccgagggccg gtgctgctg gacctgatta acatcctgca gagcatagtg gtgcaggagc   11760
gcagcctgag cctggccgac aaggtggcgg ccatcaacta ctcgatgctg agcctgggca   11820
agttttacgc gcgcaagatc taccagacgc cgtacgtgcc catagacaag gaggtgaaga   11880
tcgacggttt ttacatgcgc atggcgctga agtgctcac cctaagcgac gacctgggcg    11940
tgtaccgcaa cgagcgcatc cacaaggccg tgagcgtgag ccggcggcgc gagctgagcg   12000
accgcgagct gatgcatagc ctgcagcggg cgctggcggg cgccggcagc ggcgacaggg   12060
aggcggagtc ctacttcgat gcggggggcgg acctgcgctg ggcgcccagc cggcgggccc   12120
tggaggccgc gggggtccgc gaggactatg acgaggacgg cgaggaggat gaggagtacg   12180
agctagagga gggcgagtac ctggactaaa ccgcggggtgg tgtttccggt agatgcaaga   12240
```

-continued

```
cccgaacgtg gtggacccgg cgctgcgggc ggctctgcag agccagccgt ccggccttaa    12300
ctcctcagac gactggcgac aggtcatgga ccgcatcatg tcgctgacgg cgcgtaaccc    12360
ggacgcgttc cggcagcagc cgcaggccaa caggctctcc gccatcctgg aggcggtggt    12420
gcctgcgcgc tcgaaccccca cgcacgagaa ggtgctggcc atagtgaacg cgctggccga    12480
gaacagggcc atccgcccgg acgaggccgg gctggtgtac gacgcgctgc tgcagcgcgt    12540
ggcccgctac aacagcggca acgtgcagac caacctggac cggctggtgg gggacgtgcg    12600
cgaggcggtg gcgcagcgcg agcgcgcgga tcggcagggc aacctgggct ccatggtggc    12660
gctgaatgcc ttcctgagca cgcagccggc caacgtgccg cggggcagg aagactacac    12720 caactttgtg agcgcgctgc ggctgatggt gaccgagacc ccccagagcg aggtgtacca    12780
gtcgggtccg gactacttct tccagaccag cagacagggc ctgcagacgg tgaacctgag    12840
ccaggctttc aagaacctgc gggggctgtg gggcgtgaag gcgcccaccg cgaccgggc    12900 gacggtgtcc agcctgctga cgcccaactc gcgcctgctg ctgctgctga tcgcgccgtt    12960
cacggacagc ggcagcgtgt cccgggacac ctacctgggg cacctgctga ccctgtaccg    13020
cgaggccatc gggcaggcgc aggtggacga gcacaccttc caggagatca ccagcgttag    13080
ccgcgcgctg gggcaggagg acacgagcag cctggaggcg actctgaact acctgctgac    13140
caaccggcgg cagaagattc cctcgctgca cagcctgacc tccgaggagg agcgcatctt    13200
gcgctacgtg cagcagagcg tgagcctgaa cctgatcgcg cacggggtga cgcccagtgt    13260
ggcgctggac atgaccgcgc gcaacatgga accgggcatg tacgccgcgc accggccttta    13320 catcaaccgc tgatggact acctgcatcg cgcggcggcc gtgaacccc agtactttac    13380 caacgccatc ctgaacccgc actggctccc gccgcccggg ttctacagcg ggggcttcga    13440
ggtcccggag gccaacgatg gcttcctgtg ggacgcatg gacgacagcg tgttctcccc    13500
gcggccgcag gcgctggcgg aagcgtccct gctgcgtccc aagaaggagg aggaggcgag    13560
tcgccgccgc ggcagcagcg gcgtggcttc tctgtccgag ctgggggcgg cagccgccgc    13620 gcgcccggg tcctgggcg gcagccctt tccgagcctg tggggtctc tgcacagcga    13680 gcgcaccacc cgccctcggc tgctgggcga ggacgagtac ctgaataact ccctgctgca    13740
gccggtgcgg gagaaaaacc tgcctcccgc cttccccaac aacgggatag agagcctggt    13800
ggacaagatg agcagatgga agacctatgc gcaggagcac agggacgcgc ccgcgctccg    13860
gccgcccacg cggcgccagc gccacgaccg gcagcggggg ctggtgtggg atgacgagga    13920
ctccgcggac gatagcagcg tgctggacct ggagggagc ggcaacccgt tcgcgcacct    13980
gcgcccccgc ctggggagga tgttttaaaa aaaaaaaaa gcaagaagca tgatgcaaaa    14040
attaaataaa actcaccaag gccatggcga ccgagcgttg gtttcttgtg ttccctttcag    14100 tatgcggcgc gcggcgatgt accaggaggg acctcctccc tcttacgaga gcgtggtggg    14160
cgcggcggcg gcggcgccct cttctcccctt tgcgtcgcag ctgctggagc cgccgtacgt    14220
gcctccgcgc tacctgcggc ctacggggg gagaaacagc atccgttact cggagctggc    14280 gccccttgttc gacaccaccc gggtgtacct ggtggacaac aagtcggcgg acgtggcctc    14340
cctgaactac cagaacgacc acagcaattt tttgaccacg gtcatccaga caatgactca    14400
cagcccgagc gaggccagca cccagaccat caatctggat gaccggtcgc actggggcgg    14460
cgacctgaaa accatcctgc acaccaacat gcccaacgtg aacgagttca tgttcaccaa    14520
taagttcaag gcgcgggtga tggtgtcgcg ctcgcacacc aaggaagacc gggtggagct    14580
gaagtacgag tgggtggagt tcgagctgcc agagggcaac tactccgaga ccatgaccat    14640
```

```
tgacctgatg aacaacgcga tcgtggagca ctatctgaaa gtgggcaggc agaacggggt   14700
cctggagagc gacatcgggg tcaagttcga caccaggaac ttccgcctgg ggctggaccc   14760
cgtgaccggg ctggttatgc cggggtgta caccaacgag gccttccatc ccgacatcat   14820
cctgctgccc ggctgcgggg tggacttcac ttacagccgc ctgagcaacc tcctgggcat   14880
ccgcaagcgg cagcccttcc aggagggctt caggatcacc tacgaggacc tggaggggg    14940 caacatcccc gcgctcctcg atgtggaggc ctaccaggat agcttgaagg aaaatgaggc   15000
gggacaggag gataccgccc ccgccgcctc cgccgccgcc gagcagggcg aggatgctgc   15060
tgacaccgcg gccgcggacg gggcggaggc cgaccccgct atggtggtgg aggctgccga   15120
gcaggaggag gacatgaatg acagtgcggt gcgcggagac accttcgtca cccgggggga   15180
ggaaaagcaa gcggaggccg aggccgcggc cgaggaaaag caactggcgg cagcagcggc   15240
ggcggcggcg ttggccgcgg cggaggctga gtctgagggg accaagcccg ccaaggagcc   15300
cgtgattaag cccctgaccg aagatagcaa gaagcgcagt tacaacctgc tcaaggacag   15360
caccaacacc gcgtaccgca gctggtacct ggcctacaac tacggcgacc cgtcgacggg   15420
ggtgcgctcc tggaccctgc tgtgcacgcc ggacgtgacc tgcggctcgg agcaggtgta   15480
ctggtcgctg cccgacatga tgcaagaccc cgtgaccttc cgctccacgc ggcaggtcag   15540
caacttcccg gtggtgggcg ccgagctgct gcccgtgcac tccaagagct tctacaacga   15600
ccaggccgtc tactcccagc tcatccgcca gttcacctct ctgacccacg tgttcaatcg   15660 cttttcctgag aaccagattc tggcgcgccc gcccgcccccc accatcacca ccgtcagtga   15720
aaacgttcct gctctcacag atcacgggac gctaccgctg cgcaacagca tcggaggagt   15780
ccagcgagtg accgttactg acgccagacg ccgcacctgc ccctacgttt acaaggcctt   15840
gggcatagtc tcgccgcgcg tcctttccag ccgcactttt tgagcaacac caccatcatg   15900
tccatcctga tctcacccag caataactcc ggctggggac tgctgcgcgc gcccagcaag   15960
atgttcggag gggcgaggaa gcgttccgag cagcaccccg tgcgcgtgcg cgggcacttc   16020
cgcgccccct ggggagcgca caaacgcggc cgcgcggggc gcaccaccgt ggacgacgcc   16080
atcgactcgg tggtggagca ggcgcgcaac tacaggcccc cggtctctac cgtgacgcg    16140 gccatccaga ccgtggtgcg gggcgcgcgg cggtacgcca agctgaagag ccgccggaag   16200
cgcgtggccc gccgccaccg ccgccgaccc ggggccgccg ccaaacgcgc cgccgcggcc   16260
ctgcttcgcc gggccaagcg cacgggccgc cgcgccgcca tgagggccgc gcgccgcttg   16320
gccgccggca tcaccgccgc caccatggcc ccccgtaccc gaagacgcgc ggccgccgcc   16380
gccgccgccg ccatcagtga catggccagc aggcgccggg gcaacgtgta ctgggtgcgc   16440
gactcggtga ccgcacgcg cgtgcccgtg cgcttccgcc cccgcggac ttgagatgat    16500 gtgaaaaaac aacactgagt ctcctgctgt tgtgtgtatc ccagcggcgg cggcggcgcg   16560
cgcagcgtca tgtccaagcg caaaatcaaa gaagagatgc tccaggtcgt cgcgccggag   16620
atctatgggc ccccgaagaa ggaagagcag gattcgaagc cccgcaagat aaagcgggtc   16680
aaaaagaaaa agaaagatga tggcgatgcc gatgggaggg tggagttcct gcgcgccacg   16740
gcgcccaggc gcccggtgca gtggaagggc cggcgcgtaa agcgcgtcct gcgccccggc   16800
accgcggtgg tcttcacgcc cggcgagcgc tccacccgga cttcaagcg cgtctatgac    16860 gaggtgtacg gcgacgaaga cctgctggag caggccaacg agcgcttcgg agagtttgct   16920
tacgggaagc gtcagcggcc gctggggaag gaggacctgc tggcgctgcc gctggaccag   16980
```

```
ggcaacccca cccccagtct gaagcccgtg accctgcagc aggtgctgcc gagcagcgca   17040
ccctccgagg cgaagcgggg tctgaagcgc gagggcggcg acctggcgcc caccgtgcag   17100
ctcatggtgc ccaagcggca gaggctggag gatgtgctgg agaaaatgaa agtagacccc   17160
ggtctgcagc cggacatcag ggtccgtccc atcaagcagg tggcgccggg cctcggcgtg   17220
cagaccgtgg acgtggtcat ccccaccggc aactccccg ccgccaccac cactaccgct    17280
gcctccacgg acatggagac acagaccgat cccgccgcag ccgccgccac cgccgccgcc   17340
gcgacctcct cggcggaggt gcagacggac ccctggctgc cgccggcgat gtcagctccc   17400
cgcgcgcgtc gcgggcgcag gaagtacggc gccgccaacg cgctcctgcc cgagtacgcc   17460
ttgcatcctt ccatcgcgcc cacccccggc taccgaggct atacctaccg cccgcgaaga   17520
gccaagggtt ccaccgccg tccccgccga cgcgccgccg ccaccacccg ccgccgccgc    17580
cgcagacgcc agcccgcact ggctccagtc tccgtgagga gagtggcgcg cgacggacac   17640
accctggtgc tgcccagggc gcgctaccac cccagcatcg tttaaaagcc tgttgtggtt   17700
cttgcagata tggccctcac ttgccgcctc cgtttcccgg tgccgggata ccgaggagga   17760
agatcgcgcc gcaggagggg tctggccggc cgcggcctga gcggaggcag ccgccgcgcg   17820
caccggcgga gacgcgccac cagccgacgc atgcgcggcg gggtgctgcc cctgttaatc   17880 ccctgatcg ccgcggcgat cggcgccgtg cccgggatcg cctccgtggc cttgcaggcg    17940
tcccagaggc attgacagac ttgcaaactt gcaaatatgg aaaaaaaccc caataaaaaa   18000
gtctagactc tcacgctcgc ttggtcctgt gactattttg tagaatggaa gacatcaact   18060
ttgcgtcgct ggccccgcgt cacggctcgc gcccgttcct gggacactgg aacgatatcg   18120
gcaccagcaa catgagcggt ggcgccttca gttgggggctc tctgtggagc ggcattaaaa   18180
gtatcgggtc tgccgttaaa aattacggct cccgggcctg gaacagcagc acgggccaga   18240
tgttgagaga caagttgaaa gagcagaact tccagcagaa ggtggtggag ggcctggcct   18300
ccggcatcaa cggggtggtg gacctggcca accaggccgt gcagaataag atcaacagca   18360
gactggaccc ccggccgccg gtggaggagg tgccgccggc gctggagacg gtgtcccccg   18420
atgggcgtgg cgagaagcgc ccgcggcccg atagggaaga gaccactctg gtcacgcaga   18480
ccgatgagcc gccccgtat gaggaggccc tgaagcaagg tctgcccacc acgcggccca    18540
tcgcgcccat ggccaccggg gtggtgggcc gccacacccc cgccacgctg gacttgcctc   18600
cgcccgccga tgtgccgcag cagcagcaga aggcggcaca gccgggcccg cccgtgaccg   18660
cctcccgttc ctccgccggt cctctgcgcc gcgcggccag cggccccgc ggggggtcg     18720 cgaggcacgg caactggcag agcacgctga acagcatcgt gggtctgggg gtgcggtccg   18780
tgaagcgccg ccgatgctac tgaatagctt agctaacgtg ttgtatgtgt gtatgcgccc   18840
tatgtcgccg ccagaggagc tgctgagtcg ccgccgttcg cgcgcccacc accaccaccg   18900
ccactccgcc cctcaagatg gcgacccat cgatgatgcc gcagtggtcg tacatgcaca    18960 tctcggggcca ggacgcctcg gagtacctga gccccgggct ggtgcagttc gcccgcgcca   19020
ccgagagcta cttcagcctg agtaacaagt ttaggaaccc cacggtggcg cccacgcacg   19080
atgtgaccac cgaccggtct cagcgcctga cgctgcggtt cattcccgtg accgcgagg    19140 acaccgcgta ctcgtacaag gcgcggttca ccctggccgt gggcgacaac cgcgtgctgg   19200
acatggcctc cacctacttt gacatccgcg gggtgctgga ccggggcccc actttcaagc   19260
cttactctgg caccgcctac aactccctgg cccccaaggg cgctcccaac tcctgcgagt   19320
gggagcaatt agaagaagcc caggccgctg tggaagacga agaattagaa gatgaagacg   19380
```

```
aggaaccaca ggatgaggca cctgtgaaaa aaacccatgt atacgctcag gctccccttt   19440
ctggagaaga aattactaaa aacggtttgc aaatagggtc agataacaca gaagcccagt   19500
ctaagcccat atatgcagat cctacattcc agcctgaacc ccaaatcggg gaatcccagt   19560
ggaatgaggc agatgctaca gttgccggcg gtagagtgct aaagaaatcc actcccatga   19620
agccatgcta tggttcctat gcaagaccca caaactccaa tggaggtcaa ggtgtgctgg   19680
tggctgatga taagggggtt cttcaatcta agttgaatt gcaattttt tcaaatacta    19740 ctactcttaa tcagcgggag ggtaacgata caaaaccaaa agtggtgctg tatagcgaag   19800
atgtgcacat ggaaactcca gacacccaca tttcttacaa gcccacaaaa agcgatgaca   19860
attcaaaaat catgctgggt cagcagtcca tgcccaacag acctaattac atcggcttca   19920
gagacaactt tatcggcctc atgtattaca atagcactgg caacatggga gtgcttgcag   19980
gtcaggcctc tcagttgaat gcagtggtgg acttgcaaga cagaaacaca gaactgtcct   20040
accagctctt gcttgattcc atgggtgaca gaaccagata cttttccatg tggaatcagg   20100
cagtggacag ttatgaccca gatgtcagaa ttattgaaaa tcatggaact gaagacgagc   20160
tccccaacta ttgtttccct ctgggcggca taggggtaac tgacacttac caggccatta   20220
aaaccaatgg caatggtcaa gaaaacccaa cctgggaaaa agatacagag tttgcagacc   20280
gcaatgaaat aggggtggga aacaatttcg ctatggagat caacctcagt gccaacctgt   20340
ggagaaactt cctgtactcc aacgtggcgc tgtacctgcc agacaagctt aagtacaacc   20400
cctccaatgt ggacatctct gacaacccca acacctacga ttacatgaac aagcgagtgg   20460
tggccccggg gctggtggac tgctacatca acctgggcgc gcgctggtcg ctggactaca   20520
tggacaacgt caacccccttc aaccaccacc gcaatgcggg cctgcgctac cgctccatgc   20580
tcctgggcaa cgggcgctac gtgcccttcc acatccaggt gccccagaag ttctttgcca   20640
tcaagaacct cctcctcctg ccgggctcct acacctacga gtggaacttc aggaaggatg   20700
tcaacatggt cctccagagc tctctgggta cgatctcag ggtggacggg gccagcatca   20760
agttcgagag catctgcctc tacgccacct tcttccccat ggcccacaac acggcctcca   20820
cgctcgaggc catgctcagg aacgacacca acgaccagtc cttcaatgac tacctctccg   20880
ccgccaacat gctctacccc ataccccgcca acgccaccaa cgtccccatc tccatcccct   20940
cgcgcaactg ggcggcctcc cgcggctggg ccttcacccg cctcaagacc aaggagaccc   21000
cctccctggg ctcgggattc gacccctact acacctactc gggctccatt ccctacctgg   21060
acggcaccct ctacctcaac cacactttca gaaggtctc ggtcaccttc gactcctcgg   21120
tcagctggcc gggcaacgac cgtctgctca cccccaacga gttcgaaatc aagcgctcgg   21180
tcgacgggga gggctacaac gtggcccagt gcaacatgac caaggactgg ttcctggtcc   21240
agatgctggc caactacaac atcggctacc agggcttcta catcccagag agctacaagg   21300
acaggatgta ctccttcttc aggaacttcc agcccatgag ccgcaggtg gtggaccaga   21360 ccaagtacaa ggactaccag gaggtgggca tcatccacca gcacaacaac tcgggcttcg   21420
tgggctacct cgcccccacc atgcgcgagg acaggcccta ccccgccaac ttcccctacc   21480
cgctcatagg caagaccgcg tcgacagca tcacccagaa aaagttcctc tgcgatcgca   21540
ccctctggcg catccccttc tccagcaact tcatgtccat gggtgcgctc tcggacctgg   21600
gccagaactt gctctacgcc aactccgccc acgccctcga catgaccttc gaggtcgacc   21660
ccatggacga gcccacccctt ctctatgttc tgttcgaagt ctttgacgtg gtccgggtcc   21720
```

```
accagccgca ccgcggcgtc atcgagaccg tgtacctgcg tacgcccttc tcggccggca   21780
acgccaccac ctaaagaagc aagccgcagt catcgccgcc tgcatgccgt cgggttccac   21840
cgagcaagag ctcagggcca tcgtcagaga cctgggatgc gggccctatt ttttgggcac   21900
tttcgacaag cgcttccctg gctttgtctc cccacacaag ctggcctgcg ccatcgtcaa   21960
cacggccggc cgcgagaccg ggggcgtgca ctggctggcc ttcgcctgga acccgcgctc   22020
caaaacatgc ttcctctttg accccttcgg cttttcggac cagcggctca agcaaatcta   22080
cgagttcgag tacgagggct gctgcgtcg cagcgccatc gcctcctcgc ccgaccgctg    22140
cgtcaccctc gaaaagtcca cccagaccgt gcagggcccc gactcggccg cctgcggtct   22200
cttctgctgc atgtttctgc acgcctttgt gcactggcct cagagtccca tggaccgcaa   22260
ccccaccatg aacttgctga cggggtgcc caactccatg ctccagagcc cccaggtcga    22320
gcccaccctg cgccgcaacc aggagcagct ctacagcttc ctggagcgcc actcgcccta   22380
cttccgccgc cacagcgcac agatcaggag ggccacctcc ttctgccact tgcaagagat   22440
gcaagaaggg taataacgat gtacacactt ttttctcaat aaatggcatt ttttattta    22500 tacaagctct ctggggtatt catttcccac caccaccacc accgccgtt gtcgccatct    22560 ggctctattt agaaatcgaa agggttctgc cgggagtcgc cgtgcgccac gggcagggac   22620
acgttgcgat actggtagcg ggtgccccac ttgaactcgg gcaccaccag gcgaggcagc   22680
tcggggaagt tttcgctcca caggctgcgg gtcagcacca gcgcgttcat caggtcgggc   22740
gccgagatct tgaagtcgca gttggggccg ccgccctgcg cgcgcgagtt gcggtacacc   22800
gggttgcagc actggaacac caacagcgcc gggtgcttca cgctagccag cacgctgcgg   22860
tcggagatca gctcggcgtc caggtcctcc gcgttgctca gcgcgaacgg ggtcatcttg   22920
ggcacttgcc tccccaggaa gggcgcgtgc cccggtttcg agttgcagtc gcagcgcagc   22980
gggatcagca ggtgcccatg cccggactcg gcgttgggt acagcgcgcg catgaaggcc    23040
tgcatctggc ggaaggccat ctgggccttg gcgcccctccg agaagaacat gccgcaggac   23100
ttgcccgaga actggtttgc ggggcagctg gcgtcgtgca ggcagcagcg cgcgtcggtg   23160
ttggcgatct gcaccacgtt gcgccccac cggttcttca cgatcttggc cttggacgat    23220
tgctccttca gcgcgcgctg cccgttctcg ctggtcacat ccatctcgat cacatgttcc   23280
ttgttcacca tgctgctgcc gtgcaggcac ttcagctcgc cctccgtctc ggtgcagcgg   23340
tgctgccaca gcgcgcagcc cgtgggctcg aaagacttgt aggtcacctc cgcgaaggac   23400
tgcaggtacc cctgcaaaaa gcggcccatc atggtcacga aggtcttgtt gctgctgaag   23460
gtcagctgca gcccgcggtg ctcctcgttc agccaggtct tgcacacggc cgccagcgcc   23520
tccacctggt cgggcagcat cttgaagttc accttcagct cattctccac gtggtacttg   23580
tccatcagcg tgcgcgccgc ctccatgccc ttctcccagg ccgacaccag cggcaggctc   23640
acggggttct tcaccatcac cgtggccgcc gcctccgccg cgctttcgct ttccgccccg   23700
ctgttctctt cctcttcctc ctcttcctcg ccgccgccca ctcgcagccc ccgcaccacg   23760
gggtcgtctt cctgcaggcg ctgcaccttg cgcttgccgt tgcgcccctg cttgatgcgc   23820
acgggcgggt tgctgaagcc caccatcacc agcgcggcct cttcttgctc gtcctcgctg   23880
tccagaatga cctccgggga ggggggttg gtcatcctca gtaccgaggc acgcttcttt    23940
ttcttcctgg gggcgttcgc cagctccgcg gctgcggccg ctgccgaggt cgaaggccga   24000
gggctgggcg tgcgcggcac cagcgcgtcc tgcgagccgt cctcgtcctc ctcggactcg   24060
agacggaggc gggcccgctt cttcgggggc gcgcggggcg gcggaggcgg cggcggcgac   24120
```

```
ggagacgggg acgagacatc gtccagggtg ggtggacggc gggccgcgcc gcgtccgcgc    24180 tcggggtgg  tctcgcgctg gtcctcttcc cgactggcca tctcccactg ctccttctcc    24240
tataggcaga aagagatcat ggagtctctc atgcgagtcg agaaggagga ggacagccta    24300
accgccccct ctgagccctc caccaccgcc gccaccaccg ccaatgccgc cgcggacgac    24360
gcgcccaccg agaccaccgc cagtaccacc nnnctcccca gcgacgcacc cccgctcgag    24420
aatgaagtgc tgatcgagca ggacccgggt tttgtgagcg agaggagga  tgaggtggat    24480 gagaaggaga aggaggaggt cgccgcctca gtgccaaaag aggataaaaa gcaagaccag    24540
gacgacgcag ataaggatga  gacagcagtc gggcggggga acggaagcca tgatgctgat   24600
gacggctacc tagacgtggg agacgacgtg ctgcttaagc acctgcaccg ccagtgcgtc    24660
atcgtctgcg acgcgctgca ggagcggtgc gaagtgcccc tggacgtggc ggaggtcagc    24720
cgcgcctacg agcggcacct cttcgcgccg cacgtgcccc ccaagcgccg ggagaacggc    24780
acctgcgagc ccaaccccgcg tctcaacttc tacccggtct tcgcggtacc cgaggtgctg    24840
gccacctacc acatcttttt ccaaaactgc aagatccccc tctcctgccg cgctaaccgc    24900
acccgcgccg acaaaaccct gaccctgcgg cagggcgccc acatacctga tattgcctct    24960
ctggaggaag tgcccaagat cttcgagggt ctcggtcgcg acgagaaacg ggcggcgaac    25020
gctctgcacg gagacagcga aaacgagagt cactcggggg tgctggtgga gctcgagggc    25080
gacaacgcgc gcctggccgt actcaagcgc agcatagagg tcacccactt tgcctacccg    25140
gcgctcaacc tgcccccccaa ggtcatgagt gtggtcatgg gcgagctcat catgcgccgc    25200
gcccagcccc tggccgcgga tgcaaacttg caagagtcct cagaggaagg cctgcccgcg    25260
gtcagcgacg agcagctggc gcgctggctg gagacccgcg accccgcgca gctggaggag    25320
cggcgcaagc tcatgatggc cgcggtgctg gtcaccgtgg agctcgagtg tctgcagcgc    25380
ttcttcgcgg accccgagat gcagcgcaag ctcgaggaga ccctgcacta caccttccgc    25440
cagggctacg tgcgccaggc ctgcaagatc tccaacgtgg agctctgcaa cctggtctcc    25500
tacctgggca tcctgcacga gaaccgcctc gggcagaacg tcctgcactc cacccctcaaa   25560 ggggaggcgc gccgcgacta catccgcgac tgcgcctacc tcttcctctg ctacacctgg    25620
cagacggcca tgggggtctg gcagcagtgc ctggaggagc gcaacctcaa ggagctggaa    25680
aagctcctca gcgcgcaccct cagggacctc tggacgggct tcaacgagcg ctcggtggcc    25740
gccgcgctgg cggacatcat cttccccgag cgcctgctca agaccctgca gcagggcctg    25800
cccgacttca ccagcagag  catgctgcag aacttcagga ctttcatcct ggagcgctcg    25860
ggcatcctgc cggccacttg ctgcgcgctg cccagcgact tcgtgcccat caagtacagg    25920
gagtgcccgc cgccgctctg gggccactgc tacctcttcc agctggccaa ctacctcgcc    25980
taccactcgg acctcatgga agacgtgagc ggcgagggcc tgctcgagtg ccactgccgc    26040
tgcaacctct gcacgcccca ccgctctcta gtctgcaacc cgcagctgct cagcgagagt    26100
cagattatcg gtaccttcga gctgcagggt ccctcgcctg acgagaagtc cgcggctccg    26160
gggctgaaac tcactccggg gctgtggact tccgcctacc tacgcaaatt tgtacctgag    26220
gactaccacc cccacgagat caggttctac gaagaccaat cccgcccgcc caaggcgag   26280 ctcaccgcct gcgtcatcac ccaggggcac atcctgggcc aattgcaagc catcaacaaa    26340
gcccgccgag agttcttgct gaaaaagggt cgggggtgt  acctgaccc  ccagtccggc    26400 gaggagctaa acccgctacc cccgccgccg ccccagcagc gggaccttgc ttcccaggat    26460
```

```
ggcacccaga aagaagcagc agccgccgcc gcagccatac atgcttctgg aggaagagga    26520
ggaggactgg gacagtcagg cagaggagat gatggaagac tgggaggagg acagcagcct    26580
agacgaggaa gcttcagagg ccgaagaggt ggcagacgca acaccatcac cctcggtcgc    26640 agcccctcg  ccggggcccc tgaaatcctc cgaacccagc accagcgcta taacctccgc    26700
tcctccggcg ccggcgccac ccgcccgcag acccaaccgt agatgggaca ccacaggaac    26760
cggggtcggt aagtccaagt gcccgccgcc gccaccgcag cagcagcagc agcagcgcca    26820
gggctaccgc tcgtggcgcg ggcacaagaa cgccatagtc gcctgcttgc aagactgcgg    26880
gggcaacatc tctttcgccc gccgcttcct gctattccac cacggggtcg cctttccccg    26940
caatgtcctg cattactacc gtcatctcta cagccctac  tgcagcggcg acccagaggc    27000
ggcagcggca gccacagcgg cgaccaccac ctaggaagat atcctccgcg ggcaagacag    27060
cggcagcagc ggccaggaga cccgcggcag cagcggcggg agcggtgggc gcactgcgcc    27120
tctcgcccaa cgaacccctc tcgacccggg agctcagaca caggatcttc ccactttgt     27180 atgccatctt ccaacagagc agaggccagg agcaggagct gaaaataaaa aacagatctc    27240
tgcgctccct cacccgcagc tgtctgtatc acaaaagcga agatcagctt cggcgcacgc    27300
tggaggacgc ggaggcactc ttcagcaaat actgcgcgct cactcttaaa gactagctcc    27360
gcgcccttct cgaatttagg cgggagaaaa ctacgtcatc gccggccgcc gcccagcccg    27420
cccagccgag atgagcaaag agattccac  gccatacatg tggagctacc agccgcagat    27480
gggactcgcg gcgggagcgg cccaggacta ctccaccgc  atgaactaca tgagcgcggg    27540
accccacatg atctcacagg tcaacgggat ccgcgcccag cgaaaccaaa tactgctgga    27600
acaggcggcc atcaccgcca cgccccgcca taatctcaac cccgaaatt  ggcccgccgc    27660 cctagtgtac caggaaaccc cctccgccac caccgtacta cttccgcgtg acgcccaggc    27720
cgaagtccag atgactaact caggggcgca gctcgcgggc ggctttcgtc acggggcgcg    27780
gccgctccga ccaggtataa gacacctgat gatcagaggc cgaggtatcc agctcaacga    27840
cgagtcggtg agctcttcgc tcggtctccg tccggacgga actttccagc tcgccggatc    27900
cggtcgctct tcgttcacgc cccgccaggc gtacctgact ctgcagacct cgtcctcgga    27960
gccccgctcc ggcggcatcg gaaccctcca gttcgtggag gagttcgtgc cctcggtcta    28020 cttcaaccc  ttctcgggac ctccggacg  ctaccccgac cagttcattc cgaactttga    28080
cgcggtgaag gactcggcgg acggctacga ctgaatgtca ggtgccgagg cagagcagct    28140
tcgcctgaga cacctcgagc actgccgccg ccacaagtgc ttcgcccgcg gttccggtga    28200
gttctgctac tttcagctac ccgaggagca taccgagggg ccggcgcacg gcgtccgcct    28260
gaccacccag ggcgaggtta cctgttccct catccgggag ttcaccctcc gtccctgct    28320 agtggagcgg gagcggggtc cctgtgtcct aactatcgcc tgcaactgcc ctaaccctgg    28380
attacatcaa gatctttgct gtcatctctg tgctgagttt aataaacgct gagatcagaa    28440
tctactgggg ctcctgtcgc catcctgtga acgccaccgt cttcacccac cccgaccagg    28500
cccaggcgaa cctcacctgc ggtctgcatc ggaggtccaa gaagtacctc acctggtact    28560 tcaacgcac  cccctttgtg gtttacaaca gcttcgacgg ggacggagtc tccctgaaag    28620
accagctctc cggtctcagc tactccatcc acaagaacac caccctccaa ctcttccctc    28680
cctacctgcc gggaacctac gagtgcgtca ccggccgctg cacccacctc acccgcctga    28740
tcgtaaacca gagctttccg ggaacagata actccctctt cccagaaaca ggaggtgagc    28800
tcaggaaact ccccggggac cagggcggag acgtaccttc gaccccttgtg gggttaggat    28860
```

```
tttttattac cggggttgctg gctcttttaa tcaaagcttc cttgagatttt gttctttcct   28920
tctacgtgta tgaacacctc agcctccaat aactctaccc tttcttcggg atcaggtgac   28980
ttttctgaaa tcgggcttgg tgtgctgctt actctgttga ttttttttcct tatcatactc   29040
agccttctgt gcctcaggct cgccgcctgc tgcgcacaca tctatatcta ctgctggttg   29100
ctcaagtgca ggggtcgcca cccaagatga acaggtacat ggtcctatcg atcctaggcc   29160
tgctggccct gcggcctgc agcgccgcca aaaagagat tacctttgag gagcccgctt     29220
gcaatgtaac tttcaagccc gagggtgacc aatgcaccac cctcgtcaaa tgcgttacca   29280
atcatgagaa gctgcgcatc gactacaaaa acaaaactgg ccggtttgcg gtctatagtg   29340
tgtttacgcc cggagacccc tctaactact ctgtcaccgt cttccagggc ggacagtcta   29400
agatattcaa ttacactttc ccttttttatg agttgtgcga tgcggtcatg tacatgtcaa   29460
aacagtacaa cctgtggcct ccctctcccc aggcgtgtgt ggaaaatact gggtcttact   29520
gctgtatggc tttggcaatc actacgctcg ctctaatctg cacggtgcta tatataaaat   29580
tcaggcagag gcgaatctttt atcgatgaaa agaaaatgcc ttgatcgcta acaccggctt   29640
tctatctgca gaatgaatgc aatcacctcc ctactaatca ccaccaccct ccttgcgatt   29700
gcccatgggt tgacacgaat cgaagtgcca gtggggtcca atgtcaccat ggtgggcccc   29760
gccggcaatt ccaccctcat gtgggaaaaa tttgtccgca atcaatgggt tcatttctgc   29820
tctaaccgaa tcagtatcaa gcccagagcc atctgcgatg ggcaaaatct aactctgatc   29880
aatgtgcaaa tgatggatgc tgggtactat tacgggcagc ggggagaaat cattaattac   29940
tggcgacccc acaaggacta catgctgcat gtagtcgagg cacttcccac taccaccccc   30000
actaccacct ctcccaccac cactaccact actactacta ctactaccac taccgctgcc   30060
cgccataccc gcaaaagcac catgattagc acaaagcccc ctcgtgctca ctcccacgcc   30120
ggcgggccca tcggtgcgac ctcagaaacc accgagcttt gcttctgcca atgcactaac   30180
gccagcgctc atgaactgtt cgacctggag aatgaggatg cccagcagag ctccgcttgc   30240
ctgacccagg aggctgtgga gcccgttgcc ctgaagcaga tcggtgattc aataattgac   30300
tcttcttctt ttgccactcc cgaataccct cccgattcta ctttccacat cacgggtacc   30360
aaagaccta acctctcttt ctacctgatg ctgctgctct gtatctctgt ggtctcttcc   30420
gcgctgatgt tactggggat gttctgctgc ctgatctgcc gcagaaagag aaaagctcgc   30480
tctcagggcc aaccactgat gcccttcccc taccccccgg attttgcaga taacaagata   30540
tgagctcgct gctgacacta accgctttac tagcctgcgc tctaaccctt gtcgcttgcg   30600
actcgagatt ccacaatgtc acagctgtgg caggagaaaa tgttactttc aactccacgg   30660
ccgataccca gtggtcgtgg agtggctcag gtagctactt aactatctgc aatagctcca   30720
cttccccccag catatcccca accaagtacc aatgcaatgc cagcctgttc accctcatca   30780
acgcttccac cctggacaat ggactctatg taggctatgt acccttttggt gggcaaggaa   30840
agacccacgc ttacaacctg gaagttcgcc agcccagaac cactacccaa gctwcymcca   30900
ycaccagcac cagcagcagc agccacagca gcagcagcag attattgact ttggttttgg   30960
ccagctcatc tgccgctacc caggccatct acagctctgt gcccgaaacc actcagaccc   31020
accgcccaga aacgaccacc gccaccaccc tacacacctc cagcgatcag atgccgacca   31080
acatcacccc cttggctctt caaatgggac ttacaagccc cactccaaaa ccagtggatg   31140
cggccgaggt ctccgccctc gtcaatgact gggcggggct gggaatgtgg tggttcgcca   31200
```

-continued

```
taggcatgat ggcgctctgc ctgcttctgc tctggctcat ctgctgcctc caccgcaggc    31260
gagccagacc ccccatctat agacccatca ttgtcctgaa ccccgataat gatgggatcc    31320
atagattgga tggcctgaaa aacctacttt tttcttttac agtatgataa attgagacat    31380
gcctcgcatt ttcttgtaca tgttccttct cccacctttt ctggggtgtt ctacgctggc    31440
cgctgtgtct cacctggagg tagactgcct ctcacccttc actgtctacc tgctttacgg    31500
attggtcacc ctcactctca tctgcagcct aatcacagta atcatcgcct tcatccagtg    31560
cattgattac atctgtgtgc gcctcgcata cttcagacac cacccgcagt accgagacag    31620
gaacattgcc caacttctaa gactgctcta atcatgcata agactgtgat ctgccttctg    31680
atcctctgca tcctgcccac cctcacctcc tgccagtaca ccacaaaatc tccgcgcaaa    31740
agacatgcct cctgccgctt cacccaactg tggaatatac ccaaatgcta caacgaaaag    31800
agcgagctct ccgaagcttg gctgtatggg gtcatctgtg tcttagtttt ctgcagcact    31860
gtctttgccc tcatgatcta cccctacttt gatttgggat ggaacgcgat cgatgccatg    31920
aattacccca cctttcccgc acccgagata attccactgc acaagttgt acccgttgtc     31980
gttaatcaac gccccccatc ccctacgccc actgaaatca gctactttaa cctaacaggc    32040
ggagatgact gacgccctag atctagaaat ggacggcatc agtaccgagc agcgtctcct    32100
agagaggcgc aggcaggcgg ctgagcaaga gcgcctcaat caggagctcc gagatctcgt    32160
taacctgcac cagtgcaaaa gaggcatctt ttgtctggta aagcaggcca aagtcaccta    32220
cgagaagacc ggcaacagcc accgcctcag ttacaaattg cccacccagc gccagaagct    32280
ggtgctcatg gtgggtgaga atcccatcac cgtcacccag cactcggtag agaccgaggg    32340
gtgtctgcac tccccctgtc ggggtccaga agacctctgc accctggtaa agaccctgtg    32400
cggtctcaga gatttagtcc cctttaacta atcaaacact ggaatcaata aaagaatca    32460
cttacttaaa atcagacagc aggtctctgt ccagtttatt cagcagcacc tccttcccct    32520
cctcccaact ctggtactcc aaacgccttc tggcggcaaa cttcctccac accctgaagg    32580
gaatgtcaga ttcttgctcc tgtccctccg cacccactat cttcatgttg ttgcagatga    32640
agcgcaccaa aacgtctgac gagagcttca accccgtgta cccctatgac acggaaagcg    32700
gccctccctc cgtcccttc ctcacccctc ccttcgtgtc tcccgatgga ttccaagaaa    32760
gtcccccgg ggtcctgtct ctgaacctgg ccgagcccct ggtcacttcc cacggcatgc    32820
tcgccctgaa aatgggaagt ggcctctccc tggacgacgc tggcaacctc acctctcaag    32880
atatcaccac cgctagccct cccctcaaaa aaaccaagac caacctcagc ctagaaacct    32940
catccccct aactgtgagc acctcaggcg ccctcaccgt agcagccgcc gctcccctgg    33000
cggtggccgg cacctccctc accatgcaat cagaggcccc cctgacagta caggatgcaa    33060
aactcaccct ggccaccaaa ggccccctga ccgtgtctga aggcaaactg gccttgcaaa    33120
catcggcccc gctgacggcc gctgacagca gcaccctcac cgttagcgcc acaccaccaa    33180
ttaatgtaag cagtggaagt ttaggcttag acatggaaga ccctatgtat actcacaatg    33240
gaaaactggg aataagaatt gggggtccac taagagtagt agacagcttg catacactca    33300
ctgtagttac cggaaatgga ctaactgtag ataacaatgc cctccaaact aaagttacgg    33360
gcgccctagg ttatgacaca tcaggaaatc tacaattaag agctgcagga ggtatgcgaa    33420
ttgacgcaaa tggccaactt atccttaatg tggcataccc atttgatgct cagaacaatc    33480
tcagccttag acttggtcag ggaccctgt atataaacac agaccacaac ctggatttga    33540
attgcaacag aggtctaacc acaactacca ccaacaacac aaaaaaactt gagactaaaa    33600
```

```
ttagctcagg cttagactat gacaccaatg gtgctgtcat tattaaactt ggcactggtc  33660
taagcttcga caacacaggc gccctaactg tgggaaacac tggtgatgat aaactgactc  33720
tgtggacgac cccagaccca tctccaaatt gcagaattca ctcagacaaa gactgcaagt  33780
ttactctagt cctaactaag tgtggaagcc aaatcctggc ctctgtcgcc gccctagcgg  33840
tatcaggaaa tctggcttcg ataacaggca ccgttgccag cgttaccatc tttctcagat  33900
ttgatcagaa tggagtgctt atggaaaact cctcgctaga caggcagtac tggaacttca  33960
gaaatggcaa ctcaactaac gctgccccct acaccaatgc agttgggttc atgccaaacc  34020
tcgcagcata ccccaaaacg caaagccaga ctgctaaaaa caacattgta agtcaggttt  34080
acttgaatgg agacaaatcc aaacccatga cccttaccat caccctcaat ggaactaatg  34140
aatccagtga aactagccag gtgagtcact actccatgtc atttacatgg gcttgggaaa  34200
gtgggcaata tgccactgaa acctttgcca ccaactcctt cacctttttct tacattgctg  34260 aacaataaaa agcatgacac tgatgttcat ttctgattct tatttttatta ttttcaaaca  34320 caacaaaatc attcaagtca ttcttccatc ttagcttaat agacacagta gcttaataga  34380
cccagtagtg caaagcccca ttctagctta taactagtgg agaagtactc gcctacatgg  34440
gggtagagtc ataatcgtgc atcaggatag ggcggtggtg ctgcagcagc gcgcgaataa  34500
actgctgccg ccgccgctcc gtcctgcagg aatacaacat ggcagtggtc tcctcagcga  34560
tgattcgcac cgcccgcagc ataaggcgcc ttgtcctccg ggcacagcag cgcaccctga  34620
tctcacttaa atcagcacag taactgcagc acagcaccac aatattgttc aaaatcccac  34680
agtgcaaggc gctgtatcca aagctcatgg cggggaccac agaacccacg tggccatcat  34740
accacaagcg caggtagatt aagtggcgac ccctcataaa cacgctggac ataaacatta  34800
cctcttttgg catgttgtaa ttcaccacct cccggtacca tataaacctc tgattaaaca  34860
tggcgccatc caccaccatc ctaaaccagc tggccaaaac ctgcccgccg gctatacact  34920
gcagggaacc gggactggaa caatgacagt ggagagccca ggactcgtaa ccatggatca  34980
tcatgctcgt catgatatca atgttggcac aacacaggca cacgtgcata cacttcctca  35040
ggattacaag ctcctcccgc gttagaacca tatcccaggg aacaacccat tcctgaatca  35100
gcgtaaatcc cacactgcag ggaagacctc gcacgtaact cacgttgtgc attgtcaaag  35160
tgttacattc gggcagcagc ggatgatcct ccagtatggt agcgcgggtt tctgtctcaa  35220
aaggaggtag acgatcccta ctgtacggag tgcgccgaga caaccgagat cgtgttggtc  35280
gtagtgtcat gccaaatgga acgccggacg tagtcatatt tcctgaagtc ttagatctct  35340
caacgcagca ccagcaccaa cacttcgcag tgtaaaaggc caagtgccga gagagtatat  35400
ataggaataa aaagtgacgt aaacgggcaa agtccaaaaa acgcccagaa aaaccgcacg  35460
cgaacctacg ccccgaaacg aaagccaaaa aacactagac actcccttcc ggcgtcaact  35520 tccgcttttcc cacgctacgt cacttgcccc agtcaaacaa actacatatc ccgaacttcc  35580
aagtcgccac gcccaaaaca ccgcctacac ctccccgccc gccggcccgc cccaaaccc   35640 gcctcccgcc ccgcgcccccg ccccgcgccg ccatctctcat tatcatattg gcttcaatcc  35700
aaaataaggt atattattga tgatggttta acggatcca attcttgaag acgaaagggc  35760
ctcgtgatac gcctatttttt ataggttaat gtcatgataa taatggtttc ttagacgtca  35820
ggtggcactt tcggggaaa tgtgcgcgga acccctatttt gtttatttttt ctaaatacat  35880 tcaaatatgt atccgctcat gagacaataa ccctgataaa tgcttcaata atattgaaaa  35940
```

-continued aggaagagta tgagtattca acatttccgt gtcgccctta ttcccttttt tgcggcattt 36000
tgccttcctg tttttgctca cccagaaacg ctggtgaaag taaaagatgc tgaagatcag 36060
ttgggtgcac gagtgggtta catcgaactg gatctcaaca gcggtaagat ccttgagagt 36120
tttcgccccg aagaacgttt tccaatgatg agcactttta aagttctgct atgtggcgcg 36180
gtattatccc gtgttgacgc cgggcaagag caactcggtc gccgcataca ctattctcag 36240
aatgacttgg ttgagtactc accagtcaca gaaaagcatc ttacggatgg catgacagta 36300
agagaattat gcagtgctgc cataaccatg agtgataaca ctgcggccaa cttacttctg 36360
acaacgatcg gaggaccgaa ggagctaacc gcttttttgc acaacatggg ggatcatgta 36420
actcgccttg atcgttggga accggagctg aatgaagcca taccaaacga cgagcgtgac 36480
accacgatgc ctgtagcaat ggcaacaacg ttgcgcaaac tattaactgg cgaactactt 36540
actctagctt cccggcaaca attaatagac tggatggagg cggataaagt tgcaggacca 36600
cttctgcgct cggcccttcc ggctggctgg tttattgctg ataaatctgg agccggtgag 36660
cgtgggtctc gcggtatcat tgcagcactg gggccagatg gtaagccctc ccgtatcgta 36720
gttatctaca cgacggggag tcaggcaact atggatgaac gaaatagaca gatcgctgag 36780
ataggtgcct cactgattaa gcattggtaa ctgtcagacc aagtttactc atatatactt 36840
tagattgatt taaaaggatc taggtgaaga tcctttttga taatctcatg accaaaatcc 36900
cttaacgtga gttttcgttc cactgagcgt cagaccccgt agaaaagatc aaaggatctt 36960
cttgagatcc tttttttctg cgcgtaatct gctgcttgca aacaaaaaaa ccaccgctac 37020
cagcggtggt ttgtttgccg gatcaagagc taccaactct ttttccgaag gtaactggct 37080
tcagcagagc gcagatacca aatactgtcc ttctagtgta gccgtagtta ggccaccact 37140
tcaagaactc tgtagcaccg cctacatacc tcgctctgct aatcctgtta ccagtggctg 37200
ctgccagtgg cgataagtcg tgtcttaccg ggttggactc aagacgatag ttaccggata 37260
aggcgcagcg gtcgggctga acggggggtt cgtgcacaca gcccagcttg gagcgaacga 37320
cctacaccga actgagatac ctacagcgtg agctatgaga aagcgccacg cttcccgaag 37380
ggagaaaggc ggacaggtat ccggtaagcg gcagggtcgg aacaggagag cgcacgaggg 37440
agcttccagg gggaaacgcc tggtatcttt atagtcctgt cgggtttcgc cacctctgac 37500
ttgagcgtcg atttttgtga tgctcgtcag gggggcggag cctatggaaa aacgccagca 37560
acgcggcctt tttacggttc ctggcctttt gctggccttg aagctgtccc tgatggtcgt 37620
catctacctg cctggacagc atggcctgca acgcgggcat cccgatgccg ccggaagcga 37680
gaagaatcat aatggggaag gccatccagc ctcgcgtcgc agatccgaat tcgtttaaac 37740

<210> SEQ ID NO 23
<211> LENGTH: 1572
<212> TYPE: DNA
<213> ORGANISM: Rabies virus

<400> SEQUENCE: 23
atggtgcctc aagccctgct gttcgtgccc ctgctggtct tctccctctg ctttggcaag 60
ttccccatct acaccatccc tgacaagctc ggcccctggt cccccattga catacatcac 120
ctcagctgcc ccaacaacct ggtggtggag gatgagggct gcacaaacct gagcggcttc 180
tcctatatgg aactcaaggt gggctatatc tccgccatca aggtcaatgg attcacatgc 240
accggcgtcg tgacagaggc tgaaacatac accaactttg tgggctacgt caccaccaca 300
ttcaagagga agcacttcag gcccacccct gacgcttgca gggctgccta caattggaag 360

```
atggctggcg acccccaggta tgaggagtcc ctgcacaatc cctaccccga ctaccattgg    420
ctcaggacag tcaagaccac caaggagtcc ctggtcatta tctcccctag cgtggccgac    480
ctagacccgt atgacaaaag cctgcactcc agggtcttcc ctagcggcaa atgctccggc    540
attacagtga gctccaccta ctgcagcaca aaccacgact acaccatctg gatgcctgag    600
aatcctaggc tcggcacctc ctgtgacata tttacaaata gcaggggcaa gagggcttcc    660
aaaggcagca aaacctgcgg ctttgtcgac gaaagaggcc tgtacaagtc cctcaagggc    720
gcttgtaaac tcaagctgtg cggagtgctg ggactcagac tcatggacgg cacatgggtg    780
gccatgcaga ccagcgatga gaccaagtgg tgcccccccg atcagctggt gaatctgcac    840
gacttcaggt ccgacgaaat tgagcacctc gtggtcgagg agctggtgaa gagagagaa     900 gagtgcctgg atgctctgga gtccatcatg accaccaaat ccgtgtcctt cagaaggctg    960
agccacctca ggaagctggt ccccggcttt ggcaaggcct acacaatttt caataagaca    1020
ctgatggagg ccgatgctca ctacaaatcc gtgaggacct ggaacgagat catcccctcc    1080
aaaggctgcc tgagggtggg aggaagatgc cacccccacg tcaacggcgt cttcttcaac    1140
ggcattatcc tcggacccga tgccatgtc ctgatccctg aaatgcaaag ctccctgctg     1200
cagcagcaca tggaactcct ggagagctcc gtcatccccc tgatgcaccc tctcgctgac    1260
cccagcaccg tgtttaaaga cggcgatgag gccgaggact tcgtggaagt gcatctgcct    1320
gatgtgcata agcaagtcag cggcgtcgat ctgggcctgc ctaattgggg caagtatgtc    1380
ctgctctccg ccggagctct gattgccctg atgctgatca tcttcctgat gacctgctgc    1440
agaagagtca acagacctga gagcacccaa agatccctcg gcggaaccgg aaggaaggtc    1500
agcgtgacca gccagtccgg caaagtgatt tcctcctggg agagctataa aagcggcgga    1560
gagaccaggc tg                                                        1572

<210> SEQ ID NO 24
<211> LENGTH: 37536
<212> TYPE: DNA
<213> ORGANISM: Pan troglodytes
<220> FEATURE:
<221> NAME/KEY: misc_feature
<222> LOCATION: (24187)..(24189)
<223> OTHER INFORMATION: n is a, c, g, or t

<400> SEQUENCE: 24
catcatcaat aatataccttt attttggatt gaagccaata tgataatgag atgggcggcg    60
cggggcgggg cgcggggcgg gaggcgggtt tggggcgggg ccggcgggcg gggcggtgtg    120
gcggaagtgg actttgtaag tgtggcggat gtgacttgct agtgccgggc gcggtaaaag    180
tgacgttttc cgtgcgcgac aacgccccccg ggaagtgaca tttttcccgc ggttttttacc  240 ggatgttgta gtgaatttgg gcgtaaccaa gtaagatttg gccattttcg cgggaaaact    300
gaaacgggga agtgaaatct gattaatttt gcgttagtca taccgcgtaa tatttgtcta    360
gggccgaggg actttggccg attacgtgga ggactcgccc aggtgttttt tgaggtgaat    420
ttccgcgttc cgggtcaaag tctgcgtttt attattatag gatatcccat tgcatacgtt    480
gtatccatat cataatatgt acatttatat tggctcatgt ccaacattac cgccatgttg    540
acattgatta ttgactagtt attaatagta atcaattacg gggtcattag ttcatagccc    600
atatatggag ttccgcgtta cataacttac ggtaaatggc ccgcctggct gaccgcccaa    660
cgacccccgc ccattgacgt caataatgac gtatgttccc atagtaacgc caatagggac    720
```

```
tttccattga cgtcaatggg tggagtattt acggtaaact gcccacttgg cagtacatca      780
agtgtatcat atgccaagta cgcccctat tgacgtcaat gacggtaaat ggcccgcctg       840
gcattatgcc cagtacatga ccttatggga ctttcctact tggcagtaca tctacgtatt     900
agtcatcgct attaccatgg tgatgcggtt ttggcagtac atcaatgggc gtggatagcg     960
gtttgactca cggggatttc caagtctcca ccccattgac gtcaatggga gtttgttttg    1020
gaaccaaaat caacgggact ttccaaaatg tcgtaacaac tccgccccat tgacgcaaat    1080
gggcggtagg cgtgtacggt gggaggtcta taagcagag ctctcccta tcagtgatag      1140 agatctccct atcagtgata gagatcgtcg acgagctcgt ttagtgaacc gtcagatcgc    1200
ctggagacgc catccacgct gttttgacct ccatagaaga caccgggacc gatccagcct    1260
ccgcggccgg gaacggtgca ttggaacgcg gattccccgt gccaagagtg agatcttccg    1320
tttatctagg taccagatat cgccaccatg gtgcctcaag ccctgctgtt cgtgcccctg    1380
ctggtcttct ccctctgctt tggcaagttc cccatctaca ccatccctga caagctcggc    1440
ccctggtccc ccattgacat acatcacctc agctgcccca caacctggt ggtggaggat     1500 gagggctgca caaacctgag cggcttctcc tatatggaac tcaaggtggg ctatatctcc    1560
gccatcaagg tcaatggatt cacatgcacc ggcgtcgtga cagaggctga acatacacc     1620 aactttgtgg gctacgtcac caccacattc aagaggaagc acttcaggcc caccctgac    1680 gcttgcaggg ctgcctacaa ttggaagatg gctggcgacc caggtatga ggagtccctg    1740 cacaatccct accccgacta ccattggctc aggacagtca agaccaccaa ggagtccctg    1800
gtcattatct cccctagcgt ggccgaccta gacccgtatg acaaaagcct gcactccagg    1860
gtcttcccta gcggcaaatg ctccggcatt acagtgagct ccacctactg cagcacaaac    1920
cacgactaca ccatctggat gcctgagaat cctaggctcg gcacctcctg tgacatattt    1980
acaaatagca ggggcaagag ggcttccaaa gcagcaaaa cctgcggctt tgtcgacgaa     2040
agaggcctgt acaagtccct caagggcgct tgtaaactca agctgtgcgg agtgctggga    2100
ctcagactca tggacggcac atgggtggcc atgcagacca gcgatgagac caagtggtgc    2160 cccccgatc agctggtgaa tctgcacgac ttcaggtccg acgaaattga gcacctcgtg     2220
gtcgaggagc tggtgaagaa gagagaagag tgcctggatg ctctggagtc catcatgacc    2280
accaaatccg tgtccttcag aaggctgagc cacctcagga agctggtccc cggctttggc    2340
aaggcctaca caattttcaa taagacactg atggaggccg atgctcacta caaatccgtg    2400
aggacctgga acgagatcat cccctccaaa ggctgcctga gggtgggagg aagatgccac    2460
ccccacgtca acggcgtctt cttcaacggc attatcctcg acccgatgg ccatgtcctg    2520 atccctgaaa tgcaaagctc cctgctgcag cagcacatgg aactcctgga gagctccgtc    2580 atcccctga tgcaccctct cgctgacccc agcaccgtgt taaagacgg cgatgaggcc     2640 gaggacttcg tggaagtgca tctgcctgat gtgcataagc aagtcagcgg cgtcgatctg    2700
ggcctgccta ttggggcaa gtatgtcctg ctctccgccg gagctctgat tgccctgatg    2760
ctgatcatct tcctgatgac ctgctgcaga agagtcaaca gacctgagag cacccaaaga    2820
tccctcggcg gaaccggaag gaaggtcagc gtgaccagcc agtccggcaa agtgatttcc    2880
tcctgggaga gctataaaag cggcggagag accaggctgt gatgagcggc cgcgatctgc    2940
tgtgccttct agttgccagc catctgttgt ttgcccctcc ccgtgccctt ccttgaccct    3000
ggaaggtgcc actcccactg tccttttccta ataaaatgag gaaattgcat cgcattgtct    3060
gagtaggtgt cattctattc tggggggtgg ggtggggcag gacagcaagg gggaggattg    3120
```

```
ggaagacaat agcaggcatg ctggggatgc ggtgggctct atggccgatc agcgatcgct    3180
gaggtgggtg agtgggcgtg gcctggggtg gtcatgaaaa tatataagtt ggggtctta    3240
gggtctcttt atttgtgttg cagagaccgc cggagccatg agcgggagca gcagcagcag    3300
cagtagcagc agcgccttgg atggcagcat cgtgagccct tatttgacga cgcggatgcc    3360
ccactgggcc ggggtgcgtc agaatgtgat gggctccagc atcgacggcc gacccgtcct    3420
gcccgcaaat tccgccacgc tgacctatgc gaccgtcgcg gggacgccgt tggacgccac    3480
cgccgccgcc gccgccaccg cagccgcctc ggccgtgcgc agcctggcca cggactttgc    3540
attcctggga ccactggcga cagggggctac ttctcgggcc gctgctgccg ccgttcgcga    3600
tgacaagctg accgccctgc tggcgcagtt ggatgcgctt actcgggaac tgggtgacct    3660
ttctcagcag gtcatggccc tgcgccagca ggtctcctcc ctgcaagctg gcgggaatgc    3720
ttctcccaca aatgccgttt aagataaata aaaccagact ctgtttggat taagaaaag    3780
tagcaagtgc attgctctct ttatttcata attttccgcg cgcgataggc cctagaccag    3840
cgttctcggt cgttgagggt gcggtgtatc ttctccagga cgtggtagag gtggctctgg    3900
acgttgagat acatgggcat gagcccgtcc cgggggtgga ggtagcacca ctgcagagct    3960
tcatgctccg gggtggtgtt gtagatgatc cagtcgtagc aggagcgctg gcatggtgc    4020
ctaaaaatgt ccttcagcag caggccgatg gccaggggga ggcccttggt gtaagtgttt    4080
acaaaacggt taagttggga agggtgcatt cggggagaga tgatgtgcat cttggactgt    4140
atttttagat tggcgatgtt tccgcccaga tcccttctgg gattcatgtt gtgcaggacc    4200
accagtacag tgtatccggt gcacttgggg aatttgtcat gcagcttaga gggaaaagcg    4260
tggaagaact tggagacgcc cttgtggcct cccagatttt ccatgcattc gtccatgatg    4320
atggcaatgg gcccgcggga ggcagcttgg gcaaagatat ttctggggtc gctgacgtcg    4380
tagttgtgtt ccagggtgag gtcgtcatag gccattttta caaagcgcgg gcggagggtg    4440
cccgactggg ggatgatggt cccctctggc cccggggcgt agttgccctc gcagatctgc    4500
atttcccagg ccttaatctc ggagggggga atcatatcca cctgcgggc gatgaagaaa    4560
acggtttccg gagccgggga gattaactgg gatgagagca ggtttctaag cagctgtgat    4620
tttccacaac cggtgggccc ataaataaca cctataaccg gttgcagctg gtagtttaga    4680
gagctgcagc tgccgtcgtc ccggaggagg ggggccacct cgttgagcat gtccctgacg    4740
cgcatgttct ccccgaccag atccgccaga aggcgctcgc cgcccaggga cagcagctct    4800
tgcaaggaag caaagttttt cagcggcttg aggccgtccg ccgtgggcat gttttttcagg    4860
gtctggctca gcagctccag gcggtcccag agctcggtga cgtgctctac ggcatctcta    4920
tccagcatat ctcctcgttt cgcggggtttgg ggcgactttc gctgtagggc accaagcggt    4980
ggtcgtccag cgggggccaga gtcatgtcct tccatgggcg cagggtcctc gtcagggtgg    5040
tctgggtcac ggtgaagggg tgcgctccgg gctgagcgct tgccaaggtg cgcttgaggc    5100
tggttctgct ggtgctgaag cgctgccggt cttcgccctg cgcgtcggcc aggtagcatt    5160
tgaccatggt gtcatagtcc agcccctccg cggcgtgtcc cttggcgcgc agcttgccct    5220
tggaggtggc gccgcacgag gggcagagca ggctcttgag cgcgtagagc ttggggcga    5280
ggaagaccga ttcgggggag taggcgtccg cgccgcagac cccgcacacg gtctcgcact    5340
ccaccagcca ggtgagctcg gggcgcgccg ggtcaaaaac caggtttccc ccatgctttt    5400
tgatgcgttt cttacctcgg gtctccatga ggtggtgtcc ccgctcggtg acgaagaggc    5460
```

```
tgtccgtgtc tccgtagacc gacttgaggg gtcttttctc caggggggtc cctcggtctt    5520
cctcgtagag gaactcggac cactctgaga cgaaggcccg cgtccaggcc aggacgaagg    5580
aggctatgtg ggaggggtag cggtcgttgt ccactagggg gtccaccttc tccaaggtgt    5640
gaagacacat gtcgccttcc tcggcgtcca ggaaggtgat tggcttgtag gtgtaggcca    5700
cgtgaccggg ggttcctgac gggggggtat aaaagggggt ggggcgcgc tcgtcgtcac    5760
tctcttccgc atcgctgtct gcgagggcca gctgctgggg tgagtattcc ctctcgaagg    5820
cgggcatgac ctccgcgctg aggttgtcag tttccaaaaa cgaggaggat ttgatgttca    5880
cctgtcccga ggtgatacct ttgagggtac ccgcgtccat ctggtcagaa aacacgatct    5940
ttttattgtc cagcttggtg gcgaacgacc cgtagagggc gttggagagc agcttggcga    6000
tggagcgcag ggtctggttc ttgtccctgt cggcgcgctc cttggccgcg atgttgagct    6060
gcacgtactc gcgcgcgacg cagcgccact cggggaagac ggtggtgcgc tcgtcgggca    6120
ccaggcgcac gcgccagccg cggttgtgca gggtgaccag gtccacgctg gtggcgacct    6180
cgccgcgcag gcgctcgttg gtccagcaga gacggccgcc cttgcgcgag cagaaggggg    6240
gcaggggtc gagctgggtc tcgtccgggg ggtccgcgtc cacggtgaaa accccggggc    6300
gcaggcgcgc gtcgaagtag tctatcttgc aaccttgcat gtccagcgcc tgctgccagt    6360
cgcgggcggc gagcgcgcgc tcgtaggggt tgagcggcgg gccccagggc atggggtggg    6420
tgagtgcgga ggcgtacatg ccgcagatgt catagacgta gaggggctcc cgcaggaccc    6480
cgatgtaggt ggggtagcag cggccgccgc ggatgctggc gcgcacgtag tcatacagct    6540
cgtgcgaggg ggcgaggagg tcggggccca ggttggtgcg ggcggggcgc tccgtgcgga    6600
agacgatctg cctgaagatg gcatgcgagt tggaagagat ggtggggcgc tggaagacgt    6660
tgaagctggc gtcctgcagg ccgacggcgt cgcgcacgaa ggaggcgtag gagtcgcgca    6720
gcttgtgtac cagctcggcg gtgacctgca cgtcgagcgc gcagtagtcg agggtctcgc    6780
ggatgatgtc atatttagcc tgccccttct ttttccacag ctcgcggttg aggacaaact    6840
cttcgcggtc tttccagtac tcttggatcg ggaaaccgtc cggttccgaa cggtaagagc    6900
ctagcatgta gaactggttg acggcctggt aggcgcagca gcccttctcc acggggaggg    6960
cgtaggcctg cgcggccttg cggagcgagg tgtgggtcag ggcgaaggtg tccctgacca    7020
tgactttgag gtactggtgc ttgaagtcgg agtcgtcgca gccgccccgc tcccagagcg    7080
agaagtcggt gcgcttcttg gagcgggggt tgggcagagc gaaggtgaca tcgttgaaga    7140
ggattttgcc cgcgcgggc atgaagttgc gggtgatgcg gaaggccccc ggcacttcag    7200
agcggttgtt gatgacctgg gcggcgagca cgatctcgtc gaagccgttg atgttgtggc    7260
ccacgatgta gagttccagg aagcggggcc ggcccttac ggtgggcagc ttctttagct    7320
cttcgtaggt gagctcctcg ggcgaggcga ggccgtgctc ggccagggcc cagtccgcga    7380
ggtgcgggtt gtctctgagg aaggactccc agaggtcgcg ggccaggagg gtctgcaggc    7440
ggtccctgaa ggtcctgaac tggcggccca cggccatttt tcgggggtg atgcagtaga    7500
aggtgagggg gtcttgctgc cagcggtccc agtcgagctg cagggcgagg tcgcgcgcgg    7560
cggtgaccag cgctcgtcg cccccgaatt tcatgaccag catgaagggc acgagctgct    7620
ttccgaaggc ccccatccaa gtgtaggtct ctacatcgta ggtgacaaag aggcgctccg    7680
tgcgaggatg cgagccgatc gggaagaact ggatctcccg ccaccagttg gaggagtggc    7740
tgttgatgtg gtggaagtag aagtcccgtc gccgggccga acactcgtgc tggcttttgt    7800
aaaagcgagc gcagtactgg cagcgctgca cgggctgtac ctcatgcacg agatgcacct    7860
```

```
ttcgcccgcg cacgaggaag ccgagggaa atctgagccc cccgcctggc tcgcggcatg    7920
gctggtgctc ttctactttg gatgcgtgtc cgtctccgtc tggctcctcg aggggtgtta    7980
cggtggagcg gaccaccacg ccgcgcgagc cgcaggtcca gatatcggcg cgcggcggtc    8040
ggagtttgat gacgacatcg cgcagctggg agctgtccat ggtctggagc tcccgcggcg    8100
gcggcaggtc agccgggagt tcttgcaggt tcacctcgca gagtcgggcc agggcgcggg    8160
gcaggtctag gtggtacctg atctctaggg gcgtgttggt ggcggcgtcg atggcttgca    8220
ggagcccgca gccccggggg gcgacgacgg tgccccgcgg ggtggtggtg gtggtggcgg    8280
tgcagctcag aagcggtgcc gcgggcggcc ccccggaggt agggggggct ccggtcccgc    8340
gggcaggggc ggcagcggca cgtcggcgtg gagcgcgggc aggagttggt gctgtgcccg    8400
gaggttgctg gcgaaggcga cgacgcgcg gttgatctcc tggatctggc gcctctgcgt    8460
gaagacgacg ggcccggtga gcttgaacct gaaagagagt tcgacagaat caatctcggt    8520
gtcattgacc gcgcctggc gcaggatctc ctgcacgtct cccgagttgt cttggtaggc    8580
gatctcggcc atgaactgct cgatctcttc ctcctggagg tctccgcgtc cggcgcgttc    8640
cacggtggcc gccaggtcgt tggagatgcg ccccatgagc tgcgagaagg cgttgagtcc    8700
gccctcgttc cagactcggc tgtagaccac gccccctgg tcatcgcggg cgcgcatgac    8760
cacctgcgcg aggttgagct ccacgtgccg cgcgaagacg gcgtagttgc gcagacgctg    8820
gaagaggtag ttgagggtgg tggcggtgtg ctcggccacg aagaagttca tgacccagcg    8880
gcgcaacgtg gattcgttga tgtcccccaa ggcctccagc cgttccatgg cctcgtagaa    8940
gtccacggcg aagttgaaaa actgggagtt gcgcgccgac acggtcaact cctcctccag    9000
aagacggatg agctcggcga cggtgtcgcg cacctcgcgc tcgaaggcta tgggatctc    9060 ttcctccgct agcatcacca cctcctcctc ttcctcctct tctggcactt ccatgatggc    9120
ttcctcctct tcgggggtg gcggcggcgg cggtggggga gggggcgctc tgcgccggcg    9180
gcggcgcacc gggaggcggt ccacgaagcg cgcgatcatc tccccgcggc ggcggcgcat    9240
ggtctcggtg acggcgcggc cgttctcccg ggggcgcagt tggaagacgc cgccggacat    9300
ctggtgctgg ggcgggtggc cgtgaggcag cgagacggcg ctgacgatgc atctcaacaa    9360
ttgctgcgta ggtacgccgc cgagggacct gagggagtcc atatccaccg gatccgaaaa    9420
cctttcgagg aaggcgtcta accagtcgca gtcgcaaggt aggctgagca ccgtggcggg    9480
cggcgggggg tgggggagt gtctggcgga ggtgctgctg atgatgtaat tgaagtaggc    9540
ggacttgaca cggcggatgg tcgacaggag caccatgtcc ttgggtccgg cctgctggat    9600
gcggaggcgg tcggctatgc cccaggcttc gttctggcat cggcgcaggt ccttgtagta    9660
gtcttgcatg agccttttcca ccggcacctc ttctccttcc tcttctgctt cttccatgtc    9720
tgcttcggcc ctggggcggc gccgcgcccc cctgcccccc atgcgcgtga ccccgaaccc    9780
cctgagcggt tggagcaggg ccaggtcggc gacgacgcgc tcggccagga tggcctgctg    9840
cacctgcgtg agggtggttt ggaagtcatc caagtccacg aagcggtggt aggcgcccgt    9900
gttgatggtg taggtgcagt tggccatgac ggaccagttg acggtctggt ggcccggttg    9960
cgacatctcg gtgtacctga gtcgcgagta ggcgcggag tcgaagacgt agtcgttgca   10020
agtccgcacc aggtactggt agcccaccag gaagtgcggc ggcggctggc ggtagagggg   10080
ccagcgcagg gtgcgggggg ctccgggggc caggtcttcc agcatgaggc ggtggtaggc   10140
gtagatgtac ctggacatcc aggtgatacc cgcggcggtg gtggaggcgc gcgggaagtc   10200
```

-continued

```
gcgcacccgg ttccagatgt tgcgcagggg cagaaagtgc tccatggtag gcgtgctctg   10260
tccagtcaga cgcgcgcagt cgttgatact ctagaccagg gaaaacgaaa gccggtcagc   10320
gggcactctt ccgtggtctg gtgaatagat cgcaagggta tcatggcgga gggcctcggt   10380 tcgagcccccg gtccgggcc ggacggtccg ccatgatcca cgcggttacc gcccgcgtgt   10440
cgaacccagg tgtgcgacgt cagacaacgg tggagtgttc cttttggcgt ttttctggcc   10500
gggcgccggc gccgcgtaag agactaagcc gcgaaagcga aagcagtaag tggctcgctc   10560
cccgtagccg gagggatcct tgctaagggt tgcgttgcgg cgaaccccgg ttcgaatccc   10620
gtactcgggc cggccggacc cgcggctaag gtgttggatt ggcctccccc tcgtataaag   10680
accccgcttg cggattgact ccggacacgg ggacgagccc cttttatttt tgctttcccc   10740
agatgcatcc ggtgttgcga cagatgcgcc ccccgcccca gcagcagcaa caacaccagc   10800
aagagcggca gcaacagcag cgggagtcat gcagggcccc ctcacccacc ctcggcggcc   10860
cggccacctc ggcgtccgcg gccgtgtctg gcgcctgcgg cggcggcggc gggggggccgg   10920 ctgacgaccc cgaggagccc ccgcggcgca gggccagaca ctacctggac ctggaggagg   10980
gcgagggcct ggcgcggctg ggggcgccgt ctcccgagcg ccaccgcgg gtgcagctaa   11040 agcgcgactc gcgcgaggcg tacgtgcctc ggcagaacct gttcagggac cgcgcggggcg   11100 aggagcccga ggagatgcgg gacaggaggt tcagcgcggg gcgggagctg cggcaggggc   11160
tgaaccgcga gcggctgctg cgcgaggagg actttgagcc cgacgcgcgg acggggatca   11220
gccccgcgcg cgcgcacgtg gcggccgccg acctggtgac ggcgtacgag cagacggtga   11280
accaggagat caacttccaa aagagtttca caaccacgt gcgcacgctg gtggcgcgcg   11340
aggaggtgac catcgggctg atgcacctgt gggactttgt gagcgcgctg gtgcagaacc   11400
ccaatagcaa gcctctgacg gcgcagctgt tcctgatagt gcagcacagc agggacaacg   11460
aggcgtttag ggacgcgctg ctgaacatca ccgagcccga gggccggtgg ctgctggacc   11520
tgattaacat cctgcagagc atagtggtgc aggagcgcag cctgagcctg ccgacaagg   11580 tggcggccat caactactcg atgctgagcc tgggcaagtt ttacgcgcgc aagatctacc   11640
agacgccgta cgtgcccata gacaaggagg tgaagatcga cggttttttac atgcgcatgg   11700 cgctgaaggt gctcacccta agcgacgacc tgggcgtgta ccgcaacgag cgcatccaca   11760
aggccgtgag cgtgagccgg cggcgcgagc tgagcgaccg cgagctgatg catagcctgc   11820
agcgggcgct ggcgggcgcc ggcagcggcg acagggaggc ggagtcctac ttcgatgcgg   11880
gggcggacct cgcgctgggcg cccagccggc gggccctgga ggccgcgggg gtccgcgagg   11940
actatgacga ggacggcgag gaggatgagg agtacgagct agaggagggc gagtacctgg   12000
actaaaccgc gggtggtgtt tccggtagat gcaagacccg aacgtggtgg acccggcgct   12060 gcgggcgget ctgcagagcc agccgtccgg ccttaactcc tcagacgact ggcgacaggt   12120 catgaccgc atcatgtcgc tgacggcgcg taacccggac gcgttccggc agcagccgca   12180
ggccaacagg ctctccgcca tcctggaggc ggtggtgcct cgcgcgctcga accccacgca   12240 cgagaaggtg ctggccatag tgaacgcgct ggccgagaac agggccatcc gcccggacga   12300
ggccgggctg gtgtacgacg cgctgctgca gcgcgtggcc cgctacaaca gcggcaacgt   12360
gcagaccaac ctggaccggc tggtggggga cgtgcgcgag gcggtggcgc agcgcgagcg   12420
cgcggatcgg cagggcaacc tgggctccat ggtggcgctg aatgccttcc tgagcacgca   12480
gccgccaaac gtgccgcggg ggcaggaaga ctacaccaac tttgtgagcg cgctgcggct   12540
gatggtgacc gagacccccc agagcgaggt gtaccagtcg ggtccggact acttcttcca   12600
```

```
gaccagcaga cagggcctgc agacggtgaa cctgagccag gctttcaaga acctgcgggg    12660 gctgtgggggc gtgaaggcgc ccaccggcga ccgggcgacg gtgtccagcc tgctgacgcc    12720
caactcgcgc ctgctgctgc tgctgatcgc gccgttcacg gacagcggca gcgtgtcccg    12780
ggacacctac ctggggcacc tgctgaccct gtaccgcgag gccatcgggc aggcgcaggt    12840
ggacgagcac accttccagg agatcaccag cgttagccgc gcgctggggc aggaggacac    12900
gagcagcctg gaggcgactc tgaactacct gctgaccaac cggcggcaga agattccctc    12960
gctgcacagc ctgacctccg aggaggagcg catcttgcgc tacgtgcagc agagcgtgag    13020
cctgaacctg atgcgcgacg gggtgacgcc cagtgtggcg ctggacatga ccgcgcgcaa    13080
catggaaccg ggcatgtacg ccgcgcaccg gccttacatc aaccgcctga tggactacct    13140
gcatcgcgcg gcgccgtga accccgagta ctttaccaac gccatcctga cccgcactg    13200 gctcccgccg cccgggttct acagcggggg cttcgaggtc ccggaggcca acgatggctt    13260
cctgtgggac gacatggacg acagcgtgtt ctccccgcgg ccgcaggcgc tggcggaagc    13320
gtccctgctg cgtcccaaga aggaggagga ggcgagtcgc cgccgcggca gcagcggcgt    13380
ggcttctctg tccgagctgg gggcggcagc cgccgcgcgc cccgggtccc tgggcggcag    13440
cccctttccg agcctggtgg ggtctctgca cagcgagcgc accacccgcc ctcggctgct    13500
gggcgaggac gagtacctga taactccct gctgcagccg gtgcgggaga aaaacctgcc    13560
tcccgccttc cccaacaacg ggatagagag cctggtggac aagatgagca gatggaagac    13620
ctatgcgcag gagcacaggg acgcgcccgc gctccggccg cccacgcggc gccagcgcca    13680
cgaccggcag cggggggctgg tgtgggatga cgaggactcc gcggacgata gcagcgtgct    13740
ggacctggga gggagcggca acccgttcgc gcacctgcgc ccccgcctgg ggaggatgtt    13800
ttaaaaaaaa aaaaaagcaa gaagcatgat gcaaaaatta ataaaactc accaaggcca    13860 tggcgaccga gcgttggttt cttgtgttcc cttcagtatg cggcgcgcgg cgatgtacca    13920
ggagggacct cctccctctt acgagagcgt ggtgggcgcg gcggcggcgg cgccctcttc    13980 tcccttttgcg tcgcagctgc tggagccgcc gtacgtgcct ccgcgctacc tgcggcctac    14040
gggggggaga acagcatcc gttactcgga gctggcgccc ctgttcgaca ccacccgggt    14100
gtacctggtg gacaacaagt cggcggacgt ggcctccctg aactaccaga acgaccacag    14160
caattttttg accacggtca tccagaacaa tgactacagc ccgagcgagg ccagcaccca    14220
gaccatcaat ctggatgacc ggtcgcactg gggcggcgac ctgaaaacca tcctgcacac    14280
caacatgccc aacgtgaacg agttcatgtt caccaataag ttcaaggcgc gggtgatggt    14340
gtcgcgctcg cacaccaagg aagaccgggt ggagctgaag tacgagtggg tggagttcga    14400
gctgccagag ggcaactact ccgagaccat gaccattgac ctgatgaaca cgcgatcgt    14460 ggagcactat ctgaaagtgg gcaggcagaa cggggtcctg gagagcgaca tcgggtcaa    14520 gttcgacacc aggaacttcc gcctggggct ggacccgtg accggctgg ttatgcccgg    14580 ggtgtacacc aacgaggcct tccatcccga catcatcctg ctgcccggct gcggggtgga    14640
cttcacttac agccgcctga gcaacctcct gggcatccgc aagcggcagc ccttccagga    14700
gggcttcagg atcacctacg aggacctgga gggggcaac atccccgcgc tcctcgatgt    14760
ggaggcctac caggatagct tgaaggaaaa tgaggcggga caggaggata ccgccccgc    14820 cgcctccgcc gccgccgagc agggcgagga tgctgctgac accgcggccg cggacgggggc    14880 ggaggccgac cccgctatgg tggtggaggc tgccgagcag gaggaggaca tgaatgacag    14940
```

```
tgcggtgcgc ggagacacct tcgtcacccg gggggaggaa aagcaagcgg aggccgaggc   15000
cgcggccgag gaaaagcaac tggcggcagc agcggcggcg gcggcgttgg ccgcggcgga   15060
ggctgagtct gagggggacca agcccgccaa ggagcccgtg attaagcccc tgaccgaaga   15120
tagcaagaag cgcagttaca acctgctcaa ggacagcacc aacaccgcgt accgcagctg   15180
gtacctggcc tacaactacg gcgacccgtc gacggggtg cgctcctgga ccctgctgtg    15240
cacgccggac gtgacctgcg gctcggagca ggtgtactgg tcgctgcccg acatgatgca   15300
agaccccgtg accttccgct ccacgcggca ggtcagcaac ttcccggtgg tgggcgccga   15360
gctgctgccc gtgcactcca agagcttcta caacgaccag gccgtctact cccagctcat   15420
ccgccagttc acctctctga cccacgtgtt caatcgcttt cctgagaacc agattctggc   15480
gcgcccgccc gcccccacca tcaccaccgt cagtgaaaac gttcctgctc tcacagatca   15540
cgggacgcta ccgctgcgca acagcatcgg aggagtccag cgagtgaccg ttactgacgc   15600
cagacgccgc acctgcccct acgtttacaa ggccttgggc atagtctcgc gcgcgtcct    15660 ttccagccgc acttttgag caacaccacc atcatgtcca tcctgatctc acccagcaat    15720
aactccggct ggggactgct gcgcgcgccc agcaagatgt cggagggc gaggaagcgt     15780 tccgagcagc accccgtgcg cgtgcgcggg cacttccgcg cccctgggg agcgcacaaa    15840 cgcggccgcg cggggcgcac caccgtggac gacgccatcg actcggtggt ggagcaggcg   15900
cgcaactaca gcccgcggt ctctaccgtg gacgcggcca tccagaccgt ggtgcggggc    15960
gcgcggcggt acgccaagct gaagagccgc cggaagcgcg tggcccgccg ccaccgccgc   16020
cgacccgggg ccgccgccaa acgcgccgcc gcggccctgc ttcgccgggc caagcgcacg   16080
ggccgccgcg ccgccatgag ggccgcgcgc cgcttggccg ccggcatcac cgccgccacc   16140
atggcccccc gtacccgaag acgcgcgcc gccgccgccg ccgccgccat cagtgacatg      16200
gccagcaggc gccggggcaa cgtgtactgg gtgcgcgact cggtgaccgg cacgcgcgtg   16260
cccgtgcgct tccgcccccc gcggacttga gatgatgtga aaaacaaca ctgagtctcc     16320 tgctgttgtg tgtatcccag cggcggcggc ggcgcgcgca gcgtcatgtc caagcgcaaa    16380
atcaaagaag agatgctcca ggtcgtcgcg ccggagatct atgggccccc gaagaaggaa    16440
gagcaggatt cgaagccccg caagataaag cgggtcaaaa agaaaaagaa agatgatggc    16500
gatgccgatg gggaggtgga gttcctgcgc gccacggcgc ccaggcgccc ggtgcagtgg    16560
aagggccggc gcgtaaagcg cgtcctgcgc cccggcaccg cggtggtctt cacgcccggc    16620
gagcgctcca cccggacttt caagcgcgtc tatgacgagg tgtacggcga cgaagacctg    16680
ctggagcagg ccaacgagcg cttcggagag tttgcttacg ggaagcgtca gcggccgctg    16740
gggaaggagg acctgctggc gctgccgctg gaccagggca accccacccc cagtctgaag   16800
cccgtgaccc tgcagcaggt gctgccgagc agcgcaccct ccgaggcgaa gcggggtctg    16860
aagcgcgagg gcggcgacct ggcgcccacc gtgcagctca tggtgcccaa gcggcagagg    16920
ctggaggatg tgctggagaa aatgaaagta gaccccggtc tgcagccgga catcagggtc    16980
cgtcccatca gcaggtggc gccgggcctc ggcgtgcaga ccgtggacgt ggtcatcccc      17040
accggcaact ccccgccgc caccaccact accgctgcct ccacggacat ggagacacag      17100
accgatcccg ccgcagccgc cgccaccgcc gccgccgcga cctcctcggc ggaggtgcag    17160
acggacccct ggctgccgcc ggcgatgtca gctccccgcg cgcgtcgcgg gcgcaggaag     17220
tacgcgcccg ccaacgcgct cctgcccgag tacgccttgc atccttccat cgcgcccacc     17280
cccggctacc gaggctatac ctaccgcccg cgaagagcca agggttccac ccgccgtccc    17340
```

```
cgccgacgcg ccgccgccac cacccgccgc cgccgccgca gacgccagcc cgcactggct    17400
ccagtctccg tgaggagagt ggcgcgcgac ggacacaccc tggtgctgcc cagggcgcgc    17460
taccacccca gcatcgttta aaagcctgtt gtggttcttg cagatatggc cctcacttgc    17520
cgcctccgtt tcccggtgcc gggataccga ggaggaagat cgcgccgcag gaggggtctg    17580
gccggccgcg gcctgagcgg aggcagccgc cgcgcgcacc ggcggcgacg cgccaccagc    17640
cgacgcatgc gcggcggggt gctgcccctg ttaatccccc tgatcgccgc ggcgatcggc    17700
gccgtgcccg ggatcgcctc cgtggccttg caggcgtccc agaggcattg acagacttgc    17760
aaacttgcaa atatggaaaa aaaccccaat aaaaagtct agactctcac gctcgcttgg    17820
tcctgtgact attttgtaga atggaagaca tcaactttgc gtcgctggcc ccgcgtcacg    17880
gctcgcgccc gttcctggga cactggaacg atatcggcac cagcaacatg agcggtggcg    17940
ccttcagttg gggctctctg tggagcggca ttaaaagtat cgggtctgcc gttaaaaatt    18000
acggctcccg ggcctggaac agcagcacgg gccagatgtt gagagacaag ttgaaagagc    18060
agaacttcca gcagaaggtg gtggagggcc tggcctccgg catcaacggg gtggtggacc    18120
tggccaacca ggccgtgcag aataagatca acagcagact ggaccccccgg ccgccggtgg    18180 aggaggtgcc gccggcgctg gagacggtgt ccccccgatgg gcgtggcgag aagcgcccgc    18240
ggcccgatag ggaagagacc actctggtca cgcagaccga tgagccgccc cgtatgagg    18300 aggccctgaa gcaaggtctg cccaccacgc ggcccatcgc gcccatggcc accggggtgg    18360
tgggccgcca cacccccgcc acgctggact tgcctccgcc cgccgatgtg ccgcagcagc    18420
agcagaaggc ggcacagccg ggcccgcccg tgaccgcctc ccgttcctcc gccggtcctc    18480
tgcgccgcgc ggccagcggc ccccgcgggg gggtcgcgag gcacggcaac tggcagagca    18540
cgctgaacag catcgtgggt ctgggggtgc ggtccgtgaa gcgccgccga tgctactgaa    18600
tagcttagct aacgtgttgt atgtgtgtat gcgccctatg tcgccgccag aggagctgct    18660
gagtcgccgc cgttcgcgcg cccaccacca ccaccgccac tccgcccctc aagatggcga    18720
ccccatcgat gatgccgcag tggtcgtaca tgcacatctc gggccaggac gcctcggagt    18780
acctgagccc cgggctggtg cagttcgccc gcgccaccga gagctacttc agcctgagta    18840
acaagtttag gaaccccacg gtggcgccca cgcacgatgt gaccaccgac cggtctcagc    18900
gcctgacgct gcggttcatt cccgtggacc gcgaggacac cgcgtactcg tacaaggcgc    18960
ggttcaccct ggccgtgggc gacaaccgcg tgctggacat ggcctccacc tactttgaca    19020
tccgcggggt gctggaccgg ggccccactt tcaagcctta ctctggcacc gcctacaact    19080
ccctggcccc caagggcgct cccaactcct gcgagtggga gcaattagaa gaagcccagg    19140
ccgctgtgga agacgaagaa ttagaagatg aagacgagga accacaggat gaggcacctg    19200
tgaaaaaaac ccatgtatac gctcaggctc ccctttctgg agaagaaatt actaaaaacg    19260
gtttgcaaat agggtcagat aacacagaag cccagtctaa gccatatat gcagatccta    19320 cattccagcc tgaaccccaa atcggggaat cccagtggaa tgaggcagat gctacagttg    19380
ccggcggtag agtgctaaag aaatccactc ccatgaagcc atgctatggt tcctatgcaa    19440
gacccacaaa ctccaatgga ggtcaaggtg tgctggtggc tgatgataag ggggttcttc    19500
aatctaaagt tgaattgcaa ttttttttcaa atactactac tcttaatcag cgggagggta    19560
acgatacaaa accaaaagtg gtgctgtata gcgaagatgt gcacatggaa actccagaca    19620
cccacatttc ttacaagccc acaaaaagcg atgacaattc aaaaatcatg ctgggtcagc    19680
```

```
agtccatgcc caacagacct aattacatcg gcttcagaga caactttatc ggcctcatgt   19740
attacaatag cactggcaac atgggagtgc ttgcaggtca ggcctctcag ttgaatgcag   19800
tggtggactt gcaagacaga aacacagaac tgtcctacca gctcttgctt gattccatgg   19860
gtgacagaac cagatacttt tccatgtgga atcaggcagt ggacagttat gacccagatg   19920
tcagaattat tgaaaatcat ggaactgaag acgagctccc caactattgt ttccctctgg   19980
gcggcatagg ggtaactgac acttaccagg ccattaaaac caatggcaat ggtcaagaaa   20040
acccaacctg ggaaaaagat acagagtttg cagaccgcaa tgaaataggg gtgggaaaca   20100
atttcgctat ggagatcaac ctcagtgcca acctgtggag aaacttcctg tactccaacg   20160
tggcgctgta cctgccagac aagcttaagt acaacccctc caatgtggac atctctgaca   20220
accccaacac ctacgattac atgaacaagc gagtggtggc cccggggctg gtggactgct   20280
acatcaacct gggcgcgcgc tggtcgctgg actacatgga caacgtcaac cccttcaacc   20340
accaccgcaa tgcgggcctg cgctaccgct ccatgctcct gggcaacggg cgctacgtgc   20400
ccttccacat ccaggtgccc cagaagttct ttgccatcaa gaacctcctc ctcctgccgg   20460
gctcctacac ctacgagtgg aacttcagga aggatgtcaa catggtcctc cagagctctc   20520
tgggtaacga tctcagggtg gacggggcca gcatcaagtt cgagagcatc tgcctctacg   20580
ccaccttctt ccccatggcc cacaacacgg cctccacgct cgaggccatg ctcaggaacg   20640
acaccaacga ccagtccttc aatgactacc tctccgccgc caacatgctc taccccatac   20700
ccgccaacgc caccaacgtc cccatctcca tcccctcgcg caactgggcg ccttccgcg   20760
gctgggcctt caccccgcctc aagaccaagg agacccctc cctgggctcg ggattcgacc   20820
cctactacac ctactcgggc tccattccct acctggacgg caccttctac ctcaaccaca   20880
cttttcaagaa ggtctcggtc accttcgact cctcggtcag ctggccgggc aacgaccgtc   20940
tgctcacccc caacgagttc gaaatcaagc gctcggtcga cggggagggc tacaacgtgg   21000
cccagtgcaa catgaccaag gactggttcc tggtccagat gctggccaac tacaacatcg   21060
gctaccaggg cttctacatc ccagagagct acaaggacag gatgtactcc ttcttcagga   21120
acttccagcc catgagccgg caggtggtgg accagaccaa gtacaaggac taccaggagg   21180
tgggcatcat ccaccagcac aacaactcgg gcttcgtggg ctacctcgcc cccaccatgc   21240
gcgagggaca ggcctacccc gccaacttcc cctacccgct cataggcaag accgcggtcg   21300
acagcatcac ccagaaaaag ttcctctgcg atcgcaccct ctggcgcatc cccttctcca   21360
gcaacttcat gtccatgggt gcgctctcgg acctgggcca gaacttgctc tacgccaact   21420
ccgcccacgc cctcgacatg accttcgagg tcgaccccat ggacgagccc acccttctct   21480
atgttctgtt cgaagtcttt gacgtggtcc gggtccacca gccgcaccgc ggcgtcatcg   21540
agaccgtgta cctgcgtacg cccttctcgg ccggcaacgc caccacctaa gaagcaagc   21600
cgcagtcatc gccgcctgca tgccgtcggg ttccaccgag caagagctca gggccatcgt   21660
cagagacctg ggatgcgggc cctattttt gggcactttc gacaagcgct tccctggctt   21720
tgtctcccca cacaagctgg cctgcgccat cgtcaacacg gccggccgcg agaccggggg   21780
cgtgcactgg ctggccttcg cctggaaccc gcgctccaaa acatgcttcc tctttgaccc   21840
cttcggcttt tcggaccagc ggctcaagca aatctacgag ttcgagtacg agggcttgct   21900
gcgtcgcagc gccatcgcct cctcgcccga ccgctgcgtc accctcgaaa agtccaccca   21960
gaccgtgcag gggcccgact cggccgcctg cggtctcttc tgctgcatgt ttctgcacgc   22020
ctttgtgcac tggcctcaga gtcccatgga ccgcaacccc accatgaact tgctgacggg   22080
```

```
ggtgcccaac tccatgctcc agagccccca ggtcgagccc accctgcgcc gcaaccagga    22140
gcagctctac agcttcctgg agcgccactc gccctacttc cgccgccaca gcgcacagat    22200
caggagggcc acctccttct gccacttgca agagatgcaa gaagggtaat aacgatgtac    22260
acactttttt ctcaataaat ggcattttt tatttataca agctctctgg ggtattcatt     22320
tcccaccacc accaccaccc gccgttgtcg ccatctggct ctatttagaa atcgaaaggg    22380
ttctgccggg agtcgccgtg cgccacgggc agggacacgt tgcgatactg gtagcgggtg    22440
ccccacttga actcgggcac caccaggcga ggcagctcgg ggaagttttc gctccacagg    22500
ctgcgggtca gcaccagcgc gttcatcagg tcgggcgccg agatcttgaa gtcgcagttg    22560
gggccgccgc cctgcgcgcg cgagttgcgg tacaccgggt tgcagcactg gaacaccaac    22620
agcgccgggt gcttcacgct agccagcacg ctgcggtcgg agatcagctc ggcgtccagg    22680
tcctccgcgt tgctcagcgc gaacgggtc atcttgggca cttgcctccc caggaagggc     22740
gcgtgccccg gtttcgagtt gcagtcgcag cgcagcggga tcagcaggtg cccatgcccg    22800
gactcggcgt tggggtacag cgcgcgcatg aaggcctgca tctggcggaa ggccatctgg    22860
gccttggcgc cctccgagaa gaacatgccg caggacttgc ccgagaactg gtttgcgggg    22920
cagctggcgt cgtgcaggca gcagcgcgcg tcggtgttgg cgatctgcac cacgttgcgc    22980
ccccaccggt tcttcacgat cttggccttg gacgattgct ccttcagcgc gcgctgcccg    23040
ttctcgctgg tcacatccat ctcgatcaca tgttccttgt tcaccatgct gctgccgtgc    23100
aggcacttca gctcgccctc cgtctcggtg cagcggtgct gccacagcgc gcagcccgtg    23160
ggctcgaaag acttgtaggt cacctccgcg aaggactgca ggtaccctg caaaaagcgg     23220 cccatcatgg tcacgaaggt cttgttgctg ctgaaggtca gctgcagccc gcggtgctcc    23280
tcgttcagcc aggtcttgca cacggccgcc agcgcctcca cctggtcggg cagcatcttg    23340
aagttcacct tcagctcatt ctccacgtgg tacttgtcca tcagcgtgcg cgccgcctcc    23400
atgcccttct cccaggccga caccagcggc aggctcacgg ggttcttcac catcaccgtg    23460
gccgccgcct ccgccgcgct ttcgcttcc gcccgctgt tctcttcctc ttcctcctct       23520
tcctcgccgc cgcccactcg cagccccgc accacgggt cgtcttcctg caggcgctgc      23580
accttgcgct tgccgttgcg cccctgcttg atgcgcacgg gcgggttgct gaagcccacc    23640
atcaccagcg cggcctcttc ttgctcgtcc tcgctgtcca gaatgacctc cggggagggg    23700
gggttggtca tcctcagtac cgaggcacgc ttcttttcct tcctgggggc gttcgccagc    23760
tccgcggctg cggccgctgc cgaggtcgaa ggccgagggc tgggcgtgcg cggcaccagc    23820
gcgtcctgcg agccgtcctc gtcctcctcg gactcgagac ggaggcgggc ccgcttcttc    23880
gggggcgcgc gggcggcgg aggcggcggc ggcgacggag acgggacga gacatcgtcc      23940 agggtgggtg gacggcgggc cgcgccgcgt ccgcgctcgg gggtggtctc gcgctggtcc    24000
tcttcccgac tggccatctc ccactgctcc ttctcctata ggcagaaaga gatcatggag    24060
tctctcatgc gagtcgagaa ggaggaggac agcctaaccg ccccctctga gccctccacc    24120
accgccgcca ccaccgccaa tgccgccgcg gacgacgcgc ccaccgagac caccgccagt    24180
accaccnnnc tccccagcga cgcaccccg ctcgagaatg aagtgctgat cgagcaggac      24240
ccgggttttg tgagcggaga ggaggatgag gtggatgaga aggagaagga ggaggtcgcc    24300
gcctcagtgc caaagagga taaaaagcaa gaccaggacg acgcagataa ggatgagaca     24360
gcagtcgggc gggggaacgg aagccatgat gctgatgacg gctacctaga cgtgggagac    24420
```

```
gacgtgctgc ttaagcacct gcaccgccag tgcgtcatcg tctgcgacgc gctgcaggag  24480
cggtgcgaag tgcccctgga cgtggcggag gtcagccgcg cctacgagcg caccctcttc  24540
gcgccgcacg tgcccccaa gcgccgggag aacggcacct gcgagcccaa cccgcgtctc  24600
aacttctacc cggtcttcgc ggtacccgag gtgctggcca cctaccacat cttttttccaa  24660
aactgcaaga tcccctctc ctgccgcgct aaccgcaccc gcgccgacaa aaccctgacc  24720
ctgcggcagg gcgcccacat acctgatatt gcctctctgg aggaagtgcc caagatcttc  24780
gagggtctcg gtcgcgacga gaaacgggcg gcgaacgctc tgcacggaga cagcgaaaac  24840
gagagtcact cggggggtgct ggtggagctc gagggcgaca acgcgcgcct ggccgtactc  24900
aagcgcagca tagaggtcac ccactttgcc tacccggcgc tcaacctgcc ccccaaggtc  24960
atgagtgtgg tcatgggcga gctcatcatg cgccgcgccc agccctggc cgcggatgca  25020
aacttgcaag agtcctcaga ggaaggcctg cccgcggtca gcgacgagca gctggcgcgc  25080
tggctggaga cccgcgaccc cgcgcagctg gaggagcggc gcaagctcat gatggccgcg  25140
gtgctggtca ccgtggagct cgagtgtctg cagcgcttct tcgcggaccc cgagatgcag  25200
cgcaagctcg aggagaccct gcactacacc ttccgccagg gctacgtgcg ccaggcctgc  25260
aagatctcca acgtggagct ctgcaacctg gtctcctacc tgggcatcct gcacgagaac  25320
cgcctcgggc agaacgtcct gcactccacc ctcaaagggg aggcgcgccg cgactacatc  25380
cgcgactgcg cctacctctt cctctgctac acctggcaga cggccatggg ggtctggcag  25440
cagtgcctgg aggagcgcaa cctcaaggag ctggaaaagc tcctcaagcg caccctcagg  25500
gacctctgga cgggcttcaa cgagcgctcg gtggccgccg cgctggcgga catcatcttc  25560
cccgagcgcc tgctcaagac cctgcagcag ggcctgcccg acttcaccag ccagagcatg  25620
ctgcagaact tcaggacttt catcctggag cgctcgggca tcctgccggc cacttgctgc  25680
gcgctgccca gcgacttcgt gcccatcaag tacagggagt gcccgccgcc gctctgggc  25740
cactgctacc tcttccagct ggccaactac ctcgcctacc actcggacct catggaagac  25800
gtgagcggcg agggcctgct cgagtgccac tgccgctgca acctctgcac gccccaccgc  25860
tctctagtct gcaacccgca gctgctcagc gagagtcaga ttatcggtac cttcgagctg  25920
cagggtccct cgcctgacga gaagtccgcg gctccggggc tgaaactcac tccggggctg  25980
tggacttccg cctacctacg caaatttgta cctgaggact accacgccca cgagatcagg  26040
ttctacgaag accaatcccg cccgcccaag gcggagctca ccgcctgcgt catcacccag  26100
gggcacatcc tgggccaatt gcaagccatc aacaaagccc gccgagagtt cttgctgaaa  26160
aagggtcggg gggtgtacct ggaccccag tccggcgagg agctaaaccc gctaccccg  26220
ccgccgcccc agcagcggga ccttgcttcc caggatggca cccagaaaga agcagcagcc  26280
gccgccgcag ccatacatgc ttctggagga agaggaggag gactgggaca gtcaggcaga  26340
ggagatgatg gaagactggg aggaggacag cagcctagac gaggaagctt cagaggccga  26400
agaggtggca gacgcaacac catcaccctc ggtcgcagcc cctcgccgg ggcccctgaa  26460
atcctccgaa cccagcacca gcgctataac ctccgctcct ccggcgccgg cgccacccgc  26520
ccgcagaccc aaccgtagat gggacaccac aggaaccggg gtcggtaagt ccaagtgccc  26580
gccgccgcca ccgcagcagc agcagcagca gcgccagggc taccgctcgt ggcgcgggca  26640
caagaacgcc atagtcgcct gcttgcaaga ctgcgggggc aacatctctt tcgcccgccg  26700
cttcctgcta ttccaccacg gggtcgcctt tccccgcaat gtcctgcatt actaccgtca  26760
tctctacagc ccctactgca gcggcgaccc agaggcggca gcggcagcca cagcggcgac  26820
```

```
caccacctag gaagatatcc tccgcgggca agacagcggc agcagcgcc aggagacccg    26880 cggcagcagc ggcgggagcg gtgggcgcac tgcgcctctc gcccaacgaa cccctctcga    26940
cccgggagct cagacacagg atcttcccca ctttgtatgc catcttccaa cagagcagag    27000
gccaggagca ggagctgaaa ataaaaaaca gatctctgcg ctccctcacc cgcagctgtc    27060
tgtatcacaa aagcgaagat cagcttcggc gcacgctgga ggacgcggag gcactcttca    27120
gcaaatactg cgcgctcact cttaaagact agctccgcgc ccttctcgaa tttaggcggg    27180
agaaaactac gtcatcgccg gccgccgccc agcccgccca gccgagatga gcaaagagat    27240
tcccacgcca tacatgtgga gctaccagcc gcagatggga ctcgcggcgg gagcggccca    27300
ggactactcc acccgcatga actacatgag cgcgggaccc cacatgatct cacaggtcaa    27360
cgggatccgc gcccagcgaa accaaatact gctggaacag cggccatca ccgccacgcc     27420 ccgccataat ctcaaccccc gaaattggcc cgccgcccta gtgtaccagg aaacccctc     27480 cgccaccacc gtactacttc cgcgtgacgc ccaggccgaa gtccagatga ctaactcagg    27540
ggcgcagctc gcgggcggct tcgtcacgg ggcgcggccg ctccgaccag gtataagaca     27600
cctgatgatc agaggccgag gtatccagct caacgacgag tcggtgagct cttcgctcgg    27660
tctccgtccg gacggaactt tccagctcgc cggatccggt cgctcttcgt tcacgccccg    27720
ccaggcgtac ctgactctgc agacctcgtc ctcggagccc cgctccggcg gcatcggaac    27780
cctccagttc gtggaggagt tcgtgccctc ggtctacttc aaccccttct cgggacctcc    27840
cggacgctac cccgaccagt tcattccgaa ctttgacgcg gtgaaggact cggcggacgg    27900
ctacgactga atgtcaggtg ccgaggcaga gcagcttcgc ctgagacacc tcgagcactg    27960
ccgccgccac aagtgcttcg cccgcggttc cggtgagttc tgctactttc agctaccga    28020 ggagcatacc gaggggccgg cgcacggcgt ccgcctgacc acccagggcg aggttacctg    28080
ttccctcatc cggagttca ccctccgtcc cctgctagtg gagcgggagc ggggtccctg     28140
tgtcctaact atcgcctgca actgccctaa ccctggatta catcaagatc tttgctgtca    28200
tctctgtgct gagtttaata aacgctgaga tcagaatcta ctgggctcc tgtcgccatc     28260 ctgtgaacgc caccgtcttc acccaccccg accaggccca ggcgaacctc acctgcggtc    28320
tgcatcggag gtccaagaag tacctcacct ggtacttcaa cggcaccccc tttgtggttt    28380
acaacagctt cgacggggac ggagtctccc tgaaagacca gctctccggt ctcagctact    28440
ccatccacaa gaacaccacc ctccaactct ccctccccta cctgccggga acctacgagt    28500
gcgtcaccgg ccgctgcacc cacctcaccc gcctgatcgt aaaccagagc tttccgggaa    28560
cagataactc cctcttcccc agaacaggag gtgagctcag gaaactcccc ggggaccagg    28620
gcggagacgt accttcgacc cttgtggggt taggattttt tattaccggg ttgctggctc    28680
ttttaatcaa agcttccttg agatttgttc tttccttcta cgtgtatgaa cacctcagcc    28740 tccataact ctacccttc ttcgggatca ggtgactttt ctgaaatcgg gcttggtgtg       28800
ctgcttactc tgttgatttt tttccttatc atactcagcc ttctgtgcct caggctcgcc    28860
gcctgctgcg cacacatcta tatctactgc tggttgctca agtgcagggg tcgccaccca    28920
agatgaacag gtacatggtc ctatcgatcc taggcctgct ggccctggcg gcctgcagcg    28980
ccgccaaaaa agagattacc tttgaggagc ccgcttgcaa tgtaactttc aagcccgagg    29040
gtgaccaatg caccacccctc gtcaaatgcg ttaccaatca tgagaagctg cgcatcgact    29100
acaaaaacaa aactggccgg tttgcggtct atagtgtgtt tacgcccgga gacccctcta    29160
```

```
actactctgt caccgtcttc cagggcggac agtctaagat attcaattac actttccctt   29220
tttatgagtt gtgcgatgcg gtcatgtaca tgtcaaaaca gtacaacctg tggcctccct   29280
ctccccaggc gtgtgtggaa atactgggt cttactgctg tatggctttg gcaatcacta   29340
cgctcgctct aatctgcacg gtgctatata taaaattcag gcagaggcga atctttatcg   29400
atgaaaagaa aatgccttga tcgctaacac cggctttcta tctgcagaat gaatgcaatc   29460
acctccctac taatcaccac caccctcctt gcgattgccc atgggttgac acgaatcgaa   29520
gtgccagtgg ggtccaatgt caccatggtg ggccccgccg gcaattccac cctcatgtgg   29580
gaaaaatttg tccgcaatca atgggttcat ttctgctcta accgaatcag tatcaagccc   29640
agagccatct gcgatgggca aaatctaact ctgatcaatg tgcaaatgat ggatgctggg   29700
tactattacg ggcagcgggg agaaatcatt aattactggc gaccccacaa ggactacatg   29760
ctgcatgtag tcgaggcact tcccactacc accccacta ccacctctcc caccaccact   29820
accactacta ctactactac taccactacc gctgcccgcc ataccgcaa aagcaccatg   29880 attagcacaa agcccctcg tgctcactcc cacgccggcg ggccatcgg tgcgacctca   29940 gaaaccaccg agctttgctt ctgccaatgc actaacgcca gcgctcatga actgttcgac   30000
ctggagaatg aggatgccca gcagagctcc gcttgcctga cccaggaggc tgtggagccc   30060
gttgccctga agcagatcgg tgattcaata attgactctt cttcttttgc cactcccgaa   30120
taccctcccg attctacttt ccacatcacg ggtaccaaag accctaacct ctctttctac   30180
ctgatgctgc tgctctgtat ctctgtggtc tcttccgcgc tgatgttact ggggatgttc   30240
tgctgcctga tctgccgcag aaagagaaaa gctcgctctc agggccaacc actgatgccc   30300
ttcccctacc ccccggattt tgcagataac aagatatgag ctcgctgctg acactaaccg   30360
ctttactagc ctgcgctcta acccttgtcg cttgcgactc gagattccac aatgtcacag   30420
ctgtggcagg agaaaatgtt actttcaact ccacggccga tacccagtgg tcgtggagtg   30480
gctcaggtag ctacttaact atctgcaata gctccacttc ccccagcata tccccaacca   30540
agtaccaatg caatgccagc ctgttcaccc tcatcaacgc ttccaccctg acaatggac   30600 tctatgtagg ctatgtaccc tttggtgggc aaggaaagac ccacgcttac aacctggaag   30660
ttcgccagcc cagaaccact acccaagctw cymccaycac cagcaccagc agcagcagcc   30720
acagcagcag cagcagatta ttgactttgg ttttggccag ctcatctgcc gctacccagg   30780
ccatctacag ctctgtgccc gaaaccactc agacccaccg cccagaaacg accaccgcca   30840
ccaccctaca cacctccagc gatcagatgc cgaccaacat caccccctg gctcttcaaa   30900 tgggacttac aagcccact ccaaaaccag tggatgcggc cgaggtctcc gccctcgtca   30960
atgactgggc ggggctggga atgtggtggt tcgccatagg catgatggcg ctctgcctgc   31020
ttctgctctg gctcatctgc tgcctccacc gcaggcgagc cagaccccc atctatagac   31080 ccatcattgt cctgaacccc gataatgatg ggatccatag attggatggc ctgaaaaacc   31140
tacttttttc ttttacagta tgataaattg agacatgcct cgcatttct tgtacatgtt   31200 ccttctccca ccttttctgg ggtgttctac gctggccgct gtgtctcacc tggaggtaga   31260
ctgcctctca cccttcactg tctacctgct ttacggattg gtcaccctca ctctcatctg   31320
cagcctaatc acagtaatca tcgccttcat ccagtgcatt gattacatct gtgtgcgcct   31380
cgcatacttc agacaccacc cgcagtaccg agacaggaac attgcccaac ttctaagact   31440
gctctaatca tgcataagac tgtgatctgc cttctgatcc tctgcatcct gcccaccctc   31500
acctcctgcc agtacaccac aaaatctccg cgcaaaagac atgcctcctg ccgcttcacc   31560
```

```
caactgtgga atatacccaa atgctacaac gaaaagagcg agctctccga agcttggctg   31620
tatggggtca tctgtgtctt agttttctgc agcactgtct ttgccctcat gatctacccc   31680
tactttgatt tgggatggaa cgcgatcgat gccatgaatt accccacctt tcccgcaccc   31740
gagataattc cactgcgaca agttgtaccc gttgtcgtta atcaacgccc ccatcccct    31800 acgcccactg aaatcagcta ctttaaccta acaggcggag atgactgacg ccctagatct   31860
agaaatggac ggcatcagta ccgagcagcg tctcctagag aggcgcaggc aggcggctga   31920
gcaagagcgc ctcaatcagg agctccgaga tctcgttaac ctgcaccagt gcaaaagagg   31980
catcttttgt ctggtaaagc aggccaaagt cacctacgag aagaccggca acagccaccg   32040
cctcagttac aaattgccca cccagcgcca gaagctggtg ctcatggtgg gtgagaatcc   32100
catcaccgtc acccagcact cggtagagac cgaggggtgt ctgcactccc cctgtcgggg   32160
tccagaagac ctctgcaccc tggtaaagac cctgtgcggt ctcagagatt tagtcccctt   32220
taactaatca aacactggaa tcaataaaaa gaatcactta cttaaaatca gacagcaggt   32280
ctctgtccag tttattcagc agcacctcct tcccctcctc ccaactctgg tactccaaac   32340
gccttctggc ggcaaacttc ctccacaccc tgaagggaat gtcagattct tgctcctgtc   32400
cctccgcacc cactatcttc atgttgttgc agatgaagcg caccaaaacg tctgacgaga   32460
gcttcaaccc cgtgtacccc tatgacacgg aaagcggccc tccctccgtc cctttcctca   32520
cccctccctt cgtgtctccc gatggattcc aagaaagtcc ccccggggtc ctgtctctga   32580
acctggccga gcccctggtc acttcccacg gcatgctcgc cctgaaaatg ggaagtggcc   32640
tctccctgga cgacgctggc aacctcacct ctcaagatat caccaccgct agccctcccc   32700
tcaaaaaaac caagaccaac ctcagcctag aaacctcatc cccctaact gtgagcacct   32760 caggcgccct caccgtagca gccgccgctc ccctggcggt ggccggcacc tccctcacca   32820
tgcaatcaga ggcccccctg acagtacagg atgcaaaact caccctggcc accaaaggcc   32880
ccctgaccgt gtctgaaggc aaactggcct tgcaaacatc ggccccgctg acggccgctg   32940
acagcagcac cctcaccgtt agcgccacac caccaattaa tgtaagcagt ggaagtttag   33000
gcttagacat ggaagaccct atgtatactc acaatggaaa actgggaata agaattgggg   33060
gtccactaag agtagtagac agcttgcata cactcactgt agttaccgga aatggactaa   33120
ctgtagataa caatgccctc caaactaaag ttacgggcgc cctaggttat gacacatcag   33180
gaaatctaca attaagagct gcaggaggta tgcgaattga cgcaaatggc caacttatcc   33240
ttaatgtggc atacccattt gatgctcaga acaatctcag ccttagactt ggtcagggac   33300
ccctgtatat aaacacagac cacaacctgg atttgaattg caacagaggt ctaaccacaa   33360
ctaccaccaa caacacaaaa aaacttgaga ctaaaattag ctcaggctta gactatgaca   33420
ccaatggtgc tgtcattatt aaacttggca ctggtctaag cttcgacaac acaggcgccc   33480
taactgtggg aaacactggt gatgataaac tgactctgtg gacgaccca gacccatctc   33540 caaattgcag aattcactca gacaaagact gcaagtttac tctagtccta actaagtgtg   33600
gaagccaaat cctggcctct gtcgccgccc tagcggtatc aggaaatctg cttcgataa    33660 caggcaccgt tgccagcgtt accatctttc tcagatttga tcagaatgga gtgcttatgg   33720
aaaactcctc gctagacagg cagtactgga acttcagaaa tggcaactca actaacgctg   33780
ccccctacac caatgcagtt gggttcatgc caaacctcgc agcataccc aaaacgcaaa    33840 gccagactgc taaaaacaac attgtaagtc aggtttactt gaatggagac aaatccaaac   33900
```

```
ccatgaccct taccatcacc ctcaatggaa ctaatgaatc cagtgaaact agccaggtga    33960
gtcactactc catgtcattt acatgggctt gggaaagtgg gcaatatgcc actgaaacct    34020
ttgccaccaa ctccttcacc ttttcttaca ttgctgaaca ataaaaagca tgacactgat    34080
gttcatttct gattcttatt ttattatttt caaacacaac aaaatcattc aagtcattct    34140
tccatcttag cttaatagac acagtagctt aatagaccca gtagtgcaaa gccccattct    34200
agcttataac tagtggagaa gtactcgcct acatggggt agagtcataa tcgtgcatca     34260
ggatagggcg gtggtgctgc agcagcgcgc gaataaactg ctgccgccgc cgctccgtcc    34320
tgcaggaata caacatggca gtggtctcct cagcgatgat tcgcaccgcc cgcagcataa    34380
ggcgccttgt cctccgggca cagcagcgca ccctgatctc acttaaatca gcacagtaac    34440
tgcagcacag caccacaata ttgttcaaaa tcccacagtg caaggcgctg tatccaaagc    34500
tcatggcggg gaccacagaa cccacgtggc catcatacca caagcgcagg tagattaagt    34560
ggcgacccct cataaacacg ctggacataa acattacctc ttttggcatg ttgtaattca    34620
ccacctcccg gtaccatata aacctctgat taaacatggc gccatccacc accatcctaa    34680
accagctggc caaaacctgc cgccggcta tacactgcag ggaaccggga ctggaacaat     34740
gacagtggag agcccaggac tcgtaaccat ggatcatcat gctcgtcatg atatcaatgt    34800
tggcacaaca caggcacacg tgcatacact tcctcaggat tacaagctcc tcccgcgtta    34860
gaaccatatc ccagggaaca acccattcct gaatcagcgt aaatcccaca ctgcaggaa    34920
gacctcgcac gtaactcacg ttgtgcattg tcaaagtgtt acattcgggc agcagcggat    34980
gatcctccag tatggtagcg cgggtttctg tctcaaaagg aggtagacga tccctactgt    35040
acggagtgcg ccgagacaac cgagatcgtg ttggtcgtag tgtcatgcca aatggaacgc    35100
cggacgtagt catatttcct gaagtcttag atctctcaac gcagcaccag caccaacact    35160
tcgcagtgta aaaggccaag tgccgagaga gtatatatag gaataaaaag tgacgtaaac    35220
gggcaaagtc caaaaaacgc ccagaaaaac cgcacgcgaa cctacgcccc gaaacgaaag    35280
ccaaaaaaca ctagacactc ccttccggcg tcaacttccg ctttcccacg ctacgtcact    35340
tgccccagtc aaacaaacta catatcccga acttccaagt cgccacgccc aaaacaccgc    35400
ctacacctcc ccgcccgccg gcccgccccc aaacccgcct cccgcccgc gccccgcccc     35460
gcgccgccca tctcattatc atattggctt caatccaaaa taaggtatat tattgatgat    35520
ggtttaaacg gatccaattc ttgaagacga aagggcctcg tgatacgcct atttttatag    35580
gttaatgtca tgataataat ggtttcttag acgtcaggtg gcacttttcg gggaaatgtg    35640
cgcggaaccc ctatttgttt attttttctaa atacattcaa atatgtatcc gctcatgaga    35700
caataaccct gataaatgct tcaataatat tgaaaaagga agagtatgag tattcaacat    35760
ttccgtgtcg cccttattcc cttttttgcg gcattttgcc ttcctgtttt tgctcaccca    35820
gaaacgctgg tgaaagtaaa agatgctgaa gatcagttgg gtgcacgagt gggttacatc    35880
gaactggatc tcaacagcgg taagatcctt gagagttttc gccccgaaga acgttttcca    35940
atgatgagca cttttaaagt tctgctatgt ggcgcggtat tatcccgtgt tgacgccggg    36000
caagagcaac tcggtcgccg catacactat tctcagaatg acttggttga gtactcacca    36060
gtcacagaaa agcatcttac ggatggcatg acagtaagag aattatgcag tgctgccata    36120
accatgagtg ataacactgc ggccaactta cttctgacaa cgatcggagg accgaaggag    36180
ctaaccgctt ttttgcacaa catgggggat catgtaactc gccttgatcg ttgggaaccg    36240
gagctgaatg aagccatacc aaacgacgag cgtgacacca cgatgcctgt agcaatggca    36300
```

```
acaacgttgc gcaaactatt aactggcgaa ctacttactc tagcttcccg gcaacaatta    36360
atagactgga tggaggcgga taaagttgca ggaccacttc tgcgctcggc ccttccggct    36420
ggctggttta ttgctgataa atctggagcc ggtgagcgtg gtctcgcgg tatcattgca     36480 gcactggggc cagatggtaa gccctcccgt atcgtagtta tctacacgac ggggagtcag    36540
gcaactatgg atgaacgaaa tagacagatc gctgagatag gtgcctcact gattaagcat    36600
tggtaactgt cagaccaagt ttactcatat atactttaga ttgatttaaa aggatctagg    36660
tgaagatcct ttttgataat ctcatgacca aaatccctta acgtgagttt cgttccact    36720 gagcgtcaga ccccgtagaa aagatcaaag gatcttcttg agatcctttt tttctgcgcg    36780
taatctgctg cttgcaaaca aaaaaaccac cgctaccagc ggtggtttgt ttgccggatc    36840
aagagctacc aactcttttt ccgaaggtaa ctggcttcag cagagcgcag ataccaaata    36900
ctgtccttct agtgtagccg tagttaggcc accacttcaa gaactctgta gcaccgccta    36960
catacctcgc tctgctaatc ctgttaccag tggctgctgc cagtggcgat aagtcgtgtc    37020
ttaccgggtt ggactcaaga cgatagttac cggataaggc gcagcggtcg ggctgaacgg    37080
ggggttcgtg cacacagccc agcttggagc gaacgaccta caccgaactg agatacctac    37140
agcgtgagct atgagaaagc gccacgcttc ccgaagggag aaaggcggac aggtatccgg    37200
taagcggcag ggtcggaaca ggagagcgca cgagggagct tccaggggga aacgcctggt    37260
atctttatag tcctgtcggg tttcgccacc tctgacttga gcgtcgattt tgtgatgct    37320 cgtcaggggg gcggagccta tggaaaaacg ccagcaacgc ggccttttta cggttcctgg    37380
ccttttgctg gccttgaagc tgtccctgat ggtcgtcatc tacctgcctg acagcatgg    37440 cctgcaacgc gggcatcccg atgccgccgg aagcgagaag aatcataatg gggaaggcca    37500
tccagcctcg cgtcgcagat ccgaattcgt ttaaac                              37536
```

<210> SEQ ID NO 25
<211> LENGTH: 29
<212> TYPE: DNA
<213> ORGANISM: Human cytomegalovirus

<400> SEQUENCE: 25
catctacgta ttagtcatcg ctattacca                                          29

<210> SEQ ID NO 26
<211> LENGTH: 21
<212> TYPE: DNA
<213> ORGANISM: Human cytomegalovirus

<400> SEQUENCE: 26
gacttggaaa tccccgtgag t                                                  21

<210> SEQ ID NO 27
<211> LENGTH: 543
<212> TYPE: PRT
<213> ORGANISM: Pan troglodytes

<400> SEQUENCE: 27

Met Lys Arg Thr Lys Thr Ser Asp Glu Ser Phe Asn Pro Val Tyr Pro
1               5                   10                  15

Tyr Asp Thr Glu Ser Gly Pro Pro Ser Val Pro Phe Leu Thr Pro Pro
            20                  25                  30

Phe Val Ser Pro Asp Gly Phe Gln Glu Ser Pro Pro Gly Val Leu Ser
        35                  40                  45

```
Leu Asn Leu Ala Glu Pro Leu Val Thr Ser His Gly Met Leu Ala Leu
 50                  55                  60

Lys Met Gly Ser Gly Leu Ser Leu Asp Asp Ala Gly Asn Leu Thr Ser
 65                  70                  75                  80

Gln Asp Ile Thr Thr Ala Ser Pro Pro Leu Lys Lys Thr Lys Thr Asn
                 85                  90                  95

Leu Ser Leu Glu Thr Ser Ser Pro Leu Thr Val Ser Thr Ser Gly Ala
                100                 105                 110

Leu Thr Val Ala Ala Ala Ala Pro Leu Ala Val Ala Gly Thr Ser Leu
            115                 120                 125

Thr Met Gln Ser Glu Ala Pro Leu Thr Val Gln Asp Ala Lys Leu Thr
130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Thr Leu Thr Val
                165                 170                 175

Ser Ala Thr Pro Pro Ile Asn Val Ser Ser Gly Ser Leu Gly Leu Asp
                180                 185                 190

Met Glu Asp Pro Met Tyr Thr His Asp Gly Lys Leu Gly Ile Arg Ile
            195                 200                 205

Gly Gly Pro Leu Arg Val Val Asp Ser Leu His Thr Leu Thr Val Val
210                 215                 220

Thr Gly Asn Gly Leu Thr Val Asp Asn Asn Ala Leu Gln Thr Arg Val
225                 230                 235                 240

Thr Gly Ala Leu Gly Tyr Asp Thr Ser Gly Asn Leu Gln Leu Arg Ala
                245                 250                 255

Ala Gly Gly Met Arg Ile Asp Ala Asn Gly Gln Leu Ile Leu Asn Val
            260                 265                 270

Ala Tyr Pro Phe Asp Ala Gln Asn Asn Leu Ser Leu Arg Leu Gly Gln
            275                 280                 285

Gly Pro Leu Tyr Ile Asn Thr Asp His Asn Leu Asp Leu Asn Cys Asn
            290                 295                 300

Arg Gly Leu Thr Thr Thr Thr Asn Asn Thr Lys Lys Leu Glu Thr
305                 310                 315                 320

Lys Ile Ser Ser Gly Leu Asp Tyr Asp Thr Asn Gly Ala Val Ile Ile
                325                 330                 335

Lys Leu Gly Thr Gly Leu Ser Phe Asp Asn Thr Gly Ala Leu Thr Val
                340                 345                 350

Gly Asn Thr Gly Asp Asp Lys Leu Thr Leu Trp Thr Thr Pro Asp Pro
            355                 360                 365

Ser Pro Asn Cys Arg Ile His Ser Asp Lys Asp Cys Lys Phe Thr Leu
    370                 375                 380

Val Leu Thr Lys Cys Gly Ser Gln Ile Leu Ala Ser Val Ala Ala Leu
385                 390                 395                 400

Ala Val Ser Gly Asn Leu Ala Ser Ile Thr Gly Thr Val Ala Ser Val
                405                 410                 415

Thr Ile Phe Leu Arg Phe Asp Gln Asn Gly Val Leu Met Glu Asn Ser
            420                 425                 430

Ser Leu Asp Arg Gln Tyr Trp Asn Phe Arg Asn Gly Asn Ser Thr Asn
            435                 440                 445

Ala Ala Pro Tyr Thr Asn Ala Val Gly Phe Met Pro Asn Leu Ala Ala
    450                 455                 460
```

Tyr Pro Lys Thr Gln Ser Gln Thr Ala Lys Asn Asn Ile Val Ser Gln
465                 470                 475                 480

Val Tyr Leu Asn Gly Asp Lys Ser Lys Pro Met Thr Leu Thr Ile Thr
            485                 490                 495

Leu Asn Gly Thr Asn Glu Ser Ser Glu Thr Ser Gln Val Ser His Tyr
        500                 505                 510

Ser Met Ser Phe Thr Trp Ala Trp Glu Ser Gly Gln Tyr Ala Thr Glu
    515                 520                 525

Thr Phe Ala Thr Asn Ser Phe Thr Phe Ser Tyr Ile Ala Glu Gln
530                 535                 540

<210> SEQ ID NO 28
<211> LENGTH: 542
<212> TYPE: PRT
<213> ORGANISM: Pan paniscus

<400> SEQUENCE: 28

Met Lys Arg Ala Lys Thr Ser Asp Glu Thr Phe Asn Pro Val Tyr Pro
1               5                   10                  15

Tyr Asp Thr Glu Asn Gly Pro Pro Ser Val Pro Phe Leu Thr Pro Pro
            20                  25                  30

Phe Val Ser Pro Asp Gly Phe Gln Glu Ser Pro Pro Gly Val Leu Ser
        35                  40                  45

Leu Arg Leu Ser Glu Pro Leu Val Thr Ser His Gly Met Leu Ala Leu
50                  55                  60

Lys Met Gly Asn Gly Leu Ser Leu Asp Asp Ala Gly Asn Leu Thr Ser
65                  70                  75                  80

Gln Asp Val Thr Thr Val Thr Pro Pro Leu Lys Lys Thr Lys Thr Asn
                85                  90                  95

Leu Ser Leu Gln Thr Ser Ala Pro Leu Thr Val Ser Ser Gly Ser Leu
            100                 105                 110

Thr Val Ala Ala Ala Pro Leu Ala Val Ala Gly Thr Ser Leu Thr
        115                 120                 125

Met Gln Ser Gln Ala Pro Leu Thr Val Gln Asp Ala Lys Leu Gly Leu
130                 135                 140

Ala Thr Gln Gly Pro Leu Thr Val Ser Glu Gly Lys Leu Thr Leu Gln
145                 150                 155                 160

Thr Ser Ala Pro Leu Thr Ala Ala Asp Ser Ser Thr Leu Thr Val Gly
            165                 170                 175

Thr Thr Pro Pro Ile Ser Val Ser Ser Gly Ser Leu Gly Leu Asp Met
        180                 185                 190

Glu Asp Pro Met Tyr Thr His Asp Gly Lys Leu Gly Ile Arg Ile Gly
    195                 200                 205

Gly Pro Leu Gln Val Val Asp Ser Leu His Thr Leu Thr Val Val Thr
210                 215                 220

Gly Asn Gly Ile Thr Val Ala Asn Asn Ala Leu Gln Thr Lys Val Ala
225                 230                 235                 240

Gly Ala Leu Gly Tyr Asp Ser Ser Gly Asn Leu Glu Leu Arg Ala Ala
            245                 250                 255

Gly Gly Met Arg Ile Asn Thr Gly Gly Gln Leu Ile Leu Asp Val Ala
        260                 265                 270

Tyr Pro Phe Asp Ala Gln Asn Asn Leu Ser Leu Arg Leu Gly Gln Gly
    275                 280                 285

Pro Leu Tyr Val Asn Thr Asn His Asn Leu Asp Leu Asn Cys Asn Arg
290                 295                 300

Gly Leu Thr Thr Thr Thr Ser Ser Asn Thr Thr Lys Leu Glu Thr Lys
305                 310                 315                 320

Ile Asp Ser Gly Leu Asp Tyr Asn Ala Asn Gly Ala Ile Ile Ala Lys
            325                 330                 335

Leu Gly Thr Gly Leu Thr Phe Asp Asn Thr Gly Ala Ile Thr Val Gly
            340                 345                 350

Asn Thr Gly Asp Asp Lys Leu Thr Leu Trp Thr Thr Pro Asp Pro Ser
            355                 360                 365

Pro Asn Cys Arg Ile His Ala Asp Lys Asp Cys Lys Phe Thr Leu Val
            370                 375                 380

Leu Thr Lys Cys Gly Ser Gln Ile Leu Ala Ser Val Ala Ala Leu Ala
385                 390                 395                 400

Val Ser Gly Asn Leu Ser Ser Met Thr Gly Thr Val Ser Ser Val Thr
            405                 410                 415

Ile Phe Leu Arg Phe Asp Gln Asn Gly Val Leu Met Glu Asn Ser Ser
            420                 425                 430

Leu Asp Lys Glu Tyr Trp Asn Phe Arg Asn Gly Asn Ser Thr Asn Ala
            435                 440                 445

Thr Pro Tyr Thr Asn Ala Val Gly Phe Met Pro Asn Leu Ser Ala Tyr
            450                 455                 460

Pro Lys Thr Gln Ser Gln Thr Ala Lys Asn Asn Ile Val Ser Glu Val
465                 470                 475                 480

Tyr Leu His Gly Asp Lys Ser Lys Pro Met Ile Leu Thr Ile Thr Leu
            485                 490                 495

Asn Gly Thr Asn Glu Ser Ser Glu Thr Ser Gln Val Ser His Tyr Ser
            500                 505                 510

Met Ser Phe Thr Trp Ser Trp Asp Ser Gly Lys Tyr Ala Thr Glu Thr
            515                 520                 525

Phe Ala Thr Asn Ser Phe Thr Phe Ser Tyr Ile Ala Glu Gln
            530                 535                 540

<210> SEQ ID NO 29
<211> LENGTH: 543
<212> TYPE: PRT
<213> ORGANISM: Pan troglodytes

<400> SEQUENCE: 29

Met Lys Arg Thr Lys Thr Ser Asp Glu Ser Phe Asn Pro Val Tyr Pro
1               5                   10                  15

Tyr Asp Thr Glu Ser Gly Pro Pro Ser Val Pro Phe Leu Thr Pro Pro
            20                  25                  30

Phe Val Ser Pro Asp Gly Phe Gln Glu Ser Pro Pro Gly Val Leu Ser
            35                  40                  45

Leu Asn Leu Ala Glu Pro Leu Val Thr Ser His Gly Met Leu Ala Leu
50                  55                  60

Lys Met Gly Ser Gly Leu Ser Leu Asp Asp Ala Gly Asn Leu Thr Ser
65                  70                  75                  80

Gln Asp Ile Thr Ser Thr Thr Pro Leu Lys Lys Thr Lys Thr Asn
            85                  90                  95

Leu Ser Leu Glu Thr Ser Ser Pro Leu Thr Val Ser Thr Ser Gly Ala
            100                 105                 110

Leu Thr Val Ala Ala Ala Ala Pro Leu Ala Val Ala Gly Thr Ser Leu
            115                 120                 125

Thr Met Gln Ser Glu Ala Pro Leu Ala Val Gln Asp Ala Lys Leu Thr

```
              130                 135                 140
Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Thr Leu Thr Val
                165                 170                 175

Ser Ser Thr Pro Pro Ile Ser Val Ser Ser Gly Ser Leu Gly Leu Asp
            180                 185                 190

Met Glu Asp Pro Met Tyr Thr His Asp Gly Lys Leu Gly Ile Arg Ile
        195                 200                 205

Gly Gly Pro Leu Arg Val Val Asp Ser Leu His Thr Leu Thr Val Val
210                 215                 220

Thr Gly Asn Gly Leu Thr Val Asp Asn Asn Ala Leu Gln Thr Arg Val
225                 230                 235                 240

Thr Gly Ala Leu Gly Tyr Asp Thr Ser Gly Asn Leu Gln Leu Arg Ala
                245                 250                 255

Ala Gly Gly Met Arg Ile Asp Ala Asn Gly Gln Leu Ile Leu Asp Val
            260                 265                 270

Ala Tyr Pro Phe Asp Ala Gln Asn Asn Leu Ser Leu Arg Leu Gly Gln
        275                 280                 285

Gly Pro Leu Tyr Val Asn Thr Asp His Asn Leu Asp Leu Asn Cys Asn
    290                 295                 300

Arg Gly Leu Thr Thr Thr Thr Asn Asn Thr Lys Lys Leu Glu Thr
305                 310                 315                 320

Lys Ile Ser Ser Gly Leu Asp Tyr Asp Thr Asn Gly Ala Val Ile Ile
                325                 330                 335

Lys Leu Gly Thr Gly Leu Ser Phe Asp Asn Thr Gly Ala Leu Thr Val
            340                 345                 350

Gly Asn Thr Gly Asp Asp Lys Leu Thr Leu Trp Thr Thr Pro Asp Pro
        355                 360                 365

Ser Pro Asn Cys Arg Ile His Ser Asp Lys Asp Cys Lys Phe Thr Leu
    370                 375                 380

Val Leu Thr Lys Cys Gly Ser Gln Ile Leu Ala Ser Val Ala Ala Leu
385                 390                 395                 400

Ala Val Ser Gly Asn Leu Ala Ser Ile Thr Gly Val Ala Ser Val
                405                 410                 415

Thr Ile Phe Leu Arg Phe Asp Gln Asn Gly Val Leu Met Glu Asn Ser
            420                 425                 430

Ser Leu Asp Lys Gln Tyr Trp Asn Phe Arg Asn Gly Asn Ser Thr Asn
        435                 440                 445

Ala Ala Pro Tyr Thr Asn Ala Val Gly Phe Met Pro Asn Leu Ala Ala
    450                 455                 460

Tyr Pro Lys Thr Gln Ser Gln Thr Ala Lys Asn Ile Val Ser Gln
465                 470                 475                 480

Val Tyr Leu Asn Gly Asp Lys Ser Lys Pro Met Thr Leu Thr Ile Thr
                485                 490                 495

Leu Asn Gly Thr Asn Glu Ser Ser Glu Thr Ser Gln Val Ser His Tyr
            500                 505                 510

Ser Met Ser Phe Thr Trp Ala Trp Glu Ser Gly Gln Tyr Ala Thr Glu
        515                 520                 525

Thr Phe Ala Thr Asn Ser Phe Thr Phe Ser Tyr Ile Ala Glu Gln
    530                 535                 540

<210> SEQ ID NO 30
```

<211> LENGTH: 543
<212> TYPE: PRT
<213> ORGANISM: Pan troglodytes

<400> SEQUENCE: 30

```
Met Lys Arg Thr Lys Thr Ser Asp Lys Ser Phe Asn Pro Val Tyr Pro
1               5                   10                  15

Tyr Asp Thr Glu Asn Gly Pro Pro Ser Val Pro Phe Leu Thr Pro Pro
            20                  25                  30

Phe Val Ser Pro Asp Gly Phe Gln Glu Ser Pro Pro Gly Val Leu Ser
        35                  40                  45

Leu Asn Leu Ala Glu Pro Leu Val Thr Ser His Gly Met Leu Ala Leu
    50                  55                  60

Lys Met Gly Ser Gly Leu Ser Leu Asp Asp Ala Gly Asn Leu Thr Ser
65                  70                  75                  80

Gln Asp Val Thr Thr Thr Pro Pro Leu Lys Lys Thr Lys Thr Asn
            85                  90                  95

Leu Ser Leu Glu Thr Ser Ala Pro Leu Thr Val Ser Thr Ser Gly Ala
            100                 105                 110

Leu Thr Leu Ala Ala Ala Pro Leu Ala Val Ala Gly Thr Ser Leu
        115                 120                 125

Thr Met Gln Ser Glu Ala Pro Leu Thr Val Gln Asp Ala Lys Leu Thr
130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Thr Leu Thr Val
            165                 170                 175

Ser Ala Thr Pro Pro Ile Ser Val Ser Ser Gly Ser Leu Gly Leu Asp
            180                 185                 190

Met Glu Asp Pro Met Tyr Thr His Asp Gly Lys Leu Gly Ile Arg Ile
            195                 200                 205

Gly Gly Pro Leu Arg Val Val Asp Ser Leu His Thr Leu Thr Val Val
    210                 215                 220

Thr Gly Asn Gly Ile Ala Val Asp Asn Asn Ala Leu Gln Thr Arg Val
225                 230                 235                 240

Thr Gly Ala Leu Gly Tyr Asp Thr Ser Gly Asn Leu Gln Leu Arg Ala
            245                 250                 255

Ala Gly Met Arg Ile Asp Ala Asn Gly Gln Leu Ile Leu Asp Val
            260                 265                 270

Ala Tyr Pro Phe Asp Ala Gln Asn Asn Leu Ser Leu Arg Leu Gly Gln
        275                 280                 285

Gly Pro Leu Tyr Val Asn Thr Asp His Asn Leu Asp Leu Asn Cys Asn
    290                 295                 300

Arg Gly Leu Thr Thr Thr Thr Asn Asn Thr Lys Lys Leu Glu Thr
305                 310                 315                 320

Lys Ile Gly Ser Gly Leu Asp Tyr Asp Thr Asn Gly Ala Val Ile Ile
            325                 330                 335

Lys Leu Gly Thr Gly Val Ser Phe Asp Ser Thr Gly Ala Leu Ser Val
        340                 345                 350

Gly Asn Thr Gly Asp Asp Lys Leu Thr Leu Trp Thr Thr Pro Asp Pro
    355                 360                 365

Ser Pro Asn Cys Arg Ile His Ser Asp Lys Asp Cys Lys Phe Thr Leu
370                 375                 380

Val Leu Thr Lys Cys Gly Ser Gln Ile Leu Ala Ser Val Ala Ala Leu
```

```
                385                 390                 395                 400
        Ala Val Ser Gly Asn Leu Ala Ser Ile Thr Gly Thr Val Ser Ser Val
                        405                 410                 415

Thr Ile Phe Leu Arg Phe Asp Gln Asn Gly Val Leu Met Glu Asn Ser
                        420                 425                 430

Ser Leu Asp Lys Gln Tyr Trp Asn Phe Arg Asn Gly Asn Ser Thr Asn
                        435                 440                 445

Ala Thr Pro Tyr Thr Asn Ala Val Gly Phe Met Pro Asn Leu Ala Ala
                        450                 455                 460

Tyr Pro Lys Thr Gln Ser Gln Thr Ala Lys Asn Asn Ile Val Ser Gln
        465                 470                 475                 480

Val Tyr Leu Asn Gly Asp Lys Ser Lys Pro Met Thr Leu Thr Ile Thr
                        485                 490                 495

Leu Asn Gly Thr Asn Glu Ser Ser Glu Thr Ser Gln Val Ser His Tyr
                        500                 505                 510

Ser Met Ser Phe Thr Trp Ala Trp Glu Ser Gly Gln Tyr Ala Thr Glu
                        515                 520                 525

Thr Phe Ala Thr Asn Ser Phe Thr Phe Ser Tyr Ile Ala Glu Gln
                        530                 535                 540

<210> SEQ ID NO 31
<211> LENGTH: 543
<212> TYPE: PRT
<213> ORGANISM: Pan troglodytes

<400> SEQUENCE: 31

Met Lys Arg Thr Lys Thr Ser Asp Glu Ser Phe Asn Pro Val Tyr Pro
        1               5                   10                  15

Tyr Asp Thr Glu Asn Gly Pro Pro Ser Val Pro Phe Leu Thr Pro Pro
                        20                  25                  30

Phe Val Ser Pro Asp Gly Phe Gln Glu Ser Pro Pro Gly Val Leu Ser
                        35                  40                  45

Leu Asn Leu Ala Glu Pro Leu Val Thr Ser His Gly Met Leu Ala Leu
        50                  55                  60

Lys Met Gly Ser Gly Leu Ser Leu Asp Asp Ala Gly Asn Leu Thr Ser
        65                  70                  75                  80

Gln Asp Val Thr Thr Thr Pro Pro Leu Lys Lys Thr Lys Thr Asn
                        85                  90                  95

Leu Ser Leu Glu Thr Ser Ala Pro Leu Thr Val Ser Thr Ser Gly Ala
                        100                 105                 110

Leu Thr Leu Ala Ala Ala Ala Pro Leu Ala Val Ala Gly Thr Ser Leu
                        115                 120                 125

Thr Met Gln Ser Glu Ala Pro Leu Thr Val Gln Asp Ala Lys Leu Thr
                130                 135                 140

Leu Ala Thr Lys Gly Pro Leu Thr Val Ser Glu Gly Lys Leu Ala Leu
        145                 150                 155                 160

Gln Thr Ser Ala Pro Leu Thr Ala Ala Asp Ser Ser Thr Leu Thr Val
                        165                 170                 175

Ser Ala Thr Pro Pro Ile Asn Val Ser Ser Gly Ser Leu Gly Leu Asp
                        180                 185                 190

Met Glu Asn Pro Met Tyr Thr His Asp Gly Lys Leu Gly Ile Arg Ile
                        195                 200                 205

Gly Gly Pro Leu Arg Val Val Asp Ser Leu His Thr Leu Thr Val Val
                        210                 215                 220
```

```
Thr Gly Asn Gly Ile Ala Val Asp Asn Asn Ala Leu Gln Thr Arg Val
225                 230                 235                 240

Thr Gly Ala Leu Gly Tyr Asp Thr Ser Gly Asn Leu Gln Leu Arg Ala
            245                 250                 255

Ala Gly Gly Met Arg Ile Asp Ala Asn Gly Gln Leu Ile Leu Asp Val
        260                 265                 270

Ala Tyr Pro Phe Asp Ala Gln Asn Asn Leu Ser Leu Arg Leu Gly Gln
    275                 280                 285

Gly Pro Leu Tyr Val Asn Thr Asp His Asn Leu Asp Leu Asn Cys Asn
290                 295                 300

Arg Gly Leu Thr Thr Thr Thr Asn Asn Thr Lys Lys Leu Glu Thr
305                 310                 315                 320

Lys Ile Gly Ser Gly Leu Asp Tyr Asp Thr Asn Gly Ala Val Ile Ile
            325                 330                 335

Lys Leu Gly Thr Gly Val Ser Phe Asp Ser Thr Gly Ala Leu Ser Val
            340                 345                 350

Gly Asn Thr Gly Asp Asp Lys Leu Thr Leu Trp Thr Thr Pro Asp Pro
        355                 360                 365

Ser Pro Asn Cys Arg Ile His Ser Asp Lys Asp Cys Lys Phe Thr Leu
    370                 375                 380

Val Leu Thr Lys Cys Gly Ser Gln Ile Leu Ala Ser Val Ala Ala Leu
385                 390                 395                 400

Ala Val Ser Gly Asn Leu Ala Ser Ile Thr Gly Thr Val Ser Ser Val
                405                 410                 415

Thr Ile Phe Leu Arg Phe Asp Gln Asn Gly Val Leu Met Glu Asn Ser
            420                 425                 430

Ser Leu Asp Lys Gln Tyr Trp Asn Phe Arg Asn Gly Asn Ser Thr Asn
        435                 440                 445

Ala Thr Pro Tyr Thr Asn Ala Val Gly Phe Met Pro Asn Leu Ala Ala
    450                 455                 460

Tyr Pro Lys Thr Gln Ser Gln Thr Ala Lys Asn Asn Ile Val Ser Gln
465                 470                 475                 480

Val Tyr Leu Asn Gly Asp Lys Ser Lys Pro Met Ile Leu Thr Ile Thr
                485                 490                 495

Leu Asn Gly Thr Asn Glu Ser Ser Glu Thr Ser Gln Val Ser His Tyr
            500                 505                 510

Ser Met Ser Phe Thr Trp Ala Trp Glu Ser Gly Gln Tyr Ala Thr Glu
        515                 520                 525

Thr Phe Ala Thr Asn Ser Phe Thr Phe Ser Tyr Ile Ala Glu Gln
    530                 535                 540

<210> SEQ ID NO 32
<211> LENGTH: 578
<212> TYPE: PRT
<213> ORGANISM: Pan troglodytes

<400> SEQUENCE: 32

Met Lys Arg Thr Lys Thr Ser Asp Glu Ser Phe Asn Pro Val Tyr Pro
1               5                   10                  15

Tyr Asp Thr Glu Asn Gly Pro Pro Ser Val Pro Phe Leu Thr Pro Pro
            20                  25                  30

Phe Val Ser Pro Asp Gly Phe Gln Glu Ser Pro Pro Gly Val Leu Ser
        35                  40                  45

Leu Asn Leu Ala Glu Pro Leu Val Thr Ser His Gly Met Leu Ala Leu
    50                  55                  60
```

```
Lys Met Gly Ser Gly Leu Ser Leu Asp Asp Ala Gly Asn Leu Thr Ser
65              70                  75                  80

Gln Asp Val Thr Thr Thr Pro Pro Leu Lys Lys Thr Lys Thr Asn
            85              90              95

Leu Ser Leu Glu Thr Ser Ala Pro Leu Thr Val Ser Thr Ser Gly Ala
            100             105             110

Leu Thr Leu Ala Ala Ala Val Pro Leu Ala Val Ala Gly Thr Ser Leu
            115             120             125

Thr Met Gln Ser Glu Ala Pro Leu Thr Val Gln Asp Ala Lys Leu Thr
            130             135             140

Leu Ala Thr Lys Gly Pro Leu Thr Val Ser Glu Gly Lys Leu Ala Leu
145             150             155                         160

Gln Thr Ser Ala Pro Leu Thr Ala Ala Asp Ser Ser Thr Leu Thr Ile
                165             170             175

Ser Ala Thr Pro Pro Leu Ser Thr Ser Asn Gly Ser Leu Gly Ile Asp
            180             185             190

Met Gln Ala Pro Ile Tyr Thr Thr Asn Gly Lys Leu Gly Leu Asn Phe
            195             200             205

Gly Ala Pro Leu His Val Val Asp Ser Leu Asn Ala Leu Thr Val Val
210             215             220

Thr Gly Gln Gly Leu Thr Ile Asn Gly Thr Ala Leu Gln Thr Arg Val
225             230             235             240

Ser Gly Ala Leu Asn Tyr Asp Ser Ser Gly Asn Leu Glu Leu Arg Ala
                245             250             255

Ala Gly Gly Met Arg Val Asp Ala Asn Gly Lys Leu Ile Leu Asp Val
            260             265             270

Ala Tyr Pro Phe Asp Ala Gln Asn Asn Leu Ser Leu Arg Leu Gly Gln
            275             280             285

Gly Pro Leu Phe Val Asn Ser Ala His Asn Leu Asp Val Asn Tyr Asn
290             295             300

Arg Gly Leu Tyr Leu Phe Thr Ser Gly Asn Thr Lys Lys Leu Glu Val
305             310             315             320

Asn Ile Lys Thr Ala Lys Gly Leu Ile Tyr Asp Thr Ala Ile Ala
                325             330             335

Ile Asn Pro Gly Asp Gly Leu Glu Phe Gly Ser Gly Ser Asp Thr Asn
            340             345             350

Pro Leu Lys Thr Lys Leu Gly Leu Gly Leu Glu Tyr Asp Ser Ser Arg
            355             360             365

Ala Ile Ile Ala Lys Leu Gly Thr Gly Leu Ser Phe Asp Asn Thr Gly
            370             375             380

Ala Ile Thr Val Gly Asn Lys Asn Asp Lys Leu Thr Leu Trp Thr
385             390             395             400

Thr Pro Asp Pro Ser Pro Asn Cys Arg Ile Tyr Ser Glu Lys Asp Ala
            405             410             415

Lys Phe Thr Leu Val Leu Thr Lys Cys Gly Ser Gln Val Leu Ala Ser
            420             425             430

Val Ser Val Leu Ser Val Lys Gly Ser Leu Ala Pro Ile Ser Gly Thr
            435             440             445

Val Thr Ser Ala Gln Ile Ile Leu Arg Phe Asp Glu Asn Gly Val Leu
            450             455             460

Leu Ser Asn Ser Ser Leu Asp Pro Gln Tyr Trp Asn Tyr Arg Lys Gly
465             470             475             480
```

```
Asp Leu Thr Glu Gly Thr Ala Tyr Thr Asn Ala Val Gly Phe Met Pro
                485                 490                 495

Asn Leu Thr Ala Tyr Pro Lys Thr Gln Ser Gln Thr Ala Lys Ser Asn
            500                 505                 510

Ile Val Ser Gln Val Tyr Leu Asn Gly Asp Lys Ser Lys Pro Met Ile
            515                 520                 525

Leu Thr Ile Thr Leu Asn Gly Thr Asn Glu Thr Gly Asp Ala Thr Val
        530                 535                 540

Ser Thr Tyr Ser Met Ser Phe Ser Trp Asn Trp Asn Gly Ser Asn Tyr
545                 550                 555                 560

Ile Asn Glu Thr Phe Gln Thr Asn Ser Phe Thr Phe Ser Tyr Ile Ala
                565                 570                 575

Gln Glu

<210> SEQ ID NO 33
<211> LENGTH: 578
<212> TYPE: PRT
<213> ORGANISM: Pan troglodytes

<400> SEQUENCE: 33

Met Lys Arg Thr Lys Thr Ser Asp Glu Ser Phe Asn Pro Val Tyr Pro
1               5                   10                  15

Tyr Asp Thr Glu Ser Gly Pro Pro Ser Val Pro Phe Leu Thr Pro Pro
            20                  25                  30

Phe Val Ser Pro Asp Gly Phe Gln Glu Ser Pro Pro Gly Val Leu Ser
        35                  40                  45

Leu Asn Leu Ala Glu Pro Leu Val Thr Ser His Gly Met Leu Ala Leu
50                  55                  60

Lys Met Gly Ser Gly Leu Ser Leu Asp Asp Ala Gly Asn Leu Thr Ser
65                  70                  75                  80

Gln Asp Ile Thr Thr Ala Ser Pro Pro Leu Lys Lys Thr Lys Thr Asn
                85                  90                  95

Leu Ser Leu Glu Thr Ser Ser Pro Leu Thr Val Ser Thr Ser Gly Ala
            100                 105                 110

Leu Thr Val Ala Ala Ala Ala Pro Leu Ala Val Ala Gly Thr Ser Leu
        115                 120                 125

Thr Met Gln Ser Glu Ala Pro Leu Thr Val Gln Asp Ala Lys Leu Thr
130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Thr Leu Thr Val
                165                 170                 175

Ser Ala Thr Pro Pro Leu Ser Thr Ser Asn Gly Ser Leu Gly Ile Asp
            180                 185                 190

Met Gln Ala Pro Ile Tyr Thr Thr Asn Gly Lys Leu Gly Leu Asn Phe
        195                 200                 205

Gly Ala Pro Leu His Val Val Asp Ser Leu Asn Ala Leu Thr Val Val
210                 215                 220

Thr Gly Gln Gly Leu Thr Ile Asn Gly Thr Ala Leu Gln Thr Arg Val
225                 230                 235                 240

Ser Gly Ala Leu Asn Tyr Asp Thr Ser Gly Asn Leu Glu Leu Arg Ala
                245                 250                 255

Ala Gly Gly Met Arg Val Asp Ala Asn Gly Gln Leu Ile Leu Asp Val
            260                 265                 270
```

Ala Tyr Pro Phe Asp Ala Gln Asn Asn Leu Ser Leu Arg Leu Gly Gln
            275                 280                 285

Gly Pro Leu Phe Val Asn Ser Ala His Asn Leu Asp Val Asn Tyr Asn
    290                 295                 300

Arg Gly Leu Tyr Leu Phe Thr Ser Gly Asn Thr Lys Lys Leu Glu Val
305                 310                 315                 320

Asn Ile Lys Thr Ala Lys Gly Leu Ile Tyr Asp Asp Thr Ala Ile Ala
                325                 330                 335

Ile Asn Ala Gly Asp Gly Leu Gln Phe Asp Ser Gly Ser Asp Thr Asn
            340                 345                 350

Pro Leu Lys Thr Lys Leu Gly Leu Gly Leu Asp Tyr Asp Ser Ser Arg
    355                 360                 365

Ala Ile Ile Ala Lys Leu Gly Thr Gly Leu Ser Phe Asp Asn Thr Gly
370                 375                 380

Ala Ile Thr Val Gly Asn Lys Asn Asp Asp Lys Leu Thr Leu Trp Thr
385                 390                 395                 400

Thr Pro Asp Pro Ser Pro Asn Cys Arg Ile Tyr Ser Glu Lys Asp Ala
                405                 410                 415

Lys Phe Thr Leu Val Leu Thr Lys Cys Gly Ser Gln Val Leu Ala Ser
            420                 425                 430

Val Ser Val Leu Ser Val Lys Gly Ser Leu Ala Pro Ile Ser Gly Thr
    435                 440                 445

Val Thr Ser Ala Gln Ile Val Leu Arg Phe Asp Glu Asn Gly Val Leu
450                 455                 460

Leu Ser Asn Ser Ser Leu Asp Pro Gln Tyr Trp Asn Tyr Arg Lys Gly
465                 470                 475                 480

Asp Leu Thr Glu Gly Thr Ala Tyr Thr Asn Ala Val Gly Phe Met Pro
                485                 490                 495

Asn Leu Thr Ala Tyr Pro Lys Thr Gln Ser Gln Thr Ala Lys Ser Asn
            500                 505                 510

Ile Val Ser Gln Val Tyr Leu Asn Gly Asp Lys Ser Lys Pro Met Thr
    515                 520                 525

Leu Thr Ile Thr Leu Asn Gly Thr Asn Glu Thr Gly Asp Ala Thr Val
530                 535                 540

Ser Thr Tyr Ser Met Ser Phe Ser Trp Asn Trp Asn Gly Ser Asn Tyr
545                 550                 555                 560

Ile Asn Glu Thr Phe Gln Thr Asn Ser Phe Thr Ser Tyr Ile Ala
                565                 570                 575

Gln Glu

<210> SEQ ID NO 34
<211> LENGTH: 578
<212> TYPE: PRT
<213> ORGANISM: Pan troglodytes

<400> SEQUENCE: 34

Met Lys Arg Thr Lys Thr Ser Asp Glu Ser Phe Asn Pro Val Tyr Pro
1               5                   10                  15

Tyr Asp Thr Glu Ser Gly Pro Pro Ser Val Pro Phe Leu Thr Pro Pro
            20                  25                  30

Phe Val Ser Pro Asp Gly Phe Gln Glu Ser Pro Pro Gly Val Leu Ser
        35                  40                  45

Leu Asn Leu Ala Glu Pro Leu Val Thr Ser His Gly Met Leu Ala Leu
    50                  55                  60

-continued

```
Lys Met Gly Ser Gly Leu Ser Leu Asp Asp Ala Gly Asn Leu Thr Ser
 65                  70                  75                  80

Gln Asp Ile Thr Thr Ala Ser Pro Pro Leu Lys Lys Thr Lys Thr Asn
                 85                  90                  95

Leu Ser Leu Glu Thr Ser Ser Pro Leu Thr Val Ser Thr Ser Gly Ala
            100                 105                 110

Leu Thr Val Ala Ala Ala Ala Pro Leu Ala Val Ala Gly Thr Ser Leu
            115                 120                 125

Thr Met Gln Ser Glu Ala Pro Leu Thr Val Gln Asp Ala Lys Leu Thr
    130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Thr Leu Thr Val
                165                 170                 175

Ser Ala Thr Pro Pro Leu Ser Thr Ser Asn Gly Ser Leu Gly Ile Asp
            180                 185                 190

Met Gln Ala Pro Ile Tyr Thr Thr Asn Gly Lys Leu Gly Leu Asn Phe
        195                 200                 205

Gly Ala Pro Leu His Val Val Asp Ser Leu Asn Ala Leu Thr Val Val
    210                 215                 220

Thr Gly Gln Gly Leu Thr Ile Asn Gly Thr Ala Leu Gln Thr Arg Val
225                 230                 235                 240

Ser Gly Ala Leu Asn Tyr Asp Thr Ser Gly Asn Leu Glu Leu Arg Ala
                245                 250                 255

Ala Gly Gly Met Arg Val Asp Ala Asn Gly Gln Leu Ile Leu Asp Val
            260                 265                 270

Ala Tyr Pro Phe Asp Ala Gln Asn Asn Leu Ser Leu Arg Leu Gly Gln
        275                 280                 285

Gly Pro Leu Phe Val Asn Ser Ala His Asn Leu Asp Val Asn Tyr Asn
    290                 295                 300

Arg Gly Leu Tyr Leu Phe Thr Ser Gly Asn Thr Lys Lys Leu Glu Val
305                 310                 315                 320

Asn Ile Lys Thr Ala Lys Gly Leu Ile Tyr Asp Asp Thr Ala Ile Ala
                325                 330                 335

Ile Asn Ala Gly Asp Gly Leu Gln Phe Asp Ser Gly Ser Asp Thr Asn
            340                 345                 350

Pro Leu Lys Thr Lys Leu Gly Leu Gly Leu Asp Tyr Asp Ser Ser Arg
        355                 360                 365

Ala Ile Ile Ala Lys Leu Gly Thr Gly Leu Ser Phe Asp Asn Thr Gly
    370                 375                 380

Ala Ile Thr Val Gly Asn Lys Asn Asp Asp Lys Leu Thr Leu Trp Thr
385                 390                 395                 400

Thr Pro Asp Pro Ser Pro Asn Cys Arg Ile Tyr Ser Glu Lys Asp Ala
                405                 410                 415

Lys Phe Thr Leu Val Leu Thr Lys Cys Gly Ser Gln Val Leu Ala Ser
            420                 425                 430

Val Ser Val Leu Ser Val Lys Gly Ser Leu Ala Pro Ile Ser Gly Thr
        435                 440                 445

Val Thr Ser Ala Gln Ile Val Leu Arg Phe Asp Glu Asn Gly Val Leu
    450                 455                 460

Leu Ser Asn Ser Ser Leu Asp Pro Gln Tyr Trp Asn Tyr Arg Lys Gly
465                 470                 475                 480

Asp Leu Thr Glu Gly Thr Ala Tyr Thr Asn Ala Val Gly Phe Met Pro
```

```
                    485                 490                 495
Asn Leu Thr Ala Tyr Pro Lys Thr Gln Ser Gln Thr Ala Lys Ser Asn
                500                 505                 510

Ile Val Ser Gln Val Tyr Leu Asn Gly Asp Lys Ser Lys Pro Met Thr
            515                 520                 525

Leu Thr Ile Thr Leu Asn Gly Thr Asn Glu Thr Gly Asp Ala Thr Val
        530                 535                 540

Ser Thr Tyr Ser Met Ser Phe Ser Trp Asn Trp Asn Gly Ser Asn Tyr
545                 550                 555                 560

Ile Asn Glu Thr Phe Gln Thr Asn Ser Phe Thr Phe Ser Tyr Ile Ala
                565                 570                 575

Gln Glu

<210> SEQ ID NO 35
<211> LENGTH: 577
<212> TYPE: PRT
<213> ORGANISM: Pan paniscus

<400> SEQUENCE: 35

Met Lys Arg Ala Lys Thr Ser Asp Glu Thr Phe Asn Pro Val Tyr Pro
1               5                   10                  15

Tyr Asp Thr Glu Asn Gly Pro Pro Ser Val Pro Phe Leu Thr Pro Pro
            20                  25                  30

Phe Val Ser Pro Asp Gly Phe Gln Glu Ser Pro Pro Gly Val Leu Ser
        35                  40                  45

Leu Arg Leu Ser Glu Pro Leu Val Thr Ser His Gly Met Leu Ala Leu
50                  55                  60

Lys Met Gly Asn Gly Leu Ser Leu Asp Asp Ala Gly Asn Leu Thr Ser
65                  70                  75                  80

Gln Asp Val Thr Thr Val Thr Pro Pro Leu Lys Lys Thr Lys Thr Asn
                85                  90                  95

Leu Ser Leu Gln Thr Ser Ala Pro Leu Thr Val Ser Ser Gly Ser Leu
            100                 105                 110

Thr Val Ala Ala Ala Pro Leu Ala Val Ala Gly Thr Ser Leu Thr
        115                 120                 125

Met Gln Ser Gln Ala Pro Leu Thr Val Gln Asp Ala Lys Leu Gly Leu
130                 135                 140

Ala Thr Gln Gly Pro Leu Thr Val Ser Glu Gly Lys Leu Thr Leu Gln
145                 150                 155                 160

Thr Ser Ala Pro Leu Thr Ala Ala Asp Ser Ser Thr Leu Thr Val Ser
                165                 170                 175

Ala Thr Pro Pro Leu Ser Thr Ser Asn Gly Ser Leu Ser Ile Asp Met
            180                 185                 190

Gln Ala Pro Ile Tyr Thr Thr Asn Gly Lys Leu Ala Leu Asn Ile Gly
        195                 200                 205

Ala Pro Leu His Val Val Asp Thr Leu Asn Ala Leu Thr Val Val Thr
210                 215                 220

Gly Gln Gly Leu Thr Ile Asn Gly Arg Ala Leu Gln Thr Arg Val Thr
225                 230                 235                 240

Gly Ala Leu Ser Tyr Asp Thr Glu Gly Asn Ile Gln Leu Gln Ala Gly
                245                 250                 255

Gly Gly Met Arg Ile Asp Asn Asn Gly Gln Leu Ile Leu Asn Val Ala
            260                 265                 270

Tyr Pro Phe Asp Ala Gln Asn Asn Leu Ser Leu Arg Leu Gly Gln Gly
```

```
            275                 280                 285
Pro Leu Ile Val Asn Ser Ala His Asn Leu Asp Leu Asn Leu Asn Arg
    290                 295                 300

Gly Leu Tyr Leu Phe Thr Ser Gly Asn Thr Lys Lys Leu Glu Val Asn
305                 310                 315                 320

Ile Lys Thr Ala Lys Gly Leu Phe Tyr Asp Gly Thr Ala Ile Ala Ile
                325                 330                 335

Asn Ala Gly Asp Gly Leu Gln Phe Gly Ser Gly Ser Asp Thr Asn Pro
            340                 345                 350

Leu Gln Thr Lys Leu Gly Leu Gly Leu Glu Tyr Asp Ser Asn Lys Ala
        355                 360                 365

Ile Ile Thr Lys Leu Gly Thr Gly Leu Ser Phe Asp Asn Thr Gly Ala
    370                 375                 380

Ile Thr Val Gly Asn Lys Asn Asp Lys Leu Thr Leu Trp Thr Thr
385                 390                 395                 400

Pro Asp Pro Ser Pro Asn Cys Arg Ile Asn Ser Glu Lys Asp Ala Lys
                405                 410                 415

Leu Thr Leu Val Leu Thr Lys Cys Gly Ser Gln Val Leu Ala Ser Val
            420                 425                 430

Ser Val Leu Ser Val Lys Gly Ser Leu Ala Pro Ile Ser Gly Thr Val
        435                 440                 445

Thr Ser Ala Gln Ile Val Leu Arg Phe Asp Glu Asn Gly Val Leu Leu
    450                 455                 460

Ser Asn Ser Ser Leu Asp Pro Gln Tyr Trp Asn Tyr Arg Lys Gly Asp
465                 470                 475                 480

Ser Thr Glu Gly Thr Ala Tyr Thr Asn Ala Val Gly Phe Met Pro Asn
                485                 490                 495

Leu Thr Ala Tyr Pro Lys Thr Gln Ser Gln Thr Ala Lys Ser Asn Ile
            500                 505                 510

Val Ser Gln Val Tyr Leu Asn Gly Asp Lys Thr Lys Pro Met Thr Leu
        515                 520                 525

Thr Ile Thr Leu Asn Gly Thr Asn Glu Thr Gly Asp Ala Thr Val Ser
    530                 535                 540

Thr Tyr Ser Met Ser Phe Ser Trp Asn Trp Asn Gly Ser Asn Tyr Ile
545                 550                 555                 560

Asn Asp Thr Phe Gln Thr Asn Ser Phe Thr Phe Ser Tyr Ile Ala Gln
                565                 570                 575

Glu

<210> SEQ ID NO 36
<211> LENGTH: 577
<212> TYPE: PRT
<213> ORGANISM: Pan paniscus

<400> SEQUENCE: 36

Met Lys Arg Ala Lys Thr Ser Asp Glu Thr Phe Asn Pro Val Tyr Pro
1               5                   10                  15

Tyr Asp Thr Glu Asn Gly Pro Pro Ser Val Pro Phe Leu Thr Pro Pro
            20                  25                  30

Phe Val Ser Pro Asp Gly Phe Gln Glu Ser Pro Pro Gly Val Leu Ser
        35                  40                  45

Leu Arg Leu Ser Glu Pro Leu Val Thr Ser His Gly Met Leu Ala Leu
    50                  55                  60

Lys Met Gly Asn Gly Leu Ser Leu Asp Asp Ala Gly Asn Leu Thr Ser
```

```
                65                   70                   75                   80
Gln Asp Val Thr Thr Val Thr Pro Pro Leu Lys Lys Thr Lys Thr Asn
                        85                   90                   95
Leu Ser Leu Gln Thr Ser Ala Pro Leu Thr Val Ser Ser Gly Ser Leu
                100                  105                  110
Thr Val Ala Ala Ala Pro Leu Ala Val Ala Gly Thr Ser Leu Thr
                115                  120                  125
Met Gln Ser Gln Ala Pro Leu Thr Val Gln Asp Ala Lys Leu Gly Leu
    130                  135                  140
Ala Thr Gln Gly Pro Leu Thr Val Ser Glu Gly Lys Leu Thr Leu Gln
145                  150                  155                  160
Thr Ser Ala Pro Leu Thr Ala Ala Asp Ser Ser Thr Leu Thr Val Ser
                    165                  170                  175
Ala Thr Pro Pro Leu Ser Thr Ser Asn Gly Ser Leu Ser Ile Asp Met
                180                  185                  190
Gln Ala Pro Ile Tyr Thr Thr Asn Gly Lys Leu Ala Leu Asn Ile Gly
                195                  200                  205
Ala Pro Leu His Val Val Asp Thr Leu Asn Ala Leu Thr Val Val Thr
210                  215                  220
Gly Gln Gly Leu Thr Ile Asn Gly Arg Ala Leu Gln Thr Arg Val Thr
225                  230                  235                  240
Gly Ala Leu Ser Tyr Asp Thr Glu Gly Asn Ile Gln Leu Gln Ala Gly
                245                  250                  255
Gly Gly Met Arg Ile Asp Asn Asn Gly Gln Leu Ile Leu Asn Val Ala
                260                  265                  270
Tyr Pro Phe Asp Ala Gln Asn Asn Leu Ser Leu Arg Leu Gly Gln Gly
            275                  280                  285
Pro Leu Ile Val Asn Ser Ala His Asn Leu Asp Leu Asn Leu Asn Arg
            290                  295                  300
Gly Leu Tyr Leu Phe Thr Ser Gly Asn Thr Lys Lys Leu Glu Val Asn
305                  310                  315                  320
Ile Lys Thr Ala Lys Gly Leu Phe Tyr Asp Gly Thr Ala Ile Ala Ile
                325                  330                  335
Asn Ala Gly Asp Gly Leu Gln Phe Gly Ser Gly Ser Asp Thr Asn Pro
                340                  345                  350
Leu Gln Thr Lys Leu Gly Leu Gly Leu Glu Tyr Asp Ser Asn Lys Ala
                355                  360                  365
Ile Ile Thr Lys Leu Gly Thr Gly Leu Ser Phe Asp Asn Thr Gly Ala
            370                  375                  380
Ile Thr Val Gly Asn Lys Asn Asp Asp Lys Leu Thr Leu Trp Thr Thr
385                  390                  395                  400
Pro Asp Pro Ser Pro Asn Cys Arg Ile Asn Ser Glu Lys Asp Ala Lys
                    405                  410                  415
Leu Thr Leu Val Leu Thr Lys Cys Gly Ser Gln Val Leu Ala Ser Val
                420                  425                  430
Ser Val Leu Ser Val Lys Gly Ser Leu Ala Pro Ile Ser Gly Thr Val
            435                  440                  445
Thr Ser Ala Gln Ile Val Leu Arg Phe Asp Glu Asn Gly Val Leu Leu
            450                  455                  460
Ser Asn Ser Ser Leu Asp Pro Gln Tyr Trp Asn Tyr Arg Lys Gly Asp
465                  470                  475                  480
Ser Thr Glu Gly Thr Ala Tyr Thr Asn Ala Val Gly Phe Met Pro Asn
                485                  490                  495
```

Leu Thr Ala Tyr Pro Lys Thr Gln Ser Gln Thr Ala Lys Ser Asn Ile
            500                 505                 510

Val Ser Gln Val Tyr Leu Asn Gly Asp Lys Thr Lys Pro Met Thr Leu
            515                 520                 525

Thr Ile Thr Leu Asn Gly Thr Asn Glu Thr Gly Asp Ala Thr Val Ser
        530                 535                 540

Thr Tyr Ser Met Ser Phe Ser Trp Asn Trp Asn Gly Ser Asn Tyr Ile
545                 550                 555                 560

Asn Asp Thr Phe Gln Thr Asn Ser Phe Thr Phe Ser Tyr Ile Ala Gln
                565                 570                 575

Glu

<210> SEQ ID NO 37
<211> LENGTH: 845
<212> TYPE: DNA
<213> ORGANISM: Human cytomegalovirus

<400> SEQUENCE: 37
ccattgcata cgttgtatcc atatcataat atgtacattt atattggctc atgtccaaca     60
ttaccgccat gttgacattg attattgact agttattaat agtaatcaat tacgggtca    120 ttagttcata gcccatatat ggagttccgc gttacataac ttacggtaaa tggcccgcct    180
ggctgaccgc ccaacgaccc ccgcccattg acgtcaataa tgacgtatgt tcccatagta    240
acgccaatag ggactttcca ttgacgtcaa tgggtggagt atttacggta aactgcccac    300
ttggcagtac atcaagtgta tcatatgcca gtacgcccc ctattgacgt caatgacggt    360
aaatggcccg cctggcatta tgcccagtac atgaccttat gggactttcc tacttggcag    420
tacatctacg tattagtcat cgctattacc atggtgatgc ggttttggca gtacatcaat    480
gggcgtggat agcggtttga ctcacgggga tttccaagtc tccaccccat tgacgtcaat    540
gggagtttgt tttggcacca aaatcaacgg gactttccaa aatgtcgtaa caactccgcc    600
ccattgacgc aaatgggcgg taggcgtgta cggtgggagg tctatataag cagagctctc    660
cctatcagtg atagagatct ccctatcagt gatagagatc gtcgacgagc tcgtttagtg    720
aaccgtcaga tcgcctggag acgccatcca cgctgttttg acctccatag aagacaccgg    780
gaccgatcca gcctccgcgg ccgggaacgg tgcattggaa cgcggattcc ccgtgccaag    840
agtga                                                                845

<210> SEQ ID NO 38
<211> LENGTH: 15422
<212> TYPE: DNA
<213> ORGANISM: Pan troglodytes

<400> SEQUENCE: 38
tgcccgcttt ccagtcggga aacctgtcgt gccagctgca ttaatgaatc ggccaacgcg     60
cggggagagg cggtttgcgt attgggcgct agatctccca tcacatatac ctgccgttca    120
ctattattta gtgaaatgag atattatgat attttctgaa ttgtgattaa aaaggcaact    180
ttatgcccat gcaacagaaa ctataaaaaa tacagaaat gaaaagaaac agatagattt    240
tttagttctt taggcccgta gtctgcaaat ccttttatga ttttctatca aacaaaagag    300
gaaaatagac cagttgcaat ccaaacgaga gtctaataga atgaggtcga aaagtaaatc    360
gcgcgggttt gttactgata aagcaggcaa gacctaaaat gtgtaaaggg caaagtgtat    420
actttggcgt caccccttac atattttagg tctttttta ttgtgcgtaa ctaacttgcc    480

```
atcttcaaac aggagggctg gaagaagcag accgctaaca cagtacataa aaaaggagac    540
atgaacgatg aacatcaaaa agtttgcaaa acaagcaaca gtattaacct ttactaccgc    600
actgctggca ggaggcgcaa ctcaagcgtt tgcgaaagaa acgaaccaaa agccatataa    660
ggaaacatac ggcatttccc atattacacg ccatgatatg ctgcaaatcc ctgaacagca    720
aaaaaatgaa aaatatcaag ttcctgaatt cgattcgtcc acaattaaaa atatctcttc    780
tgcaaaaggc ctggacgttt gggacagctg gccattacaa aacgctgacg gcactgtcgc    840
aaactatcac ggctaccaca tcgtctttgc attagccgga gatcctaaaa atgcggatga    900
cacatcgatt tacatgttct atcaaaaagt cggcgaaact tctattgaca gctggaaaaa    960
cgctggccgc gtctttaaag acagcgacaa attcgatgca aatgattcta tcctaaaaga   1020
ccaaacacaa gaatggtcag gttcagccac atttacatct gacggaaaaa tccgtttatt   1080
ctacactgat ttctccggta acattacgg caaacaaaca ctgacaactg cacaagttaa    1140
cgtatcagca tcagacagct cttttgaacat caacggtgta gaggattata atcaatctt    1200 tgacggtgac ggaaaaacgt atcaaaatgt acagcagttc atcgatgaag caactacag    1260 ctcaggcgac aaccatacgc tgagagatcc tcactacgta aagataaag ccacaaata     1320 cttagtattt gaagcaaaca ctggaactga agatggctac caaggcgaag aatctttatt   1380
taacaaagca tactatggca aaagcacatc attcttccgt caagaaagtc aaaaacttct   1440
gcaaagcgat aaaaaacgca cggctgagtt agcaaacggc gctctcggta tgattgagct   1500
aaacgatgat tacacactga aaaaagtgat gaaaccgctg attgcatcta acacagtaac   1560
agatgaaatt gaacgcgcga acgtctttaa aatgaacggc aaatggtacc tgttcactga   1620
ctcccgcgga tcaaaaatga cgattgacgg cattacgtct aacgatattt acatgcttgg   1680
ttatgtttct aattctttaa ctggcccata caagccgctg aacaaaactg ccttgtgtt    1740 aaaaatggat cttgatccta acgatgtaac ctttacttac tcacacttcg ctgtacctca   1800
agcgaaagga aacaatgtcg tgattacaag ctatatgaca aacagaggat tctacgcaga   1860
caaacaatca acgtttgcgc caagcttcct gctgaacatc aaaggcaaga aaacatctgt   1920
tgtcaaagac agcatccttg aacaaggaca attaacagtt aacaaataat agggataaca   1980
gggtaatgct agaagacccg agtcttacca gtaaaagaaa aaagatctct caacgcagca   2040
ccagcaccaa cacttcgcag tgtaaaaggc caagtgccga gagagtatat ataggaataa   2100
aaagtgacgt aaacgggcaa agtccaaaaa acgcccagaa aaaccgcacg cgaacctacg   2160
ccccgaaacg aaagccaaaa aacactagac actcccttcc ggcgtcaact tccgctttcc   2220
cacgctacgt cacttgcccc agtcaaacaa actacatatc ccgaacttcc aagtcgccac   2280
gcccaaaaca ccgcctacac ctcccgccc gcggcccgc ccccaaaccc gcctcccgcc     2340
ccgcgccccg ccccgcgccg cccatctcat tatcatattg gcttcaatcc aaaataaggt   2400
atattattga tgatggttta acggatcct ctagagtcga cctgcaggca tgcaagcttg    2460
agtattctat agtgtcacct aaatagcttg gcgtaatcat ggtcatagct gtttcctgtg   2520
tgaaattgtt atccgctcac aattccacac aacatacgag ccggaagcat aaagtgtaaa   2580
gcctggggtg cctaatgagt gagctaactc acattaattg cgttgcgctc actgcccgct   2640
ttccagtcgg gaaacctgtc gtgccagctg cattaatgaa tcggccaacg cgaaccccctt   2700 gcggccgccc gggccgtcga ccaattctca tgtttgacag cttatcatcg aatttctgcc   2760
attcatccgc ttattatcac ttattcaggc gtagcaacca ggcgtttaag ggcaccaata   2820
```

```
actgccttaa aaaaattacg ccccgccctg ccactcatcg cagtactgtt gtaattcatt    2880
aagcattctg ccgacatgga agccatcaca aacggcatga tgaacctgaa tcgccagcgg    2940
catcagcacc ttgtcgcctt gcgtataata tttgcccatg gtgaaaacgg gggcgaagaa    3000
gttgtccata ttggccacgt ttaaatcaaa actggtgaaa ctcacccagg gattggctga    3060
gacgaaaaac atattctcaa taaacccttt agggaaatag gccaggtttt caccgtaaca    3120
cgccacatct tgcgaatata tgtgtagaaa ctgccggaaa tcgtcgtggt attcactcca    3180
gagcgatgaa aacgtttcag tttgctcatg gaaaacggtg taacaagggt gaacactatc    3240
ccatatcacc agctcaccgt ctttcattgc catacggaat tccggatgag cattcatcag    3300
gcgggcaaga atgtgaataa aggccggata aaacttgtgc ttattttttct ttacggtctt    3360
taaaaaggcc gtaatatcca gctgaacggt ctggttatag gtacattgag caactgactg    3420
aaatgcctca aaatgttctt tacgatgcca ttgggatata tcaacggtgg tatatccagt    3480
gatttttttc tccattttag cttccttagc tcctgaaaat ctcgataact caaaaaatac    3540
gcccggtagt gatcttattt cattatggtg aaagttggaa cctcttacgt gccgatcaac    3600
gtctcatttt cgccaaaagt tggcccaggg cttcccggta tcaacaggga caccaggatt    3660
tatttattct gcgaagtgat cttccgtcac aggtatttat tcgcgataag ctcatggagc    3720
ggcgtaaccg tcgcacagga aggacagaga aagcgcggat ctgggaagtg acggacagaa    3780
cggtcaggac ctggattggg gaggcggttg ccgccgctgc tgctgacggt gtgacgttct    3840
ctgttccggt cacaccacat acgttccgcc attcctatgc gatgcacatg ctgtatgccg    3900
gtataccgct gaaagttctg caaagcctga tgggacataa gtccatcagt tcaacggaag    3960
tctacacgaa ggttttttgcg ctggatgtgg ctgcccggca ccgggtgcag tttgcgatgc    4020
cggagtctga tgcggttgcg atgctgaaac aattatcctg agaataaatg ccttggcctt    4080
tatatggaaa tgtggaactg agtggatatg ctgttttttgt ctgttaaaca gagaagctgg    4140
ctgttatcca ctgagaagcg aacgaaacag tcgggaaaat ctcccattat cgtagagatc    4200
cgcattatta atctcaggag cctgtgtagc gtttatagga agtagtgttc tgtcatgatg    4260
cctgcaagcg gtaacgaaaa cgatttgaat atgccttcag gaacaataga aatcttcgtg    4320
cggtgttacg ttgaagtgga gcggattatg tcagcaatgg acagaacaac ctaatgaaca    4380
cagaaccatg atgtggtctg tccttttaca gccagtagtg ctcgccgcag tcgagcgaca    4440
gggcgaagcc ctcgagtgag cgaggaagca ccagggaaca gcacttatat attctgctta    4500
cacacgatgc ctgaaaaaac ttcccttggg gttatccact tatccacggg gatatttta    4560
taattatttt ttttatagtt tttagatctt cttttttaga gcgccttgta ggcctttatc    4620
catgctggtt ctagagaagg tgttgtgaca aattgccctt tcagtgtgac aaatcaccct    4680
caaatgacag tcctgtctgt gacaaattgc ccttaaccct gtgacaaatt gccctcagaa    4740
gaagctgttt tttcacaaag ttatccctgc ttattgactc ttttttattt agtgtgacaa    4800
tctaaaaact tgtcacactt cacatggatc tgtcatggcg aaacagcgg ttatcaatca    4860
caagaaacgt aaaaatagcc cgcgaatcgt ccagtcaaac gacctcactg aggcggcata    4920
tagtctctcc cggatcaaa aacgtatgct gtatctgttc gttgaccaga tcagaaaatc    4980
tgatggcacc ctacaggaac atgacggtat ctgcgagatc catgttgcta aatatgctga    5040
aatattcgga ttgaccctctg cggaagccag taaggatata cggcaggcat tgaagagttt    5100
cgcggggaag gaagtggttt tttatcgccc tgaagaggat gccggcgatg aaaaaggcta    5160
tgaatctttt ccttggttta tcaaacgtgc gcacagtcca tccagagggc tttacagtgt    5220
```

```
acatatcaac ccatatctca ttcccttctt tatcgggtta cagaaccggt ttacgcagtt    5280
tcggcttagt gaaacaaaag aaatcaccaa tccgtatgcc atgcgtttat acgaatccct    5340
gtgtcagtat cgtaagccgg atggctcagg catcgtctct ctgaaaatcg actggatcat    5400
agagcgttac cagctgcctc aaagttacca gcgtatgcct gacttccgcc gccgcttcct    5460
gcaggtctgt gttaatgaga tcaacagcag aactccaatg cgcctctcat acattgagaa    5520
aaagaaaggc cgccagacga ctcatatcgt attttccttc cgcgatatca cttccatgac    5580
gacaggatag tctgagggtt atctgtcaca gatttgaggg tggttcgtca catttgttct    5640
gacctactga gggtaatttg tcacagtttt gctgtttcct tcagcctgca tggattttct    5700
catacttttt gaactgtaat ttttaaggaa gccaaatttg agggcagttt gtcacagttg    5760
atttccttct ctttcccttc gtcatgtgac ctgatatcgg gggttagttc gtcatcattg    5820
atgagggttg attatcacag tttattactc tgaattggct atccgcgtgt gtacctctac    5880
ctggagtttt tcccacggtg gatatttctt cttgcgctga gcgtaagagc tatctgacag    5940
aacagttctt ctttgcttcc tcgccagttc gctcgctatg ctcggttaca cggctgcggc    6000
gagcgctagt gataataagt gactgaggta tgtgctcttc ttatctcctt ttgtagtgtt    6060
gctcttattt taaacaactt tgcggttttt tgatgacttt gcgattttgt tgttgctttg    6120
cagtaaattg caagatttaa taaaaaaacg caaagcaatg attaaaggat gttcagaatg    6180
aaactcatgg aaacacttaa ccagtgcata aacgctggtc atgaaatgac gaaggctatc    6240
gccattgcac agtttaatga tgacagcccg gaagcgagga aaataacccg cgctggagaa    6300
ataggtgaag cagcggattt agttggggtt tcttctcagg ctatcagaga tgccgagaaa    6360
gcagggcgac taccgcaccc ggatatggaa attcgaggac gggttgagca acgtgttggt    6420
tatacaattg aacaaattaa tcatatgcgt gatgtgtttg gtacgcgatt gcgacgtgct    6480
gaagacgtat ttccaccggt gatcggggtt gctgcccata aggtggcgt ttacaaaacc    6540 tcagtttctg ttcatcttgc tcaggatctg gctctgaagg ggctacgtgt tttgctcgtg    6600
gaaggtaacg accccaggg aacagcctca atgtatcacg gatgggtacc agatcttcat    6660
attcatgcag aagacactct cctgccttc tatcttgggg aaaaggacga tgtcacttat    6720
gcaataaagc ccacttgctg gccgggggctt gacattattc cttcctgtct ggctctgcac    6780
cgtattgaaa ctgagttaat gggcaaattt gatgaaggta aactgccac cgatccacac    6840 ctgatgctcc gactggccat tgaaactgtt gctcatgact atgatgtcat agttattgac    6900
agcgcgccta acctgggtat cggcacgatt aatgtcgtat gtgctgctga tgtgctgatt    6960
gttcccacgc tgctgagtt gtttgactac acctccgcac tgcagttttt cgatatgctt    7020
cgtgatctgc tcaagaacgt tgatcttaaa gggttcgagc ctgatgtacg tattttgctt    7080
accaaataca gcaatagtaa tggctctcag tccccgtgga tggaggagca aattcgggat    7140
gcctggggaa gcatggttct aaaaaatgtt gtacgtgaaa cggatgaagt tggtaaaggt    7200
cagatccgga tgagaactgt ttttgaacag gccattgatc aacgctcttc aactggtgcc    7260
tggagaaatg ctcttttctat ttgggaacct gtctgcaatg aaattttcga tcgtctgatt    7320
aaaccacgct gggagattag ataatgaagc gtgcgcctgt tattccaaaa catacgctca    7380
atactcaacc ggttgaagat acttcgttat cgacaccagc tgccccgatg gtggattcgt    7440
taattgcgcg cgtaggagta atggctcgcg gtaatgccat tactttgcct gtatgtggtc    7500
gggatgtgaa gtttactctt gaagtgctcc ggggtgatag tgttgagaag acctctcggg    7560
```

```
tatggtcagg taatgaacgt gaccaggagc tgcttactga ggacgcactg gatgatctca    7620
tcccttcttt tctactgact ggtcaacaga caccggcgtt cggtcgaaga gtatctggtg    7680
tcatagaaat tgccgatggg agtcgccgtc gtaaagctgc tgcacttacc gaaagtgatt    7740
atcgtgttct ggttggcgag ctggatgatg agcagatggc tgcattatcc agattgggta    7800
acgattatcg cccaacaagt gcttatgaac gtggtcagcg ttatgcaagc cgattgcaga    7860
atgaatttgc tggaaatatt tctgcgctgg ctgatgcgga aaatatttca cgtaagatta    7920
ttacccgctg tatcaacacc gccaaattgc ctaaatcagt tgttgctctt ttttctcacc    7980
ccggtgaact atctgcccgg tcaggtgatg cacttcaaaa agcctttaca gataaagagg    8040
aattacttaa gcagcaggca tctaaccttc atgagcagaa aaaagctggg gtgatatttg    8100
aagctgaaga agttatcact cttttaactt ctgtgcttaa aacgtcatct gcatcaagaa    8160
ctagtttaag ctcacgacat cagtttgctc ctggagcgac agtattgtat aagggcgata    8220
aaatggtgct taacctggac aggtctcgtg ttccaactga gtgtatagag aaaattgagg    8280
ccattcttaa ggaacttgaa aagccagcac cctgatgcga ccacgtttta gtctacgttt    8340
atctgtcttt acttaatgtc cttgttaca ggccagaaag cataactggc ctgaatattc    8400
tctctgggcc cactgttcca cttgtatcgt cggtctgata atcagactgg gaccacggtc    8460
ccactcgtat cgtcggtctg attattagtc tgggaccacg gtcccactcg tatcgtcggt    8520
ctgattatta gtctgggacc acggtcccac tcgtatcgtc ggtctgataa tcagactggg    8580
accacggtcc cactcgtatc gtcggtctga ttattagtct gggaccatgg tcccactcgt    8640
atcgtcggtc tgattattag tctgggacca cggtcccact cgtatcgtcg gtctgattat    8700
tagtctggaa ccacggtccc actcgtatcg tcggtctgat tattagtctg ggaccacggt    8760
cccactcgta tcgtcggtct gattattagt ctgggaccac gatcccactc gtgttgtcgg    8820
tctgattatc ggtctgggac acggtcccac cttgtattgt cgatcagact atcagcgtga    8880
gactacgatt ccatcaatgc ctgtcaaggg caagtattga catgtcgtcg taacctgtag    8940
aacggagtaa cctcggtgtg cggttgtatg cctgctgtgg attgctgctg tgtcctgctt    9000
atccacaaca ttttgcgcac ggttatgtgg acaaaatacc tggttaccca ggccgtgccg    9060
gcacgttaac cgggctgcat ccgatgcaag tgtgtcgctg tcgacgagct cgcgagctcg    9120
gacatgaggt tgcccccgtat tcagtgtcgc tgatttgtat tgtctgaagt tgttttttacg    9180 ttaagttgat gcagatcaat taatacgata cctgcgtcat aattgattat ttgacgtggt    9240
ttgatggcct ccacgcacgt tgtgatatgt agatgataat cattatcact ttacgggtcc    9300
tttccggtga tccgacaggt tacggggcgg cgacctcgcg ggttttcgct atttatgaaa    9360
attttccggt ttaaggcgtt tccgttcttc ttcgtcataa cttaatgttt ttatttaaaa    9420
taccctctga aaagaaagga aacgacaggt gctgaaagcg agcttttttgg cctctgtcgt    9480 ttcctttctc tgtttttgtc cgtggaatga caatggaag tccgagctca tcgctaataa    9540
cttcgtatag catacattat acgaagttat attcgatgcg ccgcaaggg gttcgcgtca    9600 gcgggtgttg gcgggtgtcg gggctggctt aactatgcgg catcagagca gattgtactg    9660
agagtgcacc atatgcggtg tgaaataccg cacagatgcg taaggagaaa ataccgcatc    9720
aggcgccatt cgccattcag gctgcgcaac tgtgtgggaag gcgatcggt gcgggcctct    9780 tcgctattac gccagctggc gaaggggga tgtgctgcaa ggcgattaag ttgggtaacg    9840
ccagggtttt cccagtcacg acgttgtaaa acgacggcca gtgaattgta atacgactca    9900
ctatagggcg aattcgagct cggtacccgg ggatcctcgt ttaaaccatc atcaataata    9960
```

```
taccttattt tggattgaag ccaatatgat aatgagatgg gcggcgcggg gcggggcgcg    10020
gggcgggagg cgggtttggg ggcgggccgg cgggcggggc ggtgtggcgg aagtggactt    10080
tgtaagtgtg gcggatgtga cttgctagtg ccgggcgcgg taaaagtgac gttttccgtg    10140
cgcgacaacg cccccgggaa gtgacatttt tcccgcggtt tttaccggat gttgtagtga    10200
atttgggcgt aaccaagtaa gatttggcca ttttcgcggg aaaactgaaa cggggaagtg    10260
aaatctgatt aattttgcgt tagtcatacc gcgtaatatt tgtctagggc cgagggactt    10320
tggccgatta cgtggaggac tcgcccaggt gttttttgag gtgaatttcc gcgttccggg    10380
tcaaagtctg cgtttttatta ttataggata tcccattgca tacgttgtat ccatatcata    10440
atatgtacat ttatattggc tcatgtccaa cattaccgcc atgttgacat tgattattga    10500
ctagttatta atagtaatca attacggggt cattagttca tagcccatat atggagttcc    10560
gcgttacata acttacggta aatggcccgc ctggctgacc gcccaacgac ccccgcccat    10620
tgacgtcaat aatgacgtat gttcccatag taacgccaat agggactttc cattgacgtc    10680
aatgggtgga gtatttacgg taaactgccc acttggcagt acatcaagtg tatcatatgc    10740
caagtacgcc ccctattgac gtcaatgacg gtaaatggcc cgcctggcat tatgcccagt    10800
acatgacctt atgggacttt cctacttggc agtacatcta cgtattagtc atcgctatta    10860
ccatggtgat gcggttttgg cagtacatca atgggcgtgg atagcggttt gactcacggg    10920
gatttccaag tctccacccc attgacgtca atgggagttt gttttggcac caaaatcaac    10980
gggactttcc aaaatgtcgt aacaactccg ccccattgac gcaaatgggc ggtaggcgtg    11040
tacggtggga ggtctatata agcagagctc tccctatcag tgatagagat ctccctatca    11100
gtgatagaga tcgtcgacga gctcgtttag tgaaccgtca gatcgcctgg agacgccatc    11160
cacgctgttt tgacctccat agaagacacc gggaccgatc cagcctccgc ggccgggaac    11220
ggtgcattgg aacgcggatt ccccgtgcca agagtgagat cttccgttta tctaggtacc    11280
gggccccccc tcgaggtcga cggtatcgat aagcttcacg ctgccgcaag cactcagggc    11340
gcaagggctg ctaaaggaag cggaacacgt agaaagccag tccgcagaaa cggtgctgac    11400
cccggatgaa tgtcagctac tgggctatct ggacaaggga aaacgcaagc gcaaagagaa    11460
agcaggtagc ttgcagtggg cttacatggc gatagctaga ctgggcggtt ttatggacag    11520
caagcgaacc ggaattgcca gctggggcgc cctctggtaa ggttgggaag ccctgcaaag    11580
taaactggat ggctttcttg ccgccaagga tctgatggcg caggggatca agatctaacc    11640
aggagctatt taatgcaac agttaaccag ctggtacgca aaccacgtgc tcgcaaagtt    11700
gcgaaaagca acgtgcctgc gctggaagca tgcccgcaaa acgtggcgt atgtactcgt    11760 gtatatacta ccactcctaa aaaaccgaac tccgcgctgc gtaaagtatg ccgtgttcgt    11820
ctgactaacg gtttcgaagt gacttcctac atcggtggtg aaggtcacaa cctgcaggag    11880
cactccgtga tcctgatccg tggcggtcgt gttaaagacc tcccgggtgt tcgttaccac    11940
accgtacgtg gtgcgcttga ctgctccggc gttaaagacc gtaagcaggc tcgttccaag    12000
tatggcgtga agcgtcctaa ggcttaatgg tagatctgat caagagacag gatgacggtc    12060
gtttcgcatg cttgaacaag atggattgca cgcaggttct ccggccgctt gggtggagag    12120
gctattcggc tatgactggg cacaacagac aatcggctgc tctgatgccg ccgtgttccg    12180
gctgtcagcg caggggcgcc cggttctttt tgtcaagacc gacctgtccg gtgccctgaa    12240
tgaactgcag gacgaggcag cgcggctatc gtggctggcc acgacgggcg ttccttgcgc    12300
```

```
agctgtgctc gacgttgtca ctgaagcggg aagggactgg ctgctattgg gcgaagtgcc    12360
ggggcaggat ctcctgtcat ctcaccttgc tcctgccgag aaagtatcca tcatggctga    12420
tgcaatgcgg cggctgcata cgcttgatcc ggctacctgc ccattcgacc accaagcgaa    12480
acatcgcatc gagcgagcac gtactcggat ggaagccggt cttgtcgatc aggatgatct    12540
ggacgaagag catcaggggc tcgcgccagc cgaactgttc gccaggctca aggcgcgcat    12600
gcccgacggc gaggatctcg tcgtgaccca tggcgatgcc tgcttgccga atatcatggt    12660
ggaaaatggc cgcttttctg gattcatcga ctgtggccgg ctgggtgtgg cggaccgcta    12720
tcaggacata gcgttggcta cccgtgatat tgctgaagag cttggcggcg aatgggctga    12780
ccgcttcctc gtgctttacg gtatcgccgc tcccgattcg cagcgcatcg ccttctatcg    12840
ccttcttgac gagttcttct gagcgggact ctggggttcg aaatgaccga ccaagcgacg    12900
cccaacctgc catcacgaga tttcgattcc accgccgcct tctatgaaag gttgggcttc    12960
ggaatcgttt tccgggacgc cggctggatg atcctccagc gcgggatct catgctggag     13020
ttcttcgccc accccgggct cgatcccctc ggggggaatc agaattcagt cgacagcggc    13080
cgcgatctgc tgtgccttct agttgccagc catctgttgt ttgcccctcc ccgtgccttt    13140
ccttgaccct ggaaggtgcc actcccactg tcctttccta ataaaatgag gaaattgcat    13200
cgcattgtct gagtaggtgt cattctattc tggggggtgg ggtggggcag gacagcaagg    13260
gggaggattg ggaagacaat agcaggcatg ctggggatgc ggtgggctct atggccgatc    13320
agcgatcgct gaggtgggtg agtgggcgtg gcctggggtg gtcatgaaaa tatataagtt    13380
gggggtctta gggtctcttt atttgtgttg cagagaccgc cggagccatg agcgggagca    13440
gcagcagcag cagtagcagc agcgccttgg atggcagcat cgtgagccct tatttgacga    13500
cgcggatgcc ccactgggcc ggggtgcgtc agaatgtgat gggctccagc atcgacggcc    13560
gacccgtcct gcccgcaaat tccgccacgc tgacctatgc gaccgtcgcg gggacgccgt    13620
tggacgccac cgccgccgcc gccgccaccg cagccgcctc ggccgtgcgc agcctggcca    13680
cggactttgc attcctggga ccactggcga caggggctac ttctcgggcc gctgctgccg    13740
ccgttcgcga tgacaagctg accgccctgc tggcgcagtt ggatgcgctt actcgggaac    13800
tgggtgacct ttctcagcag gtcatggccc tgcgccagca ggtctcctcc ctgcaagctg    13860
gcggaatgc ttctcccaca aatgccgttt aagggcgcgc ctaggggataa caggtgtaata   13920
cccctatttg tttattttc taaatacatt caaatatgta tccgctcatg agacaataac     13980
cctgataaat gcttcaataa tattgaaaaa ggaagagtat gagtattcaa catttccgtg    14040
tcgcccttat tccctttttt gcggcatttt gccttcctgt ttttgctcac ccagaaacgc    14100
tggtgaaagt aaaagatgct gaagatcagt tgggtgcacg agtgggttac atcgaactgg    14160
atctcaacag cggtaagatc cttgagagtt ttcgccccga agaacgtttt ccaatgatga    14220
gcacttttaa agttctgcta tgtggcgcgg tattatcccg tattgacgcc gggcaagagc    14280
aactcggtcg ccgcatacac tattctcaga atgacttggt tgagtactca ccagtcacag    14340
aaaagcatct tacgatggc atgacagtaa gagaattatg cagtgctgcc ataaccatga    14400
gtgataacac tgcggccaac ttacttctga caacgatcgg aggaccgaag gagctaaccg    14460
cttttttgca caacatgggg gatcatgtaa ctcgccttga tcgttgggaa ccggagctga    14520
atgaagccat accaaacgac gagcgtgaca ccacgatgcc tgtagcaatg gcaacaacgt    14580
tgcgcaaact attaactggc gaactactta ctctagcttc ccggcaacaa ttaatagact    14640
ggatggaggc ggataaagtt gcaggaccac ttctgcgctc ggcccttccg gctggctggt    14700
```

| | | |
|---|---|---|
| ttattgctga taaatctgga gccggtgagc gtgggtctcg cggtatcatt gcagcactgg | 14760 | |
| ggccagatgg taagccctcc cgtatcgtag ttatctacac gacggggagt caggcaacta | 14820 | |
| tggatgaacg aaatagacag atcgctgaga taggtgcctc actgattaag cattggtaac | 14880 | |
| tgtcagacca agtttactca tatatacttt agattgattt aaaatacgta tatatgtatt | 14940 | |
| agtcatcgct attaccatgg ttaatgcgcc gctacagggc gcgtccattc gccattcagg | 15000 | |
| ctgcgcaact gttgggaagg gcgatcgtg cgggcctctt cgctattacg ccagctggcg | 15060 | |
| aaaggggat gtgctgcaag gcgattaagt tgggtaacgc cagggttttc ccagtcacga | 15120 | |
| cgttgtaaaa cgacggccag tgaattgtaa tacgactcac tatagggcga attgggccct | 15180 | |
| ctagatgcat gctcgagcgg ccgccagtgt gatggatatc tgcagaattc cagcacactg | 15240 | |
| gcggccgtta ctagtggatc cgagctcggt accaagcttg gcgtaatcat ggtcatagct | 15300 | |
| gtttcctgtg tgaaattgtt atccgctcac aattccacac aacatacgag ccggaagcat | 15360 | |
| aaagtgtaaa gcctggggtg cctaatgagt gagctaactc acattaattg cgttgcgctc | 15420 | |
| ac | 15422 | |

<210> SEQ ID NO 39
<211> LENGTH: 225
<212> TYPE: DNA
<213> ORGANISM: Bos taurus

<400> SEQUENCE: 39

| | | |
|---|---|---|
| ctgtgccttc tagttgccag ccatctgttg tttgcccctc ccccgtgcct tccttgaccc | 60 | |
| tggaaggtgc cactcccact gtcctttcct aataaaatga ggaaattgca tcgcattgtc | 120 | |
| tgagtaggtg tcattctatt ctgggggtg gggtgggca ggacagcaag ggggaggatt | 180 | |
| gggaagacaa tagcaggcat gctggggatg cggtgggctc tatgg | 225 | |

<210> SEQ ID NO 40
<211> LENGTH: 3983
<212> TYPE: DNA
<213> ORGANISM: Pan troglodytes

<400> SEQUENCE: 40

| | | |
|---|---|---|
| catcatcaat aatataccct attttggatt gaagccaata tgataatgag atgggcggcg | 60 | |
| cggggcgggg cgcggggcgg gaggcgggtt tgggggcggg ccggcgggcg gggcggtgtg | 120 | |
| gcggaagtgg actttgtaag tgtggcggat gtgacttgct agtgccgggc gcggtaaaag | 180 | |
| tgacgttttc cgtgcgcgac aacgcccccg ggaagtgaca ttttttcccgc ggttttacc | 240 | |
| ggatgttgta gtgaatttgg gcgtaaccaa gtaagatttg gccattttcg cgggaaaact | 300 | |
| gaaacgggga agtgaaatct gattaatttt gcgttagtca taccgcgtaa tatttgtcta | 360 | |
| gggccgaggg actttggccg attacgtgga ggactcgccc aggtgttttt tgaggtgaat | 420 | |
| ttccgcgttc cgggtcaaag tctccgtttt attattatag gatatcccat tgcatacgtt | 480 | |
| gtatccatat cataatatgt acaggcgcgc caaagcatga cactgatgtt catttctgat | 540 | |
| tcttatttta ttattttcaa acacaacaaa atcattcaag tcattcttcc atcttagctt | 600 | |
| aatagacaca gtagcttaat agacccagta gtgcaaagcc ccattctagc ttataactag | 660 | |
| tggagaagta ctcgcctaca tgggggtaga gtcataatcg tgcatcagga tagggcggtg | 720 | |
| gtgctgcagc agcgcgcgaa taaactgctg ccgccgccgc tccgtcctgc aggaatacaa | 780 | |
| catggcagtg gtctcctcag cgatgattcg caccgcccgc agcataaggc gccttgtcct | 840 | |

```
ccgggcacag cagcgcaccc tgatctcact taaatcagca cagtaactgc agcacagcac    900
cacaatattg ttcaaaatcc cacagtgcaa ggcgctgtat ccaaagctca tggcggggac    960
cacagaaccc acgtggccat cataccacaa gcgcaggtag attaagtggc gacccctcat   1020
aaacacgctg gacataaaca ttacctcttt tggcatgttg taattcacca cctcccggta   1080
ccatataaac ctctgattaa acatggcgcc atccaccacc atcctaaacc agctggccaa   1140
aacctgcccg ccggctatac actgcaggga accgggactg gaacaatgac agtggagagc   1200
ccaggactcg taaccatgga tcatcatgct cgtcatgata tcaatgttgg cacaacacag   1260
gcacacgtgc atacacttcc tcaggattac aagctcctcc cgcgttagaa ccatatccca   1320
gggaacaacc cattcctgaa tcagcgtaaa tcccacactg cagggaagac ctcgcacgta   1380
actcacgttg tgcattgtca aagtgttaca ttcgggcagc agcggatgat cctccagtat   1440
ggtagcgcgg gtttctgtct caaaaggagg tagacgatcc ctactgtacg gagtgcgccg   1500
agacaaccga gatcgtgttg gtcgtagtgt catgccaaat ggaacgccgg acgtagtcat   1560
atttcctgaa gtcttagatc tctcaacgca gcaccagcac caacacttcg cagtgtaaaa   1620
ggccaagtgc cgagagagta tatataggaa taaaaagtga cgtaaacggg caaagtccaa   1680
aaaacgccca gaaaaccgcc acgcgaacct acgccccgaa acgaaagcca aaaaacacta   1740
gacactccct tccggcgtca acttccgctt tcccacgcta cgtcacttgc cccagtcaaa   1800
caaactacat atcccgaact tccaagtcgc cacgcccaaa acaccgccta cacctccccg   1860
cccgccggcc cgccccccaaa cccgcctccc gccccgcgcc ccgccccgcg ccgcccatct   1920
cattatcata ttggcttcaa tccaaaataa ggtatattat tgatgatggt ttaaacggat   1980
ccaattcttg aagacgaaag ggcctcgtga tacgcctatt tttataggtt aatgtcatga   2040
taataatggt ttcttagacg tcaggtggca cttttcgggg aaatgtgcgc ggaacccta   2100
tttgtttatt tttctaaata cattcaaata tgtatccgct catgagacaa taaccctgat   2160
aaatgcttca ataatattga aaaggaagag tatgagtatt caacatttc cgtgtcgccc   2220
ttattccctt ttttgcggca ttttgccttc ctgttttgc tcacccagaa acgctggtga   2280
aagtaaaaga tgctgaagat cagttgggtg cacgagtggg ttacatcgaa ctggatctca   2340
acagcggtaa gatccttgag agttttcgcc ccgaagaacg ttttccaatg atgagcactt   2400
ttaaagttct gctatgtggc gcggtattat cccgtgttga cgccgggcaa gagcaactcg   2460
gtcgccgcat acactattct cagaatgact tggttgagta ctcaccagtc acagaaaagc   2520
atcttacgga tggcatgaca gtaagagaat tatgcagtgc tgccataacc atgagtgata   2580
acactgcggc caacttactt ctgacaacga tcggaggacc gaaggagcta accgcttttt   2640
tgcacaacat gggggatcat gtaactcgcc ttgatcgttg ggaaccggag ctgaatgaag   2700
ccataccaaa cgacgagcgt gacaccacga tgcctgtagc aatggcaaca acgttgcgca   2760
aactattaac tggcgaacta cttactctag cttcccggca acaattaata gactggatgg   2820
aggcggataa agttgcagga ccacttctgc gctcggccct tccggctggc tggtttattg   2880
ctgataaatc tggagccggt gagcgtgggt ctcgcggtat cattgcagca ctggggccag   2940
atggtaagcc ctcccgtatc gtagttatct acacgacggg gagtcaggca actatggatg   3000
aacgaaatag acagatcgct gagataggtg cctcactgat taagcattgg taactgtcag   3060
accaagttta ctcatatata ctttagattg atttaaaagg atctaggtga agatccttt    3120
tgataatctc atgaccaaaa tcccttaacg tgagttttcg ttccactgag cgtcagaccc   3180
cgtagaaaag atcaaaggat cttcttgaga tcctttttt ctgcgcgtaa tctgctgctt   3240
```

```
gcaaacaaaa aaaccaccgc taccagcggt ggtttgtttg ccggatcaag agctaccaac    3300 tcttttccg aaggtaactg gcttcagcag agcgcagata ccaaatactg tccttctagt    3360
gtagccgtag ttaggccacc acttcaagaa ctctgtagca ccgcctacat acctcgctct    3420
gctaatcctg ttaccagtgg ctgctgccag tggcgataag tcgtgtctta ccgggttgga    3480
ctcaagacga tagttaccgg ataaggcgca gcggtcgggc tgaacggggg gttcgtgcac    3540
acagcccagc ttggagcgaa cgacctacac cgaactgaga tacctacagc gtgagctatg    3600
agaaagcgcc acgcttcccg aagggagaaa ggcggacagg tatccggtaa gcggcagggt    3660
cggaacagga gagcgcacga gggagcttcc agggggaaac gcctggtatc tttatagtcc    3720
tgtcgggttt cgccacctct gacttgagcg tcgattttg tgatgctcgt caggggggcg    3780
gagcctatgg aaaaacgcca gcaacgcggc ctttttacgg ttcctggcct tttgctggcc    3840
ttgaagctgt ccctgatggt cgtcatctac ctgcctggac agcatggcct gcaacgcggg    3900
catcccgatg ccgccggaag cgagaagaat cataatgggg aaggccatcc agcctcgcgt    3960
cgcagatccg aattcgttta aac                                           3983

<210> SEQ ID NO 41
<211> LENGTH: 25
<212> TYPE: DNA
<213> ORGANISM: Human cytomegalovirus

<400> SEQUENCE: 41
acatcaatgg gcgtggatag cggtt                                           25

<210> SEQ ID NO 42
<211> LENGTH: 1187
<212> TYPE: DNA
<213> ORGANISM: Human cytomegalovirus

<400> SEQUENCE: 42
ccattgcata cgttgtatcc atatcataat atgtacattt atattggctc atgtccaaca      60
ttaccgccat gttgacattg attattgact agttattaat agtaatcaat tacgggggtca    120 ttagttcata gcccatatat ggagttccgc gttacataac ttacggtaaa tggcccgcct    180
ggctgaccgc ccaacgaccc ccgcccattg acgtcaataa tgacgtatgt tcccatagta    240
acgccaatag ggactttcca ttgacgtcaa tgggtggagt atttacggta aactgcccac    300
ttggcagtac atcaagtgta tcatatgcca agtacgcccc ctattgacgt caatgacggt    360
aaatggcccg cctggcatta tgcccagtac atgaccttat gggactttcc tacttggcag    420
tacatctacg tattagtcat cgctattacc atggtgatgc ggttttggca gtacatcaat    480
gggcgtggat agcggtttga ctcacgggga tttccaagtc tccacccccat tgacgtcaat    540 gggagtttgt tttggcacca aaatcaacgg gactttccaa aatgtcgtaa caactccgcc    600
ccattgacgc aaatgggcgg taggcgtgta cggtgggagg tctatataag gcgaagcgct    660
ccctatcagt gatagagatc tccctatcag tgatagagat cgtcgacgag ctcgcggcgg    720
gcgggagtcg ctgcgcgctg ccttcgcccc gtgccccgct ccgccgccgc ctcgcgccgc    780
ccgccccggc tctgactgac cgcgttacta aaacaggtaa gtccggcctc cgcgccgggt    840
tttggcgcct cccgcgggcg ccccccctcct cacggcgagc gctgccacgt cagacgaagg    900
gcgcagcgag cgtcctgatc cttccgcccg gacgctcagg acagcggccc gctgctcata    960
agactcggcc ttagaacccc agtatcagca gaaggacatt ttaggacggg acttgggtga   1020
```

```
ctctagggca ctggttttct ttccagagag cggaacaggc gaggaaaagt agtcccttct    1080
cggcgattct gcggagggat ctccgtgggg cggtgaacgc cgatgatgcc tctactaacc    1140
atgttcatgt tttctttttt tttctacagg tcctgggtga cgaacag                  1187
```

SIMIAN ADENOVIRUS VECTORS COMPRISING THE CHAD-157 FIBER PROTEIN

FIELD OF THE INVENTION

The present invention relates to isolated polynucleotide and polypeptide sequences derived from novel chimpanzee adenovirus ChAd157, as well as to recombinant polynucleotides, vectors, adenoviruses, cells and compositions comprising said polynucleotide and polypeptide sequences.

BACKGROUND OF THE INVENTION

Adenovirus has been widely used for gene transfer applications due to its ability to achieve highly efficient gene transfer in a variety of target tissues and large transgene capacity. Conventionally, E1 genes of adenovirus are deleted and replaced with a transgene cassette consisting of the promoter of choice, cDNA sequence of the gene of interest and a poly A signal, resulting in a replication defective recombinant virus.

Recombinant adenoviruses are useful in gene therapy and as vaccines. Viral vectors based on chimpanzee adenovirus represent an alternative to the use of human derived adenovirus vectors for the development of genetic vaccines. Adenoviruses isolated from chimpanzees are closely related to adenoviruses isolated from humans as demonstrated by their efficient propagation in cells of human origin. However, since human and chimpanzee adenoviruses are close relatives, serologic cross reactivity between the two virus species is possible.

There is a demand for vectors which effectively deliver molecules to a target and minimize the effect of pre-existing immunity to selected adenovirus serotypes in the population. One aspect of pre-existing immunity that is observed in humans is humoral immunity, which can result in the production and persistence of antibodies that are specific for adenoviral proteins. The humoral response elicited by adenovirus is mainly directed against the three major structural capsid proteins: fiber, penton and hexon.

SUMMARY OF THE INVENTION

There is provided an isolated polynucleotide, wherein the polynucleotide encodes a polypeptide selected from the group consisting of:
(a) a polypeptide having the amino acid sequence according to SEQ ID NO: 1; and
(b) a functional derivative of a polypeptide having the amino acid sequence according to SEQ ID NO: 1, wherein the functional derivative has an amino acid sequence which is at least 99.8% identical over its entire length to the amino acid sequence of SEQ ID NO: 1.

Also provided is a recombinant polynucleotide comprising a polynucleotide selected from the group consisting of:
(a) a polynucleotide which encodes a polypeptide having the amino acid sequence according to SEQ ID NO: 1; and
(b) a polynucleotide which encodes a functional derivative of a polypeptide having the amino acid sequence according to SEQ ID NO: 1, wherein the functional derivative has an amino acid sequence which is at least 99.8% identical over its entire length to the amino acid sequence of SEQ ID NO: 1.

Also provided is a recombinant vector comprising a polynucleotide selected from the group consisting of:
(a) a polynucleotide which encodes a polypeptide having the amino acid sequence according to SEQ ID NO: 1; and
(b) a polynucleotide which encodes a functional derivative of a polypeptide having the amino acid sequence according to SEQ ID NO: 1, wherein the functional derivative has an amino acid sequence which is at least 99.8% identical over its entire length to the amino acid sequence of SEQ ID NO: 1.

Also provided is a recombinant adenovirus comprising at least one polynucleotide or polypeptide selected from the group consisting of:
(a) a polynucleotide which encodes a polypeptide having the amino acid sequence according to SEQ ID NO: 1;
(b) a polynucleotide which encodes a functional derivative of a polypeptide having the amino acid sequence according to SEQ ID NO: 1, wherein the functional derivative has an amino acid sequence which is at least 99.8% identical over its entire length to the amino acid sequence of SEQ ID NO: 1;
(c) a polypeptide having the amino acid sequence according to SEQ ID NO: 1; and
(d) a functional derivative of a polypeptide having the amino acid sequence according to SEQ ID NO: 1, wherein the functional derivative has an amino acid sequence which is at least 99.8% identical over its entire length to the amino acid sequence of SEQ ID NO: 1.

Also provided is a composition comprising at least one of the following:
(a) an isolated polynucleotide which encodes a polypeptide having the amino acid sequence according to SEQ ID NO: 1;
(b) an isolated polynucleotide which encodes a functional derivative of a polypeptide having the amino acid sequence according to SEQ ID NO: 1, wherein the functional derivative has an amino acid sequence which is at least 99.8% identical over its entire length to the amino acid sequence of SEQ ID NO: 1;
(c) an isolated polypeptide having the amino acid sequence according to SEQ ID NO: 1;
(d) an isolated functional derivative of a polypeptide having the amino acid sequence according to SEQ ID NO: 1, wherein the functional derivative has an amino acid sequence which is at least 99.8% identical over its entire length to the amino acid sequence of SEQ ID NO: 1;
(e) a vector comprising a polynucleotide as described in (a) or (b) above; and
(f) a recombinant adenovirus comprising a polynucleotide as described in (a) or (b) above, and a pharmaceutically acceptable excipient.

Also provided is a cell comprising at least one of the following:
(a) an isolated polynucleotide which encodes a polypeptide having the amino acid sequence according to SEQ ID NO: 1,
(b) an isolated polynucleotide which encodes a functional derivative of a polypeptide having the amino acid sequence according to SEQ ID NO: 1, wherein the functional derivative has an amino acid sequence which is at least 99.8% identical over its entire length to the amino acid sequence of SEQ ID NO: 1;
(c) a vector comprising a polynucleotide as described in (a) or (b) above, and (d) a recombinant adenovirus comprising a polynucleotide as described in (a) or (b) above.

Also provided is an isolated adenoviral polypeptide selected from the group consisting of:
(a) a polypeptide having the amino acid sequence according to SEQ ID NO: 1; and
(b) a functional derivative of a polypeptide having the amino acid sequence according to SEQ ID NO: 1, wherein the functional derivative has an amino acid sequence which is at least 99.8% identical over its entire length to the amino acid sequence of SEQ ID NO: 1.

DESCRIPTION OF THE SEQUENCES

Figure 1A:
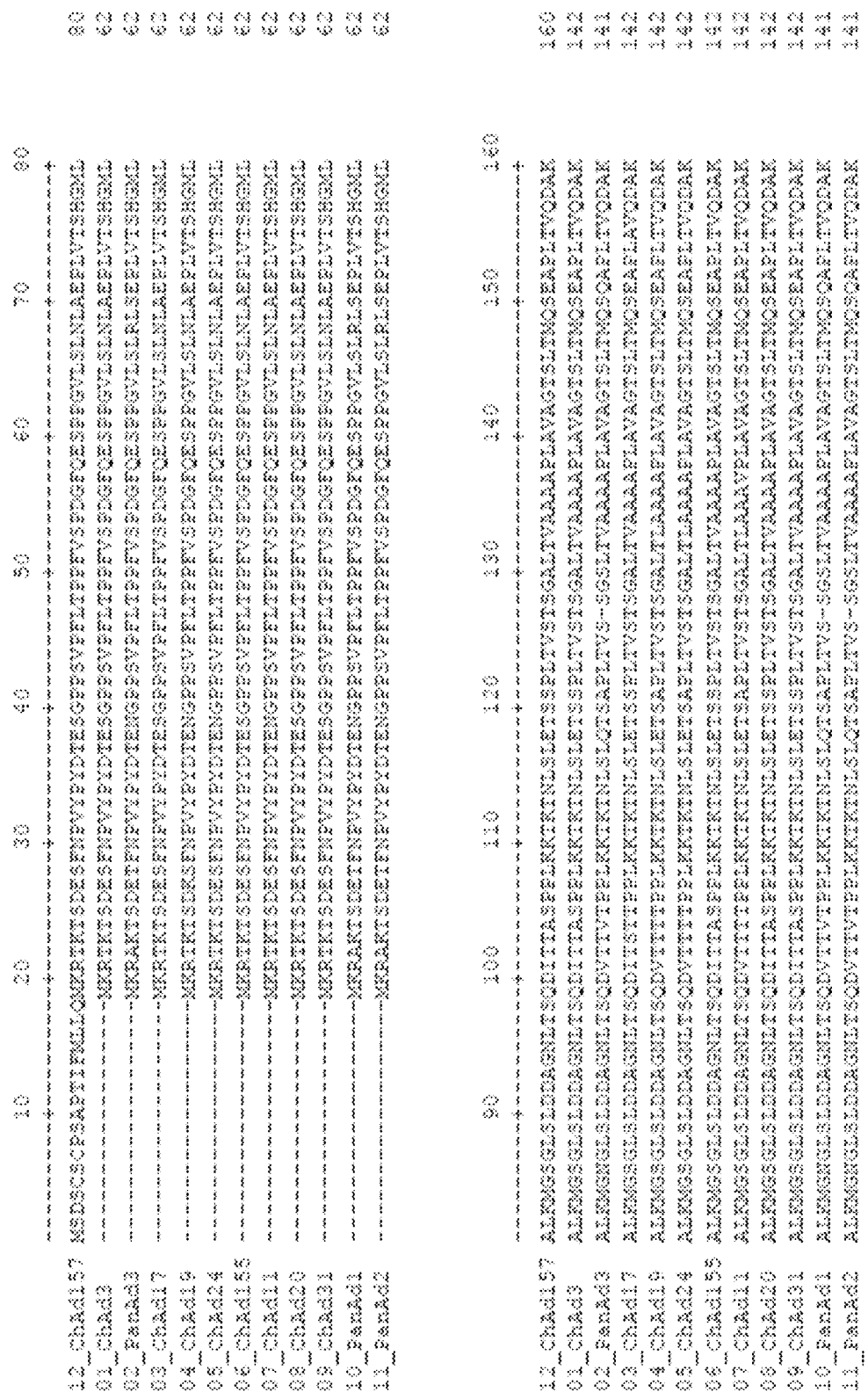
FIG. 1A-1D—Alignment of fiber protein sequences from the indicated simian adenoviruses.
ChAd157 (SEQ ID NO:1)
ChAd3 (SEQ ID NO:27)
PanAd3 (SEQ ID NO:28)
ChAd17 (SEQ ID NO:29)
ChAd19 (SEQ ID NO:30)
ChAd24 (SEQ ID NO:31)
ChAd155 (SEQ ID NO:7)
ChAd11 (SEQ ID NO:32)
ChAd20 (SEQ ID NO:33)
ChAd31 (SEQ ID NO:34)
PanAd1 (SEQ ID NO:35)
PanAd2 (SEQ ID NO:36)
FIG. 2—Subgroup C BAC Shuttle schematic representation
FIG. 3—Subgroup C Plasmid Shuttle schematic representation
FIG. 4—pChAd157 ΔE1/TetP hCMV GAG vector schematic representation
FIG. 5—pARS SpeciesC Ad5orf6-2 shuttle schematic representation
FIG. 6—plasmid carrying the ChAd157 RG schematic representation
FIG. 7—Transgene Expression by ChAd157/GAG, ChAd19/GAG and ChAd155/GAG
FIG. 8—Western Blot analysis of lysates of Hela cells infected with ChAd155/RG and ChAd157/RG
FIG. 9—Immunological potency of ChAd157/GAG, ChAd155/GAG and ChAd19 GAG in BALB/c mice
FIG. 10—Immunological potency of ChAd157/RG and ChAd155/RG in BALB/c mice
FIG. 11—Neutralization titers following preimmunization of mice with different ChAd vectors
FIG. 12—IFN-γ ELISpot following vaccination of mice with ChAd157/GAG after various preimmunization regimes
Figure 1B:
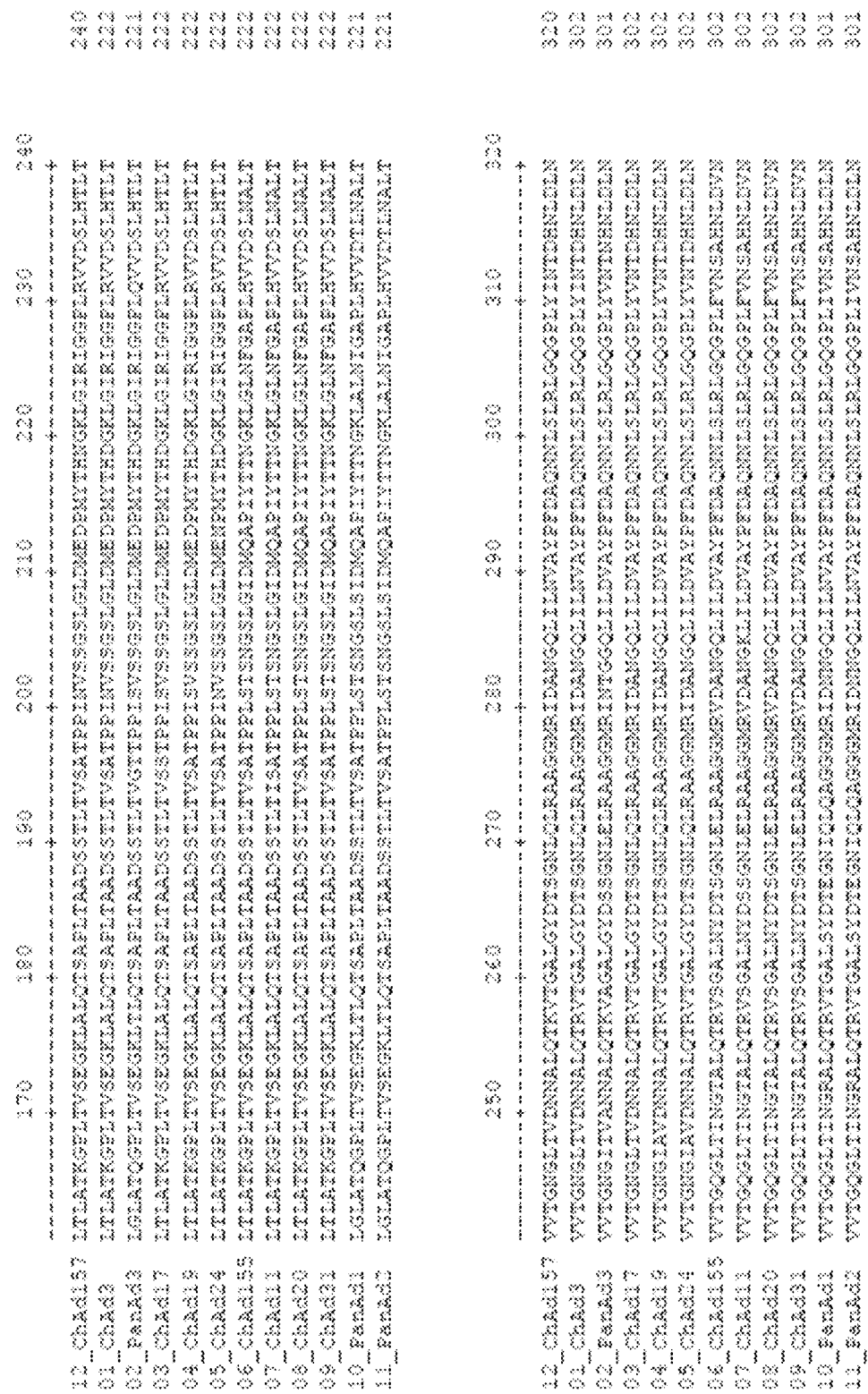
Figure 1C:
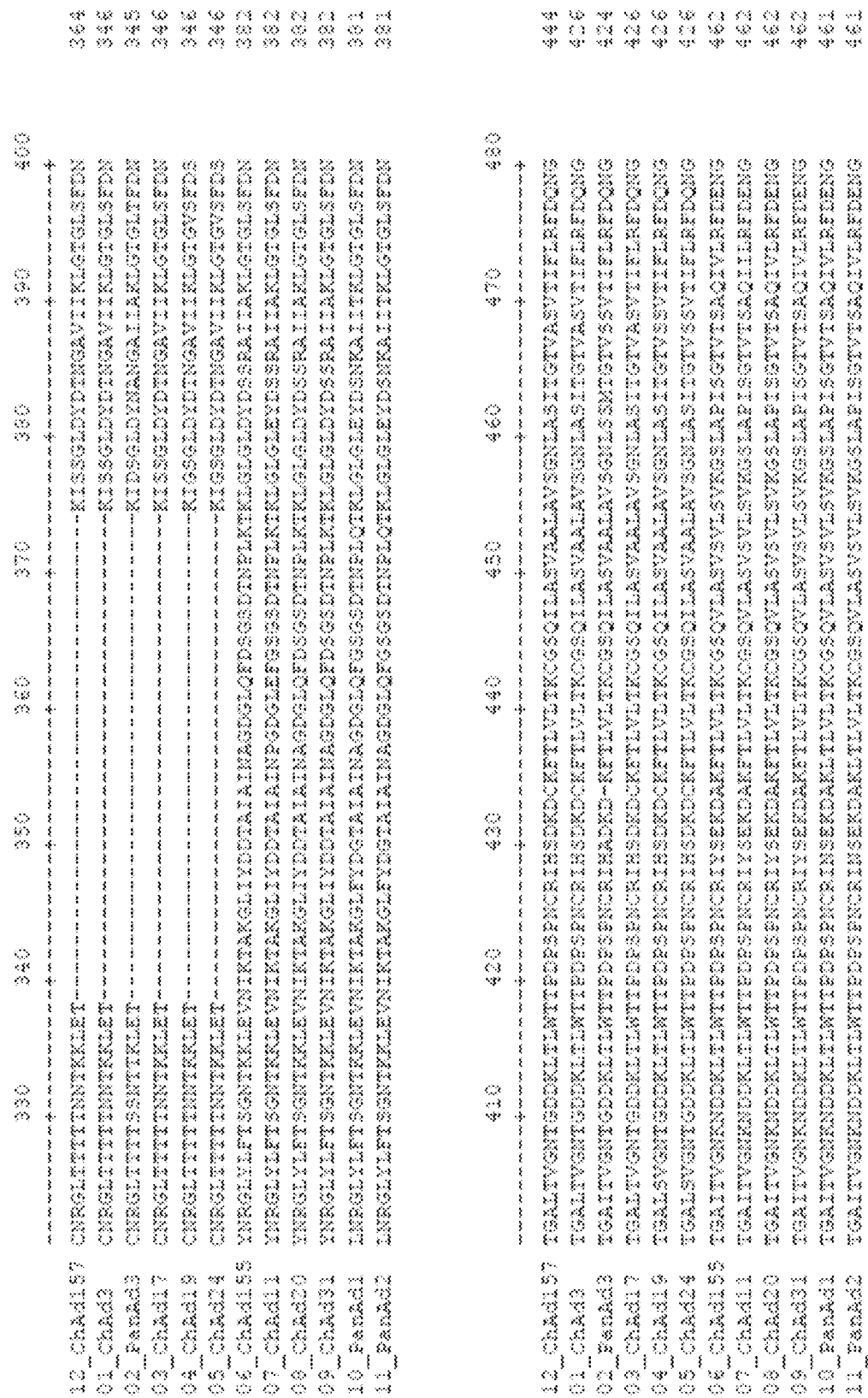
Figure 1D:
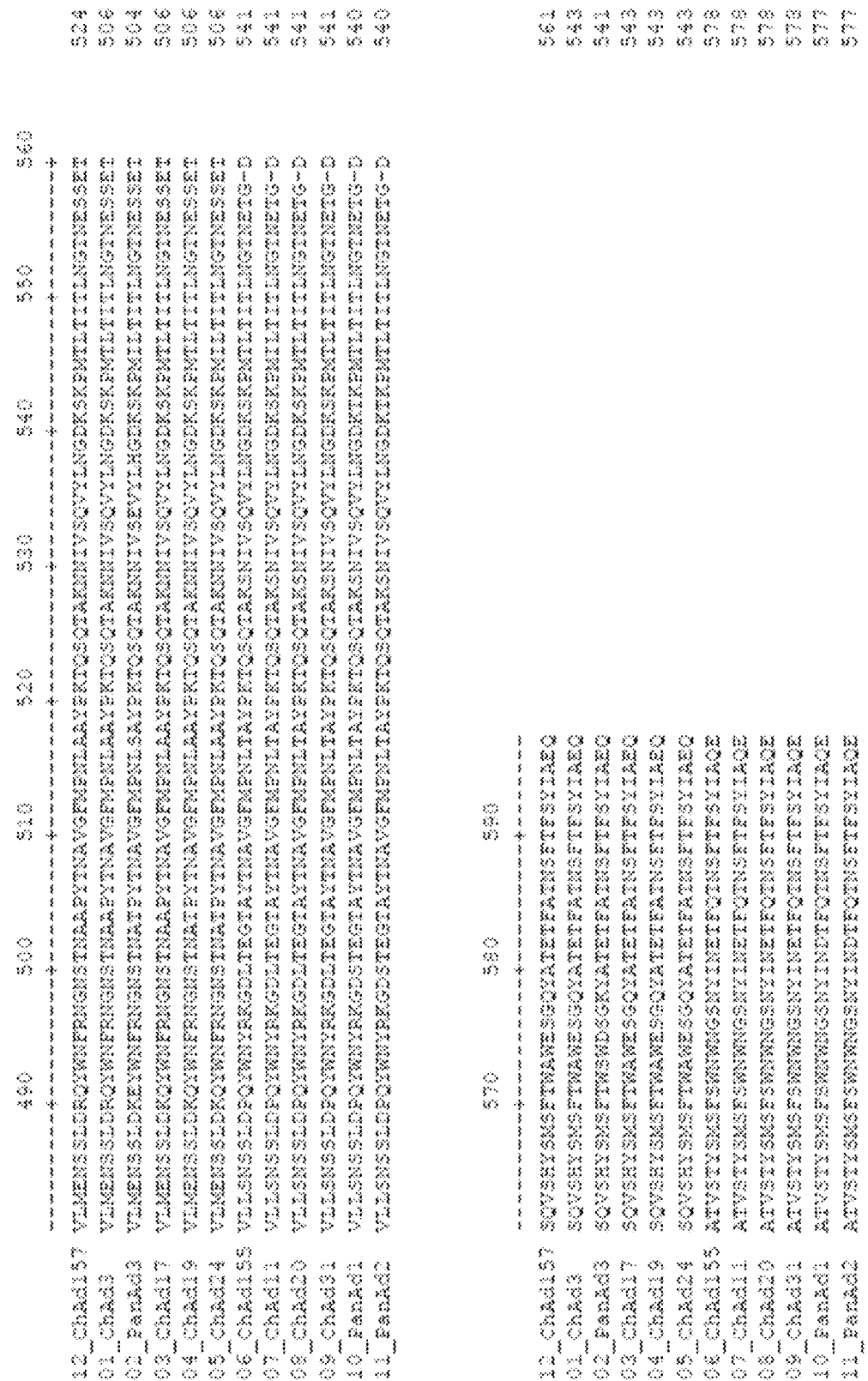

SEQ ID NO: 1—Polypeptide sequence of ChAd157 fiber
SEQ ID NO: 2—Polynucleotide sequence encoding ChAd157 fiber
SEQ ID NO: 3—Polypeptide sequence of ChAd157 penton
SEQ ID NO: 4—Polynucleotide sequence encoding ChAd157 penton
SEQ ID NO: 5—Polypeptide sequence of ChAd157 hexon
SEQ ID NO: 6—Polynucleotide sequence encoding ChAd157 hexon
SEQ ID NO: 7—Polypeptide sequence of ChAd155 fiber
SEQ ID NO: 8—Polynucleotide sequence encoding ChAd155 fiber
SEQ ID NO: 9—Polypeptide sequence of ChAd155 penton
SEQ ID NO: 10—Polynucleotide sequence encoding ChAd155 penton
SEQ ID NO: 11—Polypeptide sequence of ChAd155 hexon
SEQ ID NO: 12—Polynucleotide sequence encoding ChAd155 hexon
SEQ ID NO: 13—Polynucleotide sequence encoding wide type ChAd155
SEQ ID NO: 14—Polynucleotide sequence of Subgroup C BAC Shuttle (#1365)
SEQ ID NO: 15—Polynucleotide sequence of pChAd157ΔE1 TetO hCMV RpsL-Kana #1551
SEQ ID NO: 16—HIV Gag polynucleotide sequence
SEQ ID NO: 17—Polynucleotide sequence of pChAd157 ΔE1/TetO hCMV GAG #1557
SEQ ID NO: 18—Ad5orf6 primer 1 polynucleotide sequence
SEQ ID NO: 19—Ad5orf6 primer 2 polynucleotide sequence
SEQ ID NO: 20—Fiber-E4 polyA primer 1 polynucleotide sequence
SEQ ID NO: 21—Fiber-E4 polyA primer 2 polynucleotide sequence
SEQ ID NO: 22—Polynucleotide sequence of ChAd157 ΔE1E4_Ad5E4orf6/TetO hCMV RpsL-Kana #1594
SEQ ID NO: 23—Rabies Glycoprotein polynucleotide sequence
SEQ ID NO: 24—Polynucleotide sequence of pChAd157 ΔE1E4_Ad5E4orf6/TetO hCMV RG #1559
SEQ ID NO: 25—CMVfor primer polynucleotide sequence
SEQ ID NO: 26—CMVrev primer polynucleotide sequence
SEQ ID NO: 27—Amino acid sequence for the fiber protein of ChAd3
SEQ ID NO: 28—Amino acid sequence for the fiber protein of PanAd3
SEQ ID NO: 29—Amino acid sequence for the fiber protein of ChAd17
SEQ ID NO: 30—Amino acid sequence for the fiber protein of ChAd19
SEQ ID NO: 31—Amino acid sequence for the fiber protein of ChAd24
SEQ ID NO: 32—Amino acid sequence for the fiber protein of ChAd11
SEQ ID NO: 33—Amino acid sequence for the fiber protein of ChAd20
SEQ ID NO: 34—Amino acid sequence for the fiber protein of ChAd31
SEQ ID NO: 35—Amino acid sequence for the fiber protein of PanAd1
SEQ ID NO: 36—Amino acid sequence for the fiber protein of PanAd2
SEQ ID NO: 37—Polynucleotide sequence of hCMV (tetO)
SEQ ID NO: 38—Polynucleotide sequence of Subgroup C Plasmid Shuttle #1376
SEQ ID NO: 39—Polynucleotide sequence of BGH polyA
SEQ ID NO: 40—Polynucleotide sequence of pARS SpeciesC Ad5orf6-2
SEQ ID NO: 41—Polynucleotide sequence of CMVFAM-TAMRA probe SEQ ID NO: 42—Polynucleotide sequence encoding the enhanced hCMV promoter

DETAILED DESCRIPTION OF THE INVENTION

Vectors, compositions and methods of the present invention may have one or more following improved characteristics over the prior art, including but not limited to higher productivity, improved immunogenicity, increased transgene expression or a distinct serologic cross reactivity profile.

Vectors, compositions and methods of the present invention may demonstrate a combination of properties, such as productivity, immunogenicity, transgene expression and/or serologic cross reactivity which mean they provide are a valuable alternative to known approaches.

Adenovirus

Adenoviruses have a characteristic morphology with an icosahedral capsid comprising three major proteins, hexon (II), penton base (III) and a knobbed fiber (IV), along with a number of other minor proteins, VI, VIII, IX, IIIa and IVa2. The virus genome is a linear, double-stranded DNA. The virus DNA is intimately associated with the highly basic protein VII and a small peptide pX (formerly termed mu). Another protein, V, is packaged with this DNA-protein complex and provides a structural link to the capsid via protein VI. The virus also contains a virus-encoded protease, which is necessary for processing of some of the structural proteins to produce mature infectious virus.

The adenoviral genome is well characterized. There is general conservation in the overall organization of the adenoviral genome with respect to specific open reading frames being similarly positioned, e.g. the location of the E1A, E1B, E2A, E2B, E3, E4, L1, L2, L3, L4 and L5 genes of each virus. Each extremity of the adenoviral genome comprises a sequence known as an inverted terminal repeat (ITR), which is necessary for viral replication. The virus also comprises a virus-encoded protease, which is necessary for processing some of the structural proteins required to produce infectious virions. The structure of the adenoviral genome is described on the basis of the order in which the viral genes are expressed following host cell transduction. More specifically, the viral genes are referred to as early (E) or late (L) genes according to whether transcription occurs prior to or after onset of DNA replication. In the early phase of transduction, the E1A, E1B, E2A, E2B, E3 and E4 genes of adenovirus are expressed to prepare the host cell for viral replication. During the late phase of infection, expression of the late genes L1-L5, which encode the structural components of the virus particles, is activated.

Adenoviruses are species-specific and different serotypes, i.e., types of viruses that are not cross-neutralized by antibodies, have been isolated from a variety of mammalian species. For example, more than 50 serotypes have been isolated from humans which are divided into six subgroups (A-F; B is subdivided into B1 and B2) based on sequence homology and on their ability to agglutinate red blood cells (Tatsis and Ertl *Molecular Therapy* (2004) 10:616-629). Numerous adenoviruses have been isolated from nonhuman simians such as chimpanzees, bonobos, rhesus macaques and gorillas, and they are classified into the same human groups based on phylogenetic relationships based on hexon or fiber sequences (Colloca et al. (2012) *Science Translational Medicine* 4:1-9; Roy et al. (2004) *Virology* 324: 361-372; Roy et al. (2010) *Journal of Gene Medicine* 13:17-25).

WO2005071093 discloses chimpanzee adenoviruses including ChAd19. WO2016198621 (PCT/EP2016/063329) discloses the chimpanzee adenoviruses ChAd155, which is incorporated herein by reference for the purpose of defining ChAd155 derived vectors.

Adenovirus Capsid Proteins Including the Fiber Protein and Polynucleotides Encoding These Proteins As outlined above, the adenoviral capsid comprises three major proteins, hexon, penton and fiber. The hexon accounts for the majority of the structural components of the capsid, which consists of 240 trimeric hexon capsomeres and 12 penton bases. The hexon has three conserved double barrels, while the top has three towers, each tower containing a loop from each subunit that forms most of the capsid. The base of hexon is highly conserved between adenoviral serotypes, while the surface loops are variable (Tatsis and Ertl *Molecular Therapy* (2004) 10:616-629).

Penton is another adenoviral capsid protein that forms a pentameric base to which fiber attaches. The trimeric fiber protein protrudes from the penton base at each of the 12 vertices of the capsid and is a knobbed rod-like structure. A remarkable difference in the surface of adenovirus capsids compared to that of most other icosahedral viruses is the presence of the long, thin fiber protein. The primary role of the fiber protein is the tethering of the viral capsid to the cell surface via its interaction with a cellular receptor.

The fiber proteins of many adenovirus serotypes share a common architecture: an N-terminal tail, a central shaft made of repeating sequences, and a C-terminal globular knob domain (or "head"). The central shaft domain consists of a variable number of beta-repeats. The beta-repeats connect to form an elongated structure of three intertwined spiralling strands that is highly rigid and stable. The shaft connects the N-terminal tail with the globular knob structure, which is responsible for interaction with the target cellular receptor. The globular nature of the adenovirus knob domain presents large surfaces for binding the receptor laterally and apically. The effect of this architecture is to project the receptor-binding site far from the virus capsid, thus freeing the virus from steric constraints presented by the relatively flat capsid surface.

Although fibers of many adenovirus serotypes have the same overall architecture, they have variable amino acid sequences that influence their function as well as structure. For example, a number of exposed regions on the surface of the fiber knob present an easily adaptable receptor binding site. The globular shape of the fiber knob allows receptors to bind at the sides of the knob or on top of the fiber knob. These binding sites typically lie on surface-exposed loops connecting beta-strands that are poorly conserved among human adenoviruses. The exposed side chains on these loops give the knob a variety of surface features while preserving the tertiary and quaternary structure. For example, the electrostatic potential and charge distributions at the knob surfaces can vary due to the wide range of isoelectric points in the fiber knob sequences, from pI approximately 9 for Ad 8, Ad 19, and Ad 37 to approximately 5 for subgroup B adenoviruses. As a structurally complex virus ligand, the fiber protein allows the presentation of a variety of binding surfaces (knob) in a number of orientations and distances (shaft) from the viral capsid.

One of the most obvious variations between some serotypes is fiber length. Studies have shown that the length of the fiber shaft strongly influences the interaction of the knob and the virus with its target receptors. Further, fiber proteins between serotypes can also vary in their ability to bend. Although beta-repeats in the shaft form a highly stable and regular structure, electron microscopy (EM) studies have shown distinct hinges in the fiber. Analysis of the protein sequence from several adenovirus serotype fibers pinpoints a disruption in the repeating sequences of the shaft at the third beta-repeat from the N-terminal tail, which correlates strongly with one of the hinges in the shaft, as seen by EM. The hinges in the fiber allow the knob to adopt a variety of orientations relative to the virus capsid, which may circumvent steric hindrances to receptor engagement requiring the correct presentation of the receptor binding site on the knob. For example, the rigid fibers of subgroup D Ads thus require a flexible receptor or one prepositioned for virus attachment, as they are unable to bend themselves. (Nicklin et al *Molecular Therapy* 2005 12:384-393)

The identification of specific cell receptors for different Ad serotypes and the knowledge of how they contribute to tissue tropism have been achieved through the use of fiber pseudotyping technology. Although Ads of some subgroups use CAR as a primary receptor, it is becoming clear that many Ads use alternate primary receptors, leading to vastly different tropism in vitro and in vivo. The fibers of these serotypes show clear differences in their primary and tertiary structures, such as fiber shaft rigidity, the length of the fiber shaft, and the lack of a CAR binding site and/or the putative HSPG binding motif, together with the differences in net charge within the fiber knob. Pseudotyping Ad 5 particles with an alternate fiber shaft and knob therefore provides an opportunity to remove important cell binding domains and, in addition, may allow more efficient (and potentially more cell-selective) transgene delivery to defined cell types compared to that achieved with Ad 5. Neutralization of fiber-pseudotyped Ad particles may also be reduced if the fibers used are from Ads with lower seroprevalence in humans or experimental models, a situation that favours successful administration of the vector (Nicklin et al *Molecular Therapy* (2005) 12:384-393). Furthermore, full length fiber as well as isolated fiber knob regions, but not hexon or penton alone, are capable of inducing dendritic cell maturation and are associated with induction of a potent CD8+ T cell response (Molinier-Frenkel et al. *J. Biol. Chem.* (2003) 278:37175-37182). Taken together, adenoviral fiber plays an important role in at least receptor-binding and immunogenicity of adenoviral vectors.

Illustrating the differences between the fiber proteins of Group C simian adenoviruses is the alignment provided in FIG. 1. A striking feature is that the fiber sequences of these adenoviruses can be broadly grouped into having a short fiber, such as ChAd157, or long fiber, such as ChAd155. This length differential is due to a 36 amino acid deletion at approximately position 321 in the short fiber relative to the long fiber. In addition, there are a number of amino acid substitutions that differ between the short versus long fiber subgroup yet are consistent within each subgroup. While the exact function of these differences have not yet been elucidated, given the function and immunogenicity of fiber, they are likely to be significant. It has been shown that one of the determinants of viral tropism is the length of the fiber shaft. It has been demonstrated that an Ad5 vector with a shorter shaft has a lower efficiency of binding to CAR receptor and a lower infectivity (Ambriović-Ristov A. et al.: Virology. (2003) 312(2):425-33): It has been speculated that this impairment is the result of an increased rigidity of the shorter fiber leading to a less efficient attachment to the cell receptor (Wu, E et al.: J Virol. (2003) 77(13): 7225-7235).

In one aspect of the invention there is provided an isolated fiber polypeptide of chimpanzee adenovirus ChAd157 and isolated polynucleotides encoding the fiber polypeptide of chimpanzee adenovirus ChAd157.

The fiber protein is expected to contribute to low seroprevalence and can, thus, be used independently from the hexon and penton polypeptides from ChAd157 or in combination (with one or both of the hexon and penton) to suppress the affinity of an adenovirus to preexisting neutralizing antibodies, e.g. to manufacture a recombinant adenovirus with a reduced seroprevalence. Such a recombinant adenovirus may be a chimeric adenovirus with capsid proteins from different serotypes with at least a fiber protein from ChAd157.

The ChAd157 fiber polypeptide sequence is provided in SEQ ID NO: 1.

The ChAd157 penton polypeptide sequence is provided in SEQ ID NO: 3.

The ChAd157 hexon polypeptide sequence is provided in SEQ ID NO: 5.

Polypeptides, Recombinant Adenoviruses, Compositions or Cells Comprising Polypeptide Sequences of ChAd157 Fiber or a Functional Derivative Thereof Suitably the isolated polypeptide, recombinant adenovirus, composition or cell of the invention comprises a polypeptide having the amino acid sequence according to SEQ ID NO: 1.

The polypeptide, recombinant adenovirus, composition or cell of the invention may comprise a polypeptide which is a functional derivative of a polypeptide having the amino acid sequence according to SEQ ID NO: 1, wherein the functional derivative has an amino acid sequence which is at least 99.8% identical over its entire length to the amino acid sequence of SEQ ID NO: 1.

Alternatively, the functional derivative has no more than one addition, deletion or substitution compared to SEQ ID NO: 1, such as one substitution compared to SEQ ID NO: 1.

Suitably the polypeptide, recombinant adenovirus, composition or cell according to the invention further comprises:
  (a) a polypeptide having the amino acid sequence according to SEQ ID NO: 3; or
  (b) a functional derivative of a polypeptide having the amino acid sequence according to SEQ ID NO: 3, wherein the functional derivative has an amino acid sequence which is at least 60% identical over its entire length to the amino acid sequence of SEQ ID NO: 3, and/or
  (a) a polypeptide having the amino acid sequence according to SEQ ID NO: 5; or
  (b) a functional derivative of a polypeptide having the amino acid sequence according to SEQ ID NO: 5, wherein the functional derivative has an amino acid sequence which is at least 60% identical over its entire length to the amino acid sequence of SEQ ID NO: 5.

Suitably, the functional derivative of a polypeptide having the amino acid sequence according to SEQ ID NO: 3 has an amino acid sequence which is at least 70% identical over its entire length to the amino acid sequence of SEQ ID NO: 3, such as at least 80%, especially at least 90%, for example at least 95% or at least 98%.

Suitably, the functional derivative of a polypeptide having the amino acid sequence according to SEQ ID NO: 5 has an amino acid sequence which is at least 70% identical over its entire length to the amino acid sequence of SEQ ID NO: 5, such as at least 80%, especially at least 90%, for example at least 95% or at least 98%.

In particular, the polypeptide, recombinant adenovirus, composition or cell according to the invention further comprises:
(a) a polypeptide having the amino acid sequence according to SEQ ID NO: 3;
and/or
(b) a polypeptide having the amino acid sequence according to SEQ ID NO: 5.

Alternatively, the polypeptide, recombinant adenovirus, composition or cell of the invention may comprise a polypeptide which is a functional derivative of SEQ ID NO: 1, wherein the functional derivative consists of (i) a polypeptide having an amino acid sequence which is at least 99.8% identical over its entire length to residues 19-561 of SEQ ID NO: 1 and (ii) one or more amino acid residues directly N-terminal to the functional derivative. In one embodiment, a functional derivative consists of (i) a polypeptide having an amino acid sequence which is at least 99.8% identical over its entire length to residues 19-561 of SEQ ID NO: 1 and (ii) 1 to 18 amino acid residues directly N-terminal to the functional derivative. In one of these embodiments, a functional derivative consists of (i) a polypeptide having an amino acid sequence which is at least 99.8% identical over its entire length to residues 19-561 of SEQ ID NO: 1 and (ii) one amino acid residue directly N-terminal to the functional derivative.

Alternatively, the polypeptide, recombinant adenovirus, composition or cell of the invention may comprise a polypeptide which is a functional derivative of SEQ ID NO: 1, wherein the functional derivative consists of (i) a polypeptide having an amino acid sequence which is at least 99.8% identical over its entire length to residues 19-561 of SEQ ID NO: 1 and (ii) a sequence of eighteen amino acid residues directly N-terminal to the functional derivative, wherein the sequence of eighteen amino acid residues is at least 50%, more suitably at least 55%, more suitably at least 60%, more suitably at least 65%, more suitably at least 70%, more suitably at least 75%, more suitably at least 80%, more suitably at least 85%, more suitably at least 90% identical over its entire length to residues 1-18 of SEQ ID NO: 1.

Alternatively, the polypeptide, recombinant adenovirus, composition or cell of the invention may comprise a polypeptide which is a functional derivative of a polypeptide having the amino acid sequence according to SEQ ID NO: 1, wherein, the functional derivative has no more than 19 deletions compared to SEQ ID NO: 1. In some embodiments, the functional derivative may have no more than 18 deletions compared to SEQ ID NO: 1, for example, no more than 17, no more than 16, no more than 15, no more than 14, no more than 13, no more than 12, or no more than 11 deletions. In one embodiment, the functional derivative may have no more than 10 deletions compared to SEQ ID NO: 1, for example, no more than 9, no more than 8, no more than 7, no more than 6, no more than 5, no more than 4, no more than 3, no more than 2 or just a single deletion.

Isolated Polynucleotides, Vectors, Recombinant Adenoviruses, Compositions or Cells comprising Polynucleotides Encoding ChAd157 Fiber or a Functional Derivative Thereof Suitably the isolated polynucleotide, vector, recombinant adenovirus, composition or cell of the invention comprises a polynucleotide which encodes a polypeptide having the amino acid sequence according to SEQ ID NO: 1. Suitably the polynucleotide has a sequence according to SEQ ID NO: 2.

When the isolated polynucleotide, vector, recombinant adenovirus, composition or cell of the invention comprises a polynucleotide which encodes a functional derivative of a polypeptide having the amino acid sequence according to SEQ ID NO: 1, wherein the functional derivative has an amino acid sequence which is at least 99.8% identical over its entire length to the amino acid sequence of SEQ ID NO: 1, suitably the polynucleotide has a sequence according to SEQ ID NO: 2 wherein one codon has been added, deleted or altered to encode a different amino acid.

Suitably the polynucleotide, vector, recombinant adenovirus, composition or cell of the invention further comprises a polynucleotide encoding:
(a) a polypeptide having the amino acid sequence according to SEQ ID NO: 3; or
(b) a functional derivative of a polypeptide having the amino acid sequence according to SEQ ID NO: 3, wherein the functional derivative has an amino acid sequence which is at least 60% identical over its entire length to the amino acid sequence of SEQ ID NO: 3, and/or
(a) a polypeptide having the amino acid sequence according to SEQ ID NO: 5; or
(b) a functional derivative of a polypeptide having the amino acid sequence according to SEQ ID NO: 5, wherein the functional derivative has an amino acid sequence which is at least 60% identical over its entire length to the amino acid sequence of SEQ ID NO: 5.

Suitably, the functional derivative of a polypeptide having the amino acid sequence according to SEQ ID NO: 3 has an amino acid sequence which is at least 70% identical over its entire length to the amino acid sequence of SEQ ID NO: 3, such as at least 80%, especially at least 90%, for example at least 95% or at least 98%.

Suitably, the functional derivative of a polypeptide having the amino acid sequence according to SEQ ID NO: 5 has an amino acid sequence which is at least 70% identical over its entire length to the amino acid sequence of SEQ ID NO: 5, such as at least 80%, especially at least 90%, for example at least 95% or at least 98%.

In particular, the polynucleotide, vector, recombinant adenovirus, composition or cell of the invention further comprises a polynucleotide encoding:
(a) a polypeptide having the amino acid sequence according to SEQ ID NO: 3;
and/or
(b) a polypeptide having the amino acid sequence according to SEQ ID NO: 5.

The polynucleotide, vector, recombinant adenovirus, composition or cell of the invention may further comprise:
(a) a polynucleotide according to SEQ ID NO: 4;
and/or
(b) a polynucleotide according to SEQ ID NO: 6.

ChAd157 Backbones

The invention provides isolated polynucleotide sequences of chimpanzee adenovirus ChAd157, including that of wild type, unmodified ChAd157 and modified backbone constructs of ChAd157. These modified backbone constructs include those exemplified herein, such as pChAd157ΔE1 MUD hCMV RpsL-Kana #1551 (SEQ ID NO: 15) and ChAd157 ΔE1E4_Ad5E4orf6/TetO hCMV RpsL-Kana #1594 (SEQ ID NO: 22). ChAd157 backbones may be used in the construction of recombinant replication-competent or replication-incompetent adenoviruses for example for the delivery of transgenes.

Annotation of the pChAd157 ΔE1/TetO hCMV GAG (SEQ ID NO: 17) sequence is provided below.

| Annotations | ChAd157DE1_TetOhCMV_GAG |
|---|---|
| IX | 3187 ... 3651 |
| IVa2 | Complement (3710 ... 5045, 5325 ... 5337) |
| Pol | Complement(4816 ... 8397, 13762 ... 13770) |
| VA RNAI | 10230 ... 10391 |
| pTP | Complement(8196 ... 10199, 13762 ... 13770) |
| 48K | 10652 ... 11914 |
| pIIIa | 11938 ... 13714 |
| III | 13807 ... 15588 |
| pVII | 15603 ... 16199 |
| V | 16275 ... 17390 |
| pX | 17415 ... 17660 |
| pVI | 17750 ... 18508 |
| Hexon | 18623 ... 21499 |
| Protease | 21529 ... 22158 |
| DBP | Complement(22274 ... 23926) |
| 92K | 23976 ... 26447 |
| 22K | 26164 ... 26739 |
| 33K | Join(26164 ... 26473, 26679 ... 27061) |
| E2e promoter | Complement(27027 ... 27274) |
| pVIII | 27136 ... 27819 |
| E3 12K | 27820 ... 28137 |
| E3 CR1-alphap0 | 28635 ... 28835 |
| E3 gp18K | 28838 ... 29329 |
| E3A 11K | 30776 ... 31072 |
| E3 RID alpha | 31084 ... 31356 |
| E3 RID beta | 31359 ... 31757 |
| E3 15K | 31750 ... 32136 |
| U | exonComplement(32167 ... 32331) |
| fibre | 32288 ... 33973 |
| E4 ORF6/7 | Complement(34181 ... 34456, 35168 ... 35341) |
| E4 ORF6 | Complement(34457 ... 35341) |
| E4 ORF4 | Complement(35241 ... 35606) |
| E4 ORF3 | Complement(35622 ... 35969) |
| E4 ORF2 | Complement(35966 ... 36358) |
| E4 ORF1 | Complement(36411 ... 36797) |

In one embodiment, fragments of the sequences of SEQ ID NO: 15, 22 and their complementary strands, cDNA and RNA complementary thereto are provided. Suitably, fragments are at least 15 nucleotides in length, more suitably 30 nucleotides in length, more suitably 60 nucleotides in length, more suitably 120 nucleotides in length, more suitably 240, more suitably 480 nucleotides in length and encompass functional fragments, i.e., fragments which are of biological interest. For example, a functional fragment can express a desired adenoviral product or may be useful in production of recombinant viral vectors. Such fragments include the gene sequences listed above. In certain embodiments isolated sequences of SEQ ID NO: 15, 22 and their complementary strands, cDNA and RNA complementary thereto are provided.

Gene products of the ChAd157 adenovirus, such as proteins, enzymes, and fragments thereof, which are encoded by the adenoviral nucleic acids, and the aforementioned fragments thereof, described herein are provided. Such proteins include those encoded by the open reading frames identified above and the proteins encoded by the polynucleotides provided in the Sequence Listing.

Further ChAd157 Polynucleotides and Polypeptides

In some embodiments the polynucleotide of the invention comprises a polynucleotide encoding a fiber polypeptide; a hexon polypeptide and fiber polypeptide; penton polypeptide and fiber polypeptide; or hexon polypeptide, penton polypeptide and fiber polypeptide of the invention; and may further comprise additional adenoviral polynucleotides, suitably ChAd157 polynucleotides. Thus, suitably the polynucleotide according to the invention comprises one or more of the following:

(a) an adenoviral 5-inverted terminal repeat (ITR);
(b) an adenoviral E1A region, or a fragment thereof selected from among the E1A_280R and E1A_243R regions;
(c) an adenoviral E1B or IX region, or a fragment thereof selected from among the group consisting of the E1B_19K, E1B_55K and IX regions;
(d) an adenoviral E2B region; or a fragment thereof selected from among the group consisting of the E2B_pTP, E2B_polymerase and E2B_IVa2 regions;
(e) an adenoviral L1 region, or a fragment thereof, said fragment encoding an adenoviral protein selected from the group consisting of the L1_13.6K, L1_52K and L1_pIIIa protein;
(f) an adenoviral L2 region or a L2 region comprising a polynucleotide encoding the penton protein of the invention, or a fragment thereof, said fragment encoding an adenoviral protein selected from the group consisting of the L2_penton protein, the L2_pVII protein, the L2_V protein and the L2_pX protein;
(g) an adenoviral L3 region or a L3 region comprising a polynucleotide encoding the hexon protein of the invention, or a fragment thereof, said fragment encoding an adenoviral protein selected from the group consisting of the L3_pVI protein, the L3_hexon protein and the L3_protease protein;
(h) an adenoviral E2A region;
(i) an adenoviral L4 region, or a fragment thereof said fragment encoding an adenoviral protein selected from the group consisting of the L4_100 k protein, the L4_33K protein, the L4_22K protein and protein L4_VIII;
(j) an adenoviral E3 region, or a fragment thereof selected from the group consisting of
E3 ORF1, E3 ORF2, E3 ORF3, E3 ORF4, E3 ORF5, E3 ORF6, E3 ORF7, E3 ORF8, and E3 ORF9;
(k) an adenoviral L5 region or a L5 region comprising a polynucleotide encoding the L5_fiber fiber polypeptide of the invention
(l) an adenoviral (such as Ad5) E4 region, or a fragment thereof selected from the group consisting of E4 ORF7, E4 ORF6, E4 ORF4, E4 ORF3, E4 ORF2, and E4 ORF1; in particular ORF6 of said E4 region;
(m) an adenoviral 3'-ITR; and/or
(n) an adenoviral VAI or VAII RNA region, preferably an adenoviral VAI or VAII RNA region from an adenovirus other than ChAd157, more preferably from Ad5.

Definitions

Suitably the polynucleotides or polypeptides of the invention are isolated. An "isolated" polynucleotide is one that is removed from its original environment. For example, a naturally-occurring polynucleotide is isolated if it is separated from some or all of the coexisting materials in the natural system. A polynucleotide is considered to be isolated if, for example, it is cloned into a vector that is not a part of its natural environment or if it is comprised within cDNA.

Suitably the polynucleotides of the invention are recombinant. Recombinant means that the polynucleotide is the product of at least one of cloning, restriction or ligation steps, or other procedures that result in a polynucleotide that is distinct from a polynucleotide found in nature. A recombinant adenovirus is an adenovirus comprising a recombinant polynucleotide. A recombinant vector is a vector comprising a recombinant polynucleotide. 'A recombinant virus' includes progeny of the original recombinant virus. 'A recombinant vector' includes replicates of the original recombinant vector. 'A recombinant polynucleotide' includes replicates of the original recombinant polynucleotide.

Suitably, the polypeptide sequence of the present invention contains at least one alteration with respect to a native sequence. Suitably, the polynucleotide sequences of the present invention contain at least one alteration with respect to a native sequence. For example, a polynucleotide introduced by genetic engineering techniques into a plasmid or vector derived from a different species (and often a different genus, subfamily or family) is a heterologous polynucleotide. A promoter removed from its native coding sequence and operatively linked to a coding sequence with which it is not naturally found linked is a heterologous promoter. A specific recombination site that has been cloned into a genome of a virus or viral vector, wherein the genome of the virus does not naturally contain it, is a heterologous recombination site. A heterologous nucleic acid sequence also includes a sequence naturally found in an adenoviral genome, but located at a non-native position within the adenoviral vector.

Typically, "heterologous" means derived from a genotypically distinct entity from that of the rest of the entity to which it is being compared. A heterologous nucleic acid sequence refers to any nucleic acid sequence that is not isolated from, derived from, or based upon a naturally occurring nucleic acid sequence of the adenoviral vector. A heterologous protein sequence refers to any protein sequence that is not isolated from, derived from, or based upon a naturally occurring protein sequence of the adenoviral vector "Naturally occurring" means a sequence found in nature and not synthetically prepared or modified. A sequence is "derived" from a source when it is isolated from a source but modified (e.g., by deletion, substitution (mutation), insertion, or other modification), suitably so as not to disrupt the normal function of the source gene.

A "functional derivative" of a polypeptide suitably refers to a modified version of a polypeptide, e.g. wherein one or more amino acids of the polypeptide may be deleted, inserted, modified and/or substituted. A derivative of an unmodified adenoviral capsid protein is considered functional if, for example:

(a) an adenovirus comprising the derivative capsid protein within its capsid retains substantially the same or a lower seroprevalence compared to an adenovirus comprising the unmodified capsid protein and/or (b) an adenovirus comprising the derivative capsid protein within its capsid retains substantially the same or a higher host cell infectivity compared to an adenovirus comprising the unmodified capsid protein and/or (c) an adenovirus comprising the derivative capsid protein within its capsid retains substantially the same or a higher immunogenicity compared to an adenovirus comprising the unmodified capsid protein and/or (d) an adenovirus comprising the derivative capsid protein within its capsid retains substantially the same or a higher level of transgene productivity compared to an adenovirus comprising the unmodified capsid protein.

Properties (a)-(d) above may suitably be measured using the methods described in the Examples section below.

Suitably, the polypeptide, vector or recombinant adenovirus has a low seroprevalence in a human population. "Low seroprevalence" may mean having a reduced pre-existing neutralizing antibody level as compared to human adenovirus 5 (Ad5). Similarly or alternatively, "low seroprevalence" may mean less than about 20% seroprevalence, less than about 15% seroprevalence, less than about 10% seroprevalence, less than about 5% seroprevalence, less than about 4% seroprevalence, less than about 3% seroprevalence, less than about 2% seroprevalence, less than about 1% seroprevalence or no detectable seroprevalence. Seroprevalence can be measured as the percentage of individuals having a clinically relevant neutralizing titre (defined as a 50% neutralisation titer >200) using methods as described in Aste-Amezaga et al., Hum. Gene Ther. (2004) 15(3):293-304.

The terms polypeptide, peptide and protein are used interchangeably herein.

The term "simian" is typically meant to encompass non-human primates, for example Old World monkeys, New World monkeys, apes and gibbons. In particular, simian may refer to nonhuman apes such as chimpanzees (Pan troglodyte), bonobos (Pan paniscus) and gorillas (genus Gorilla). Non-ape simians may include rhesus macaques (*Macaca mulatta*).

Sequence Comparison

For the purposes of comparing two closely-related polynucleotide or polypeptide sequences, the "% identity" between a first sequence and a second sequence may be calculated using an alignment program, such as BLAST@ (available at blast.ncbi.nlm.nih.gov, last accessed 9 Mar. 2015) using standard settings. The % identity is the number of identical residues divided by the number of residues in the reference sequence, multiplied by 100. The % identity figures referred to above and in the claims are percentages calculated by this methodology. An alternative definition of % identity is the number of identical residues divided by the number of aligned residues, multiplied by 100. Alternative methods include using a gapped method in which gaps in the alignment, for example deletions in one sequence relative to the other sequence, are accounted for in a gap score or a gap cost in the scoring parameter. For more information, see the BLAST@ fact sheet available at ftp.ncbi.nlm.nih.govipub/factsheets/HowTo_BLASTGuide.pdf, last accessed on 9 Mar. 2015.

Sequences that preserve the functionality of the polynucleotide or a polypeptide encoded thereby are likely to be more closely identical. Polypeptide or polynucleotide sequences are said to be the same as or identical to other polypeptide or polynucleotide sequences, if they share 100% sequence identity over their entire length.

A "difference" between sequences refers to an insertion, deletion or substitution of a single amino acid residue in a position of the second sequence, compared to the first sequence. Two polypeptide sequences can contain one, two or more such amino acid differences. Insertions, deletions or substitutions in a second sequence which is otherwise identical (100% sequence identity) to a first sequence result in reduced percent sequence identity. For example, if the identical sequences are 9 amino acid residues long, one substitution in the second sequence results in a sequence identity of 88.9%. If the identical sequences are 17 amino acid residues long, two substitutions in the second sequence results in a sequence identity of 88.2%. If the identical sequences are 7 amino acid residues long, three substitutions in the second sequence results in a sequence identity of 57.1%. If first and second polypeptide sequences are 9 amino acid residues long and share 6 identical residues, the first and second polypeptide sequences share greater than 66% identity (the first and second polypeptide sequences share 66.7% identity). If first and second polypeptide sequences are 17 amino acid residues long and share 16 identical residues, the first and second polypeptide sequences share greater than 94% identity (the first and second polypeptide sequences share 94.1% identity). If first and second polypeptide sequences are 7 amino acid residues long and share 3 identical residues, the first and second polypeptide sequences share greater than 42% identity (the first and second polypeptide sequences share 42.9% identity).

Alternatively, for the purposes of comparing a first, reference polypeptide sequence to a second, comparison polypeptide sequence, the number of additions, substitutions and/or deletions made to the first sequence to produce the second sequence may be ascertained. An addition is the addition of one amino acid residue into the sequence of the first polypeptide (including addition at either terminus of the first polypeptide). A substitution is the substitution of one amino acid residue in the sequence of the first polypeptide with one different amino acid residue. A deletion is the deletion of one amino acid residue from the sequence of the first polypeptide (including deletion at either terminus of the first polypeptide).

For the purposes of comparing a first, reference polynucleotide sequence to a second, comparison polynucleotide sequence, the number of additions, substitutions and/or deletions made to the first sequence to produce the second sequence may be ascertained. An addition is the addition of one nucleotide residue into the sequence of the first polynucleotide (including addition at either terminus of the first polynucleotide). A substitution is the substitution of one nucleotide residue in the sequence of the first polynucleotide with one different nucleotide residue. A deletion is the deletion of one nucleotide residue from the sequence of the first polynucleotide (including deletion at either terminus of the first polynucleotide).

Suitably substitutions in the sequences of the present invention may be conservative substitutions. A conservative substitution comprises the substitution of an amino acid with another amino acid having a chemical property similar to the amino acid that is substituted (see, for example, Stryer et al, Biochemistry, 5th Edition 2002, pages 44-49). Preferably, the conservative substitution is a substitution selected from the group consisting of: (i) a substitution of a basic amino acid with another, different basic amino acid; (ii) a substitution of an acidic amino acid with another, different acidic amino acid; (iii) a substitution of an aromatic amino acid with another, different aromatic amino acid; (iv) a substitution of a non-polar, aliphatic amino acid with another, different non-polar, aliphatic amino acid; and (v) a substitution of a polar, uncharged amino acid with another, different polar, uncharged amino acid. A basic amino acid is preferably selected from the group consisting of arginine, histidine, and lysine. An acidic amino acid is preferably aspartate or glutamate. An aromatic amino acid is preferably selected from the group consisting of phenylalanine, tyrosine and tryptophane. A non-polar, aliphatic amino acid is preferably selected from the group consisting of glycine, alanine, valine, leucine, methionine and isoleucine. A polar, uncharged amino acid is preferably selected from the group consisting of serine, threonine, cysteine, proline, asparagine and glutamine. In contrast to a conservative amino acid substitution, a non-conservative amino acid substitution is the exchange of one amino acid with any amino acid that does not fall under the above-outlined conservative substitutions (i) through (v).

Vectors and Recombinant Adenovirus

The ChAd157 sequences of the invention are useful as therapeutic agents and in construction of a variety of vector systems, recombinant adenovirus and host cells. Suitably the term "vector" refers to a nucleic acid that has been substantially altered (e.g., a gene or functional region that has been deleted and/or inactivated) relative to a wild type sequence and/or incorporates a heterologous sequence, i.e., nucleic acid obtained from a different source (also called an "insert"), and replicating and/or expressing the inserted polynucleotide sequence, when introduced into a cell (e.g., a host cell). For example, the insert may be all or part of the ChAd157 sequences described herein. In addition or alternatively, a ChAd157 vector may be a ChAd157 adenovirus comprising one or more deletions or inactivations of viral genes, such as E1 or other viral gene or functional region described herein. Such a ChAd157, which may or may not comprise a heterologous sequence, is often called a "backbone" and may be used as is or as a starting point for additional modifications to the vector.

A vector may be any suitable nucleic acid molecule including naked DNA, a plasmid, a virus, a cosmid, phage vector such as lambda vector, an artificial chromosome such as a BAC (bacterial artificial chromosome), or an episome. Alternatively, a vector may be a transcription and/or expression unit for cell-free in vitro transcription or expression, such as a T7-compatible system. The vectors may be used alone or in combination with other adenoviral sequences or fragments, or in combination with elements from non-adenoviral sequences. The ChAd157 sequences are also useful in antisense delivery vectors, gene therapy vectors, or vaccine vectors. Thus, further provided are gene delivery vectors, and host cells which contain the ChAd157 sequences.

The term "replication-competent" adenovirus refers to an adenovirus which can replicate in a host cell in the absence of any recombinant helper proteins comprised in the cell. Suitably, a "replication-competent" adenovirus comprises the following intact or functional essential early genes: E1A, E1B, E2A, E2B, E3 and E4. Wild type adenoviruses isolated from a particular animal will be replication competent in that animal.

The term "replication-incompetent" or "replication-defective" adenovirus refers to an adenovirus which is incapable of replication because it has been engineered to comprise at least a functional deletion (or "loss-of-function" mutation), i.e. a deletion or mutation which impairs the function of a gene without removing it entirely, e.g. introduction of artificial stop codons, deletion or mutation of active sites or interaction domains, mutation or deletion of a regulatory sequence of a gene etc, or a complete removal of a gene encoding a gene product that is essential for viral replication, such as one or more of the adenoviral genes selected from E1A, E1B, E2A, E2B, E3 and E4 (such as E3 ORF1, E3 ORF2, E3 ORF3, E3 ORF4, E3 ORF5, E3 ORF6, E3 ORF7, E3 ORF8, E3 ORF9, E4 ORF7, E4 ORF6, E4 ORF4, E4 ORF3, E4 ORF2 and/or E4 ORF1). Particularly suitably E1 and optionally E3 and/or E4 are deleted. If deleted, the aforementioned deleted gene region will suitably not be considered in the alignment when determining % identity with respect to another sequence.

The present invention provides vectors such as recombinant adenovirus that deliver a protein, suitably a heterologous protein, to cells, either for therapeutic or vaccine purposes. A vector may include any genetic element including naked DNA, a phage, transposon, cosmid, episome, plasmid, or a virus. Such vectors contain DNA of ChAd157 as disclosed herein and a minigene. By "minigene" (or "expression cassette") is meant the combination of a selected heterologous gene (transgene) and the other regulatory elements necessary to drive translation, transcription and/or expression of the gene product in a host cell.

Typically, a ChAd157-derived adenoviral vector is designed such that the minigene is located in a nucleic acid molecule which contains other adenoviral sequences in the region native to a selected adenoviral gene. The minigene may be inserted into an existing gene region to disrupt the function of that region, if desired. Alternatively, the minigene may be inserted into the site of a partially or fully deleted adenoviral gene. For example, the minigene may be located in the site of a mutation, insertion or deletion which renders non-functional at least one gene of a genomic region selected from the group consisting of E1A, E1B, E2A, E2B, E3 and E4. The term "renders non-functional" means that a sufficient amount of the gene region is removed or otherwise disrupted, so that the gene region is no longer capable of producing functional products of gene expression. If desired, the entire gene region may be removed (and suitably replaced with the minigene).

For example, for a production vector useful for generation of a recombinant virus, the vector may contain the minigene and either the 5' end of the adenoviral genome or the 3' end of the adenoviral genome, or both the 5' and 3' ends of the adenoviral genome. The 5' end of the adenoviral genome contains the 5' cis-elements necessary for packaging and replication; i.e., the 5' ITR sequences (which function as origins of replication) and the native 5' packaging enhancer domains (that contain sequences necessary for packaging linear Ad genomes and enhancer elements for the E1 promoter). The 3' end of the adenoviral genome includes the 3' cis-elements (including the ITRs) necessary for packaging and encapsidation. Suitably, a recombinant adenovirus contains both 5' and 3' adenoviral cis-elements and the minigene (suitably containing a transgene) is located between the 5' and 3' adenoviral sequences. A ChAd157-based adenoviral vector may also contain additional adenoviral sequences.

Suitably, ChAd157-based vectors contain one or more adenoviral elements derived from the adenoviral ChAd157 genome of the invention. In one embodiment, the vectors contain adenoviral ITRs from ChAd157 and additional adenoviral sequences from the same adenoviral serotype. In another embodiment, the vectors contain adenoviral sequences that are derived from a different adenoviral serotype than that which provides the ITRs.

As defined herein, a pseudotyped adenovirus refers to an adenovirus in which the capsid proteins of the adenovirus are from a different adenovirus than the adenovirus which provides the ITRs.

Further, chimeric or hybrid adenoviruses may be constructed using the adenoviruses described herein using techniques known to those of skill in the art (e.g., U.S. Pat. No. 7,291,498).

ITRs and any other adenoviral sequences present in the vector of the present invention may be obtained from many sources. A variety of adenovirus strains are available from the American Type Culture Collection, Manassas, Va., or available by request from a variety of commercial and institutional sources. Further, the sequences of many such strains are available from a variety of databases including, e.g., PubMed and GenBank. Homologous adenovirus vectors prepared from other chimpanzee or from human adenoviruses are described in the published literature (for example, U.S. Pat. No. 5,240,846). The DNA sequences of a number of adenovirus types are available from GenBank, including type Ad5 (GenBank Accession Number M73370). The adenovirus sequences may be obtained from any known adenovirus serotype, such as serotypes 2, 3, 4, 7, 12 and 40, and further including any of the presently identified human types. Similarly adenoviruses known to infect nonhuman animals (e.g., simians) may also be employed in the vector constructs of this invention (e.g., U.S. Pat. No. 6,083,716). The viral sequences, helper viruses (if needed), and recombinant viral particles, and other vector components and sequences employed in the construction of the vectors described herein may be obtained as described below.

Sequence, Vector and Adenovirus Production

The sequences of the invention may be produced by any suitable means, including recombinant production, chemical synthesis, or other synthetic means. Suitable production techniques are well known to those of skill in the art. Alternatively, peptides can also be synthesized by well-known solid phase peptide synthesis methods.

The adenoviral plasmids (or other vectors) may be used to produce adenoviral vectors. In one embodiment, the adenoviral vectors are adenoviral particles which are replication-incompetent. In one embodiment, the adenoviral particles are rendered replication-incompetent by deletions in the E1A and/or E1B genes, in particular the E1A and E1B. Alternatively, the adenoviruses are rendered replication-incompetent by another means, optionally while retaining the E1A and/or E1B genes. Similarly, in some embodiments, reduction of an immune response to the vector may be accomplished by deletions in the E2B and/or DNA polymerase genes. The adenoviral vectors can also contain other mutations to the adenoviral genome, e.g., temperature-sensitive mutations or deletions in other genes. In other embodiments, it is desirable to retain an intact E1A and/or E1B region in the adenoviral vectors. Such an intact E1 region may be located in its native location in the adenoviral genome or placed in the site of a deletion in the native adenoviral genome (e.g., in the E3 region).

In the construction of adenovirus vectors for delivery of a gene to a mammalian (such as human) cell, a range of modified adenovirus nucleic acid sequences can be employed in the vectors. For example, all or a portion of the adenovirus delayed early gene E3 may be eliminated from the adenovirus sequence which forms a part of the recombinant virus. The function of E3 is believed to be irrelevant to the function and production of the recombinant virus particle. Adenovirus vectors may also be constructed having a deletion of at least the ORF6 region of the E4 gene, and more desirably because of the redundancy in the function of this region, the entire E4 region. Still another vector of the invention contains a deletion in the delayed early gene E2A. Deletions may also be made in any of the late genes L1 to L5 of the adenovirus genome. Similarly, deletions in the intermediate genes IX and IVa2 may be useful for some purposes. Other deletions may be made in the other structural or non-structural adenovirus genes. The above discussed deletions may be used individually, i.e., an adenovirus sequence for use as described herein may contain deletions in only a single region. Alternatively, deletions of entire genes or portions thereof effective to destroy their biological activity may be used in any combination. For example, in one exemplary vector, the adenovirus sequence may have deletions of the E1 genes and the E4 gene, or of the E1, E2A and E3 genes, or of the E1 and E3 genes, or of E1, E2A and E4 genes, with or without deletion of E3, and so on. Any one or more of the E genes may suitably be replaced with an E gene (or one or more E gene open reading frames) sourced from a different strain of adenovirus. Particularly suitably the ChAd157 E1 and E3 genes are deleted and the ChAd157E4 gene is replaced with E4Ad5orf6. As discussed above, such deletions and/or substitutions may be used in combination with other mutations, such as temperature-sensitive mutations, to achieve a desired result.

An adenoviral vector lacking one or more essential adenoviral sequences (e.g., E1A, E1B, E2A, E2B, E4 ORF6, L1, L2, L3, L4 and L5) may be cultured in the presence of the missing adenoviral gene products which are required for viral infectivity and propagation of an adenoviral particle. These helper functions may be provided by culturing the adenoviral vector in the presence of one or more helper constructs (e.g., a plasmid or virus) or a packaging host cell.

Complementation of Replication-Incompetent Vectors

To generate recombinant adenoviruses deleted in any of the genes described above, the function of the deleted gene region, if essential to the replication and infectivity of the virus, must be supplied to the recombinant virus by a helper virus or cell line, i.e., a complementation or packaging cell line.

Helper Viruses

Depending upon the adenovirus gene content of the viral vectors employed to carry the minigene, a helper adenovirus or non-replicating virus fragment may be used to provide sufficient adenovirus gene sequences necessary to produce an infective recombinant viral particle containing the minigene. Useful helper viruses contain selected adenovirus gene sequences not present in the adenovirus vector construct and/or not expressed by the packaging cell line in which the vector is transfected. In one embodiment, the helper virus is replication-defective and contains adenovirus genes in addition, suitably, to one or more of the sequences described herein. Such a helper virus is suitably used in combination with an E1 expressing (and optionally additionally E3 expressing) cell line.

A helper virus may optionally contain a reporter gene. A number of such reporter genes are known to the art as well as described herein. The presence of a reporter gene on the helper virus which is different from the transgene on the adenovirus vector allows both the adenoviral vector and the helper virus to be independently monitored. This reporter is used to enable separation between the resulting recombinant virus and the helper virus upon purification.

Complementation Cell Lines

In many circumstances, a cell line expressing the one or more missing genes which are essential to the replication and infectivity of the virus, such as human E1, can be used to transcomplement a chimpanzee adenoviral vector. This is particularly advantageous because, due to the diversity between the chimpanzee adenovirus sequences of the invention and the human adenovirus sequences found in currently available packaging cells, the use of the current human E1-containing cells prevents the generation of replication-competent adenoviruses during the replication and production process.

Alternatively, if desired, one may utilize the sequences provided herein to generate a packaging cell or cell line that expresses, at a minimum, the E1 gene from ChAd157 or from another adenovirus (such as human adenovirus, e.g. hAd5 E1, or another ChAd E1) under the transcriptional control of a promoter for expression in a selected parent cell line. Inducible or constitutive promoters may be employed for this purpose. Examples of such promoters are described in detail elsewhere in this document. A parent cell is selected for the generation of a novel cell line expressing any desired ChAd157 gene. Without limitation, such a parent cell line may be HeLa [ATCC Accession No. CCL 2], A549 [ATCC Accession No. CCL 185], HEK 293, KB [CCL 17], Detroit [e.g., Detroit 510, CCL 72] and WI-38 [CCL 75] cells, among others. These cell lines are all available from the American Type Culture Collection, 10801 University Boulevard, Manassas, Va. 20110-2209.

Such E1-expressing cell lines are useful in the generation of recombinant adenovirus E1 deleted vectors. Additionally, or alternatively, cell lines that express one or more adenoviral gene products, e.g., E1A, E1B, E2A, E3 and/or E4, can be constructed using essentially the same procedures as used in the generation of recombinant viral vectors. Such cell lines can be utilised to transcomplement adenovirus vectors deleted in the essential genes that encode those products, or to provide helper functions necessary for packaging of a helper-dependent virus (e.g., adeno-associated virus). The preparation of a host cell involves techniques such as assembly of selected DNA sequences.

In another alternative, the essential adenoviral gene products are provided in trans by the adenoviral vector and/or helper virus. In such an instance, a suitable host cell can be selected from any biological organism, including prokaryotic (e.g., bacterial) cells, and eukaryotic cells, including, insect cells, yeast cells and mammalian cells.

Host cells may be selected from among any mammalian species, including, without limitation, cells such as A549, WEHI, 3T3, 10'1'1/2, HEK 293 cells or Per.C6 (both of which express functional adenoviral E1) [Fallaux, F J et al, (1998), Hum Gene Ther, 9:1909-1917], Saos, C2C12, L cells, HT1080, HepG2 and primary fibroblast, hepatocyte and myoblast cells derived from mammals including human, monkey, mouse, rat, rabbit, and hamster.

A particularly suitable complementation cell line is the Procell92 cell line. The Procell92 cell line is based on HEK 293 cells which express adenoviral E1 genes, transfected with the Tet repressor under control of the human phosphoglycerate kinase-1 (PGK) promoter, and the G418-resistance gene (Vitelli et al. *PLOS One* (2013) 8(e55435):1-9). Procell92.S is adapted for growth in suspension conditions and is useful for producing adenoviral vectors expressing toxic proteins (www.okairos.com/e/inners.php?m=00084, last accessed 13 Apr. 2015).

Assembly of a Viral Particle and Transfection of a Cell Line

Generally, when delivering the vector comprising the minigene by transfection, the vector is delivered in an amount from about 5 μg to about 100 μg DNA, and preferably about 10 to about 50 μg DNA to about $1\times10^4$ cells to about $1\times10^{13}$ cells, and preferably about $10^5$ cells. However, the relative amounts of vector DNA to host cells may be adjusted, taking into consideration such factors as the selected vector, the delivery method and the host cells selected.

Introduction into the host cell of the vector may be achieved by any means known in the art, including transfection, and infection. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently.

Introduction of vectors into the host cell may also be accomplished using techniques known to the skilled person. Suitably, standard transfection techniques are used, e.g., CaPC transfection or electroporation.

Assembly of the selected DNA sequences of the adenovirus (as well as the transgene and other vector elements) into various intermediate plasmids, and the use of the plasmids and vectors to produce a recombinant viral particle are all achieved using conventional techniques. Such techniques include conventional cloning techniques of cDNA, use of overlapping oligonucleotide sequences of the adenovirus genomes, polymerase chain reaction, and any suitable method which provides the desired nucleotide sequence.

Standard transfection and co-transfection techniques are employed, e.g., CaPC precipitation techniques. Other conventional methods employed include homologous recombination of the viral genomes, plaquing of viruses in agar overlay, methods of measuring signal generation, and the like.

For example, following the construction and assembly of the desired minigene-containing viral vector, the vector is transfected in vitro in the presence of a helper virus into the packaging cell line. Homologous recombination occurs between the helper and the vector sequences, which permits the adenovirus-transgene sequences in the vector to be replicated and packaged into virion capsids, resulting in the recombinant viral vector particles. The resulting recombinant adenoviruses are useful in transferring a selected transgene to a selected cell. In in vivo experiments with the recombinant virus grown in the packaging cell lines, the E1-deleted recombinant adenoviral vectors of the invention demonstrate utility in transferring a transgene to a non-simian mammal, preferably a human, cell.

Transgenes

The transgene is a nucleic acid sequence, heterologous to the vector sequences flanking the transgene, which encodes a protein of interest. The nucleic acid coding sequence is operatively linked to regulatory components in a manner which permits transgene transcription, translation, and/or expression in a host cell.

The composition of the transgene sequence will depend upon the use to which the resulting vector will be put. For example, the transgene may be a therapeutic transgene or an immunogenic transgene. Alternatively, a transgene sequence may include a reporter sequence, which upon expression produces a detectable signal. Such reporter sequences include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc. These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry.

In one embodiment, the transgene is a non-marker sequence encoding a product which is useful in biology and medicine, such as a therapeutic transgene or an immunogenic transgene such as proteins, RNA, enzymes, or catalytic RNAs. Desirable RNA molecules include tRNA, dsRNA, ribosomal RNA, catalytic RNAs, and antisense RNAs. One example of a useful RNA sequence is a sequence which extinguishes expression of a targeted nucleic acid sequence in the treated animal.

The transgene may be used for treatment, e.g., of genetic deficiencies, as a cancer therapeutic or vaccine, for induction of an immune response, and/or for prophylactic vaccine purposes. As used herein, induction of an immune response refers to the ability of a protein to induce a T cell and/or a humoral immune response to the protein.

The term prophylaxis means the provision of a medicament in advance, this may be in advance of exposure to a pathogen (pre-exposure prophylaxis) or in advance of the development of disease symptoms (post-exposure prophylaxis). The terms treatment and therapy are used interchangeably herein and mean the administration of medicament during disease.

By the term disease is meant a disorder of structure or function in a subject, especially one that produces specific symptoms or that affects a specific location and is not simply a direct result of physical injury.

Regulatory Elements

In addition to the transgene the vector also includes conventional control elements which are operably linked to the transgene in a manner that permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (poly A) signals including rabbit beta-globin polyA; sequences that stabilize cytoplasmic mRNA; sequences that enhance translation efficiency (e.g., Kozak consensus sequence); sequences that enhance protein stability; and when desired, sequences that enhance secretion of the encoded product. Among other sequences, chimeric introns may be used.

In some embodiments, the Woodchuck Hepatitis Virus Posttranscriptional Regulatory Element (WPRE) (Zuffrey et al. (1999) *J Virol;* 73(4):2886-9) may be operably linked to the transgene. An exemplary WPRE is provided in SEQ ID NO: 26.

A "promoter" is a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A great number of expression control sequences, including promoters which are internal, native, constitutive, inducible and/or tissue-specific, are known in the art and may be utilized.

Examples of constitutive promoters include, without limitation, the TBG promoter, the retroviral Rous sarcoma virus LTR promoter (optionally with the enhancer), the cytomegalovirus (CMV) promoter (optionally with the CMV enhancer, see, e.g., Boshart et al, Cell, 41:521-530 (1985)), the CASI promoter, the SV40 promoter, the dihydrofolate reductase promoter, the β-actin promoter, the phosphoglycerol kinase (PGK) promoter, and the EF1a promoter (Invitrogen).

In some embodiments, the promoter is a CASI promoter (see, for example, WO2012/115980). The CASI promoter is a synthetic promoter which contains a portion of the CMV enhancer, a portion of the chicken beta-actin promoter, and a portion of the UBC enhancer. In some embodiments, the CASI promoter can include a nucleic acid sequence having at least about 90%, at least about 95%, at least about 96%, at least about 97%, at least about 98%, at least about 99%, or more, sequence identity to SEQ ID NO: 12. In some embodiments, the promoter comprises or consists of a nucleic acid sequence of SEQ ID NO: 12.

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. For example, inducible promoters include the zinc-inducible sheep metallothionine (MT) promoter and the dexamethasone (Dex)-inducible mouse mammary tumor virus (MMTV) promoter. Other inducible systems include the T7 polymerase promoter system (WO 98/10088); the ecdysone insect promoter (No et al, Proc. Natl. Acad. Sci. USA, 93:3346-3351 (1996)), the tetracycline-repressible system (Gossen et al, Proc. Natl. Acad. Sci. USA, 89:5547-5551 (1992)), the tetracycline-inducible system (Gossen et al, Science, 378:1766-1769 (1995), see also Harvey et al, Curr. Opin. Chem. Biol, 2:512-518 (1998)). Other systems include the FK506 dimer, VP16 or p65 using castradiol, diphenol murislerone, the RU486-inducible system (Wang et al, Nat. Biotech., 15:239-243 (1997) and Wang et al, Gene Ther., 4:432-441 (1997)) and the rapamycin-inducible system (Magari et al, J. Clin. Invest., 100:2865-2872 (1997)). The effectiveness of some inducible promoters increases over time. In such cases one can enhance the effectiveness of such systems by inserting multiple repressors in tandem, e.g., TetR linked to a TetR by an IRES.

In some embodiments the promotor is an enhanced hCMV promoter, such as provided in SEQ ID NO: 42.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

The transgene may be operably linked to a tissue-specific promoter. For instance, if expression in skeletal muscle is desired, a promoter active in muscle should be used. These include the promoters from genes encoding skeletal β-actin, myosin light chain 2A, dystrophin, muscle creatine kinase, as well as synthetic muscle promoters with activities higher than naturally occurring promoters (see Li et al, Nat. Biotech., 17:241-245 (1999)). Examples of promoters that are tissue-specific are known for liver (albumin, Miyatake et al, J. Virol, 71:5124-32 (1997); hepatitis B virus core promoter, Sandig et al, Gene Ther., 3:1002-9 (1996); alpha-fetoprotein (AFP), Arbuthnot et al., Hum. Gene Ther., 7: 1503-14 (1996)), bone osteocalcin (Stein et al, Mol. Biol. Rep., 24:185-96 (1997)); bone sialoprotein (Chen et al., J. Bone Miner. Res., 11:654-64 (1996)), lymphocytes (CD2, Hansal et al, J. Immunol, 161:1063-8 (1998); immunoglobulin heavy chain; T cell receptor chain), neuronal such as neuron-specific enolase (NSE) promoter (Andersen et al, Cell. Mol. Neurobiol, 13:503-15 (1993)), neurofilament light-chain gene (Piccioli et al, Proc. Natl. Acad. Sci. USA, 88:5611-5 (1991)), and the neuron-specific vgf gene (Piccioli et al, Neuron, 15:373-84 (1995)), among others.

Optionally, vectors carrying transgenes encoding therapeutically useful or immunogenic products may also include selectable markers or reporter genes which may include sequences encoding geneticin, hygromicin or puromycin resistance, among others. Such selectable reporters or marker genes (preferably located outside the viral genome to be packaged into a viral particle) can be used to signal the presence of the plasmids in bacterial cells, such as ampicillin resistance. Other components of the vector may include an origin of replication.

These vectors are generated using the techniques and sequences provided herein, in conjunction with techniques known to those of skill in the art. Such techniques include conventional cloning techniques of cDNA such as those described in texts, use of overlapping oligonucleotide sequences of the adenovirus genomes, polymerase chain reaction, and any suitable method which provides the desired nucleotide sequence.

Therapeutics and Prophylaxis

The recombinant ChAd157-based vectors are useful for gene transfer to a human or non-simian mammal in vitro, ex vivo, and in vivo.

The recombinant adenovirus vectors described herein can be used as expression vectors for the production of the products encoded by the heterologous transgenes in vitro. For example, the recombinant replication-incompetent adenovirus containing a transgene may be transfected into a complementation cell line as described above.

A ChAd157-derived recombinant adenoviral vector provides an efficient gene transfer vehicle that can deliver a selected transgene to a selected host cell in vivo or ex vivo even where the organism has neutralizing antibodies to one or more adenovirus serotypes. In one embodiment, the vector and the cells are mixed ex vivo; the infected cells are cultured using conventional methodologies; and the transduced cells are re-infused into the patient. These techniques are particularly well suited to gene delivery for therapeutic purposes and for immunisation, including inducing protective immunity.

Immunogenic Transgenes

The recombinant ChAd157 vectors may also be as administered in immunogenic compositions. An immunogenic composition as described herein is a composition comprising one or more recombinant ChAd157 vector capable of inducing an immune response, for example a humoral (e.g., antibody) and/or cell-mediated (e.g., a cytotoxic T cell) response, against a transgene product delivered by the vector following delivery to a mammal, suitably a human. A recombinant adenovirus may comprise (suitably in any of its gene deletions) a gene encoding a desired immunogen and may therefore be used in a vaccine. The recombinant adenoviruses can be used as prophylactic or therapeutic vaccines against any pathogen for which the antigen(s) crucial for induction of an immune response and able to limit the spread of the pathogen has been identified and for which the cDNA is available.

By the term immunogen is meant a polypeptide which is capable of eliciting an immune response. Suitably the immunogen is an antigen which comprises at least one B or T cell epitope. The elicited immune response may be an antigen specific B cell response, which produces neutralizing antibodies. The elicited immune response may be an antigen specific T cell response, which may be a systemic and/or a local response. The antigen specific T cell response may comprise a CD4+ T cell response, such as a response involving CD4+ T cells expressing a plurality of cytokines, e.g. IFNgamma, TNFalpha and/or IL2. Alternatively, or additionally, the antigen specific T cell response comprises a CD8+ T cell response, such as a response involving CD8+ T cells expressing a plurality of cytokines, e.g., IFNgamma, TNFalpha and/or IL2.

The term immunise therefore means the administration of an immunogen (or polynucleotide encoding the immunogen as appropriate to the context), to elicit an immune response.

Such vaccine or other immunogenic compositions may be formulated in a suitable delivery vehicle. Generally, doses for the immunogenic compositions are in the range defined below under 'Delivery Methods and Dosage'. The levels of immunity of the selected gene can be monitored to determine the need, if any, for boosters. Following an assessment of antibody titers in the serum, optional booster immunizations may be desired.

Optionally, a vaccine or immunogenic composition of the invention may be formulated to contain other components, including, e.g., adjuvants, stabilizers, pH adjusters, preservatives and the like. Examples of suitable adjuvants are provided below under 'Adjuvants'. Such an adjuvant can be administered with a priming DNA vaccine encoding an antigen to enhance the antigen-specific immune response compared with the immune response generated upon priming with a DNA vaccine encoding the antigen only. Alternatively, such an adjuvant can be administered with a polypeptide antigen which is administered in an administration regimen involving the ChAd157 vectors of the invention (as described below under 'Administration Regimens'.

The recombinant adenoviruses are administered in an immunogenic amount, that is, an amount of recombinant adenovirus that is effective in a route of administration to transfect the desired target cells and provide sufficient levels of expression of the selected gene to induce an immune response. Where protective immunity is provided, the recombinant adenoviruses are considered to be vaccine compositions useful in preventing infection and/or recurrent disease.

The recombinant vectors described herein are expected to be highly efficacious at inducing cytolytic T cells and antibodies directed to the inserted heterologous antigenic protein expressed by the vector.

Immunogens expressed by the inventive vectors which are useful to immunize a human or non-human animal against other pathogens include, e.g., bacteria, fungi, parasitic microorganisms or multicellular parasites which infect human and non-human vertebrates, or from a cancer cell or tumor cell. For example, immunogens may be selected from a variety of viral families. Examples of viral families against which an immune response would be desirable include Lyssaviruses such as rabies viruses, respiratory viruses such as respiratory syncytial virus (RSV) and other paramyxoviruses such as human metapneumovirus, hMPV and parainfluenza viruses (PIV).

Suitable rabies antigens which are useful as immunogens to immunize a human or non-human animal can be selected from the rabies viral glycoprotein (G), RNA polymerase (L), matrix protein (M), nucleoprotein (N) and phosphoprotein (P). The term "G protein" or "glycoprotein" or "G protein polypeptide" or "glycoprotein polypeptide" refers to a polypeptide or protein having all or part of an amino acid sequence of a rabies glycoprotein polypeptide. The term "L protein" or "RNA polymerase protein" or "L protein polypeptide" or "RNA polymerase protein polypeptide" refers to a polypeptide or protein having all or part of an amino acid sequence of a rabies RNA polymerase protein polypeptide. The term "M protein" or "matrix protein" or "M protein polypeptide" or "matrix protein polypeptide" refers to a polypeptide or protein having all or part of an amino acid sequence of a rabies matrix protein polypeptide. The term "N protein" or "nucleoprotein" or "N protein polypeptide" or "nucleoprotein polypeptide" refers to a polypeptide or protein having all or part of an amino acid sequence of a rabies nucleoprotein polypeptide. The term "P protein" or "phosphoprotein" or "P protein polypeptide" or "phosphoprotein polypeptide" refers to a polypeptide or protein having all or part of an amino acid sequence of a rabies phosphoprotein polypeptide.

Suitable antigens of RSV which are useful as immunogens to immunize a human or non-human animal can be selected from: the fusion protein (F), the attachment protein (G), the matrix protein (M2) and the nucleoprotein (N). The term "F protein" or "fusion protein" or "F protein polypeptide" or "fusion protein polypeptide" refers to a polypeptide or protein having all or part of an amino acid sequence of an RSV Fusion protein polypeptide. Similarly, the term "G protein" or "G protein polypeptide" refers to a polypeptide or protein having all or part of an amino acid sequence of an RSV Attachment protein polypeptide. The term "M protein" or "matrix protein" or "M protein polypeptide" refers to a polypeptide or protein having all or part of an amino acid sequence of an RSV Matrix protein and may include either or both of the M2-1 (which may be written herein as M2.1) and M2-2 gene products. Likewise, the term "N protein" or "Nucleocapsid protein" or "N protein polypeptide" refers to a polypeptide or protein having all or part of an amino acid sequence of an RSV Nucleoprotein.

Two groups of human RSV strains have been described, the A and B groups, based mainly on differences in the antigenicity of the G glycoprotein. Numerous strains of RSV have been isolated to date, any of which are suitable in the context of the antigens of the immunogenic combinations disclosed herein. Exemplary strains indicated by GenBank and/or EMBL Accession number can be found in US published application number 2010/0203071 (WO2008114149), which is incorporated herein by reference for the purpose of disclosing the nucleic acid and polypeptide sequences of RSV F and G proteins suitable for use in present invention. In an embodiment, the RSV F protein can be an ectodomain of an RSV F Protein (FΔTM).

Exemplary M and N protein nucleic acids and protein sequences can be found, e.g., in US published application number 2014/0141042 (WO2012/089833), which are incorporated herein for purpose of disclosing the nucleic acid and polypeptide sequences of RSV M and N proteins suitable for use in present invention.

Suitably, for use with in present invention, a nucleic acid encodes an RSV F antigen and RSV, M and N antigens. More specifically, the nucleic acid encodes an RSV FΔTM antigen and RSV M2-1 and N antigens, wherein a self-cleavage site is included between the RSV FΔTM antigen and the RSV M2-1 and a flexible linker is included between the RSV M2-1 and N antigens. In one embodiment a suitable nucleic acid encodes the polypeptide represented by SEQ ID NO:37

In one embodiment, the immunogen may be from a retrovirus, for example a lentivirus such as the Human Immunodeficiency Virus (HIV). In such an embodiment, immunogens may be derived from HIV-1 or HIV-2.

The HIV genome encodes a number of different proteins, each of which can be immunogenic in its entirety or as a fragment when expressed by vectors of the present invention. Envelope proteins include gp120, gp41 and Env precursor gp160, for example. Non-envelope proteins of HIV include for example internal structural proteins such as the products of the gag and pol genes and other non-structural proteins such as Rev, Nef, Vif and Tat. In an embodiment the vector of the invention encodes one or more polypeptides comprising HIV Gag.

The Gag gene is translated as a precursor polyprotein that is cleaved by protease to yield products that include the matrix protein (p17), the capsid (p24), the nucleocapsid (p9), p6 and two space peptides, p2 and p1, all of which are examples of fragments of Gag.

The Gag gene gives rise to the 55-kilodalton (kD) Gag precursor protein, also called p55, which is expressed from the unspliced viral mRNA. During translation, the N terminus of p55 is myristoylated, triggering its association with the cytoplasmic aspect of cell membranes. The membrane-associated Gag polyprotein recruits two copies of the viral genomic RNA along with other viral and cellular proteins that triggers the budding of the viral particle from the surface of an infected cell. After budding, p55 is cleaved by the virally encoded protease (a product of the pol gene) during the process of viral maturation into four smaller proteins designated MA (matrix [p17]), CA (capsid [p24]), NC (nucleocapsid [p9]), and p6, all of which are examples of fragments of Gag. In one embodiment, the vectors of the present invention comprise a Gag polypeptide of SEQ ID NO: 16.

Adjuvants

An "adjuvant" as used herein refers to a composition that enhances the immune response to an immunogen. Examples of such adjuvants include but are not limited to inorganic adjuvants (e.g. inorganic metal salts such as aluminium phosphate or aluminium hydroxide), organic adjuvants (e.g. saponins, such as QS21, or squalene), oil-based adjuvants (e.g. Freund's complete adjuvant and Freund's incomplete adjuvant), cytokines (e.g. IL-1β, IL-2, IL-7, IL-12, IL-18, GM-CFS, and INF-γ) particulate adjuvants (e.g. immunostimulatory complexes (ISCOMS), liposomes, or biodegradable microspheres), virosomes, bacterial adjuvants (e.g. monophosphoryl lipid A, such as 3-de-O-acylated monophosphoryl lipid A (3D-MPL), or muramyl peptides), synthetic adjuvants (e.g. non-ionic block copolymers, muramyl peptide analogues, or synthetic lipid A), synthetic polynucleotides adjuvants (e.g polyarginine or polylysine) and immunostimulatory oligonucleotides containing unmethylated CpG dinucleotides ("CpG").

One suitable adjuvant is monophosphoryl lipid A (MPL), in particular 3-de-O-acylated monophosphoryl lipid A (3D-MPL). Chemically it is often supplied as a mixture of 3-de-O-acylated monophosphoryl lipid A with either 4, 5, or 6 acylated chains. It can be purified and prepared by the methods taught in GB 2122204B, which reference also discloses the preparation of diphosphoryl lipid A, and 3-O-deacylated variants thereof. Other purified and synthetic lipopolysaccharides have been described (U.S. Pat. No. 6,005,099 and EP 0 729 473B1; Hilgers et al., 1986, Int. Arch. Allergy. Immunol., 79(4):392-6; Hilgers et al., 1987, Immunology, 60(1):141-6; and EP 0 549 074B11).

Saponins are also suitable adjuvants (see Lacaille-Dubois, M and Wagner H, A review of the biological and pharmacological activities of saponins. Phytomedicine vol 2 pp 363-386 (1996)). For example, the saponin Quil A (derived from the bark of the South American tree Quillaja *Saponaria* Molina), and fractions thereof, are described in U.S. Pat. No. 5,057,540 and Kensil, Crit. Rev. Ther. Drug Carrier Syst., 1996, 12:1-55; and EP 0 362 279B1. Purified fractions of Quil A are also known as immunostimulants, such as QS21 and QS17; methods of their production is disclosed in U.S. Pat. No. 5,057,540 and EP 0 362 279B1. Also described in these references is QS7 (a non-haemolytic fraction of Quil-A). Use of QS21 is further described in Kensil et al. (1991, J. Immunology, 146: 431-437). Combinations of QS21 and polysorbate or cyclodextrin are also known (WO 99/10008). Particulate adjuvant systems comprising fractions of QuilA, such as QS21 and QS7 are described in WO 96/33739 and WO 96/11711.

Another adjuvant is an immunostimulatory oligonucleotide containing unmethylated CpG dinucleotides ("CpG") (Krieg, Nature 374:546 (1995)). CpG is an abbreviation for cytosine-guanosine dinucleotide motifs present in DNA. CpG is known as an adjuvant when administered by both systemic and mucosal routes (WO 96/02555, EP 468520, Davis et al, J. Immunol, 1998, 160:870-876; McCluskie and Davis, J. Immunol., 1998, 161:4463-6). CpG, when formulated into vaccines, may be administered in free solution together with free antigen (WO 96/02555) or covalently conjugated to an antigen (WO 98/16247), or formulated with a carrier such as aluminium hydroxide (Brazolot-Millan et al., Proc. Natl. Acad. Sci., USA, 1998, 95:15553-8).

Adjuvants such as those described above may be formulated together with carriers, such as liposomes, oil in water emulsions, and/or metallic salts (including aluminum salts such as aluminum hydroxide). For example, 3D-MPL may be formulated with aluminum hydroxide (EP 0 689 454) or oil in water emulsions (WO 95/17210); QS21 may be formulated with cholesterol containing liposomes (WO 96/33739), oil in water emulsions (WO 95/17210) or alum (WO 98/15287); CpG may be formulated with alum (Brazolot-Millan, supra) or with other cationic carriers.

Combinations of adjuvants may be utilized in the present invention, in particular a combination of a monophosphoryl lipid A and a saponin derivative (see, e.g., WO 94/00153; WO 95/17210; WO 96/33739; WO 98/56414; WO 99/12565; WO 99/11241), more particularly the combination of QS21 and 3D-MPL as disclosed in WO 94/00153, or a composition where the QS21 is quenched in cholesterol-containing liposomes (DQ) as disclosed in WO 96/33739. Alternatively, a combination of CpG plus a saponin such as QS21 is an adjuvant suitable for use in the present invention. A potent adjuvant formulation involving QS21, 3D-MPL & tocopherol in an oil in water emulsion is described in WO 95/17210 and is another formulation for use in the present invention. Saponin adjuvants may be formulated in a liposome and combined with an immunostimulatory oligonucleotide. Thus, suitable adjuvant systems include, for example, a combination of monophosphoryl lipid A, preferably 3D-MPL, together with an aluminium salt (e.g. as described in WO00/23105). A further exemplary adjuvant comprises QS21 and/or MPL and/or CpG. QS21 may be quenched in cholesterol-containing liposomes as disclosed in WO 96/33739.

Other suitable adjuvants include alkyl Glucosaminide phosphates (AGPs) such as those disclosed in WO9850399 or U.S. Pat. No. 6,303,347 (processes for preparation of AGPs are also disclosed), or pharmaceutically acceptable salts of AGPs as disclosed in U.S. Pat. No. 6,764,840. Some AGPs are TLR4 agonists, and some are TLR4 antagonists. Both are thought to be useful as adjuvants.

It has been found (WO 2007/062656, which published as US 2011/0293704 and is incorporated by reference for the purpose of disclosing invariant chain sequences) that the fusion of the invariant chain to an antigen which is comprised by an expression system used for vaccination increases the immune response against said antigen, if it is administered with an adenovirus. Accordingly, in one embodiment of the invention, the immunogenic transgene may be co-expressed with invariant chain in a recombinant ChAd157 viral vector.

In another embodiment, the invention provides the use of the capsid of ChAd157 (optionally an intact or recombinant viral particle or an empty capsid is used) to induce an immunomodulatory effect response, or to enhance or adjuvant a cytotoxic T cell response to another active agent by delivering a ChAd157 capsid to a subject. The ChAd157 capsid can be delivered alone or in a combination regimen with an active agent to enhance the immune response thereto. Advantageously, the desired effect can be accomplished without infecting the host with an adenovirus.

Administration Regimens

Commonly, the ChAd157 recombinant adenoviral vectors will be utilized for delivery of therapeutic or immunogenic molecules (such as proteins). It will be readily understood for both applications, that the recombinant adenoviral vectors of the invention are particularly well suited for use in regimens involving repeat delivery of recombinant adenoviral vectors. Such regimens typically involve delivery of a series of viral vectors in which the viral capsids are alternated. The viral capsids may be changed for each subsequent administration, or after a pre-selected number of administrations of a particular serotype capsid (e.g. one, two, three, four or more). Thus, a regimen may involve delivery of a recombinant adenovirus with a first capsid, delivery with a recombinant adenovirus with a second capsid, and delivery with a recombinant adenovirus with a third capsid. A variety of other regimens which use the adenovirus capsids of the invention alone, in combination with one another, or in combination with other adenoviruses (which are preferably immunologically non-cross reactive) will be apparent to those of skill in the art. Optionally, such a regimen may involve administration of recombinant adenovirus with capsids of other non-human primate adenoviruses, human adenoviruses, or artificial sequences such as are described herein.

The adenoviral vectors of the invention are particularly well suited for therapeutic regimens in which multiple adenoviral-mediated deliveries of transgenes are desired, e.g., in regimens involving redelivery of the same transgene or in combination regimens involving delivery of other transgenes. Such regimens may involve administration of a ChAd157 adenoviral vector, followed by re-administration with a vector from the same serotype adenovirus. Particularly desirable regimens involve administration of a ChAd157 adenoviral vector, in which the source of the adenoviral capsid sequences of the vector delivered in the first administration differs from the source of adenoviral capsid sequences of the viral vector utilized in one or more of the subsequent administrations. For example, a therapeutic regimen involves administration of a ChAd157 vector and repeat administration with one or more adenoviral vectors of the same or different serotypes.

In another example, a therapeutic regimen involves administration of an adenoviral vector followed by repeat administration with a ChAd157 vector which has a capsid which differs from the source of the capsid in the first delivered adenoviral vector, and optionally further administration with another vector which is the same or, preferably, differs from the source of the adenoviral capsid of the vector in the prior administration steps. These regimens are not limited to delivery of adenoviral vectors constructed using the ChAd157 sequences. Rather, these regimens can readily utilize other adenoviral sequences, including, without limitation, other adenoviral sequences including other non-human primate adenoviral sequences, or human adenoviral sequences, in combination with the ChAd157 vectors.

In a further example, a therapeutic regimen may involve either simultaneous (such as co-administration) or sequential (such as a prime-boost) delivery of (i) one or more ChAd157 adenoviral vectors and (ii) a further component such as non-adenoviral vectors, non-viral vectors, and/or a variety of other therapeutically useful compounds or molecules such as antigenic proteins optionally simultaneously administered with adjuvant. Examples of co-administration include homo-lateral co-administration and contra-lateral co-administration (further described below under 'Delivery Methods and Dosage').

Suitable non-adenoviral vectors for use in simultaneous or particularly in sequential delivery (such as prime-boost) with one or more ChAd157 adenoviral vectors include one or more poxviral vectors. Suitably, the poxviral vector belongs to the subfamily chordopoxvirinae, more suitably to a genus in said subfamily selected from the group consisting of orthopox, parapox, yatapox, avipox (suitably canarypox (ALVAC) or fowlpox (FPV)) and molluscipox. Even more suitably, the poxviral vector belongs to the orthopox and is selected from the group consisting of vaccinia virus, NYVAC (derived from the Copenhagen strain of vaccinia), Modified Vaccinia Ankara (MVA), cowpoxvirus and monkeypox virus. Most suitably, the poxviral vector is MVA.

"Simultaneous" administration suitably refers to the same ongoing immune response. Preferably both components are administered at the same time (such as simultaneous administration of both DNA and protein), however, one component could be administered within a few minutes (for example, at the same medical appointment or doctor's visit), within a few hours. Such administration is also referred to as co-administration. In some embodiments, co-administration may refer to the administration of an adenoviral vector, an adjuvant and a protein component. In other embodiments, co-administration refers to the administration of an adenoviral vector and another viral vector, for example a second adenoviral vector or a poxvirus such as MVA. In other embodiments, co-administration refers to the administration of an adenoviral vector and a protein component, which is optionally adjuvanted.

A prime-boost regimen may be used. Prime-boost refers to two separate immune responses: (i) an initial priming of the immune system followed by (ii) a secondary or boosting of the immune system many weeks or months after the primary immune response has been established.

Such a regimen may involve the administration of a recombinant ChAd157 vector to prime the immune system to second, booster, administration with a traditional antigen, such as a protein (optionally co-administered with adjuvant), or a recombinant virus carrying the sequences encoding such an antigen (e.g., WO 00/11140). Alternatively, an immunization regimen may involve the administration of a recombinant ChAd157 vector to boost the immune response to a vector (either viral or DNA-based) encoding an antigen. In another alternative, an immunization regimen involves administration of a protein followed by booster with a recombinant ChAd157 vector encoding the antigen. In one example, the prime-boost regimen can provide a protective immune response to the virus, bacteria or other organism from which the antigen is derived. In another embodiment, the prime-boost regimen provides a therapeutic effect that can be measured using conventional assays for detection of the presence of the condition for which therapy is being administered.

Preferably, a boosting composition is administered about 2 to about 27 weeks after administering the priming composition to the subject. The administration of the boosting composition is accomplished using an effective amount of a boosting composition containing or capable of delivering the same antigen or a different antigen as administered by the priming vaccine. The boosting composition may be composed of a recombinant viral vector derived from the same viral source or from another source. Alternatively, the boosting composition can be a composition containing the same antigen as encoded in the priming vaccine, but in the form of a protein, which composition induces an immune response in the host. The primary requirements of the boosting composition are that the antigen of the composition is the same antigen, or a cross-reactive antigen, as that encoded by the priming composition.

A low cross-reactivity between neutralizing antibodies for ChAd157 and certain other adenoviral vectors, such as ChAd155, is beneficial in contexts where multiple vector administrations are required. Multiple administrations may be for the purpose of the separate delivery of different transgenes (e.g. encoding immunogens associated different medical indications) or delivery of the same or similar transgenes (e.g. in a prime-boost regime to increase the immune response for a particular medical indication).

Consequently, there is provided a recombinant adenoviral vector of the invention encoding a transgene, for administration to a subject which has previously been exposed to a recombinant adenoviral vector which does not comprise a ChAd157 fiber, or functional derivative thereof, as described herein (e.g. does not comprise a ChAd157 fiber, hexon or penton as described herein, such as a recombinant adenoviral vector comprising a ChAd155 fiber, hexon and/or penton, especially a recombinant adenoviral vector comprising a ChAd155 fiber, hexon and penton). In particular, there is provided a recombinant adenoviral vector of the invention encoding a transgene for administration to a subject which has previously been administered a recombinant adenoviral vector which does not comprise a ChAd157 fiber, or functional derivative thereof, as described herein (e.g. does not comprise a ChAd157 fiber, hexon or penton as described herein, such as a recombinant adenoviral vector comprising a ChAd155 fiber, hexon and/or penton, especially a recombinant adenoviral vector comprising a ChAd155 fiber, hexon and penton). Suitably the recombinant adenoviral vector which does not comprise a ChAd157 fiber is one which has low cross-reactivity with ChAd157. In one embodiment the recombinant adenoviral vector which does not comprise a ChAd157 fiber encodes a transgene directed at a different medical indication or indications as the recombinant adenoviral vector of the invention transgene. In another embodiment the recombinant adenoviral vector which does not comprise a ChAd157 fiber encodes a transgene directed at the same medical indication or indications as the recombinant adenoviral vector of the invention transgene (e.g. such as the same transgene).

Also provided is a recombinant adenoviral vector of the invention encoding a transgene for administration to a subject which may (i.e. it is intended or expected will) subsequently be exposed to a recombinant adenoviral vector which does not comprise a ChAd157 fiber, or functional derivative thereof, as described herein (e.g. does not comprise a ChAd157 fiber, hexon or penton as described herein, such as a recombinant adenoviral vector comprising a ChAd155 fiber, hexon and/or penton, especially a recombinant adenoviral vector comprising a ChAd155 fiber, hexon and penton). In particular, there is provided a recombinant adenoviral vector of the invention encoding a transgene for administration to a subject which may subsequently be administered a recombinant adenoviral vector which does not comprise a ChAd157 fiber, or functional derivative thereof, as described herein (e.g. does not comprise a ChAd157 fiber, hexon or penton as described herein, such as a recombinant adenoviral vector comprising a ChAd155 fiber, hexon and/or penton, especially a recombinant adenoviral vector comprising a ChAd155 fiber, hexon and penton). Suitably the recombinant adenoviral vector which does not comprise a ChAd157 fiber is one which has low cross-reactivity with ChAd157. In one embodiment the recombinant adenoviral vector which does not comprise a ChAd157 fiber encodes a transgene directed at a different medical indication or indications as the recombinant adenoviral vector of the invention transgene. In another embodiment the recombinant adenoviral vector which does not comprise a ChAd157 fiber encodes a transgene directed at the same medical indication or indications as the recombinant adenoviral vector of the invention transgene (e.g. such as the same transgene).

The present invention therefore provides a method for eliciting an immune response in a subject, said method comprising:
 (a) administering to the subject a recombinant adenoviral vector of the invention encoding a first transgene; and
 (b) administering to the subject a recombinant adenoviral vector which does not comprise a ChAd157 fiber, or functional derivative thereof as described herein, the vector encoding a second transgene;
 wherein steps (a) and (b) may be undertaken in either order and the first and second transgenes may be the same or different.

The first and second transgenes will typically encode immunogens which are useful to immunize a human or non-human animal against a pathogen such as bacteria, fungi, parasitic microorganisms or multicellular parasites which infect human and non-human vertebrates, or against a cancer cell or tumor cell. The first and second transgenes may encode the same or different immunogens. When encoding different immunogens, these may be directed to the same or different pathogen or cancer cell or tumor cell.

Consequently, there is also provided a method for the prophylaxis or treatment of a subject, said method comprising:
 (a) administering to the subject a recombinant adenoviral vector of the invention encoding a first transgene encoding an immunogen which is useful to immunize a human or non-human animal against a pathogen such as bacteria, fungi, parasitic microorganisms or multicellular parasites which infect human and non-human vertebrates, or against a cancer cell or tumor cell; and
 (b) administering to the subject a recombinant adenoviral vector which does not comprise a ChAd157 fiber, or functional derivative thereof as described herein, the vector encoding a second transgene encoding an immunogen which is useful to immunize a human or non-human animal against a different pathogen such as bacteria, fungi, parasitic microorganisms or multicellular parasites which infect human and non-human vertebrates, or against a cancer cell or tumor cell;
 wherein steps (a) and (b) may be undertaken in either order.

The recombinant adenoviral vector which does not comprise a ChAd157 fiber, or functional derivative thereof as described herein, suitably does not comprise a ChAd157 fiber, ChAd157 hexon or ChAd157 fiber, such as does not comprise a ChAd157 fiber, ChAd157 hexon or ChAd157 fiber or functional derivatives thereof having at least 98% identity thereto.

The recombinant adenoviral vector which does not comprise a ChAd157 fiber, or functional derivative thereof as described herein may be a recombinant adenoviral vector comprising a ChAd155 fiber, hexon and/or penton, especially a recombinant adenoviral vector comprising a ChAd155 fiber, hexon and penton.

As mentioned, a recombinant adenoviral vector of the invention may be used for delivery of therapeutic or immunogenic molecules in conjunction with a recombinant adenoviral vector comprising a ChAd155 fiber, hexon and/or penton. The recombinant adenoviral vector comprising a ChAd155 fiber, hexon and/or penton will comprise a fiber, penton and/or hexon according to SEQ ID NOs: 7, 9 and 11, in particular a fiber, penton and hexon according to SEQ ID NOs: 7, 9 and 11.

By the term low cross-reactivity is meant that immunisation with a first vector does not elicit a notable neutralising antibody response to a second vector, i.e. not significantly impacting the immunological potency of the second vector. Neutralising antibody responses can be determined with methods analogous to Example 7 herein. Desirably, immunisation with a first vector twice elicits a neutralising titer which is on average less than 50% of the level arising from immunisation with the second vector, such as less than 75%, suitably less than 90%.

By the term "subject" is meant any animal, suitably a mammal, and in particular a human.

Delivery Methods and Dosage

The vector may be prepared for administration by being suspended or dissolved in a pharmaceutically or physiologically acceptable carrier such as isotonic saline; isotonic salts solution or other formulations that will be apparent to those skilled in the art. The appropriate carrier will be evident to those skilled in the art and will depend in large part upon the route of administration. The compositions described herein may be administered to a mammal in a sustained release formulation using a biodegradable biocompatible polymer, or by on-site delivery using micelles, gels and liposomes.

In some embodiments, the recombinant adenovirus of the invention is administered to a subject by intramuscular injection, intravaginal administration, intravenous injection, intraperitoneal injection, subcutaneous injection, epicutaneous administration, intradermal administration, nasal administration, rectal administration or oral administration. Sublingual administration may also be of interest.

If the therapeutic regimen involves co-administration of one or more ChAd157 adenoviral vectors and a further component, each formulated in different compositions, they are favourably administered co-locationally at or near the same site. For example, the components can be administered (e.g. via an administration route selected from intramuscular, transdermal, intradermal, sub-cutaneous) to the same side or extremity ("co-lateral" administration) or to opposite sides or extremities ("contra-lateral" administration).

Dosages of the viral vector will depend primarily on factors such as the condition being treated, the age, weight and health of the patient, and may thus vary among patients. For example, a therapeutically effective adult human or veterinary dosage of the viral vector generally contains $1 \times 10^5$ to $1 \times 10^{15}$ viral particles, such as from $1 \times 10^8$ to $1 \times 10^{12}$ (e.g., $1 \times 10^8$, $2.5 \times 10^8$, $5 \times 10^8$, $1 \times 10^9$, $1.5 \times 10^9$, $2.5 \times 10^9$, $5 \times 10^9$, $1 \times 10^{10}$, $1.5 \times 10^{10}$, $2.5 \times 10^{10}$, $5 \times 10^{10}$, $1 \times 10^{11}$, $1.5 \times 10^{11}$, $2.5 \times 10^{11}$, $5 \times 10^{11}$, $1 \times 10^{12}$ particles). Alternatively, a viral vector can be administered at a dose that is typically from $1 \times 10^5$ to $1 \times 10^{10}$ plaque forming units (PFU), such as $1 \times 10^5$ PFU, $2.5 \times 10^5$ PFU, $5 \times 10^5$ PFU, $1 \times 10^6$ PFU, $2.5 \times 10^6$ PFU, $5 \times 10^6$ PFU, $1 \times 10^7$ PFU, $2.5 \times 10^7$ PFU, $5 \times 10^7$ PFU, $1 \times 10^8$ PFU, $2.5 \times 10^8$ PFU, $5 \times 10^8$ PFU, $1 \times 10^9$ PFU, $2.5 \times 10^9$ PFU, $5 \times 10^9$ PFU, or $1 \times 10^{10}$ PFU. Dosages will vary depending upon the size of the animal and the route of administration. For example, a suitable human or veterinary dosage (for about an 80 kg animal) for intramuscular injection is in the range of about $1 \times 10^9$ to about $5 \times 10^{12}$ particles per mL, for a single site. Optionally, multiple sites of administration may be used. In another example, a suitable human or veterinary dosage may be in the range of about $1 \times 10^{11}$ to about $1 \times 10^{15}$ particles for an oral formulation.

The viral vector can be quantified by Quantitative PCR Analysis (Q-PCR), for example with primers and probe designed on CMV promoter region using as standard curve serial dilution of plasmid DNA containing the vector genome with expression cassette including HCMV promoter. The copy number in the test sample is determined by the parallel line analysis method. Alternative methods for vector particle quantification can be analytical HPLC or spectrophotometric method based on $A_{260}$ nm.

An immunologically effective amount of a nucleic acid may suitably be between 1 ng and 100 mg. For example, a suitable amount can be from 1 μg to 100 mg. An appropriate amount of the particular nucleic acid (e.g., vector) can readily be determined by those of skill in the art. Exemplary effective amounts of a nucleic acid component can be between 1 ng and 100 μg, such as between 1 ng and 1 μg (e.g., 100 ng-1 μg), or between 1 μg and 100 μg, such as 10 ng, 50 ng, 100 ng, 150 ng, 200 ng, 250 ng, 500 ng, 750 ng, or 1 μg. Effective amounts of a nucleic acid can also include from 1 μg to 500 μg, such as between 1 μg and 200 μg, such as between 10 and 100 μg, for example 1 μg, 2 μg, 5 μg, 10 μg, 20 μg, 50 μg, 75 μg, 100 μg, 150 μg, or 200 μg. Alternatively, an exemplary effective amount of a nucleic acid can be between 100 μg and 1 mg, such as from 100 μg to 500 μg, for example, 100 μg, 150 μg, 200 μg, 250 μg, 300 μg, 400 μg, 500 μg, 600 μg, 700 μg, 800 μg, 900 μg or 1 mg.

Generally a human dose will be in a volume of between 0.1 ml and 2 ml. Thus the composition described herein can be formulated in a volume of, for example 0.1, 0.15, 0.2, 0.5, 1.0, 1.5 or 2.0 ml human dose per individual or combined immunogenic components.

One of skill in the art may adjust these doses, depending on the route of administration and the therapeutic or vaccine application for which the recombinant vector is employed. The levels of expression of the transgene, or for an adjuvant, the level of circulating antibody, can be monitored to determine the frequency of dosage administration.

If one or more priming and/or boosting steps are used, this step may include a single dose that is administered hourly, daily, weekly or monthly, or yearly. As an example, mammals may receive one or two doses containing between about 10 μg to about 50 μg of plasmid in carrier. The amount or site of delivery is desirably selected based upon the identity and condition of the mammal.

The therapeutic levels of, or level of immune response against, the protein encoded by the selected transgene can be monitored to determine the need, if any, for boosters. Following an assessment of CD8+ T cell response, or optionally, antibody titers, in the serum, optional booster immunizations may be desired. Optionally, the recombinant ChAd157 vectors may be delivered in a single administration or in various combination regimens, e.g., in combination with a regimen or course of treatment involving other active ingredients or in a prime-boost regimen.

The present invention will now be further described by means of the following non-limiting examples.

EXAMPLES

Example 1: Isolation of ChAd157 and Vector Construction 29 different wild type chimpanzee adenoviruses were isolated from healthy young chimpanzees housed in different European facilities using standard procedures as described in Colloca et al. Sci Transl Med. 2012 Jan. 4; 4(115):115ra2 and WO2010/086189, which is hereby incorporated by reference for the purpose of describing adenoviral isolation and characterization techniques.

The 29 wild type viruses were subsequently pooled; the viral genome of the pool was cloned by homologous recombination in E. coli BJ5183 cells using a BAC shuttle, to create a minilibrary of vectors carrying the deletion of E1 region. The minilibrary of ΔE1 vectors was transfected into the Procell 92 cell line; the rescued vectors were serially passaged for 16 passages of infection. At passage 16 the viral DNA was prepared from the amplified vector and cloned by homologous recombination in E. coli BJ5183 cells using a plasmid shuttle, The prevalent vector species was identified as ChAd157ΔE1 vector and subsequently modified to include the following additional modifications of the vector backbone:
  a) deletion of the E4 region (from bp 34413 to bp 37127) of the ΔE1 virus;
  b) insertion of the E4orf6 derived from human Ad5.

1.1: ΔE1 minilibrary generation

Figure 2:
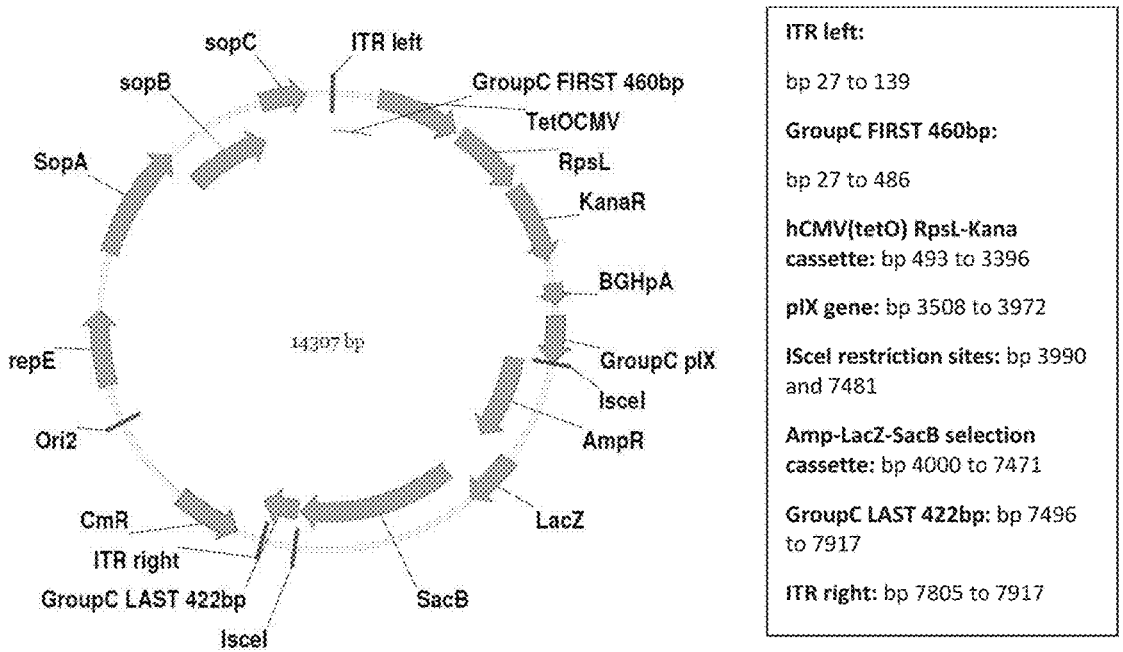

The pool of 29 wild type virus was used to obtain a pooled viral genome. The pooled viral genome was cloned into a BAC vector by homologous recombination in E. coli strain BJ5183 co-transformed with pooled viral DNA and Subgroup C BAC Shuttle (#1365) (SEQ ID NO: 14). As shown in the schematic of FIG. 2, the Subgroup C Shuttle is a BAC vector dedicated to the cloning of ChAd belonging to species C and therefore contains the pIX gene and DNA fragments derived from right and left ends (including right and left ITRs) of species C ChAd viruses.

The Species C BAC Shuttle also contains a RpsL-Kana cassette inserted between left end and the pIX gene. In addition, an Amp-LacZ-SacB selection cassette, flanked by IScel restriction sites, is present between the pIX gene and right end of the viral genome. In particular, the BAC Shuttle comprised the following features: Left ITR: bp 27 to 139, hCMV(tetO) RpsL-Kana cassette: bp 493 to 3396, pIX gene: bp 3508 to 3972, IScel restriction sites: bp 3990 and 7481, Amp-LacZ-SacB selection cassette: bp 4000 to 7471, Right ITR: bp 7805 to 7917. hCMV(tetO) is provided in SEQ ID NO: 37.

BJ5183 cells were co-transformed by electroporation with the pool of purified viral DNAs and with Subgroup C BAC Shuttle vector digested with IScel restriction enzyme and then purified from gel. Homologous recombination occurring between pIX gene and right ITR sequences (present at the ends of Species C BAC Shuttle linearized DNA) and homologous sequences present in pooled viral DNA lead to the insertion of the different viral genomic DNA in the BAC shuttle vector. At the same time, the viral E1 regions were deleted and substituted by the RpsL-Kana cassette, generating BAC/MinilibraryΔE1/TetO hCMV RpsL-Kana.

1.2: ΔE1 Minilibrary Amplification in Procell 92 Cell Line and Cloning of ChAd157ΔE1 Vector.

Figure 3:
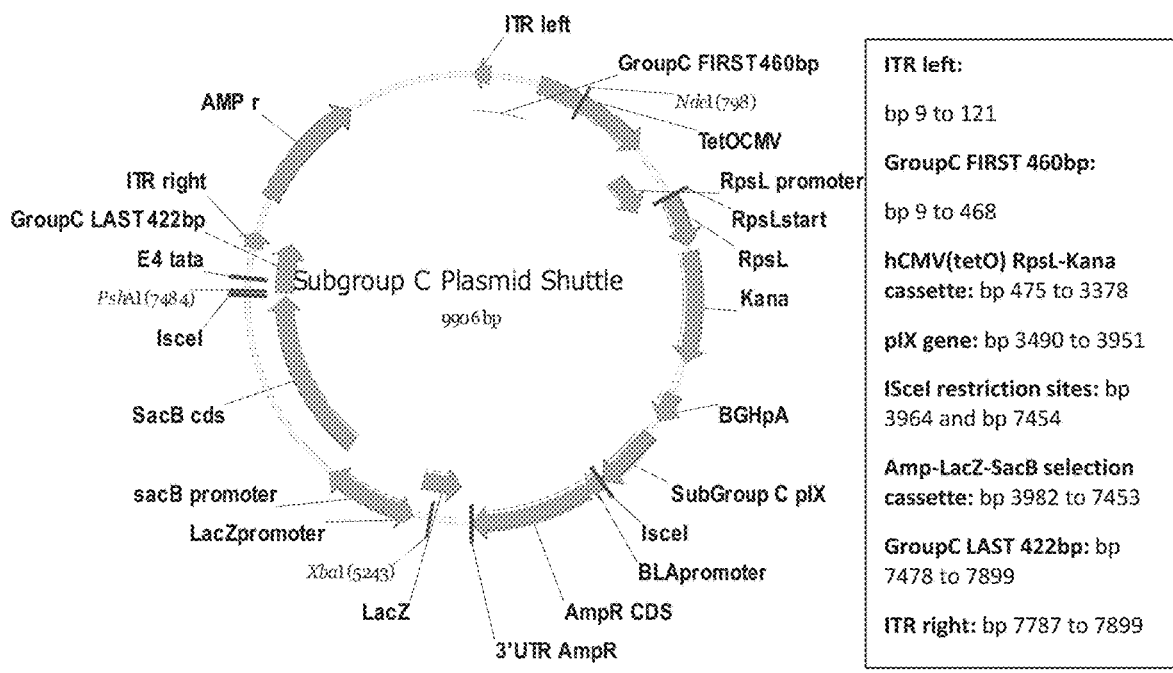

The ΔE1 minilibrary was digested with PanoI and used to transfect Procell 92 packaging cell line, in order to rescue the library of different viruses in bulk. 10 days post transfection, the cells were harvested and the cell lysate was subjected to three cycle of freeze (−70° C.) and thaw (+37° C.), clarified by centrifugation at 2000 rpm and used to infect fresh cells. 16 serial passages of virus amplification were performed, in order to select the viral species for efficiency of propagation in Procell92 cells. The virus (-es) at passage 16 were purified by two CsCl gradient centrifugations and viral DNA was extracted and cloned by homologous recombination in E. coli BJ5183 cells using a plasmid shuttle. In detail, BJ5183 cells were co-transformed with purified viral DNA and Subgroup C Plasmid Shuttle (SEQ ID NO: 38). As shown in the diagram of FIG. 3, the Subgroup C Plasmid Shuttle is a plasmid vector dedicated to the cloning of ChAd belonging to species C and therefore contains the DNA fragments derived from right and left ends (including right and left ITRs) of species C ChAd viruses.

Homologous recombination between right and left ITR DNA sequences present at the ends of linearized Subgroup C Plasmid Shuttle (digested with PshAl/NdeI/XbaI) and viral genomic DNAs allowed its insertion in the plasmid vector. 30 different clones were amplified and analysed by Restriction analysis and 9 different species were identified. 19/30 clones showed the same restriction patterns and represented the predominant species; one of these clones was selected and identified as pChAd157ΔE1 TetO hCMV RpsL-Kana #1551 (SEQ ID NO: 15).

1.3: Construction of ChAd157 ΔE1/TetO hCMV GAG #1557

The GAG cassette (GAG polynucleotide sequence SEQ ID NO: 16) was cloned into a linearised pre-adeno acceptor vector via homologous recombination in E. coli by exploiting the homology existing between HCMV promoter and BGH polyA sequences (SEQ ID NO: 39).

The plasmid pARS CV32TetOhCMV GAG was cleaved with SpeI and SphI to excise the 2.44 Kb fragment containing HCMV promoter with tetO, HIV-GAG and BGH polyA sequence.

The HIV-GAG 2.44 Kb fragment was cloned by homologous recombination into pChAd157 ΔE1/TetO hCMV RpsL-Kana (#1551) acceptor vector (SnabI digested) carrying the RpsL-Kana selection cassette under control of HCMV and BGHpA. The resulting construct was pChAd157 ΔE1/TetO hCMV GAG #1557 vector (SEQ ID NO: 17).

Figure 4:
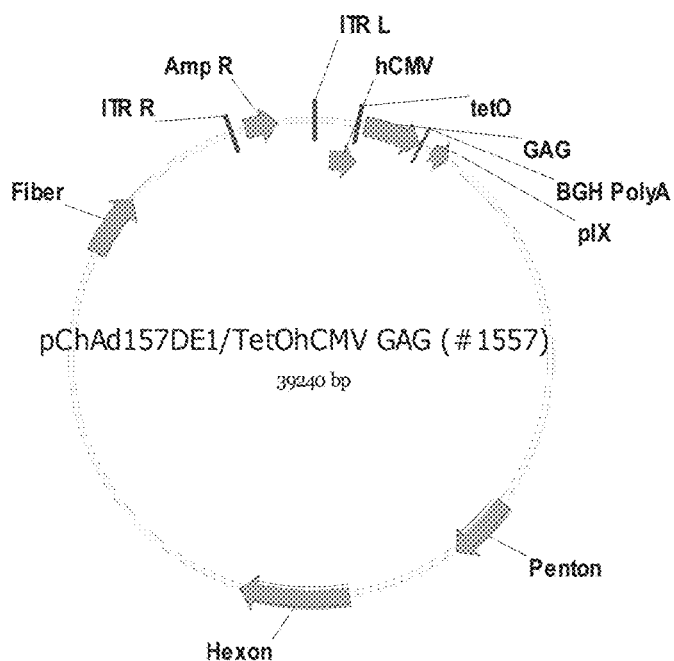
Figure 5:
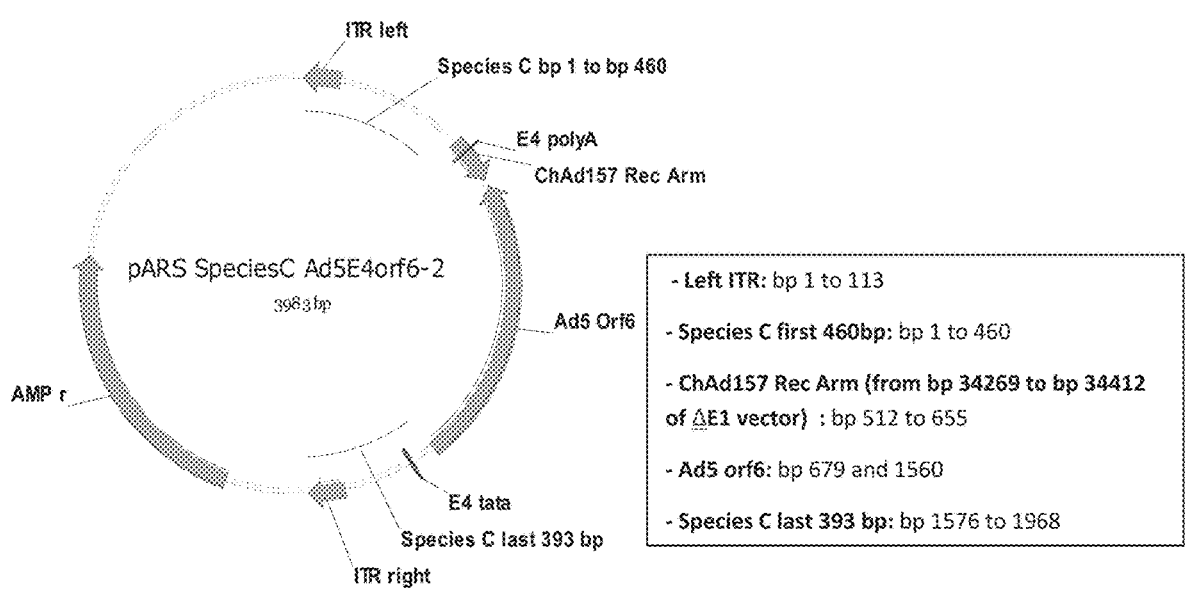

The structure of the plasmid carrying the ChAd157 GAG is reported in FIG. 4.

1.4: Construction of ChAd157 ΔE1E4 Ad5E4orf6/TetO hCMV RpsL-Kana #1594.

ChAd157ΔE1 vector was subsequently modified to carry the following modifications in the backbone:
  a) deletion of the E4 region (from bp 34413 to bp 37127) of the ΔE1 virus;
  b) insertion of the E4orf6 derived from human Ad5.

A deletion of E4 region spanning from nucleotide 34413 to 37127 (ΔE1 vector sequence coordinates) was introduced in the vector backbone by replacing the native E4 region with Ad5 E4orf6 coding sequence by using a strategy involving several steps of cloning and homologous recombination in E. coli. E4 coding region was completely deleted while E4 native promoter and polyadenylation signal were conserved. To this end, a shuttle vector was constructed to allow the insertion of Ad5orf6 by replacing ChAd157 native E4 region by homologous recombination in *E. coli* BJ5183 as detailed below.

Construction of pARS SpeciesC Ad5E4orf6-1:

Ad5orf6 containing DNA fragment was obtained by PCR using Ad5 DNA as template, with the oligonucleotides: 5'-ATACGGACTAGTGGAGAAGTACTCGCCTACATG-3' (SEQ ID NO: 18) and 5'-ATACGGAAGATCTAA-GACTTCAGGAAATATGACTAC-3' (SEQ ID NO: 19). The PCR fragment was digested with BglII and SpeI and cloned into pARS Species C RLD-EGFP shuttle digested with Bglll and SpeI, generating the plasmid pARS Species C Ad5orf6-1.

Construction of pARS SpeciesC Ad5E4orf6-2:

A 144 bp DNA fragment containing the Fiber-E4 polyA (from bp 34269 to bp 34412 of ChAd1574E1 vector) was amplified by PCR using as template the plasmid pChAd157 ΔE1/TetO hCMV RpsL-Kana (#1551) with the following oligonucleotides: 5'-ATTCAGTGTACAGGCGCGC-CAAAGCATGACACTGATGTTCATTTC-3' (SEQ ID NO: 20) and 5'-ACTAGGACTAGT-TATAAGCTAGAATGGGGCTTTGC-3' (SEQ ID NO: 21). The PCR fragment was digested with BsrGI and SpeI and cloned into pARS SubGroupC Ad5orf6-1 digested with BsrGI and SpeI, generating the plasmid pARS SpeciesC Ad5orf6-2 (SEQ ID NO: 40).

The resulting plasmid pARS SpeciesC Ad5orf6-2 was then used to replace the E4 with Ad5orf6 within ChAd157 backbone. To this end, the plasmid pChAd157ΔE1 TetO hCMV RpsL-Kana #1551 was digested with PacI and co-transformed into BJ5183 cells with the plasmid pARS SpeciesC Ad5orf6-2 BamHl/AscI digested, to obtain the pChAd157 ΔE1E4_Ad5E4orf6/TetO hCMV RpsL-Kana (#1594) preadeno plasmid (SEQ ID NO: 22).

1.5: Construction of ChAd157 ΔE1E4 Ad5E4orf6/TetO hCMV RG #1559.

The Rabies viral Glycoprotein (RG) expression cassette (Rabies Glycoprotein polynucleotide sequence SEQ ID NO: 23) was cloned into a linearised pre-adeno acceptor vector via homologous recombination in *E. coli* by exploiting the homology existing between HCMV promoter and BGH polyA sequences.

The plasmid pvjTetOhCMV-bghpolyA_RG was cleaved with SpeI and AsiSI to excise the 2.59 Kb fragment containing HCMV promoter with tetO, RG and BGHpolyA sequence.

The resulting RG 2.59 Kb fragment was cloned by homologous recombination into pChAd157 ΔE1E4_Ad5E4orf6/TetO hCMV RpsL-Kana (#1594) acceptor vector carrying the RpsL-Kana selection cassette under control of HCMV and BGHpA. The acceptor preAd plasmid was linearized with the restriction endonuclease SnaBI. The resulting construct was pChAd157 ΔE1E4_Ad5E4orf6/TetO hCMV RG #1559 vector (SEQ ID NO: 24).

Figure 6:
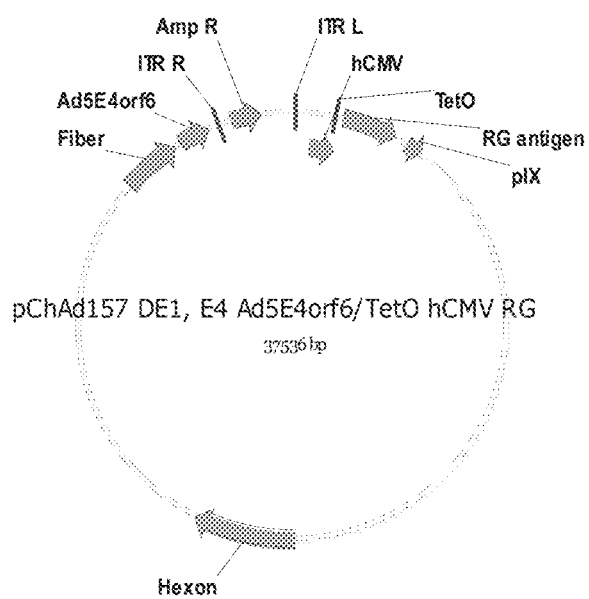

The structure of the plasmid carrying the ChAd157 RG is reported in FIG. 6.

Example 2: Vector Production

The productivity of ChAd157 was evaluated in comparison to ChAd19 and ChAd155 in the Procell 92 cell line.

2.1: Production of Vectors Comprising an HIV Gag Transgene

ChAd157/GAG, ChAd19/GAG, ChAd155/GAG (ChAd157, ChAd19 and ChAd155 vectors expressing an HIV Gag transgene) were rescued and amplified in Procell 92; the lysates were used to infect 1 T25 flask of Procell 92 cultivated in monolayer with each vector. A multiplicity of infection (MOI) of 300 vp/cell was used and the infections were performed in presence of tetracycline because ChAd19/GAG lacked the transcriptional control mediated by the insertion of the TetO operator in the hCMV promoter. The infected cells were harvested when full cytopathic effect was evident (48 hours post-infection for ChAd157/GAG and ChAd155/GAG and 5 days post-infections for ChAd19/GAG); the viruses were released from the infected cells by 3 cycles of freeze/thaw (−70° to 37° C.) then the lysate was clarified by centrifugation. The clarified lysates were quantified by Quantitative PCR Analysis with primers and probe complementary to the CMV promoter region. The oligonucleotide sequences are the following: CMVfor 5'-CATC-TACGTATTAGTCATCGCTATTACCA-3' (SEQ ID NO: 25), CMVrev 5'-GACTTGGAAATCCCCGTGAGT-3' (SEQ ID NO: 26), CMVFAM-TAMRA probe 5'-ACAT-CAATGGGCGTGGATAGCGGTT-3' (SEQ ID NO: 41) (QPCRs were run on ABI Prism 7900 Sequence detector—Applied Biosystem).

The resulting volumetric titers (vp/ml) measured on clarified lysates and the specific productivity expressed in virus particles per cell (vp/cell) are provided in Table 1 below.

TABLE 1

| GAG vector productivity. | | | |
|---|---|---|---|
| Vector | Volumetric productivity (vp/ml) | Total vp | Cell specific productivity (vp/cell) |
| ChAd157/GAG | 4.61E+09 | 2.30E+10 | 7.68E+03 |
| ChAd155/GAG | 5.42E+09 | 2.71E+10 | 9.04E+03 |
| ChAd19/GAG | 4.80E+08 | 2.40E+09 | 8.00E+02 |

2.2: Production of Vectors Comprising an RG Transgene

A different set of experiments were performed to evaluate the productivity of RG vaccine vectors in Procell 92 cultivated in suspension. The experiment compared ChAd157/RG and ChAd155/RG in parallel by infecting Procell 92 at a cell density of $5 \times 10^5$ cells/ml. A multiplicity of infection (MOI) of 300 vp/cell was used. The infected cells were harvested 4 days post infection; the virus was released from the infected cells by 3 cycles of freeze/thaw and the lysate was clarified by centrifugation. The clarified lysates were then quantified by QPCR as reported above.

The volumetric productivity and the cell specific productivity are provided in Table 2 below.

TABLE 2

| RG vector productivity. | | | |
|---|---|---|---|
| Vector | Volumetric productivity (vp/ml) | Total vp | Cell specific productivity (vp/cell) |
| ChAd157/RG | 9.39E+09 | 4.69E+11 | 1.88E+04 |
| ChAd155/RG | 1.41E+10 | 7.04E+11 | 2.81E+04 |

Example 3: Transgene Expression Levels

3.1: Expression Level of HIV Gag Transgene

Expression levels were compared in parallel experiments by infecting HeLa cells with ChAd19, ChAd155 and ChAd157 vectors comprising an HIV Gag transgene.

HeLa cells were seeded in 35 mm dishes and infected with ChAd19/GAG, ChAd157/GAG and ChAd155/GAG purified viruses using a MOI=250 vp/cell. The supernatants of infected HeLa cells were harvested 48 hours post-infection, and the production of secreted HIV GAG protein was quantified by using a commercial ELISA Kit (HIV-1 p24 ELISA Kit, PerkinElmer Life Science). The quantification was performed according to the manufacturer's instruction by using an HIV-1 p24 antigen standard curve.

Figure 7:
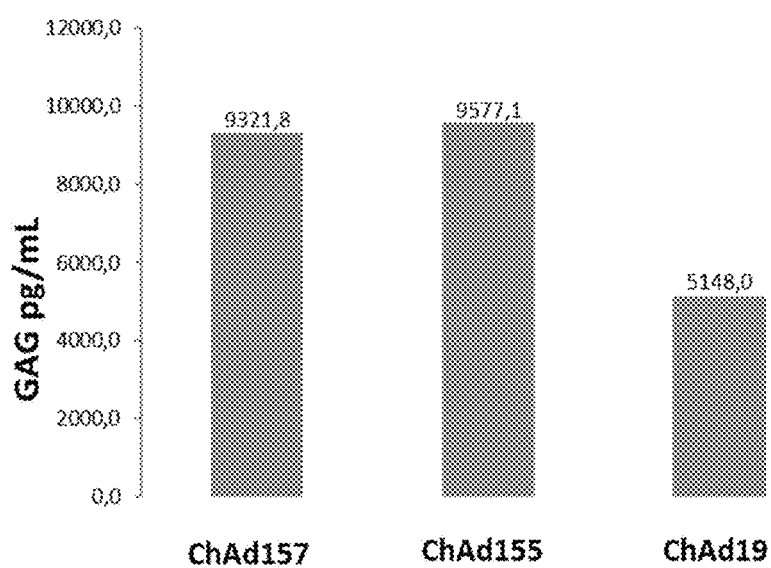

The results, expressed in pg/ml of GAG protein, are illustrated in FIG. 7.

3.2: Expression Level of RG Transgene

A western blot analysis was also performed to evaluate the rabies glycoprotein expression provided by the ChAd157/RG vector in comparison to ChAd155/RG vector. To this end, HeLa cells were seeded in 35 mm dishes and infected with ChAd157/RG and ChAd155/RG purified viruses using a MOI=250 vp/cell. Cell lysates were harvested 48 hours post-infection and the transgene expression level was evaluated by reducing SDS-PAGE followed by Western Blot analysis.

Figure 8:
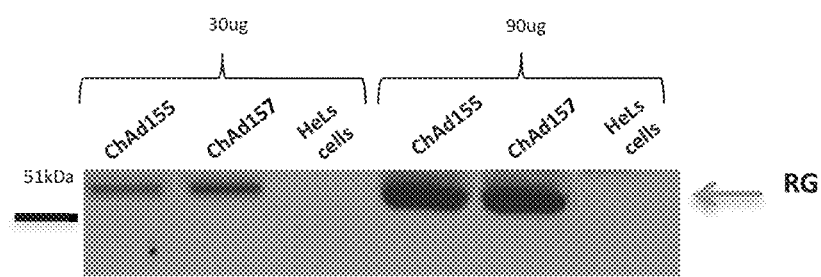

Equivalent quantities of proteins extracts were loaded on reducing SDS gel; after electrophoresis separation, the proteins were transferred to a nitrocellulose membrane to be probed with a Rabbit Polyclonal anti-GP (Cat. No. RBVGP11-S aDiagnostic, diluted 1:1000). After the incubation with primary antibody, the membrane was washed and then incubated with anti-rabbit horseradish peroxidase (HRP) conjugate secondary antibody. Finally the assay was developed by chemiluminescence using enhanced chemiluminescence (ECL) detection reagents (W3252282 PIERCE). The Western Blot results are shown in FIG. 8.

A band of about 57 kD indicated by the arrow was revealed by polyclonal antibody anti-GP, which corresponds to the expected weight of rabies glycoprotein.

The result demonstrated that the expression level of ChAd157 vector appears comparable to that provided by ChAd155.

Example 4: Evaluation of Immunological Potency by Mouse Immunization Experiments

4.1: Immunogenicity of Vectors Comprising the HIV Gag Transgene

Figure 9:
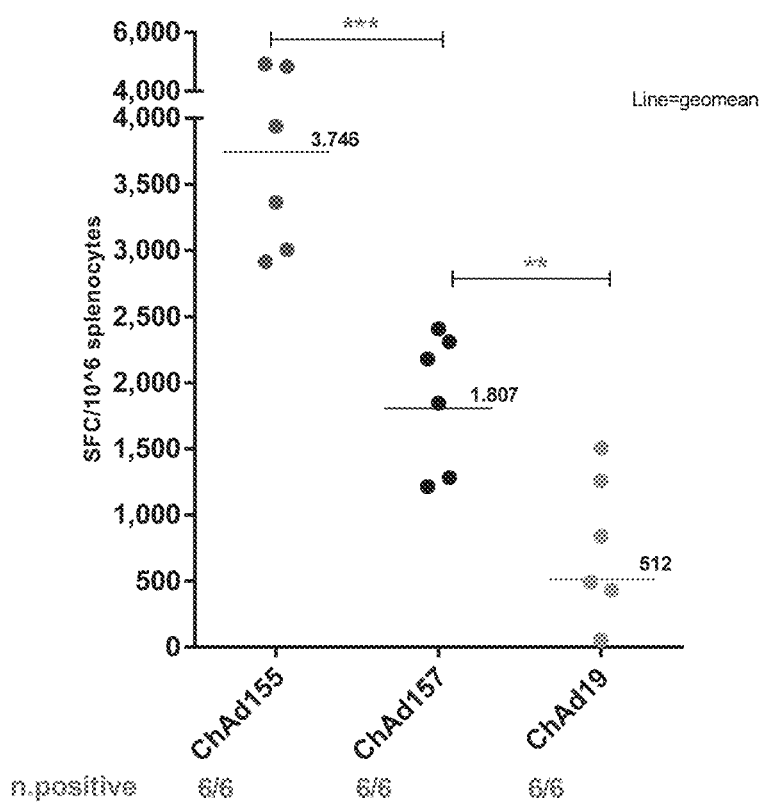

The immunogenicity ChAd157/GAG vector was evaluated in parallel with ChAd155/GAG and ChAd19/GAG in BALB/c mice (6 per group). The experiment was performed by injecting $10^7$ viral particles intramuscularly. T-cell response was measured 3 weeks after the immunization by ex vivo interferon-γ (IFN-γ) enzyme-linked immunospot (ELISpot) using a GAG CD8+ T cell epitope mapped in BALB/c mice. The results obtained are reported in FIG. 9, expressed as IFNγ Spot Forming Cells (SFC) per million of splenocytes.

Each dot represents the response in a single mouse and the line corresponds to the geomean for each dose group. Frequency of positive mice to the CD8 immunodominant peptide is shown on the x axis.

4.2 Immunogenicity of Vectors Comprising the RG Transgene

The immunological potency of ChAd157/RG and ChAd155/RG vectors was evaluated in BALB/c mice. Both vectors were injected intramuscularly with $10^7$ and $10^6$ vp doses. The splenocytes of immunized mice were isolated seven weeks after vaccination and analysed by IFNγ ELISpot (FIG. 10), using peptide pools from RG as antigen.

Figure 10:
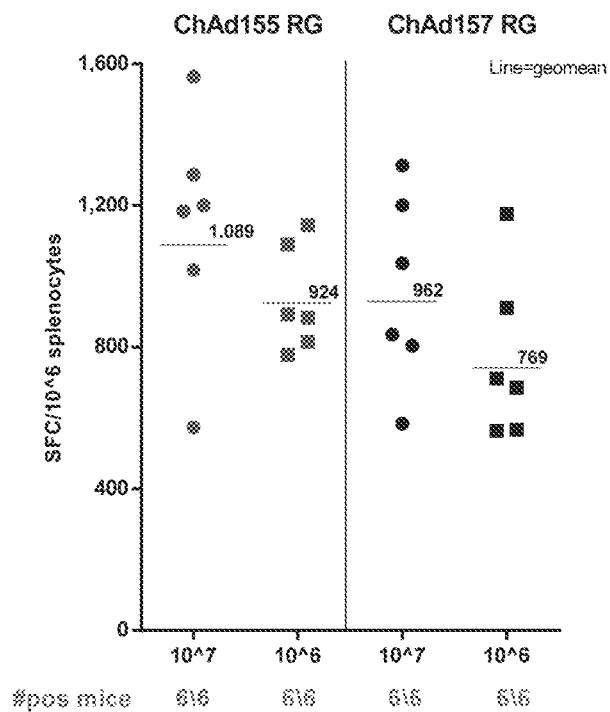

The levels of immune response were reduced in line with decreasing dosage, as expected. Moreover, ChAd155RG vector induced higher T cell response than ChAd157 RG, although they were not significantly different (FIG. 10).

Example 5: Evaluation of Infectivity

5.1 Infectivity of Vectors Comprising the HIV Gag Transgene

The infectivity of purified viruses was evaluated in adherent Procell 92 cells utilizing an antibody against adenovirus hexon protein to visualize infected cells by immunocytochemistry staining. The antibody against hexon protein recognizes all serotypes of adenoviruses. To this end, Procell92 cells were seeded in 24 well plate at a cell density of $2\times10^5$ viable cell/ml and infected in duplicate with ChAd157/GAG and ChAd155/GAG and ChAd19/GAG vectors using a MOI=1 vp/cell, 0.5 vp/cell and 0.25 vp/cell. 48 hours post-infection, infected cells were fixed by cold methanol and then labelled with the anti-hexon antibody. Excess antibody is removed. The labelled cells are then incubated with a secondary antibody conjugated with horseradish peroxidase and the detection is performed by using a commercial kit VECTOR NOVARED Substrate Kit (SK-4800). Detection is accomplished when the horseradish peroxidase enzyme label reacts with the DAB substrate resulting in a dark brown product. The labelled, dark brown cells were then quantified by light microscopy and the infectious titer calculated. The results are shown in the table below

| Virus | Vp/ml | Ifu/ml | R (vp/ifu) |
| --- | --- | --- | --- |
| ChAd155 GAG | 1.32E+11 | 1.58E+09 | 84 |
| ChAd157 GAG | 1.17E+11 | 1.23E+09 | 95 |
| ChAd19 GAG | 4.46E+10 | 3.86E+08 | 116 |

The result demonstrated that the infectivity of ChAd155 and ChAd157 viruses are comparable and higher than ChAd19.

5.2 Infectivity of Vectors Comprising the RG Transgene

The infectivity of ChAd157/RG and ChAd155/RG purified viruses was evaluated in adherent Procell 92 cells by Hexon Immunostaining as reported above. The results are shown in the table below

| Virus | Vp/ml | Ifu/ml | R (vp/ifu) |
|---|---|---|---|
| ChAd155/RG | 4.23E+11 | 4.06E+09 | 104 |
| ChAd157/RG | 1.97E+11 | 1.46E+09 | 133 |

The result demonstrated that the infectivity of ChAd155 and ChAd157 viruses are comparable

Example 6: Evaluation of Cross-Neutralization Between Chad155 and Chad157 Vectors

6.1 Testing In Vivo if ChAd155 and ChAd157 Vectors are Different Serotypes

The cross-neutralization between ChAd155 and ChAd157 vectors was assessed in BALB/c mice (6 per group). Mice were preimmunized twice at week 0 and week 3 with $10^9$ vp of ChAd155 or ChAd157 expressing RG or were mock-vaccinated with saline buffer.

Three weeks later, all mice were then immunized once with $10^9$ vp of ChAd157 encoding HIV gag

| Groups | n | Pre-immunization 2× w0 and w3 | dose (vp) | Immunization w6 | dose (vp) |
|---|---|---|---|---|---|
| 1 | 6 | PBS | — | ChAd157-GAG | $10^9$ |
| 2 | 6 | ChAd155-RG | $10^9$ | ChAd157-GAG | $10^9$ |
| 3 | 6 | ChAd157-RG | $10^9$ | ChAd157-GAG | $10^9$ |

Figure 11:
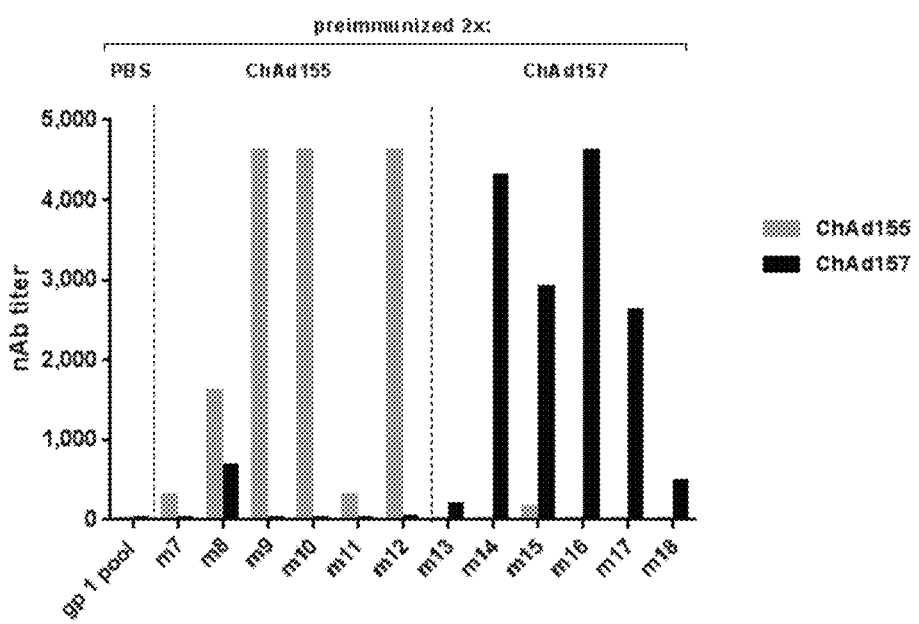
Figure 12:
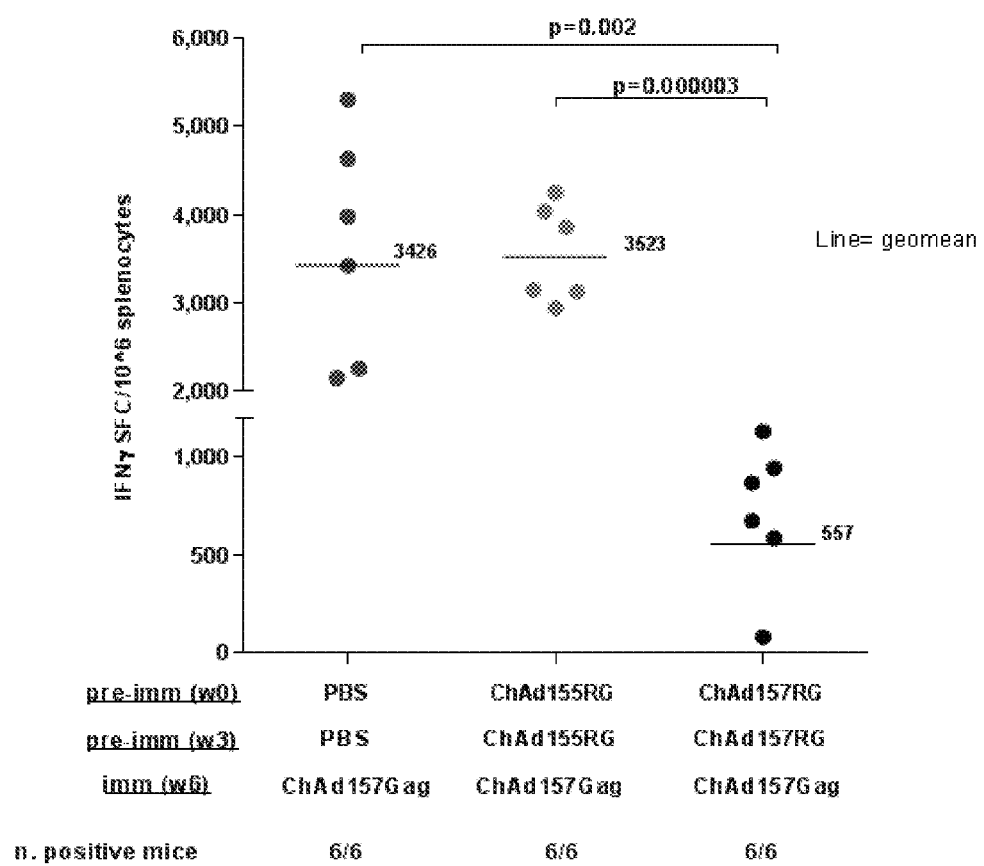

Neutralization titers to the preimmunizing vectors were measured in sera at week 5 (2 weeks post second injection) by in vitro neutralization assay (FIG. 11). Finally, T cell response against gag was tested on splenocytes 3 weeks after immunization by IFN-γ ELISpot, using a GAG CD8+ T cell epitope mapped in BALB/c mice (FIG. 12). The doses of vectors used for preimmunization were able to elicit good neutralizing activities against the two Ad vectors, although with some variability. Anti ChAd155 neutralizing antibodies do not cross-react against ChAd157 and vice-versa (FIG. 11). Moreover, ChAd157-Gag T-cell response was not affected by anti-ChAd155 preimmunity, confirming that cross-neutralization was not observed (FIG. 12).

Taken together, these data suggest that ChAd155 and ChAd157 viruses are distinct adenovirus serotypes.

---

The invention claimed is:

1. An isolated recombinant polynucleotide simian adenoviral vector, wherein the polynucleotide encodes a polypeptide having the amino acid sequence according to SEQ ID NO: 1, and
further encodes a heterologous polypeptide and the polynucleotide encoding the heterologous polypeptide is operatively linked to one or more sequences which direct expression of the heterologous polypeptide.

2. A composition according to claim 1, further comprising a pharmaceutically acceptable excipient.

3. An isolated cell comprising the isolated recombinant polynucleotide simian adenoviral vector of claim 1.

4. The isolated recombinant polynucleotide simian adenoviral vector according to claim 1, wherein the polynucleotide has a sequence according to SEQ ID NO: 2.

5. The isolated recombinant polynucleotide simian adenoviral vector according to claim 1, further comprising a polynucleotide encoding
a polypeptide having the amino acid sequence according to SEQ ID NO: 3.

6. The isolated recombinant polynucleotide simian adenoviral vector according to claim 1, wherein the polynucleotide comprises a sequence according to SEQ ID NO: 4.

7. The isolated recombinant polynucleotide simian adenoviral vector according to claim 1, further comprising a polynucleotide encoding
a polypeptide having the amino acid sequence according to SEQ ID NO: 5.

8. The isolated recombinant polynucleotide simian adenoviral vector according to claim 1, wherein the polynucleotide comprises a sequence according to SEQ ID NO: 6.

9. The isolated recombinant polynucleotide simian adenoviral vector according to claim 1, wherein the polynucleotide comprises at least one of the following:
(a) an adenoviral 5' inverted terminal repeat;
(b) an adenoviral E1A region, or a fragment thereof selected from among the E1A_280R and E1A_243R regions;
(c) an adenoviral E1B or IX region, or a fragment thereof selected from among the group consisting of the E1B_19K, E1B_55K or IX regions;
(d) an adenoviral E2b region; or a fragment thereof selected from among the group consisting of the E2B_pTP, E2B_Polymerase and E2B_IVa2 regions;
(e) an adenoviral L1 region, or a fragment thereof, said fragment encoding an adenoviral protein selected from the group consisting of the L1_13.6k protein, L1_52k and L1_IIIa protein;
an adenoviral L2 region, or a fragment thereof, said fragment encoding an adenoviral protein selected from the group consisting of the L2_penton, L2_pVII, L2_V, and L2_pX protein;
(g) an adenoviral L3 region, or a fragment thereof, said fragment encoding an adenoviral protein selected from the group consisting of the L3_pVI protein, L3_hexon protein, and L3_protease;
(h) an adenoviral E2A region;
an adenoviral L4 region, or a fragment thereof said fragment encoding an adenoviral protein selected from the group consisting of the L4_100k protein, the L4_33k protein and protein L4_VIII;
(j) an adenoviral E3 region, or a fragment thereof selected from the group consisting of E3 ORF1, E3 ORF2, E3 ORF3, E3 ORF4, E3 ORF5, E3 ORF6, E3 ORF7, E3 ORF8, and E3 ORF9;
(k) an adenoviral L5 region, or a fragment thereof said fragment encoding the L5_fiber protein;
(l) an adenoviral E4 region, or a fragment thereof selected from the group consisting of E4 ORF7, E4 ORF6, E4 ORF4, E4 ORF3, E4 ORF2, and E4 ORF1;
(m) an adenoviral 3' inverted terminal repeat; and/or
(n) an adenoviral VAI or VAII RNA region from an adenovirus other than ChAd157.

10. The isolated recombinant polynucleotide simian adenoviral vector according to claim 1, wherein the polynucleotide comprises a polynucleotide which is at least 95% identical over its entire length to a reference sequence that consists essentially of SEQ ID NO: 15 or 22.

11. The isolated recombinant polynucleotide simian adenoviral vector according to claim 10, wherein the polynucleotide comprises or consists of a polynucleotide which is at least 99.5% identical over its entire length to the reference sequence.

12. The isolated recombinant polynucleotide simian adenoviral vector according to claim 11, wherein the polynucleotide comprises or consists of a polynucleotide which is identical over its entire length to the reference sequence.

13. The isolated recombinant polynucleotide simian adenoviral vector according to claim 1, wherein the adenoviral vector is replication competent.

14. The isolated recombinant polynucleotide simian adenoviral vector according to claim 1, wherein the adenoviral vector is replication incompetent.

15. The isolated recombinant polynucleotide simian adenoviral vector according to claim 14, wherein the adenoviral vector comprises a functional inactivation.

16. The isolated recombinant polynucleotide simian adenoviral vector according to claim 1, wherein the functional inactivation is a deletion.

17. The isolated recombinant polynucleotide simian adenoviral vector according to claim 1, wherein the functional inactivation comprises a mutation or deletion which renders non-functional at least one gene of a genomic region selected from the group consisting of E1A, E1B, E2A, E2B, E3 and E4.

18. The isolated recombinant polynucleotide simian adenoviral vector according to claim 1, wherein the heterologous polypeptide is an antigenic protein or a fragment thereof.

19. The isolated recombinant polynucleotide simian adenoviral vector of claim 1, wherein the one or more sequences which direct expression of the heterologous polypeptide is selected from one or more of the group consisting of transcription initiation, transcription termination, promoter and enhancer sequences.

20. A composition according to claim 2, further comprising an adjuvant.

21. A cell according to claim 3, wherein the cell is a host cell that expresses at least one adenoviral gene selected from the group consisting of E1A, E1B, E2A, E2B, E3 E4, L1, L2, L3, L4 and L5.

22. A method for eliciting an immune response in a subject comprising
  (a) administering to the subject a recombinant adenoviral vector according to claim 1 encoding a first heterologous polypeptide; and
  (b) administering to the subject a recombinant adenoviral vector which does not comprise a ChAd157 fiber, the vector encoding a second heterologous polypeptide,
wherein steps (a) and (b) may be undertaken in either order and the first and second heterologous polypeptides may be the same or different.

23. The method according to claim 22, wherein the subject has previously been exposed to a recombinant adenoviral vector which does not comprise a ChAd157 fiber.

24. The method according to claim 23, wherein the recombinant vector to which the subject has been previously exposed is a recombinant adenoviral vector comprising a ChAd155 fiber, hexon and/or penton.

* * * * *